United States Patent
Duffy et al.

(10) Patent No.: US 7,351,575 B2
(45) Date of Patent: *Apr. 1, 2008

(54) METHODS FOR PROCESSING BIOLOGICAL MATERIALS USING PEELABLE AND RESEALABLE DEVICES

(75) Inventors: David Duffy, Cambridge, MA (US); Gregory L. Kirk, Winchester, MA (US); Stewart Campbell, Framingham, MA (US); Olivier Schueller, Somerville, MA (US); Melina Agosto, Dorchester, MA (US)

(73) Assignee: Surface Logix, Inc., Brighton, MA (US)

( * ) Notice: Subject to any disclaimer, the term of this patent is extended or adjusted under 35 U.S.C. 154(b) by 852 days.

This patent is subject to a terminal disclaimer.

(21) Appl. No.: 10/206,590

(22) Filed: Jul. 29, 2002

(65) Prior Publication Data

US 2003/0068637 A1    Apr. 10, 2003

Related U.S. Application Data

(63) Continuation-in-part of application No. 09/709,776, filed on Nov. 8, 2000, now Pat. No. 6,699,665.

(60) Provisional application No. 60/307,839, filed on Jul. 27, 2001, provisional application No. 60/323,743, filed on Sep. 21, 2001, provisional application No. 60/357,649, filed on Feb. 20, 2002, provisional application No. 60/366,260, filed on Mar. 22, 2002, provisional application No. 60/375,024, filed on Apr. 25, 2002, provisional application No. 60/380,314, filed on May 15, 2002.

(51) Int. Cl.
*C12M 1/34* (2006.01)
*C12M 3/00* (2006.01)

(52) U.S. Cl. .................. 435/288.3; 435/283.1; 435/287.1; 435/287.2; 435/288.4; 422/50; 422/61; 422/68.1

(58) Field of Classification Search .................. 435/4, 435/7.1, 283.1, 287.1, 287.2, 288.3, 288.4, 435/288.7; 422/50, 61, 68.1; 436/501, 518
See application file for complete search history.

(56) References Cited

U.S. PATENT DOCUMENTS 4,591,570 A    5/1986    Chang (Continued)

FOREIGN PATENT DOCUMENTS

WO    WO 96/02830    2/1996

(Continued)

OTHER PUBLICATIONS

MacBeath et al. Printing Small Molecules as Microarrays and Detecting Protein-Ligand Interactions en Masse, 1999, J. Am. Chem. Soc. vol. 121, pp. 7967-7968.*

(Continued)

*Primary Examiner*—Long V. Le
*Assistant Examiner*—Melanie J. Yu
(74) *Attorney, Agent, or Firm*—Kenyon & Kenyon LLP

(57) ABSTRACT

Devices and methods for performing assays on materials, particularly biological materials, are provided. The devices and methods make use of self-sealing members, which can be applied to a flat surface to form wells to facilitate immobilization of materials on the flat surface, then removed to yield a flat surface that facilitates the performance of processes on and/or detection of the immobilized material.

24 Claims, 62 Drawing Sheets

U.S. PATENT DOCUMENTS

| | | | |
|---|---|---|---|
| 4,689,310 | A | 8/1987 | Kramer et al. |
| 4,728,591 | A | 3/1988 | Clark et al. |
| 4,748,124 | A | 5/1988 | Vogler |
| 4,802,951 | A | 2/1989 | Clark et al. |
| 4,818,336 | A | 4/1989 | Rossetti |
| 4,842,633 | A | 6/1989 | Kuribayashi et al. |
| 4,886,761 | A | 12/1989 | Gustafson et al. |
| 5,079,600 | A | 1/1992 | Schnur et al. |
| 5,120,662 | A | 6/1992 | Chan et al. |
| 5,143,854 | A | 9/1992 | Pirrung et al. |
| 5,143,857 | A | 9/1992 | Finchem et al. |
| 5,154,808 | A | 10/1992 | Miyasaka et al. |
| 5,160,597 | A | 11/1992 | Colapicchioni et al. |
| 5,228,514 | A | 7/1993 | Worden et al. |
| 5,229,163 | A | 7/1993 | Fox |
| 5,229,172 | A | 7/1993 | Cahalan et al. |
| 5,242,828 | A | 9/1993 | Bergström et al. |
| 5,284,753 | A | 2/1994 | Goodwin, Jr. |
| 5,302,515 | A | 4/1994 | Goodwin, Jr. |
| 5,384,073 | A | 1/1995 | Shigekawa et al. |
| 5,384,261 | A | 1/1995 | Winkler et al. |
| 5,405,783 | A | 4/1995 | Pirrung et al. |
| 5,412,087 | A | 5/1995 | McGall et al. |
| 5,429,708 | A | 7/1995 | Linford et al. |
| 5,445,934 | A | 8/1995 | Fodor et al. |
| 5,512,131 | A | 4/1996 | Kumar et al. |
| 5,599,695 | A | 2/1997 | Pease et al. |
| 5,603,351 | A | 2/1997 | Cherukuri et al. |
| 5,605,662 | A | 2/1997 | Heller et al. |
| 5,677,196 | A | 10/1997 | Herron et al. |
| 5,677,197 | A | 10/1997 | Gordon et al. |
| 5,688,642 | A | 11/1997 | Chrisey et al. |
| 5,731,152 | A | 3/1998 | Maracas et al. |
| 5,763,191 | A | 6/1998 | Knoll et al. |
| 5,776,748 | A | 7/1998 | Singhvi et al. |
| 5,784,193 | A | 7/1998 | Ferguson |
| 5,840,256 | A | 11/1998 | Demers et al. |
| 5,893,650 | A | 4/1999 | Ohmura |
| 5,900,160 | A | 5/1999 | Whitesides et al. |
| 5,948,621 | A | 9/1999 | Turner et al. |
| 5,976,826 | A | 11/1999 | Singhvi et al. |
| 6,004,617 | A | 12/1999 | Schultz et al. |
| 6,037,171 | A | 3/2000 | Larsson |
| 6,039,897 | A | 3/2000 | Lochhead et al. |
| 6,083,763 | A | 7/2000 | Balch |
| 6,090,545 | A | 7/2000 | Wohlstadter et al. |
| 6,103,479 | A | 8/2000 | Taylor |
| 6,127,129 | A | 10/2000 | Corn et al. |
| 6,136,592 | A | 10/2000 | Leighton |
| 6,184,344 | B1 | 2/2001 | Kent et al. |
| 6,187,919 | B1 | 2/2001 | Birbaum et al. |
| 6,197,515 | B1 | 3/2001 | Bamdad et al. |
| 6,225,109 | B1 | 5/2001 | Juncosa et al. |
| 6,232,066 | B1* | 5/2001 | Felder et al. ............... 435/6 |
| 6,322,683 | B1 | 11/2001 | Wolk et al. |
| 6,329,201 | B1 | 12/2001 | Polo et al. |
| 6,558,904 | B2 | 5/2003 | Ermantraut et al. |
| 6,716,629 | B2* | 4/2004 | Hess et al. ................. 435/420 |
| 6,984,265 | B1* | 1/2006 | Raguse et al. ............... 117/73 |
| 2001/0001644 | A1 | 5/2001 | Coffman et al. |
| 2001/0031468 | A1 | 10/2001 | Chenchik et al. |
| 2001/0041349 | A1 | 11/2001 | Patron et al. |
| 2002/0012920 | A1 | 1/2002 | Gardner et al. |
| 2002/0019015 | A1 | 2/2002 | Lahiri et al. |
| 2002/0102405 | A1* | 8/2002 | Chapman et al. ......... 428/411.1 |
| 2002/0182603 | A1* | 12/2002 | Chapman et al. ............ 435/6 |
| 2003/0082604 | A1* | 5/2003 | Swanson et al. ............. 435/6 |
| 2003/0162216 | A1* | 8/2003 | Gold et al. ................. 435/6 |
| 2004/0253625 | A1* | 12/2004 | Barany et al. ............... 435/6 |
| 2006/0073610 | A1* | 4/2006 | Kopaciewicz ............... 436/518 |

FOREIGN PATENT DOCUMENTS

| | | |
|---|---|---|
| WO | WO 98/30575 | 7/1998 |
| WO | WO 98/36827 | 8/1998 |
| WO | WO 99/51773 | 10/1999 |
| WO | WO 99/54786 | 10/1999 |
| WO | WO 00/04390 | 1/2000 |
| WO | WO 00/68419 | 11/2000 |
| WO | WO 00/76662 A2 | 12/2000 |
| WO | WO 01/34302 | 5/2001 |
| WO | WO 01/70389 A2 | 9/2001 |
| WO | WO 02/26377 A2 | 4/2002 |

OTHER PUBLICATIONS

Amit et al., "Photosensitive Protecting Groups of Amino Sugars and Their Use in Glyoside Synthesis, 2-Nitrobenzyloxycarbonylamino and 6-Nitroveratryloxycarbonylamino Derivatives", J. Org. Chem., 39(2):192-196 (1974).

Becker et al., "Fabrication of microstructures with high aspect ratios and great structural heights by synchrotron radiation lithography, galvanoforming, and plastic moulding (LIGA process)", Microelectronic Engineering, 4:35-56 (1986).

Bergstrom et al., "C-5 Substituted Pyrimidine Nucleosides. 2. Synthesis via Olefin Coupling to Organopalladium Intermediates Derived from Uridine and 2'-Deoxyuridine", J. Am. Chem. Soc., 100(26):8106-8112 (1978).

Bernard et al., "Printing Patterns of Proteins", Langmuir 14(9):2225-2229 (1998).

Bishop et al., "Self-assembled monolayers: recent developments and applications", Current Opinion in Colloid & Interface Science, 1:127-136 (1996).

Blawas et al., "Step-and-Repeat Photopatterning of Protein Features Using Caged-Biotin-BSA: Characterization and Resolution", Langmuir, 14:4243-4250 (1998).

Blawas et al., "Protein patterning", Biomaterials, 19:595-609 (1998).

Bunin et al., "The combinatorial synthesis and chemical and biological evaluation of a 1,4-benzodiazepine library", Proc. Natl. Acad. Sci. USA, 91:4708-4712 (1994).

Castner et al., "Biomedical surface science: Foundations to frontiers", Surface Science, 500:28-60 (2002).

Chiu et al., "Patterned deposition of cells and proteins onto surfaces by using three-dimensional microfluidic systems",PNAS, 97(6):2408-2413 (2000).

Delamarche et al., "Golden Interfaces: The Surface of Self-Assembled Monolayers", Adv. Materials, 8(9):719-729 (1996).

Deng, et al., "Self-Assembled Monolayer of Alkanethiolates Presenting Tri (propylene sulfoxide) Groups Resist the Adsorption of Protein", J. Am. Chem. Soc., 118:5136-5137(1996).

Dubois, "Synthesis, Structure, and Properties of Model Organic Surfaces", Annu. Rev. Phys. Chem, 43:437-463 (1992).

Eteshola et al., "Development and Characterization of an ELISA assay in PDMS Microfluidic Channels", Senors and Actuators, pp. 129-133 (2001).

Folch et al., "Microengineering of Cellular Interactions", Annu. Rev. Biomed. Eng., 2:227-56 (2000).

Folch et al., "Microfabricated elastomeric stencils for micropatterning cell cultures", Journal of Biomedical Materials Research, Nov. 2000, 52:346-353.

Geysen et al., "Screening Chemically Synthesized Peptide Libraries for Biologically-Relevant Molecules", Bioorganic & Medicinal Chemistry Letters, 3(3):397-404 (1993).

Horan et al., "Nonstatistical binding of a protein to clustered carbohydrates", PNAS, 96(21):11782-11786 (1999).

Jackman et al., "Using Elastomeric Membranes as Dry Resists and for Dry Lift-Off", Langmuir, 15:2973-2984 (1999).

James et al., "Patterned Protein Layers on Solid Substrates by Thin Stamp Microcontact Printing", Langmuir 14:741-744 (1998).

Janshoff et al., "Micropatterned solid-supported membranes formed by micromolding in capillaries", Eur. Biophys. J., 29:549-554 (2000).

Kok et al., "*Immobilization of acetylcholinesterase and choline in/on pHEMA membrane for biosensor construction*", J. Biomater. Sci. Polymer Edn., 12(11):1161-1176 (2001).

Kondabagil et al., "*Proteomics and Microarrays in Cancer Research*", J. Microbiol. Biotechnol., 11(6):907-914 (2001).

Lee et al., "*Design and Fabrication of CD-Like Microfluidic Platforms for Diagnostics: Polymer-Based Microfabrication*", Biomedical Microdevices 3(4): 339-351 (2001).

Liang et al., "Measuring the forces involved in polyvalent adhesion of uropathogenic *Escherichia coli* to mannose-resenting surfaces", PNAS, 97(24):13092-96 (2000).

Libioulle et al., "*Contact-Inking Stamps for Microcontact Printing of Alkanethiols on Gold*", Langmuir, 15:300-304 (1999).

Livache et al., "*Electroconducting polymers for the construction of DNA or peptide arrays on silicon chips*", Biosensors Bioelectronics, 13:629-634 (1998).

López et al., "*Fabrication and Imaging of Two-Dimensional Patterns of Proteins Adsorbed on Self-Assembled Monolayers by Scanning Electron Microscopy*", J. Am. Chem. Soc.,115(23):10774-10781 (1993).

Luk et al., "*Self-Assembled Monolayers of Alkanethiolates Presenting Manitol Groups Are Inert to Protein Adsorption and Cell Attachment*", Langmuir, 16(24):9604-9608 (2000).

MacBeath G., "*Proteomics comes to the surface*", Nature Biotechnology, 19:828-829 (2001).

Mrkisch et al., "*Using Self-Assembled Monolayers to Understand the Interactions of Man-made Surfaces with Proteins and Cells*", Annu. Rev. Biophys. Biomol. Struct., 25:55-78 (1996).

Mrkisch et al., "*Patterning self-assembled monolayers using microcontact printing: a new technology for biosensors?*", Trends Biotechnology, 13:228-235 (1995).

Pale-Grosdemange et al., "*Formation of Self-Assembled Monolayers by Chemisorption of Derivatives of Olio (ethylene glycol) of Structure $HS(CH_2)_{11}(OCH_2\ CH_2)mOH$ on Gold[1]*". J. Am. Chem. Soc., 113(1):12-20 (1991).

Patchornik et al., "*Photosensitive Protecting Groups*", JACS, 92(21):6333-6335 (1970).

Rogers et al., "*Using an elastomeric phase mask for sub-100 nm photolithography in the optical near field*", Appl. Phys. Lett 70 (20):2658-2660 (1997).

Schindler F., "*Surface Plasmon Resonance—was steckt dahinter?*", LaborPraxis, pp. 38-42 (2000).

Service R.F., "*Protein Arrays Step Out of DNA's Shadow*", Science, 289:1673-1676 (2000).

Service R.F., "*Searching for Recipes for Protein Chips*", Science, 294:2080-2082 (2001).

Service R.F., "*High-Speed Biologists Search For Gold in Proteins*", Science, 294:2074-2083 (2001).

Shonnard et al., "*Hydrodynamic Effects on Microcapillary Motility and Chemotaxis Assays of Methylosinus trichosporium OB3b*", Applied and Environmental Microbiology, 58(9):2737-43 (1992).

Sigai et al., "*A Self-Assembled Monolayer for the Binding and Study of Histidine-Tagged Proteins by Surface Plasmon Resonance*", Anal. Chem., 68(3):490-497 (1996).

Singhvi et al., "*Engineering Cell Shape and Function*", Science, 264:696-698 (1994).

Society Updates, Journal of Biomolecular Screening, 6(2):61-67 (2001).

Stranick et al., "*Phase Separation of Mixed-Composition Self-Assembled Monolayers into Nanometer Scale Molecular Domains*", J. Phys. Chem., 98:7636-7646 (1994).

Sznaidman, "*Introduction to Carbohydrates*", Bioorganic Chemistry: Carbohydrates, pp. 1-55 (S.M. Hecht, Ed. Oxford Press, 1999).

Troughton et al. "*Monolayer Films Prepared by the Spontaneous Self-Assembly of Symmetrical and Unsymmetrical Dialky Sulfides from Solution onto Gold Substrates: Structure, Properties, and Reactivity of Constituent Functional Groups*", Langmuir, 4(2):365-385 (1988).

Ulman, "*Surface Absorption of Monolayers*", MRS Bulletin, 20(6):46-50(1995).

Ulman, "*Formation and Structure of Self-Assembled Monolayers*", Chem. Rev., 96:1533-1554 (1996).

Vo-Dinh et al., "*Nanosensors and biochips: frontiers in biomolecular diagnostics,*" Sensors and Actuators B 74, pp. 2-11 (2001).

Wagner et al., "*Bioreactive Self-Assembled Monolayers on Hydrogen-Passivated Si(III) as a New Class of Atomically Flat Substrates for Biological Scanning Probe Microscopy*", Journal of Structural Biology, 119:189-201 (1997).

Wagner et al., "*Formation and in Situ Modification of Monolayers Chemisorbed on Ultraflat Template-Stripped Gold Surfaces*", Langmuir, 11(10): 3867-3875 (1995).

Whitesides et al., "*Wet Chemical Approaches to the Characterization of Organic Surfaces: Self-Assembled Monolayers, Wetting, and the Physical-Organic Chemistry of the Solid-Liquid Interface*", Langmuir, 6:87-96 (1990).

Whitesides et al., "*Self-Assembled Monolayers: Models for Organic Surface Chemistry*", Surface Imaging and Visualization, Chapter 52, pp. 713-733.

Willner, et al., "*Integration of a Reconstituted de Novo Synthesized Hemoprotein and Native Metalloproteins with Electrode Supports for Bioelectronic and Bioelectrocatalytic Applications*", J. Am. Chem. Soc., 121:6455-6468 (1999).

Xia et al., "*Soft Lithography*", Angew. Chem. Int. Ed., 37:550-575 (1998).

Xu et al., "*The Chemistry of Self-Assembled Long-chain Alkanethiol Monolayers on Gold*", Journal of Colloid and Interface Science, 176:138-149 (1995).

Yang et al., "*Light-Activated Affinity Micropatterning of Proteins on Self-Assembled Monolayers on Gold*", Langmuir, vol. 16, No. 4, 1751-1758 (2000).

Yeo et al., "*Electroactive Monolayer Substrates that Selectively Release Adherent Cells*", Chembiochem, No. 7/8, pp. 590-593 (2001).

Yousaf et al., "*Diels—Alder Reaction for the Selective Immobilization of Protein to Electroactive Self-Assembled Monolayers*", J. Am. Chem. Soc., 121:4286-4287 (1999).

Secure Seal Hybridization Chambers, Grace Bio-Labs, Inc., P.O. Box 228, Bend, OR 97709, Publication Date May 22, 2000.

\* cited by examiner

Immobilize material of interest

Add removable member

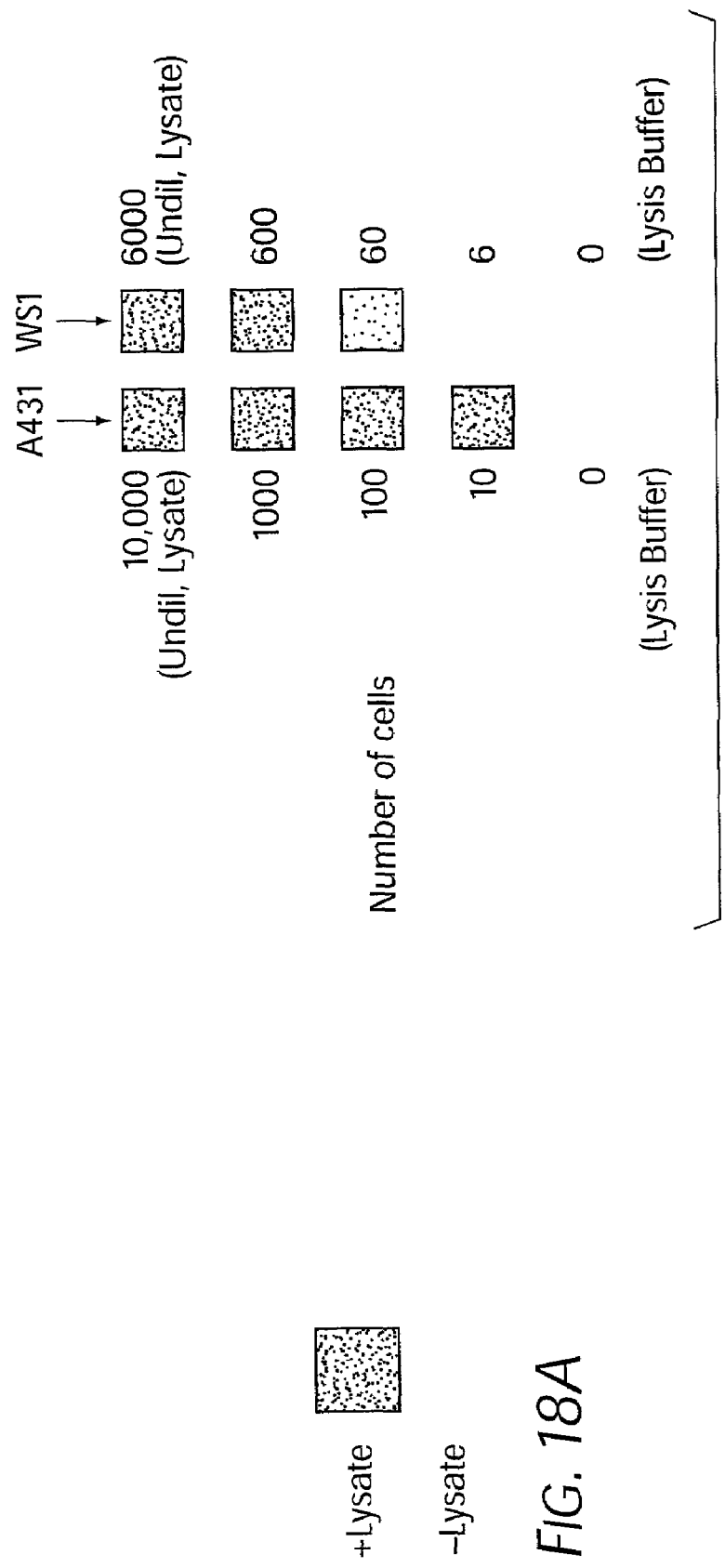

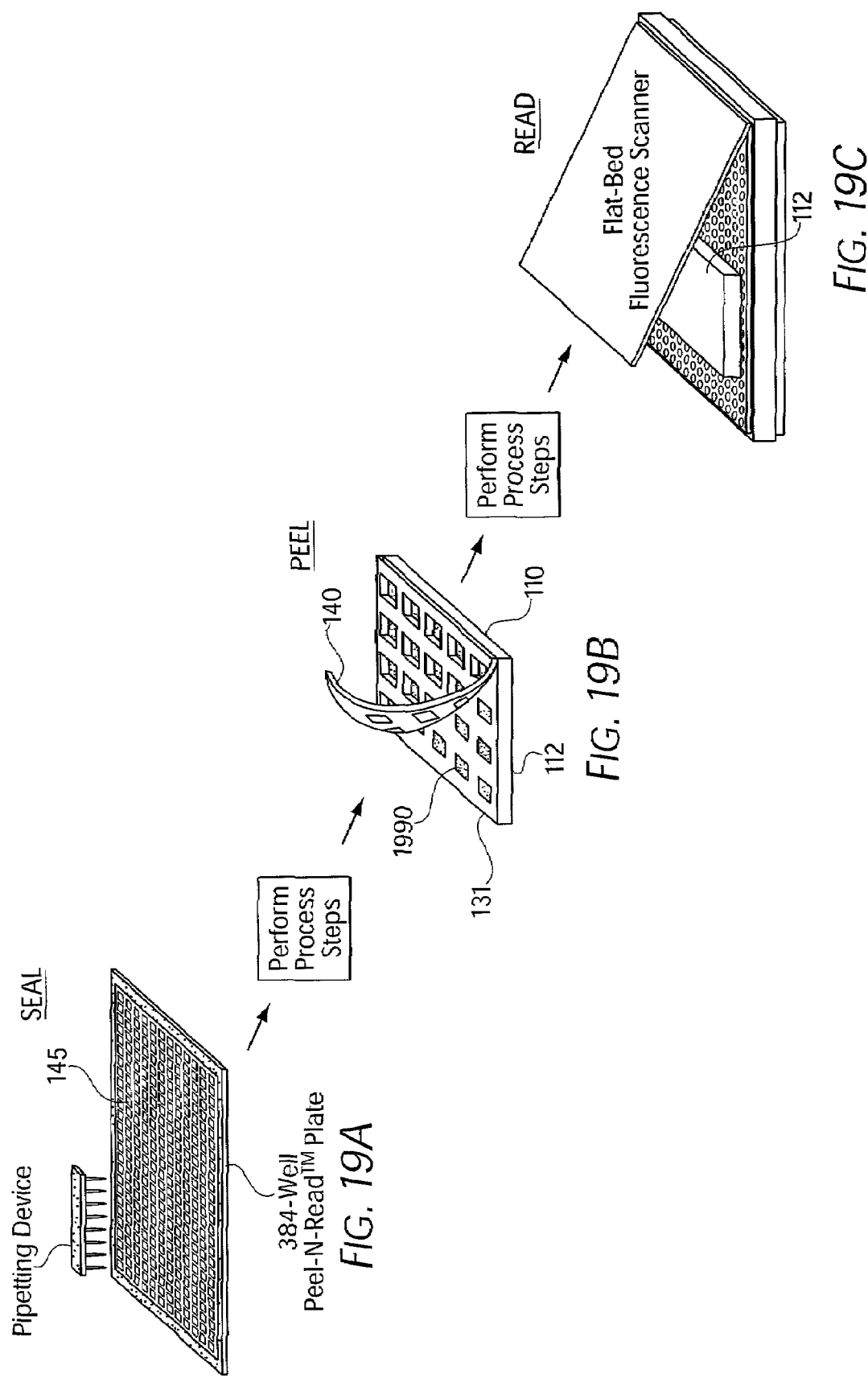

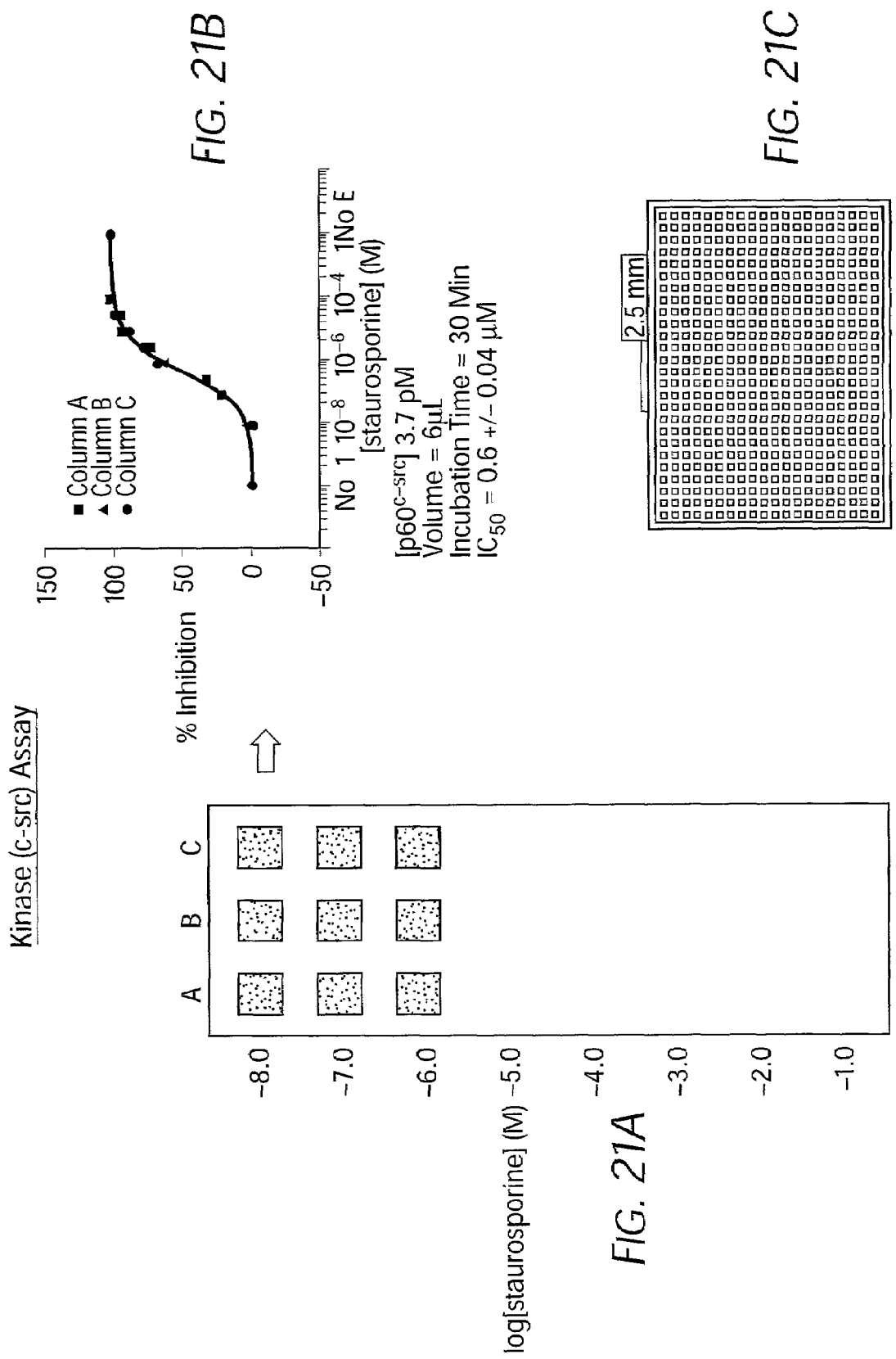

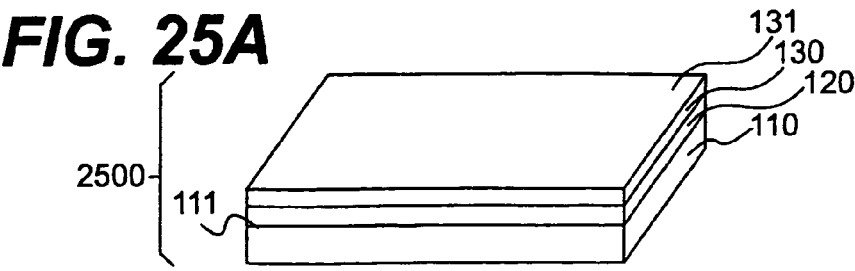
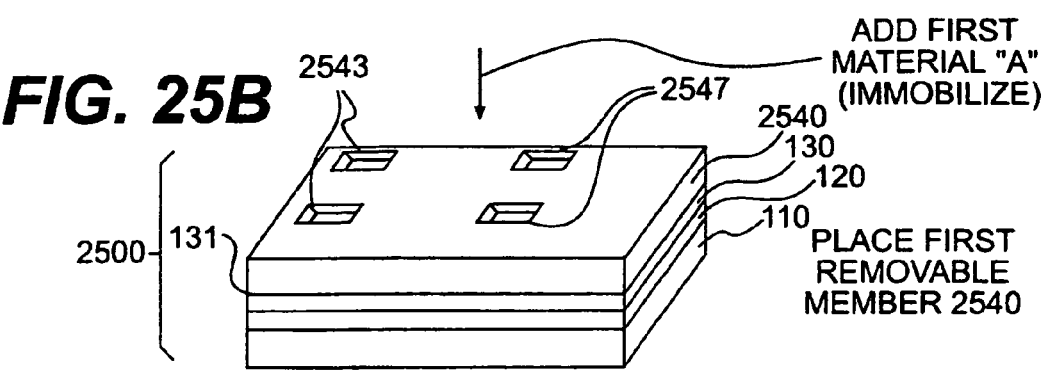
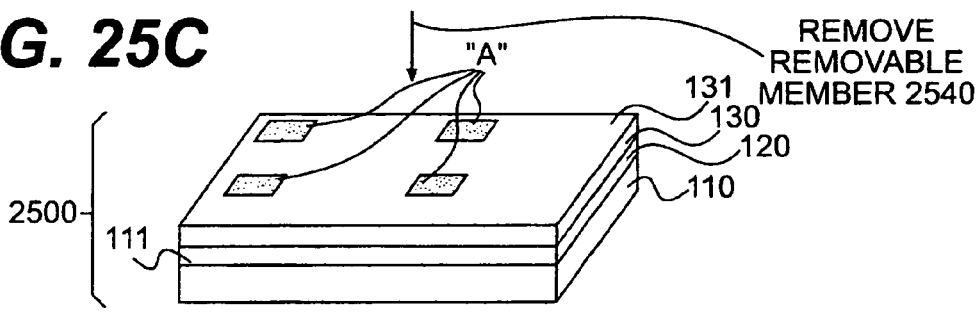
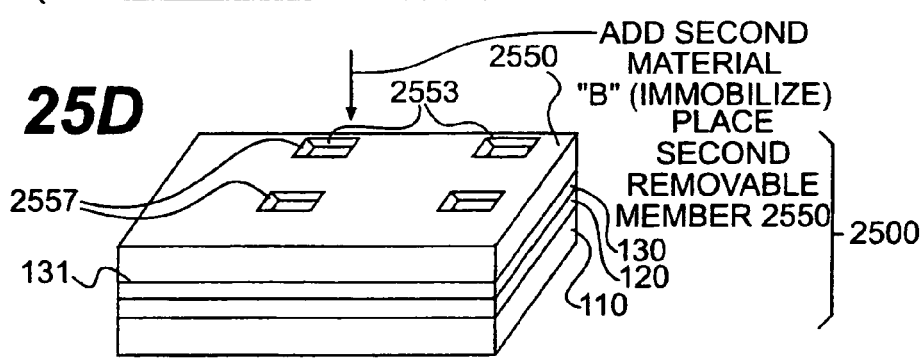
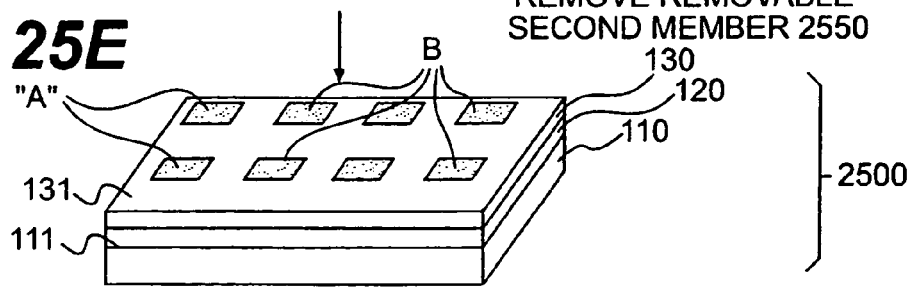

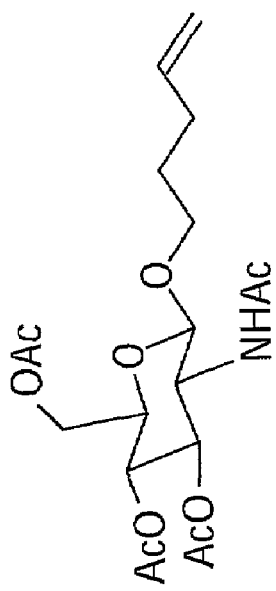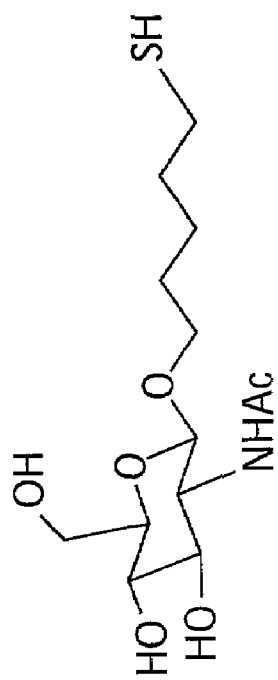
FIG. 39

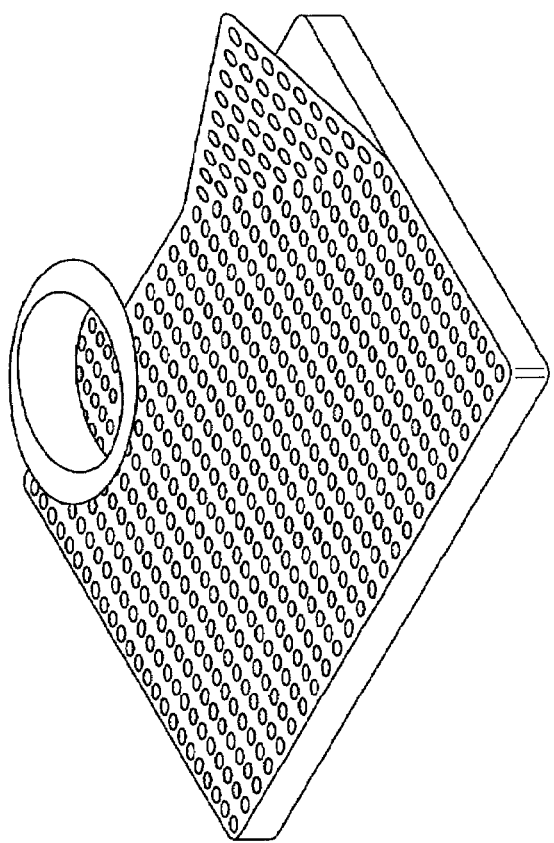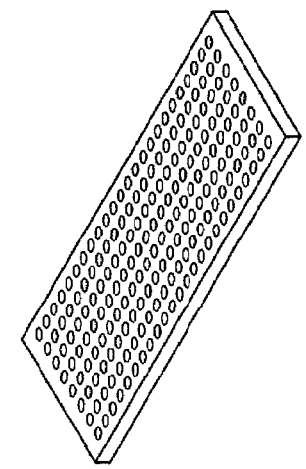
FIG. 45

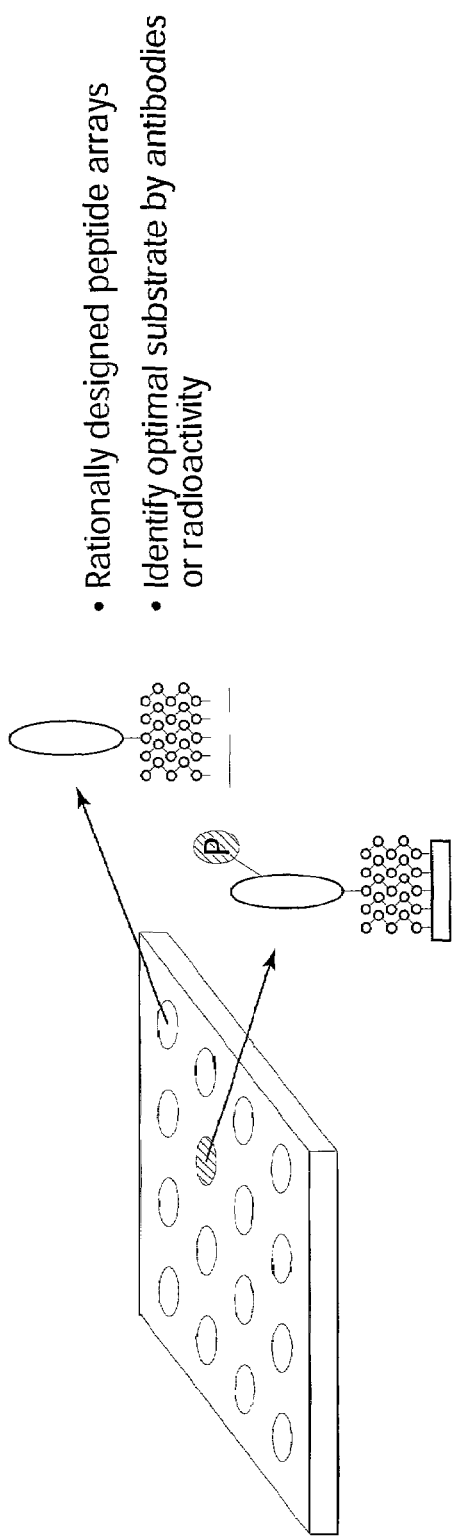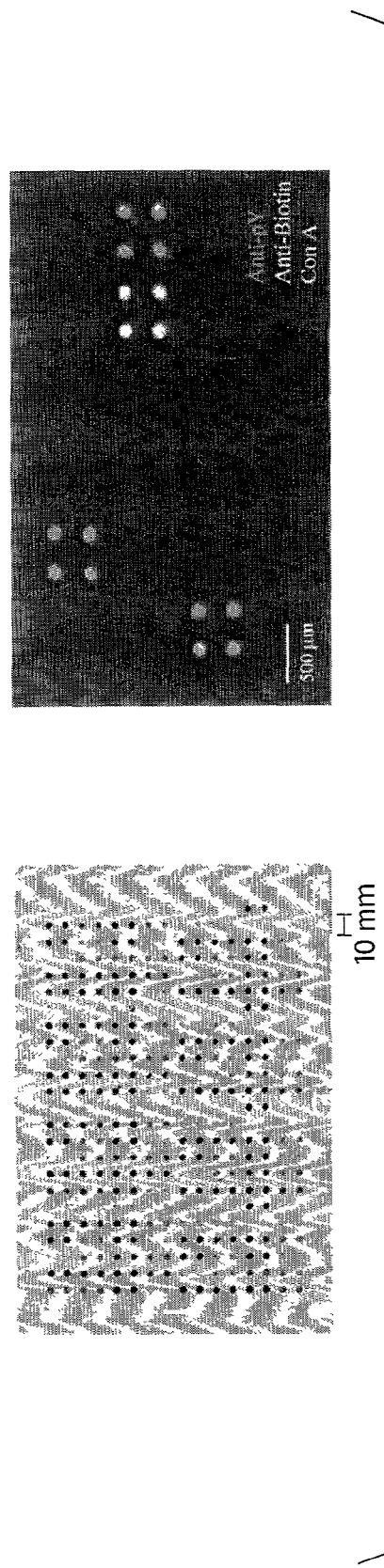
FIG. 46

Intra- and Inter- Plate Reproducibility:

Plate results

| Plate | 13 | 14 | 15 | 16 | Average |
|---|---|---|---|---|---|
| Average '+' control | 21461.96 | 15791.00 | 18430.55 | 16146.34 | 17957.46 |
| Std. '+' control | 1920.00 | 1755.63 | 1961.85 | 2124.57 | 1940.51 |
| Cv '+' control | 8.95% | 11.12% | 10.64% | 13.16% | 10.97% |
| Average '–' control | 497.65 | 474.74 | 603.72 | 531.64 | 526.94 |
| Std. '–' control | 38.68 | 55.29 | 60.99 | 34.25 | 47.30 |
| Cv '–' control | 7.77% | 11.65% | 10.10% | 6.44% | 8.99% |
| z' | 0.72 | 0.65 | 0.66 | 0.59 | 0.65 |

Inhibitor screening: IC50's
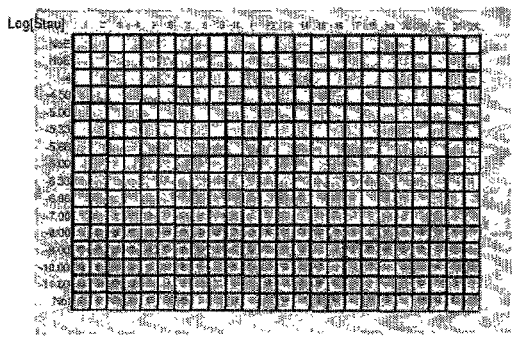 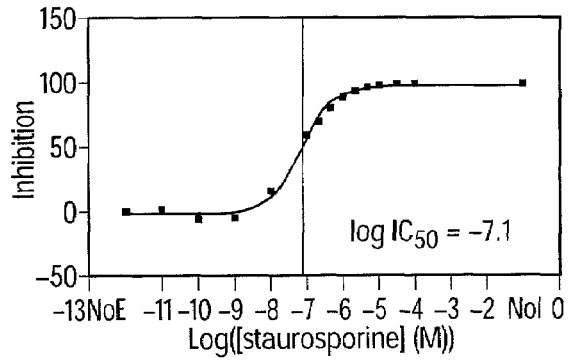
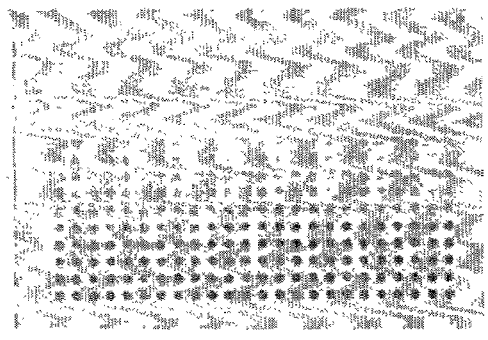 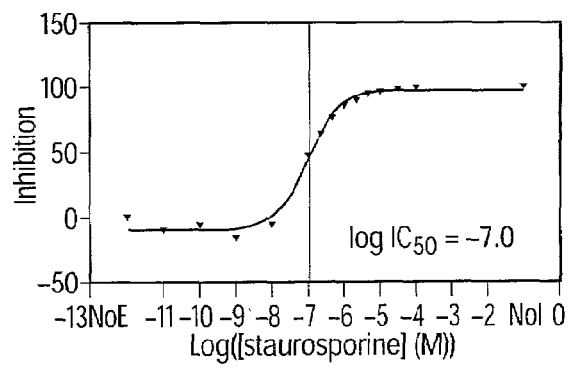
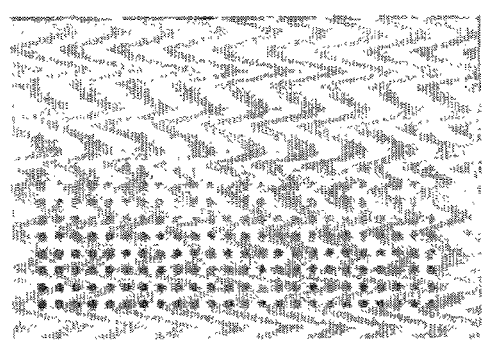 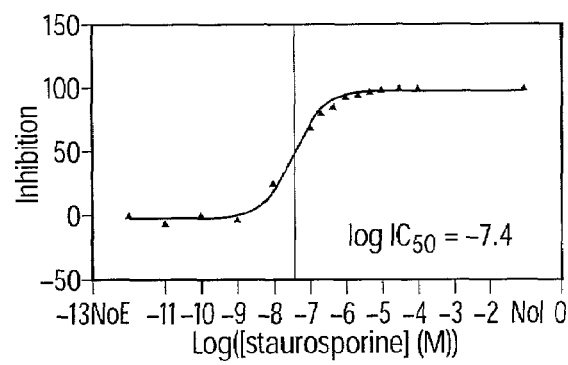
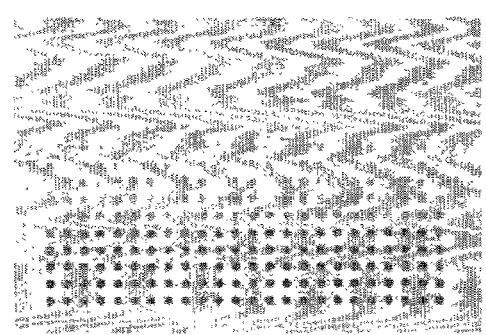 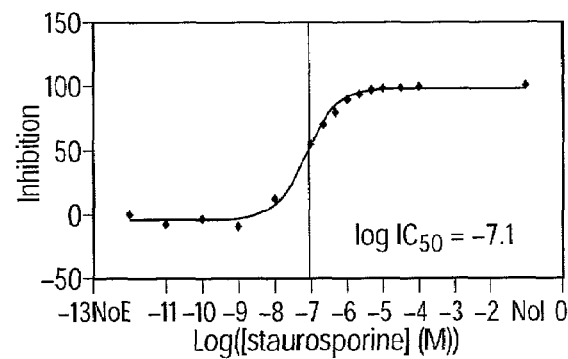
FIG. 49

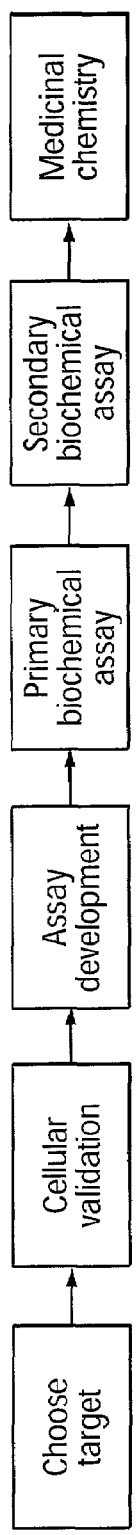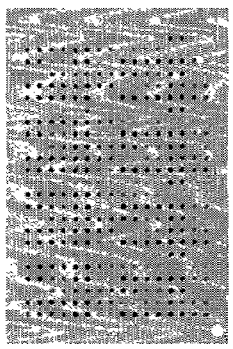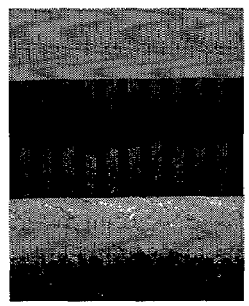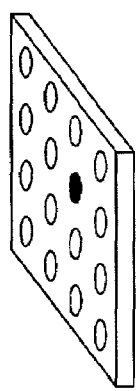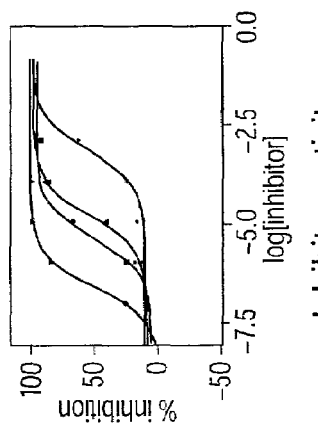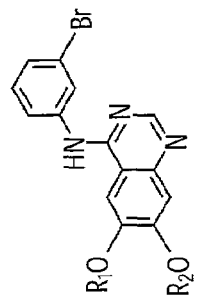
FIG. 50

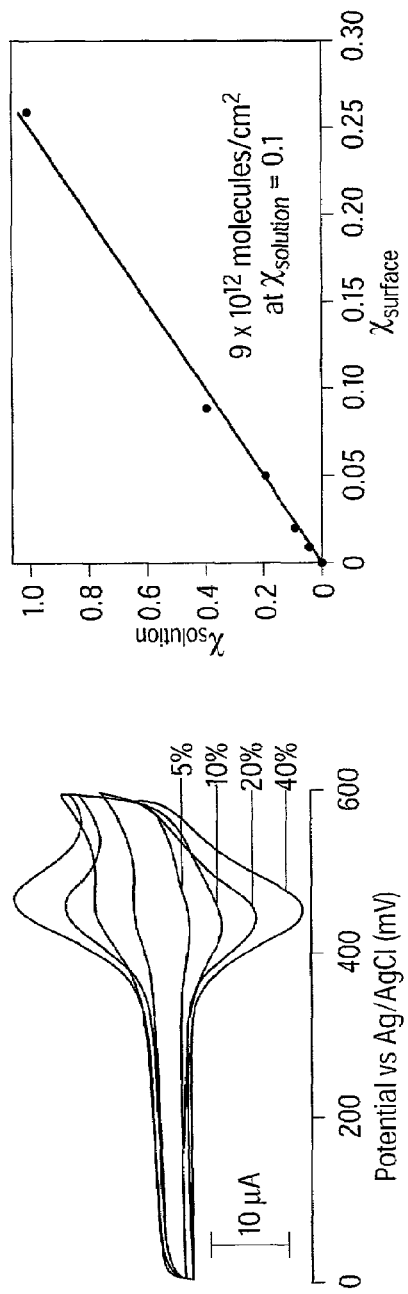
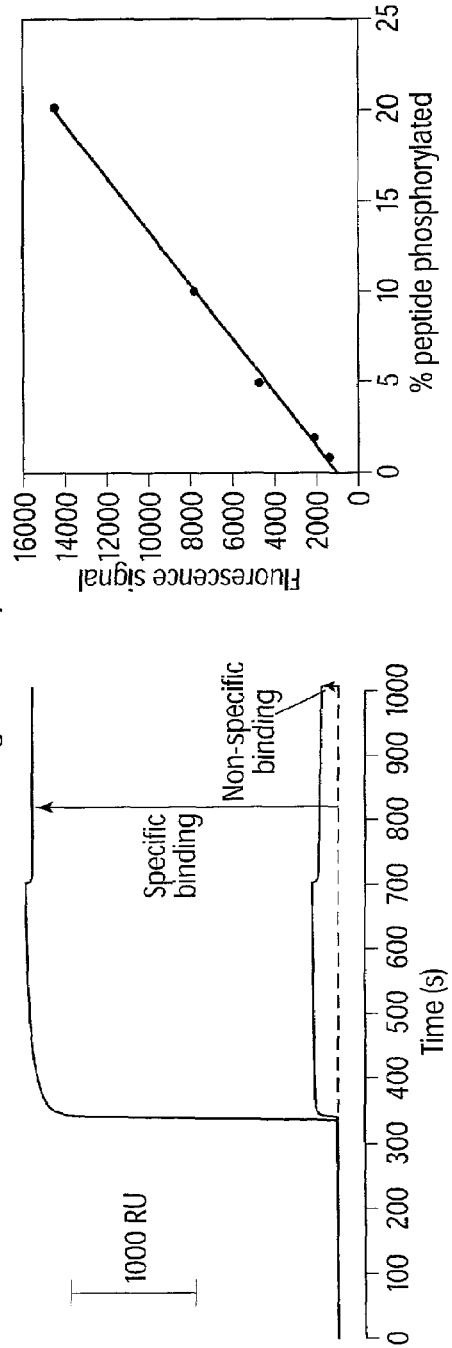
FIG. 51

Case Study 2: Identifying Ligands for Tyrosine Kinases

- Designed and synthesized generic 384-member peptide library for tyrosine kinases

| Library (N→C) | X | O | X | X | Y | X | X | X | X |
|---|---|---|---|---|---|---|---|---|---|
| Position | -4 | -3 | -2 | -1 | 0 | +1 | +2 | +3 | +4 |
| Substitutions | $X_1$ $X_2$ | | $X_1$ $X_2$ | $X_1$ $X_2$ | | $X_1$ $X_2$ $X_3$ $X_4$ | $X_1$ $X_2$ | $X_1$ $X_2$ | $X_1$ $X_2$ $X_3$ |
| No. of Variants | 2 | - | 2 | 2 | - | 4 | 2 | 2 | 3 |

Total 384

$X_n$ Design: Sample side chain space
Mimic known substrate sequences

Characterization: Purity: >90% (HPLC)
Identity: MS on random wells

FIG. 54

Case Study 2: Generalized Library for Identifying Ligands for Tyrosine Kinases
- Selecting generic and selective peptides

| Src | Lck | ZAP70 | Fyn | Lyn | | | | | | | | |
|---|---|---|---|---|---|---|---|---|---|---|---|---|
| H14 | H14 | H14 | H14 | H14 | X | O | X | X | Y | X | X | H14 |
|  |  | E3 |  |  | X | O | X | X | Y | X | X | E3 |
| E2 | E2 |  | E2 | E2 | X | O | X | X | Y | X | X | E2 |
| E6 | E6 |  | E6 | E6 | X | O | X | X | Y | X | X | E6 |
| E8 | E8 |  | E8 | E8 | X | O | X | X | Y | X | X | E8 |
| E14 | E14 |  |  | E14 | X | O | X | X | Y | X | X | E14 |
| F14 | F14 |  | F14 | F14 | X | O | X | X | Y | X | X | F14 |
| G14 | G14 |  | G14 | G14 | X | O | X | X | Y | X | X | G14 |
| L7 | L7 |  | L7 | L7 | X | O | X | X | Y | X | X | L7 |
| G2 |  |  |  |  | X | O | X | X | Y | X | X | G2 |
| G3 |  |  |  | G3 | X | O | X | X | Y | X | X | G3 |
| H15 |  |  | H15 | H15 | X | O | X | X | Y | X | X | H15 |
| K7 |  |  | K7 |  | X | O | X | X | Y | X | X | K7 |
|  |  | E11 |  |  | X | O | X | X | Y | X | X | E11 |
|  |  | E15 |  | E15 | X | O | X | X | Y | X | X | E15 |
|  |  | K15 | K15 | K15 | X | O | X | X | Y | X | X | K15 |
|  |  |  | A14 | A14 | X | O | X | X | Y | X | X | A14 |
|  |  |  | L8 | L8 | X | O | X | X | Y | X | X | L8 |
|  |  |  | L15 | L15 | X | O | X | X | Y | X | X | L15 |
|  |  |  | L23 | L23 | X | O | X | X | Y | X | X | L23 |
|  |  |  | K8 |  | X | O | X | X | Y | X | X | K8 |
|  |  |  |  | A2 | X | O | X | X | Y | X | X | A2 |
|  |  |  |  | A16 | X | O | X | X | Y | X | X | A16 |
|  |  |  |  | A20 | X | O | X | X | Y | X | X | A20 |
|  |  |  |  | L15 | X | O | X | X | Y | X | X | L15 |
|  |  |  |  | B14 | X | O | X | X | Y | X | X | B14L23 |
|  |  |  |  | C2 | X | O | X | X | Y | X | X | C2 |
|  |  |  |  | E18 | X | O | X | X | Y | X | X | E18 |
|  |  |  |  | G15 | X | O | X | X | Y | X | X | G15 |

FIG. 56

Format for Compound Screening: Inhibitor Screening Validation
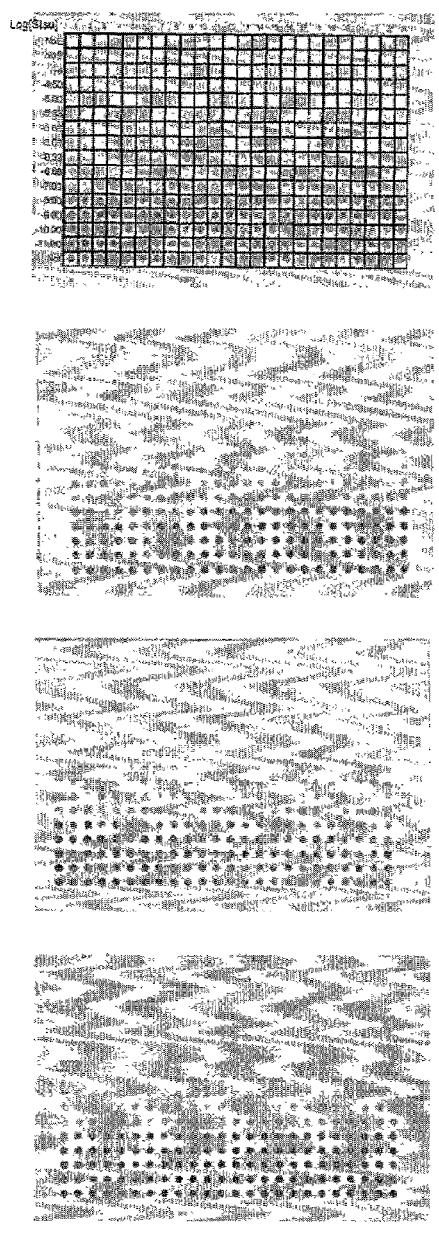
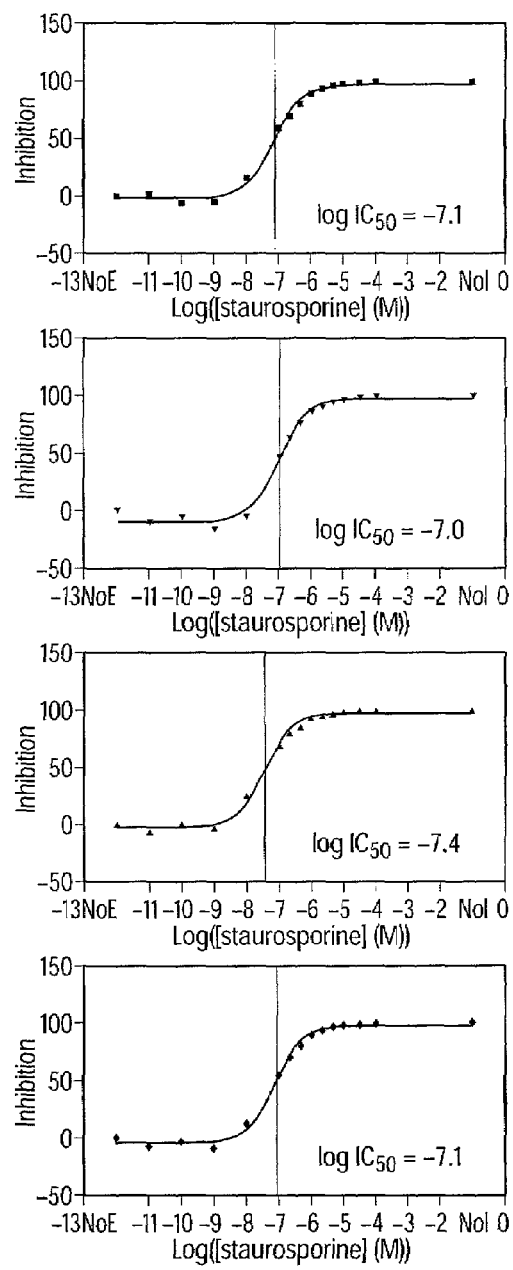
- [Staurosporine] = 0.1 mM – 10 pM (1% DMSO)
- [Src] = 12.0 pM
- [ATP] = 45 mM
|  | Plate 1 | Plate 2 | Plate 3 | Plate 11 | Average |
|---|---|---|---|---|---|
| Log IC50 | −7.14 | −7.42 | −6.99 | −7.11 | −7.17 |
| IC50 [nM] | 72.44 | 37.76 | 102.33 | 77.45 | 72.49 |
FIG. 60

METHODS FOR PROCESSING BIOLOGICAL MATERIALS USING PEELABLE AND RESEALABLE DEVICES

This application is a continuation-in-part of U.S. application Ser. No. 09/709,776 filed on Nov. 8, 2000 now U.S. Pat. No. 6,699,665. This application also claims the benefit of priority of U.S. provisional applications Nos. 60/307,839 (filed 27 Jul. 2001), 60/323,743 (filed 21 Sep. 2001), 60/357,649 (filed 20 Feb. 2002), 60/366,260 (filed 22 Mar. 2002), 60/375,024 (filed 25 Apr. 2002), 60/380,314 (filed 15 May 2002), and PCT/US01/50909 (filed 7 Nov. 2001), and these applications are hereby incorporated by reference herein.

FIELD OF THE INVENTION

This invention relates generally to biological assays, and more particularly to devices and methods for arraying and/or assaying biological materials.

BACKGROUND OF THE INVENTION

There is a need to rapidly assay or screen potential drug candidates. Drug discovery is a long, multiple step process involving the identification of specific disease targets, development of assays based on a specific target, validation of the assays, and optimization and automation of the assay to achieve screening of a large number of candidates. After high throughput screening of compound libraries using various assays, hit validation and hit compound optimization procedures are employed. Performing a screen on many thousands of compounds thus requires parallel processing of many compounds and assay component reagents. In addition, to find lead compounds for drug discovery programs, large numbers of compounds are often screened for their activity as enzyme inhibitors or receptor agonists/antagonists. Large libraries of compounds are needed for such screening. As a result of developments in this field, it is now possible to simultaneously produce combinatorial libraries containing hundreds of thousands of small molecules for screening. With such libraries on hand there is an ever increasing need to rapidly screen these new drug candidates.

One common approach to drug discovery involves presenting macromolecules implicated in causing a disease (disease targets) in bioassays in which potential drug candidates are tested for therapeutic activity. Such molecules may be receptors, enzymes, transcription factors, co-factors, DNA, RNA, growth promoters, cell-death inducers, or non-enzymatic proteins and peptides. Another approach involves presenting whole cells or organisms that are representative of the causative agent of the disease. Such agents include bacteria and tumor cell lines, for example. Thus, there is a need to be able to screen the effects of various drug candidates on assorted cells and cell lines.

Within the general drug discovery strategies, several sub-strategies have been developed. One spatially-addressable strategy that has emerged involves the generation of peptide libraries on immobilized pins that fit the dimensions of a standard 96-well microtiter plate. See PCT Patent Publication Nos. 91/17271 and 91/19818, each of which is incorporated herein by reference. This method has been used to identify peptides that mimic discontinuous epitopes as described in Geysen et al., "Screening Chemically Synthesized Peptide Libraries for Biologically Relevant Molecules," *Bioorg Med Chem. Lett.* 3: 397-404 (1993), and to generate benzodiazepine libraries as described in U.S. Pat. No. 5,288,514 and Bunin et al., "The Combinatorial Synthesis and Chemical and Biological Evaluation of a 1,4-Benzodiazepine Library," *Proc. Natl. Acad Sci.* 91:4708-4712 (1994). The structures of the individual library members can be determined from the pin location in the microtiter plate and the sequence of reaction steps (called a "synthesis histogram") performed during the synthesis.

Common therapeutic targets for high throughput screening ("HTS") are enzymes, cell surface receptors, nuclear receptors, ion channels, signal transduction proteins, cell surface glycoproteins and proteoglycans. Compounds that interact with these targets are usually identified using in vitro biochemical assays.

These assays and other conventional and HTS assays, such as DNA analysis, gene expression profiling, mapping for single nucleotide polymorphisms (SNP's), and enzyme linked immunosorbent assay (ELISA) and others rely on arraying of biomolecules.

In a recent development, the techniques of photolithography, chemistry and biology have been combined to array large collections of biocompounds on the surface of a substrate. See U.S. Pat. No. 5,143,854 and PCT patent publication Nos. 90/15070 and 92/10092, each of which is incorporated herein by reference.

"Genechip" technology as well as photolithography to generate patterns of target oligonucleotides (See U.S. Pat. No. 5,599,695) have revolutionized the ways assays are performed. Robotic spotting systems have been developed to "print" arrays of nucleic acids and other materials on surfaces for assay development. Unfortunately, both photolithography and robotic array systems require expensive equipment. In addition, processing conditions required in photolithography are often incompatible with many biochemical and biological materials. Robotic spotting systems work well when used with homogeneous fluids, but they do not work efficiently when attempting to pattern cells directly. Although silkscreen printing and ink-jet printing have recently shown much promise in the generation of biological arrays, they suffer from their inability to generate patterns having fine resolution. Obtaining sub-100 µm resolution is difficult with these techniques.

Conventional methods for assessing the effects of various agents or physiological activities on biological materials utilize standard microtiter plates. See, e.g., U.S. Pat. No. 6,083,763. Unfortunately, microtiter plates are not flat, but comprise portions which protrude substantially perpendicular from the surface on which the items to be detected are found. These perpendicular protrusions are fabricated from plastic, for example, and form the wells that separate different fluids and immobilized entities, such as cells, organic molecules, and biomolecules. These perpendicular protrusions are not removable, and they hinder the use of many detection systems, such as, microscopes including bright field, phase contrast, confocal, and epi-illuminated fluorescence microscopes, MALDI (Matrix Assisted LASER Desorbtion Ionization) mass spectrometers, surface plasmon resonance (SPR) sensors, and flat bed scanners including confocal flat bed scanners. For example, perpendicular protrusions can interfere with microscope objectives, prohibiting the user from bringing the microscope lens closer to the sample than above the height of the perpendicular protrusions.

The perpendicular protrusions in microtiter plates and the like also hinder the exposure of material immobilized in all or a plurality of wells to the same fluids bearing reagents and the like, and also hinder washing between steps. Fluids must generally be pipetted into individual wells because fluids applied to the surface of a microtiter plate will generally not enter the wells, but rather will remain on the surface, due to surface tension; this will also be the case for microtiter plates immersed in fluids. Fluids that have been pipetted into wells are difficult to remove from wells of the microtiter plates without introducing possible contamination during the fluid removal process.

There are currently efforts to overcome the aforementioned shortcomings of arrays by immobilizing materials of interest at defined locations on a flat surface. However, these efforts are limited by the difficulty of creating discrete spots of material, particularly where the material differs between spots, without physical mechanisms for separation of the spots while they are being formed. Thus, although immobilized spots remain discrete in the absence of physical barriers between them, without physical barriers, it is difficult to maintain separation between spots as they are being immobilized.

Thus, there is a need for a device that allows for the immobilization of materials in discrete areas, or spots, in a spatially defined array and which also (1) facilitates reading the results of assays and the like conducted on the device in systems which require or are better functioning when reading flat surfaces and (2) allows for easy and efficient exposure of multiple spots to a fluid or fluids.

SUMMARY OF THE INVENTION

In view of the foregoing, there is a need for a device that addresses the limitations of the prior art, particularly with respect to the desired feature of facilitating the reading, recording, observation, and the like, of materials on a surface of the device and with respect to the desired feature of efficiently exposing materials on the surface of the device to liquids.

Accordingly, in a first aspect the present invention provides a device that includes a base plate and a self-sealing, removable member on the base plate formed with an array of well orifices therein. The well orifices, which may also be referred to as "through-holes," define an array of exposed regions on the base plate. Materials may be deposited on the plate through the well orifices. In this manner, material is deposited only on the exposed regions defined by the well orifices. The walls of the well orifices and the base plate together define wells, which may be used, for example, to deposit materials in a defined area and/or to retain fluids.

The devices of the present invention can be designed to have spatial arrays corresponding to those of standard microtiter plates, such as 6-well, 12-well, 24-well, 96-well, 384-well, or 1536-well microtiter plates in the Society for Biomolecular Screening (SBS) format or other formats commonly used in the industry. See, e.g. *Journal of Biomolecular Screening*, vol. 6, No. 2, 2001, p.61-68, "Society Updates". Thus, the devices of the present invention may be, and preferably are compatible with conventional microtiter plate-related products, such as microtiter plate readers and microtiter plate robotic systems. The present invention also provides for micro-patterning of material in discrete spots of sizes in the micron range. The present invention provides a novel multilevel array system that can be used in high-throughput screening (HTS), in the study of protein-protein interaction, cell based assays, and other known biological assays.

The present invention provides low-volume, high sensitivity assays for measuring interactions between biomolecules; such as binding reactions and enzymatic reactions.

BRIEF DESCRIPTION OF THE DRAWINGS

The various features of the invention will best be appreciated by simultaneous reference to the description that follows and the accompanying drawings, in which:

FIG. 1(*a*) depicts an unassembled view, while FIG. 1(*b*) depicts an assembled view.

FIG. 17(*b*) depicts results of an assay performed using devices according to the present invention.

FIGS. 18(*a*) and (*b*) depict the results of assays performed according to the present invention.

FIGS. 19A, 19B and 19C depicts a process according to the present invention.

FIG. 21 depicts results of an assay performed using a device according to the present invention. FIG. 21(*a*) depicts a portion of the developed base plate depicted in FIG. 21(*c*). FIG. 21(*b*) is a graph of the results of the assay.

FIG. 25(a)-(i) depicts a device according to the present invention that makes use of four removable members, each having a plurality of well orifices, where the well orifices in one removable member are at different locations than the well orifices in the other removable members.

FIG. 36A) Representation of SAM after immobilization of ferrocene 13 to maleimide SAM. FIG. 36B) Normalized cyclic voltammograms of SAMs formed from different solution ratios of disulfide 1 (shown as a v/v percentage). The two waves centered at 480 mV correspond to the oxidation and reduction of the immobilized ferrocene molecules. FIG. 36C) From the normalized areas under the redox waves, the density of immobilized ferrocene group, and therefore maleimide, was determined. χsolution is the mole fraction of disulfide 1 relative to disulfide 2 in the solution from which the monolayers were formed, whereas χsurface is the mole fraction of maleimide incorporated into the surface.

FIG. 38 also shows a non-limiting example of the use of a maleimide to generate a two ligand surface by first reacting the maleimide with a thiol and then reacting the maleimide with a diene in a Deils Alder reaction.

FIG. 39 illustrates a general method of tagging carbohydrates with thiol reactive groups. Here GlcNAc is used as an example. (a) (i) AcSH, AIBN, dioxane, D; (ii) NaOH, water/dioxane.

FIG. 45 depicts kinase assay platform formats available. The kinase assays of the present invention can be arranged in standard MTP footprint arrays that use standard detection equipment such as fluorescence scanners, fluorescence plate readers, phosphor-imagers, and micro-Beta plate readers.

For kinase assays arranged in micro-array formats, detection is achieved, for example, by using a fluorescence scanner imaging SPR.

FIG. 46 depicts kinase substrate fishing as a fundamental approach for enabling assay developments. Designing peptide arrays using the present invention allows for optimal substrate identification.

Figure 47:
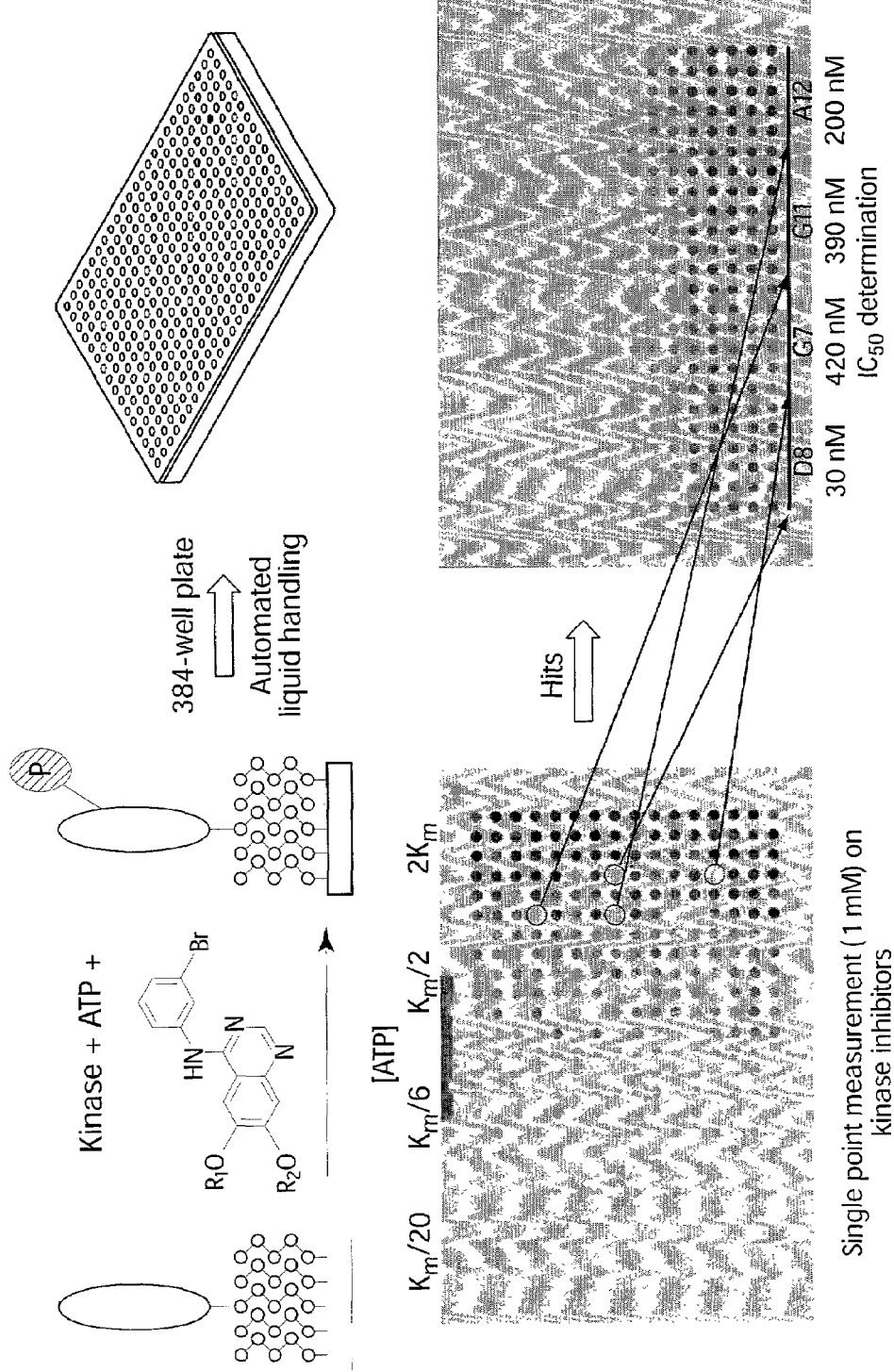

FIG. 47 schematically depicts the use of kinase assays for focused compound library screening. As illustrated in the lower 384-well plates, 90 potential inhibitors of a kinase were assayed for binding activity. $IC_{50}$ determination was then performed on a subset of four of those inhibitors (i.e. the HITS).

Figure 48:
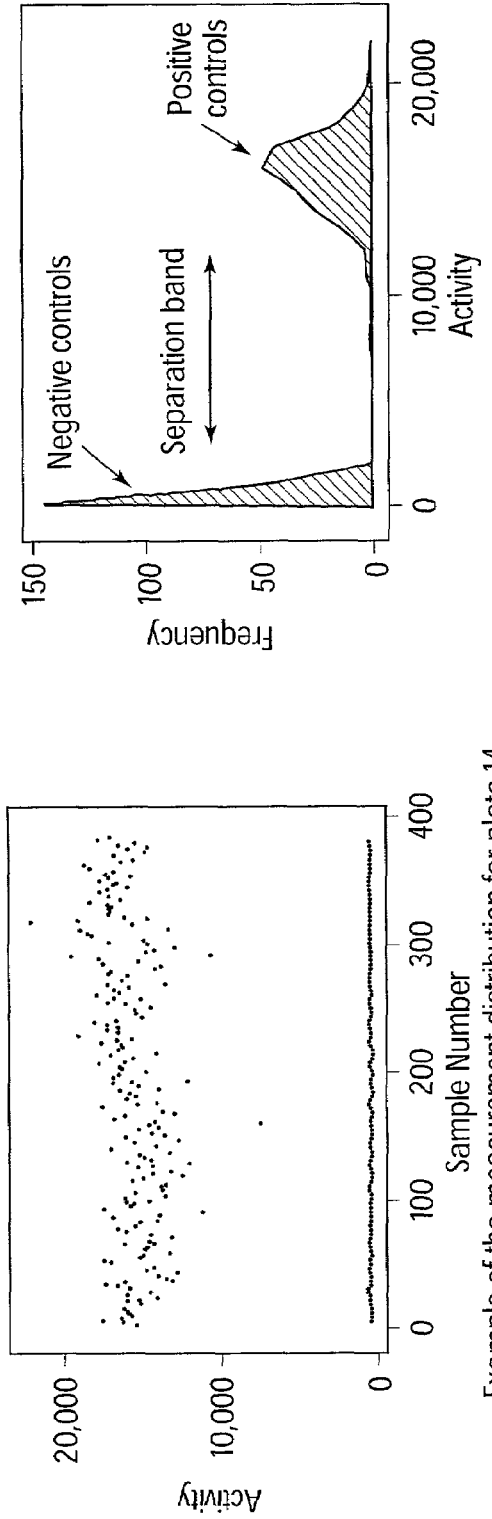

FIG. 48 represents the results of intra- and inter-plate reproducibility.

FIG. 49 depicts graphs of inhibitor screening $IC_{50}$ studies.

FIG. 50 depicts the application of the present invention throughout the various phases of drug discovery. Currently, drug discovery process involves the following steps: 1. choosing a target; 2. performing cellular validation; 3. developing assays; 4. performing primary biochemical assays; 5. performing secondary cellular assays; and 6. performing medicinal chemistry.

FIG. 51 depicts ligand density controlled by preparing a reactive surface and then immobilizing the molecule of interest. The ligand density is quantified by using electrochemically active groups and correlating the electrochemical activity to density.

Figure 52:
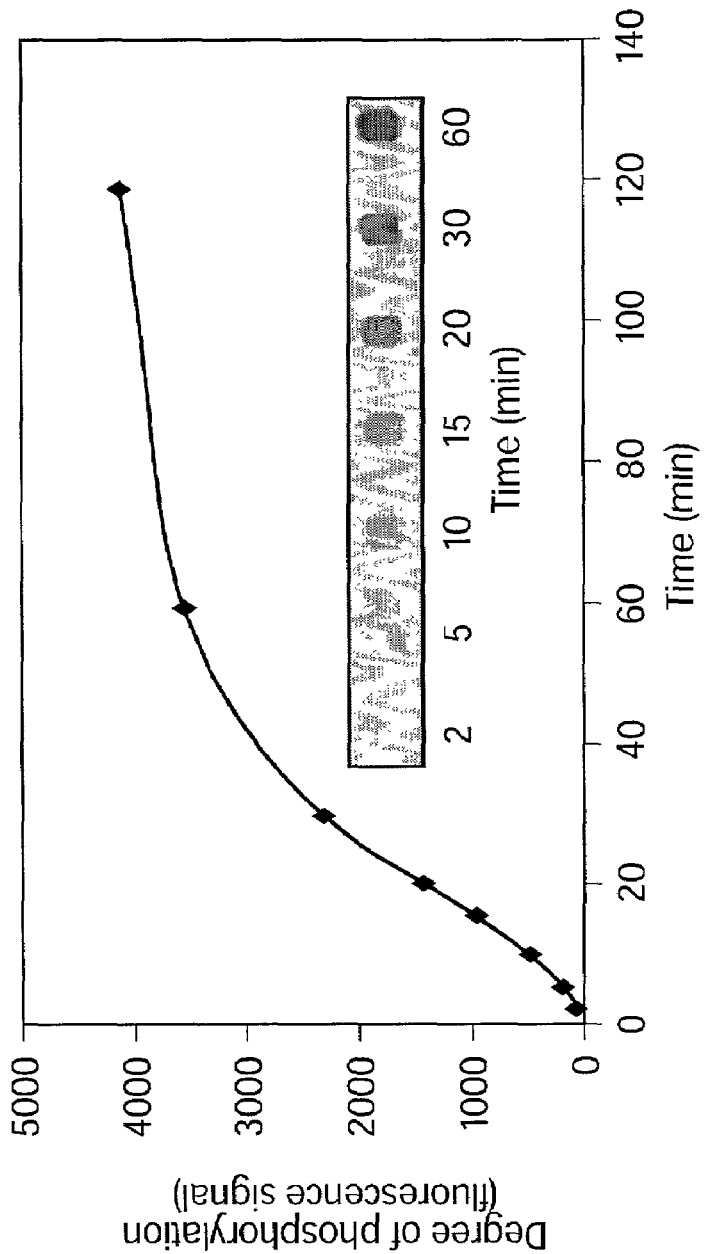

FIG. 52 depicts a method of monitoring the time course of the kinetics of a reaction. The kinetics at the surface is consistent with the "hopping" model. The hopping model is well known for enzymes that act interfacially. The enzyme "hops" from substrate to substrate by hitting the surface, turning over the substrate, releasing from the substrate, and finding another point.

Figure 53:
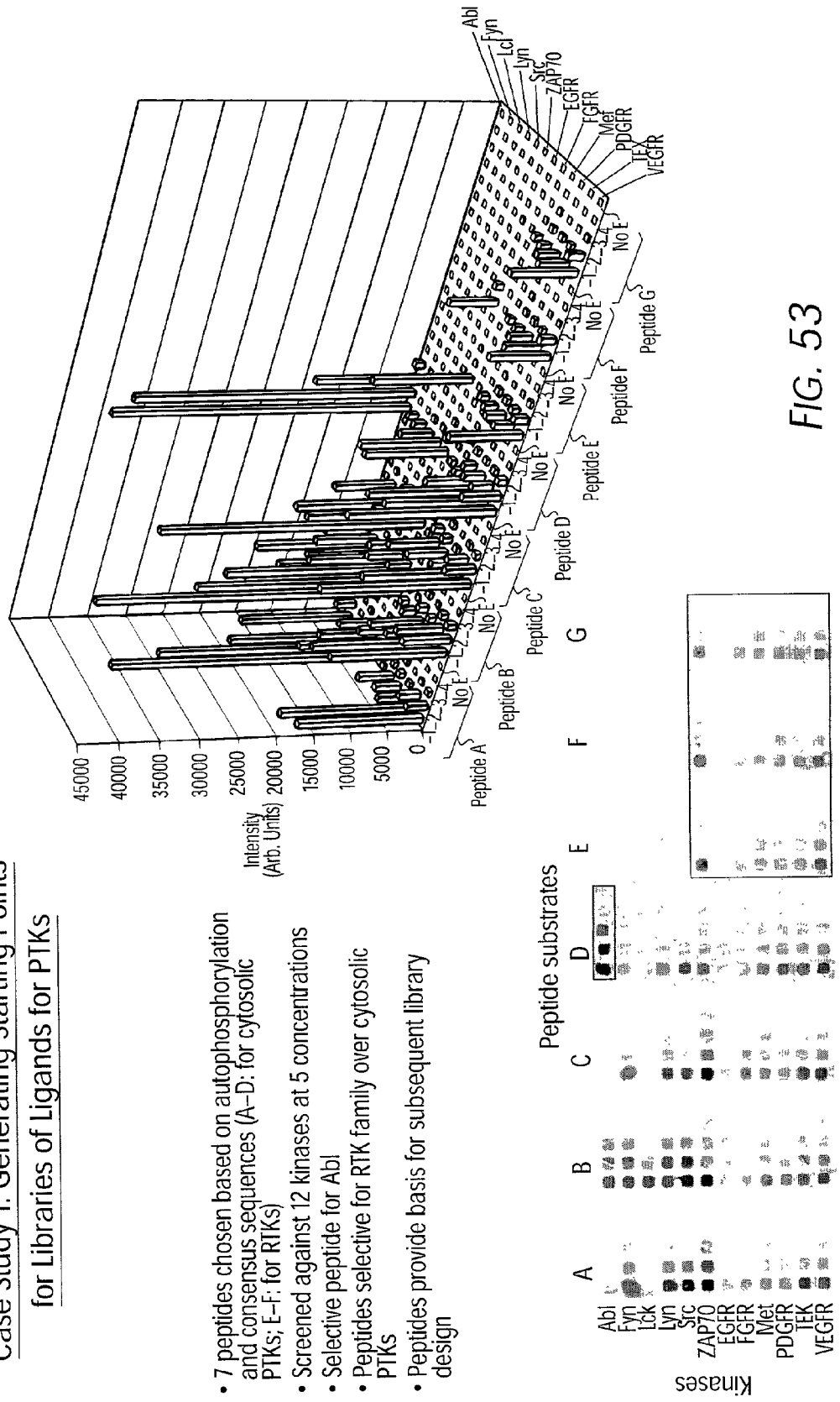

FIG. 53 depicts a design/approach to generating libraries of ligands for PTKs.

FIG. 54 depicts using the methods and devices of the present invention to identify ligands for tyrosine kinases. The libraries of ligands can be designed to have different properties for their side chains such as, for example, negative/positive charge, hydrophobic, or aromatic side chains, etc.

Figure 55:
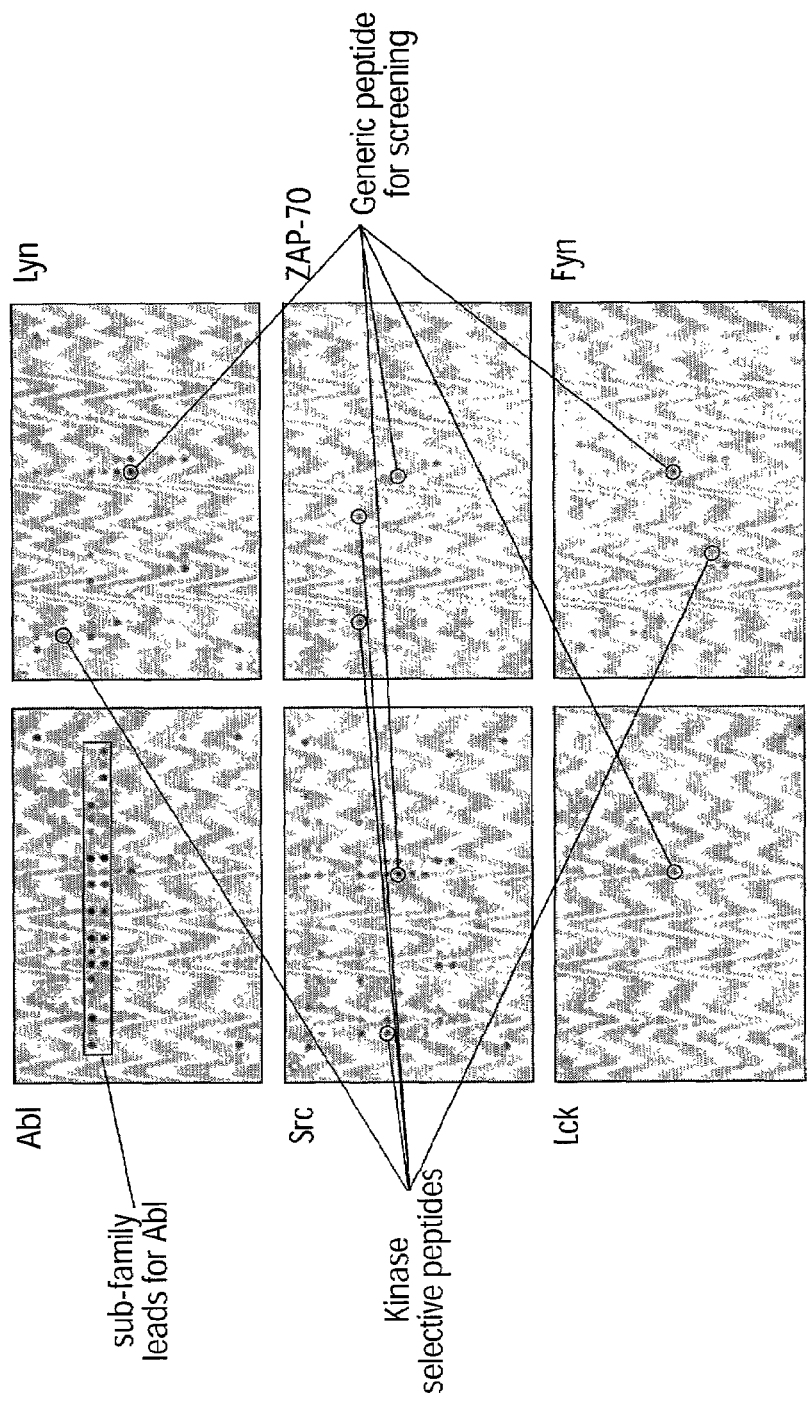

FIG. 55 depicts the use of a generalized library, designed by using methods and devices of the present invention, to identify ligands for tyrosine kinases. Since peptides are phosphorylated by many kinases, peptides are a useful substrate or starting point for designing a generic library. To design a more specific library, uniquely phosphorylated peptides provide a good starting point for a library design. In addition, they provide a good starting point for searching natural substrate candidates. Further, a "sub-family" of peptides sharing certain structural or sequence features is useful for searching for natural substrates.

FIG. 56 depicts a tabular representation of a generalized library for identifying ligand for tyrosine kinases.

Figure 57:
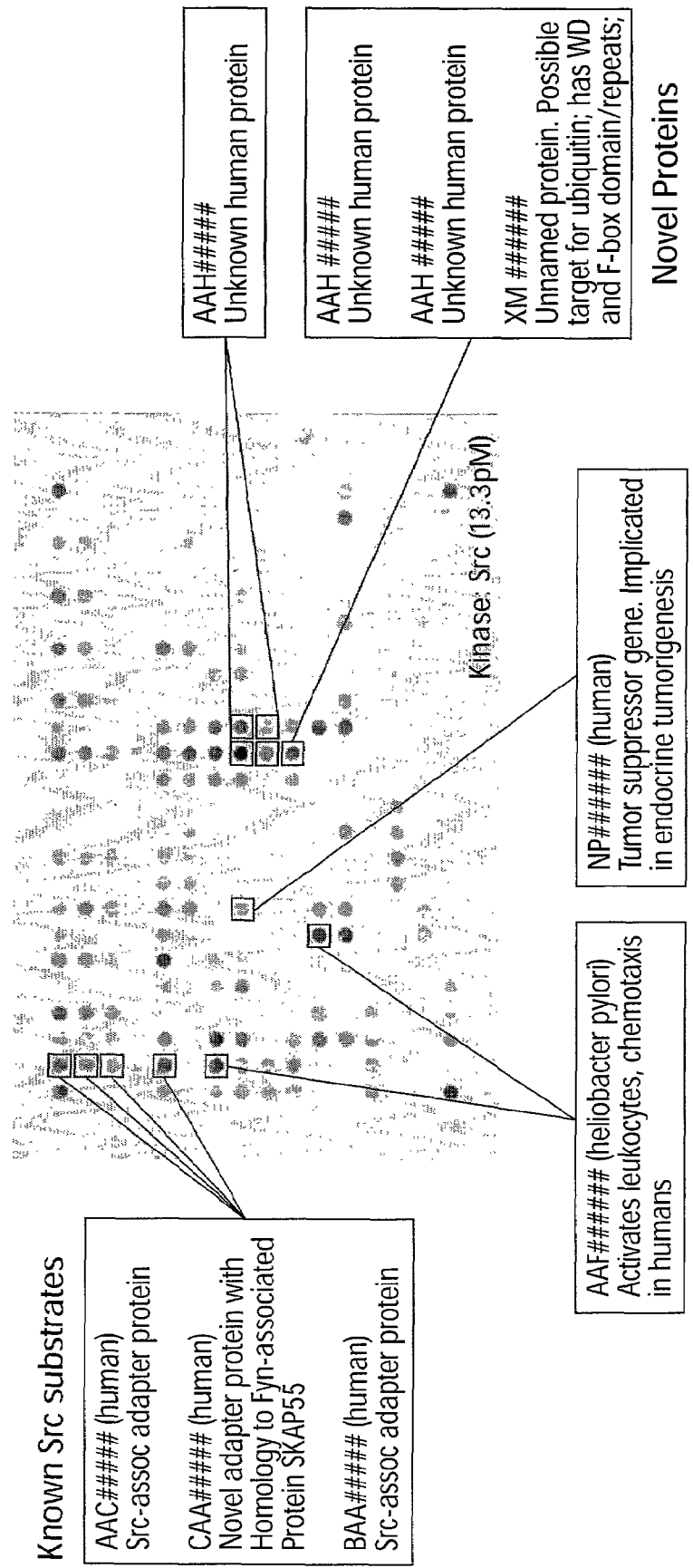

FIG. 57 depicts results from searching sequences against protein data banks to determine which proteins may be used as substrates in cells or biochemically.

Figure 58:
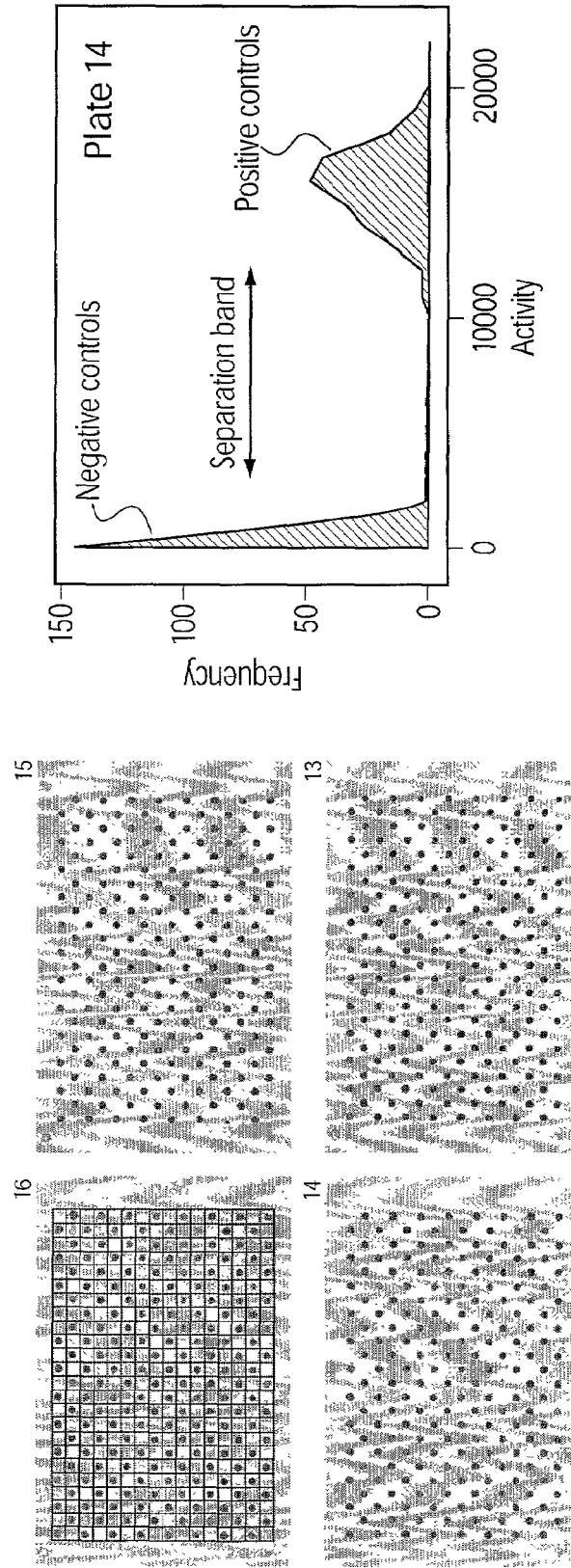

FIG. 58 represents the results of intra- and inter-plate reproducibility. This figure demonstrates that by using the methods of the present invention, there is little plate-to-plate variation.

Figure 59:
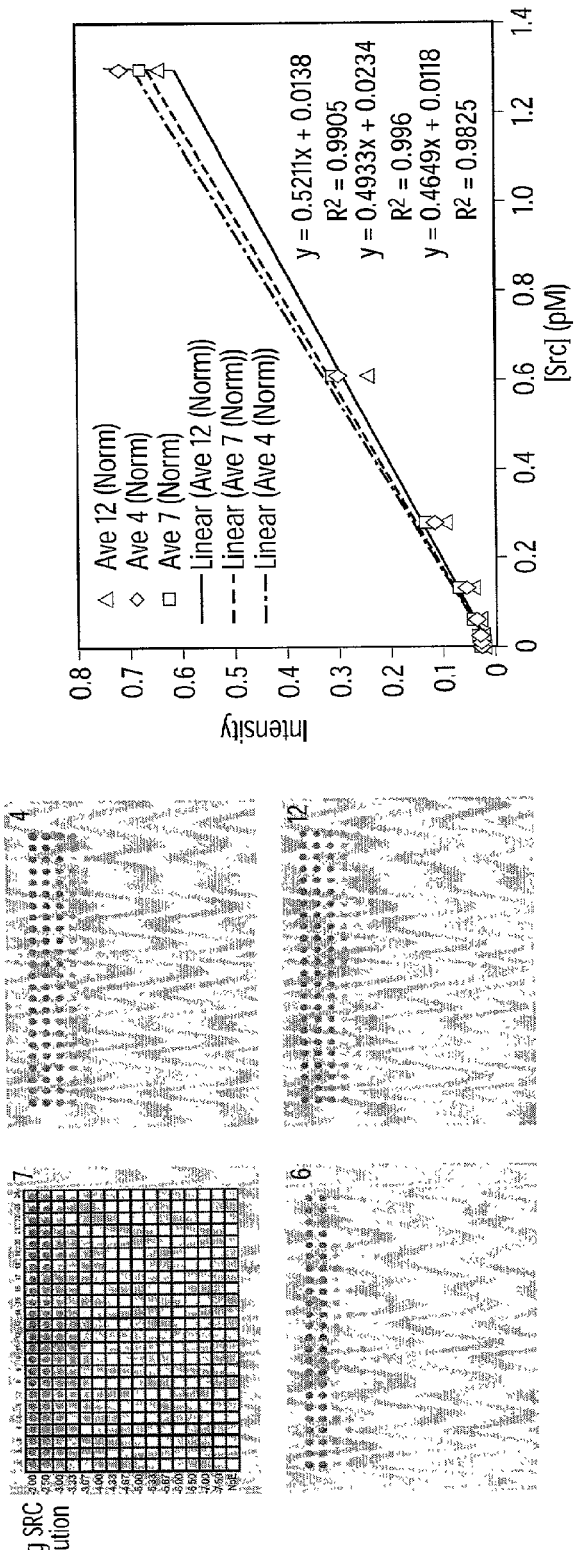

FIG. 59 represents a format for compound screening. This demonstrates that by using the methods and devices of the present invention, enzyme activity is measured. The concentration of the peptide can be predefined and measured so that the results indicate enzyme activity levels and not merely differences in peptide concentrations.

FIG. 60 depicts graphs of inhibitor screening $IC_{50}$ studies.

Figure 61:
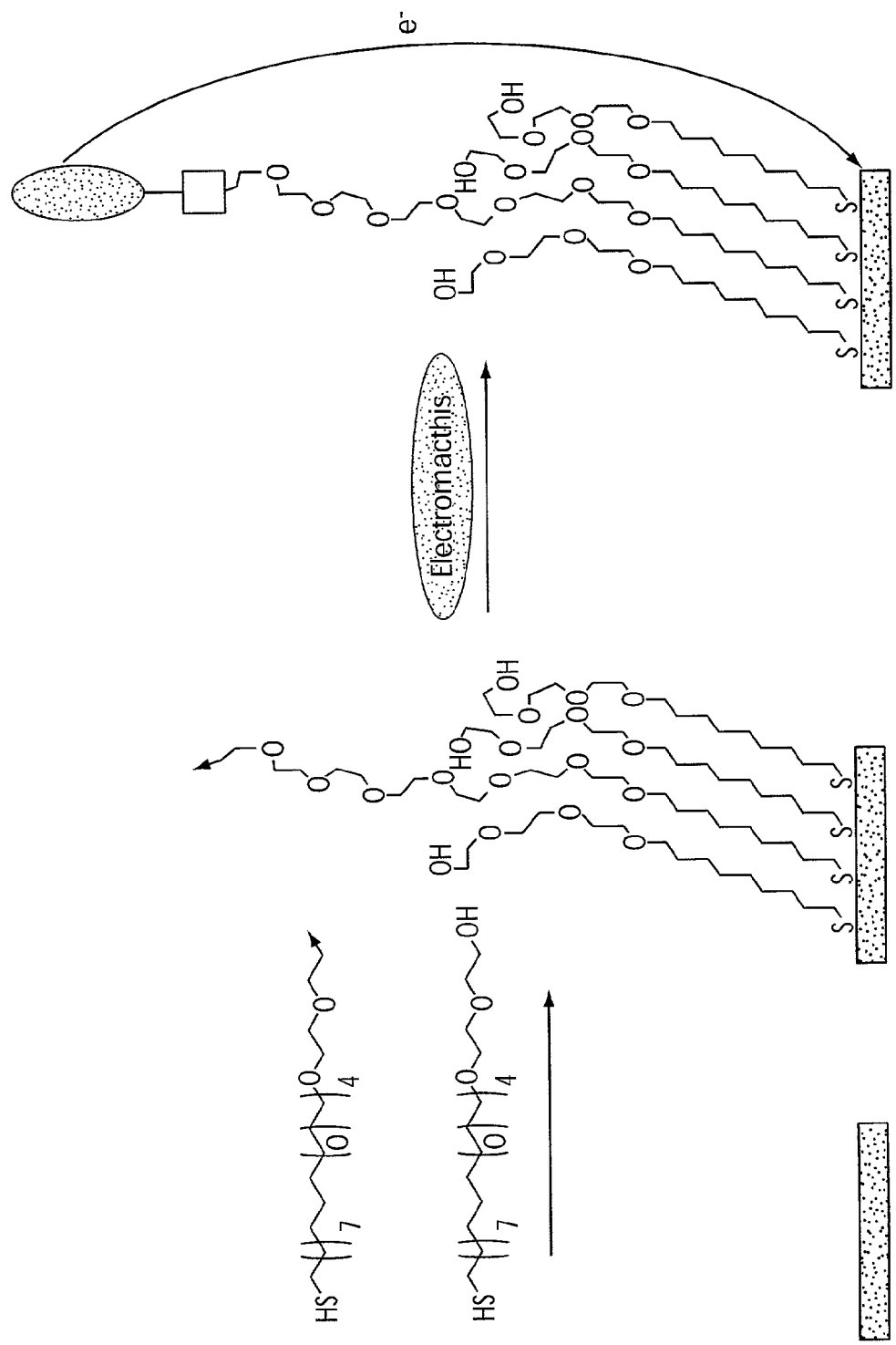

FIG. 61 schematically depicts the synthetic route used to prepare to ethyl-4-nitrophenyl (8-mercapto-octyl)phosphonate 18 used to covalently bind cutinase to a SAM. Reagents and conditions: (a) Triethyl phosphite; (b) 1. $(COCl)2$, 2.4-nitrophenol/Et3N; (c) thiolacetic acid, AIBN; (d) Hcl/MeOH.

DETAILED DESCRIPTION OF THE INVENTION

The devices and methods of the present invention may be used to perform a variety of assays and detect a variety of interactions and events. The present invention provides methods and devices for detecting the occurrence and extent of biochemical interaction in wells. Exemplary biochemical reactions include, but are not limited to, enzymatic modification such as cleavage of surface-bound substrate (e.g., cleavage by proteases, phosphatases, lipases, and/or transferases), addition and/or ligation (by, e.g., kinases, ligases, and/or transferases), restructuring (structural modification), and modifications by other enzymes, such as, but not limited to, oxidoreductases, transferases, hychrolases, lyases, and ligases. More specific, but still non-limiting examples include glycosyltransferases, glycosidases, kinases, phosphotases, phosphodiesterases, phosphoinositides, sulfotransferases, DNA modifying enzymes, restriction enzymes, ligases, polymerases, and non-peptidic kinases; other biochemical modifications, (for example, modifications not involving enzymes); binding events, such as, but not limited to, antibody-antigen, hormone-receptor, protein-protein, small molecule-protein, protein-peptide binding events; chemical modification, such as isomerization, oxidation, and reduction; and combinations of any of the above events.

Examples of specific reactions which may be measured include, but are not limited to, binding of antibodies to antigens or fragments thereof, protein binding to protein regulatory domains, enzyme-substrate binding, and protein binding to biological membrane structures and biomolecules (such as receptors) embedded therein. Examples of specific uses for devices and methods of the present invention include, but are not limited to, determination of enzymatic inhibition by a collection of compounds in solution; determination of substrates for an enzyme (fishing/selectivity), identifying binding partners for immobilized biomolecules (such as peptides, proteins, nucleic acids, antibodies, enzymes, glycoproteins, proteoglycans, and other biological materials, as well as chemical substances), identifying inhibitors of protein-protein, protein-small molecule or protein-receptor binding, determination of the activity of a collection of enzymes (in one or more than one well), and generating selectivity indices for inhibitors of enzymes or other biologically active molecules, which may preferably be performed simultaneously with the generation of inhibition data.

Devices according to the present invention will now be described with reference to the drawing figures, which are exemplary in nature and not intended to limit the scope of the invention in any respect.

Figure 1A:
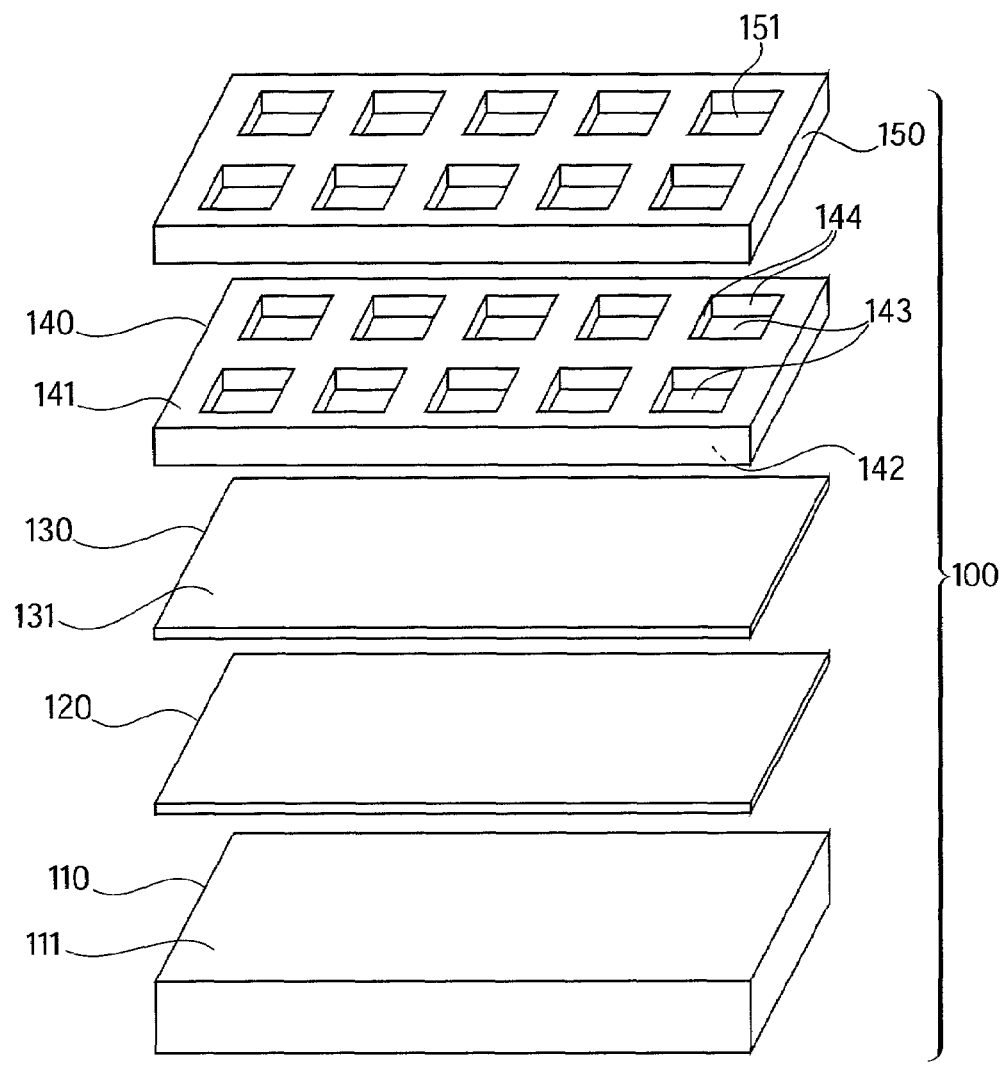
FIG. 1 depicts a device for arraying biological materials, according to an example embodiment of the present invention.
Figure 1B:
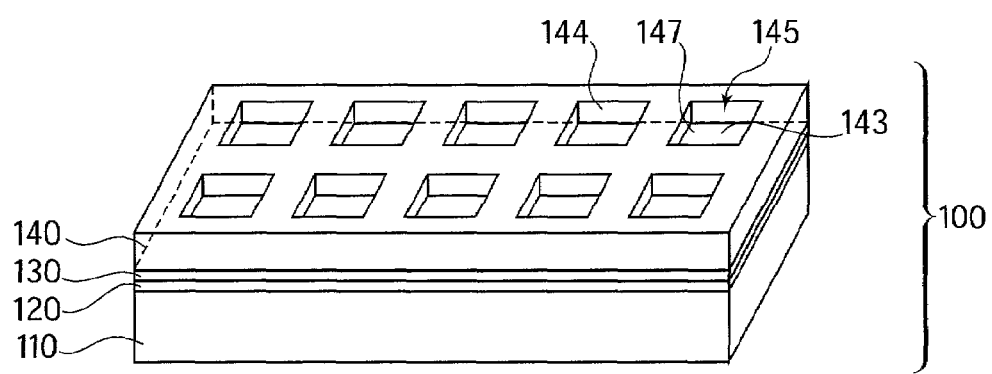

FIG. 1 depicts a device for arraying biological materials, according to an example embodiment of the present invention. FIG. 1(a) depicts an unassembled view, while FIG. 1(b) depicts an assembled view.

The elements of device 100 can additionally take on many variations and embodiments, several of which are described herein and others which will be apparent to those of skill in the art given the guidance provided herein. Like elements have been labeled with the same numbers throughout the Figures, even where they are included in different embodiments.

Device 100 comprises a base plate 110 and a removable member 140. Base plate 110 comprises upper surface 111. Surface 111 is preferably overlaid with a layer of metal 130. Layer 130 comprises surface 131. Examples of metals useful in forming layer 130 include gold, silver, platinum, palladium, and copper. Most preferably, layer 130 comprises gold. In certain embodiments, surface 111 may be overlaid with a layer of metal 120 before being overlaid with layer 130. In such embodiments, layer 120 is overlaid on surface 111 and layer 130 is overlaid on the surface of layer 120. Examples of metals useful in forming layer 120 include chromium and titanium. Other materials that are capable of adhering to the material chosen to form base plate 100 and that chosen to form layer 130 may also be used to form layer 120. Layers 120 and/or 130 may be overlaid on base plate 110 by using art-known methods, such as dunking in baths, photochemistry, and vapor deposition.

Examples of materials useful for forming base plate 110 include polymers, metals, ceramics, oxides, and the like. Base plate 110 may comprise glass, silicon wafer(s), fused silica, metal films (gold, silver, copper, platinum, etc.) alone or supported on flat surfaces, such as polystyrene, poly (methylacrylate), and polycarbonate.

Preferred substances for surface 111 and/or surface 131 are those that are biologically inert and/or capable of resisting the adsorption of biomolecules, such as proteins, by non-specific reactions. Non-specific adsorption is to be avoided as it would hamper the ability to immobilize specific biomolecules of interest and/or to immobilize biomolecules in specific locations.

Referring still to FIG. 1, surface 111 or surface 131 may be modified to support, accommodate, catalyze, or promote generation of arrays, in which adsorption, chemical reaction, or physical interaction may occur between the modified surface and array elements. Surface 111 or surface 131 may also be modified to exhibit specific interfacial characteristics, such as, but not limited to, accommodating protein adsorption, preventing non-specific protein adsorption, or promoting or resisting cellular attachment. One example of such modifications is the formation of a self-assembled monolayer (SAM) on surface 111 or surface 131. Such monolayers need not be patterned. However, such monolayers can be patterned such that, for example, proteins bind to specific areas, but not to others. Such patterning may be achieved via methods such as micro contact printing. See Andre Bernard et al,: *Langmuir,* 14(9): 2225-2229 (1998), "Printing Patterns of Proteins"; C. D. James et al,: *Langmuir,* 14: 741-744 (1998), "Patterned Protein Layers on Solid Substrates by Thin Stamp Microcontact Printing"; M. Mrksich and G. M. Whitesides, "Using Self-Assembled Monolayers to Understand the Interactions of Man-Made Surfaces with Proteins and Cells," *Annu. Rev. Biophys. Biomol Struct.,* 25: 55-78 (1996). See also, U.S. patent application Ser. No. 60/225,363. See, also, FIG. 24, which illustrates peptides immobilized using mixed SAMs. Such modifications may be performed with removable member 140 sealed to surface 111 or 131, or without removable member 140 so sealed.

Removable member 140 comprises upper surface 141 and lower surface 142. Removable member 140 defines a plurality of well orifices 143. Preferably, well orifices 143 are arranged in a spatially defined array, as can be seen in FIG. 1. For example, the spatial arrangement and dimensions of well orifices 143 may correspond to the well openings in industry standard 6-well, 12-well, 24-well, 96-well, 384-well, 1536-well plates, or even 9,600-microwell plates. Industry standard plates are those that are readily available commonly used throughout the biological, chemical, and pharmaceutical industries and in research in such areas. Well orifices 143 may also be arranged in novel configurations. Thus, the present invention provides for any configuration necessary to take advantage of today's industry standards as well as provides the flexibility to design for novel configurations.

Removable member 140 is formed of a material capable of spontaneously forming a fluid-tight seal with surface 131 or surface 111 when placed into contact with surface 131 or surface 111. Removable member 140 is self-sealing, and a fluid-tight seal between removable member 140 and surface 111 or 131 is made without the use of adhesives, ultrasound, heat or other means of sealing external to removable member 140 and surface 131 or surface 111 when removable member 140 is placed into contact with surface 111 or 131. Removable member 140 is capable of being sealed to surface 131 or surface 111, then removed therefrom (by means such as peeling and lifting, which may be performed manually or by machine) without damaging or leaving residue on surface 131 or surface 111; surface 131 or surface 111 is flat, or substantially planar, and substantially free of residue after removal of removable member 140. In an alternative embodiment, surface 111 or surface 131 may be non-planar. Examples of non-planar surface 111 or surface 131 include, for example, protrusions, ridges, concave wells, convex areas, grooves, microchannels, or the like. In certain embodiments, surface 111 has shallow concave wells. Removable member 140 is also capable of being resealed to surface 111 or 131, and a fluid-tight seal between removable member 140 and surface 111 or 131 is made without the use of adhesives, ultrasound, heat or other means of sealing external to removable member 140 and surface 131 or surface 111 when removable member 140 is placed into contact with surface 111 or 131.

Removable member 140 is also capable of being resealed to surface 131 or surface 111. As can be seen from FIG. 1, base plate 110, layers 120 and 130, and removable member 140 preferably have the same footprint as one another. By "footprint," it is meant size and shape in the plane defined by surfaces 111 and 131. Preferably, removable member 140 and base plate 110, surface 111, layer 130 and/or surface 131 comprise registration, or positioning, features. Such features may comprise components that facilitate visual, optical, magnetic, and/or mechanical registration, for example. Other suitable means of registration may also be used. Such features may comprise visual marks or structural features for example. It will often be preferable that such registration means are preferably present in embodiments of the present invention, although such means are not illustrated with every embodiment depicted and/or described herein.

Figure 15:
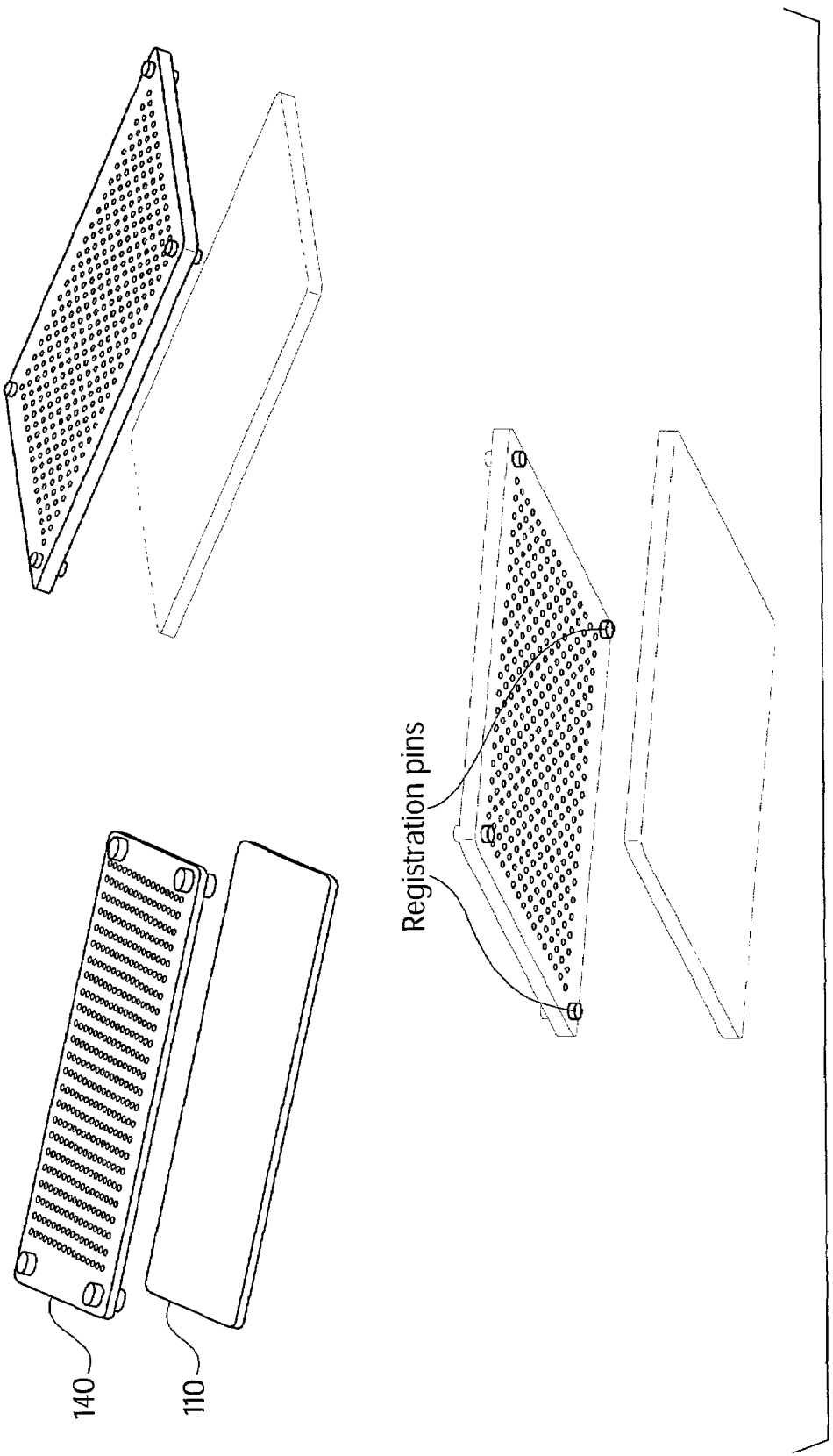
FIG. 15 depicts a base plate and removable member with registration pins.

One example of a structural feature is registration pins, which preferably ensure alignment between the components of the device within about within 200 microns, preferably within 100 microns, more preferably within 50 or fewer microns in all directions in the plane defined by surfaces 111, 141, and 131. Registration pins may, for example, be formed integrally with base plate 110 and extend through layers 120 and/or 130, and registration orifices in removable member 140, where the pins and registration orifices are positioned to facilitate positioning and re-positioning of removable member 140 on surface 111 or surface 131. As another, preferable, example, registration pins may be separate from the aforementioned components and may be removably inserted through base plate 110, through layers 120 and/or 130, through removable member 140, where the pins and registration orifices are positioned to facilitate positioning removable member 140 on surface 111 or surface 131. Such removable pins may be removed after positioning removable member 140 on surface 111 or surface 131, or they may remain in the registration orifices until it is desired to remove removable member 140. An additional exemplary embodiment having registration pins is depicted in FIG. 15.

As can be seen in FIG. 1, particularly FIG. 1(*b*), when removable member 140 is sealed to surface 131 or surface 111, a plurality of wells 145 is formed. Well orifice walls 144 form the sides of wells 145, and the well bottoms 147 are formed by surface 131 or surface 111. The spatial arrangement and shape of wells 145 correspond to the spatial arrangement and shape of well orifices 143. The spatial arrangement and location of well bottoms 147 correspond to the spatial arrangement and dimensions of well orifices 143 in the plane defined by surface 142. It will be appreciated that well bottoms 147 are constant in size, shape, and spatial arrangement, regardless of whether removable member 140 is sealed to surface 111 or 131 or is not so sealed. Therefore, well bottoms 147 is used herein to describe the portions of surface 111 or 131 corresponding in spatial arrangement and shape well orifices 143 in the plane defined by surface 142, regardless of whether removable member 140 is sealed to surface 111 or 131 or is not so sealed.

It certain embodiments, it may be desirable to coat well walls 144 with a material that inhibits binding of materials, particularly biomolecules, such that materials which are deposited into wells 145 to be immobilized on well bottoms 147 will be immobilized to well bottoms 147, and not to well walls 144. Examples of suitable materials include inert SAMs, which are discussed further herein and are known in the art.

Removable member 140 is preferably sturdy enough that it is not damaged during removal from surface 131 or surface 111, that does not degrade and that is not easily damaged by virtue of being used in multiple tests, thus allowing a removable member of the present invention to be sealed to removed from, and resealed to a surface several times during a single assay, or to be used in multiple assays; however, this is not required. Removable members 140 that are of varying degrees of sturdiness are encompassed by the present invention, and the composition of removable member 140 can be adjusted by one skilled in the art to achieve a desired balance between sturdiness and other characteristics such as adhesive characteristics, resiliency, and thickness. The desired characteristics will vary between applications.

Exemplary materials useful for fabricating removable member 140 include co-polymers or polymers, most preferably urethanes, rubber, thermoplastic rubber, molded plastic, polymethylmethacrylate (PMMA), polycarbonate, polytetrafluoroethylene (TEFLON™), polyvinylchloride (PVC), polydimethylsiloxane (PDMS), polysulfone, siloxanes, polyamides, and the like. Such materials are preferred for their ease of manufacture, low cost and disposability, as well as their general inertness to most extreme reaction conditions. Such materials may contain colored filler material to alter optical properties, such as transparency, fluorescence, and reflectivity. Such alterations may be desirable to enhance detection by certain devices and will vary according to the device and assay, as will be understood by the skilled user.

Removable member 140 may be manufactured from fabricated masters, using well known molding techniques, such as injection molding, relief molding, embossing or stamping, or by polymerizing a polymeric precursor material within the mold. Masters may be fabricated by suitable techniques, such as conventional machining, micro-machining, photolithography, injection molding, relief molding, embossing, and stamping. Numerous such techniques are known in the art. See Xia, Y. and Whitesides, G., *Angew. Chem. Int. ed.* 37: 550-575 (1998), which is herein incorporated by reference.

In many embodiments, removable member 140 is made of a material that is compliant and flexible. In such embodiments, it may be desirable to overlay removable member 140 with a more sturdy supportive member 150, as illustrated in FIG. 1(*a*). Supportive member 150 may define well orifices 151 corresponding in size and spatial arrangement to well orifices 143 in removable member 140. In such embodiments, when device 100 is assembled with supportive member 150, supportive member 150 will increase the depth of wells 145 when compared with device 100 assembled without supportive member 150, but will not alter the shape or orientation of wells 145 in the plane defined by the surface 111 of base plate 110.

Base plate 110 may be formed of any suitable material which is capable of adhering to biomolecules, gold, and/or surface treatments promoting the adherence of gold or biomolecules. Examples include glass, silicon, and plastics such as polystyrene and polycarbonate. Base plate 110 may be flat or non-planar. Preferably, base plate 100 is flat and rigid. In certain embodiments, base plate 110 is non-planar, for example, base plate 100 may be concave or convex or may have protrusions, ridges, concave wells, convex areas, grooves, channels, or the like, on surface 111. Base plate 110 may be fabricated using any suitable method. Many such methods are known in the art. Exemplary methods include those which may be used to manufacture removable member 140.

Supportive member 150 may be made from any material capable of offering support to removable member 140 and capable of being formed in the desired shape and size. In embodiments in which supportive member 150 defines well orifices 151, supportive member 150 is made from a material capable of having well orifices of the desired size and orientation formed therein, in addition to meeting the above-mentioned requirements. Supportive member 150 may be fabricated by methods described above for fabrication of removable member 140, as well as by other suitable methods.

Supportive member 150 may be permanently or removably attached to removable member 140. When supportive member 150 is permanently attached to removable member 140, it is preferable that supportive member 150 define well orifices 151. Where supportive member 150 is removable, it may be desirable to fabricate supportive member 150 without well orifices.

Referring still to FIG. 1, supportive member 150 is preferably formed of a material capable of adhering to removable member 140. Adhering may be accomplished with or without the use of adhesives, ultrasound, heat or other means of sealing external to removable member 140 and supportive member 150. However, in such embodiments, supportive member 150 preferably is capable of adhering to removable member 140, then being removed therefrom without damaging or leaving residue on removable member 140. In such embodiments, supportive member 150 preferably is capable of being resealed to removable member 140. In such embodiments, supportive member 150 preferably comprises glass and may also be coated with a metal, such as gold. Removable members 140 that have varying degrees of adhesion are encompassed by the present invention, and the composition of removable member 140 can be adjusted by one skilled in the art to achieve a desired balance between adhesive characteristics and other characteristics such as resiliency, and thickness. The desired characteristics will vary between applications.

Preferably, supportive member 150 (if present), removable member 140, base plate 110, surface 111, layer 130 and/or surface 131 comprise registration, or positioning, features. Such features may comprise components that facilitate visual, optical, magnetic, and/or mechanical registration for example. Such features may comprise visual marks, structural features, and the like. One example of a structural feature is registration pins, which preferably ensure alignment between the components of the device within 200 microns, preferably within 100 microns, more preferably within 50 or fewer microns in all directions in the plane defined by surfaces 111, 141, and 131. Registration pins may, for example, be formed integrally with base plate 110 and extend through layers 120 and/or 130, and registration orifices in removable member 140 and support member 150, where the pins and registration orifices are positioned to facilitate positioning and re-positioning removable member 140 and/or support member 150 on surface 111 or surface 131.

As another, preferable, example, which is illustrated in FIG. 2, registration pins may be separate from the aforementioned components and may be removably inserted through base plate 110, through layers 120 and/or 130, and through removable member 140, where the pins and registration orifices are positioned to facilitate positioning removable member 140 on surface 111 or surface 131. Such removable pins may be removed after positioning removable member 140 and/or support member 150 on surface 111 or surface 131, or they may be left in place until it is desired to remove removable member 140. In embodiments comprising a supportive member, an example of which is provided in FIG. 1, 150, the supportive member may define registration orifices that correspond to those in removable member 140, and the registration orifices in the supportive member may be used to facilitate positioning the supportive member on surface 141.

Figure 2A:
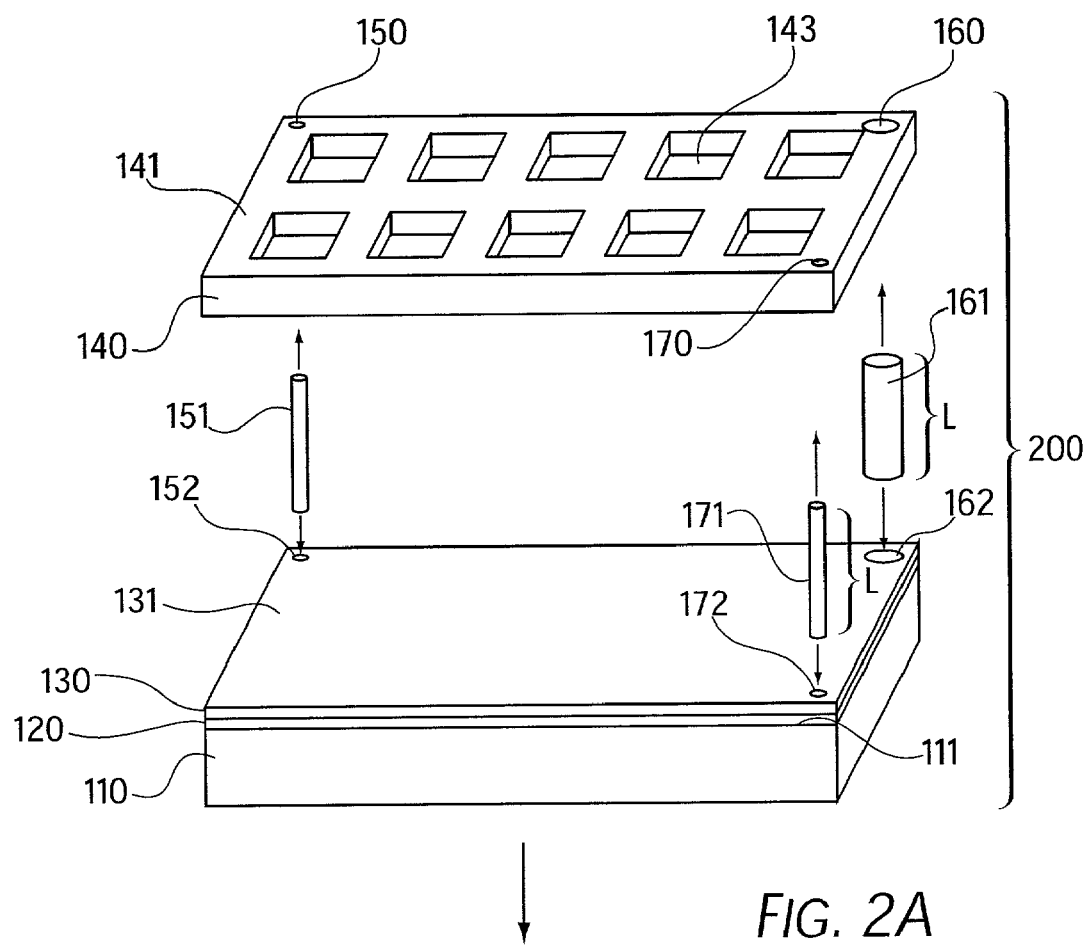
FIGS. 2A and 2B depicts a device according to the present invention, and similar to the device depicted in FIG. 1, comprising registration pins.
Figure 2B:
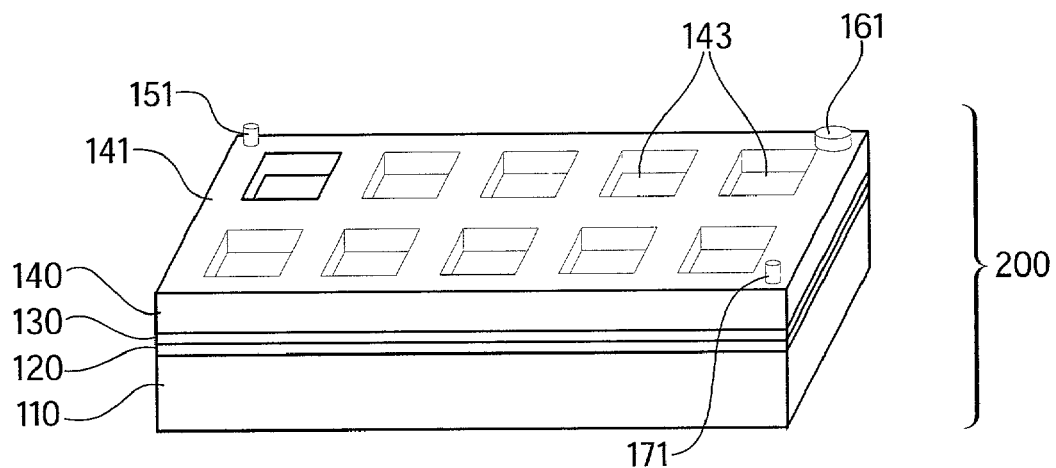

FIG. 2 depicts a device according to the present invention comprising registration pins. FIG. 2(a) shows an unassembled view of an analytical device 200 according to an embodiment of the present invention, while FIG. 2(b) depicts an assembled view. Device 200 is very similar to device 100 of FIG. 1 and comprises base plate 110, layer 120, layer 130, and removable member 140, which defines a plurality of well orifices 143. Removable member 140 also defines registration orifices 160, 170, and 180. Base plate 110 comprises registration orifices 152, 162, and 172. Layers 120 and 130 are overlaid on base plate 110 such that registration orifices 152, 162, and 172 remain open.

Registration pins 151, 161, and 171, registration orifices 160, 170, and 180, and registration orifices 152, 162, 172 are sized with relation to one another and spaced in the plane defined by surfaces 111, 131, and 141 with relation to one another such that they ensure alignment between the components of the device within 200 microns, preferably within 100 microns, more preferably within 50 or fewer microns in all directions in the plane defined by surfaces 141, 131, and 111.

In the embodiment depicted in FIG. 2, registration orifices 160 and 162 are of substantially identical shape and size in the plane defined by surfaces 141, 131, and 111. Registration orifices 152 and 172 are elongated in the plane defined by surfaces 141, 111, and 131, with one axis being longer than the other, with the long axis of registration orifice 162 being perpendicular to the long axis of orifice 172. Such elongation may serve to facilitate placement and assembly of the device. As the elongated axes of registration orifices 152 and 172 are parallel to one another, accurate registration is still provided and slippage is avoided. Registration orifices 152 and 172 may be rectangular, but are preferably oblong, with the short axis of registration orifice 152 being approximately equal in length to the diameter of registration orifice 150, and the short axis of registration orifice 172 being approximately equal in length to the diameter of registration orifice 170. Registration orifices 150, 160, 170, 152, 162, and 172 are sized and shaped in the plane of surfaces 141, 131, and 111 in relation to the size and shape of registration pins 151, 161, and 171 such that alignment between the components of the device within 200 microns, preferably within 100 microns, more preferably within 50 or fewer microns in all directions in the plane defined by surfaces 111, 141, and 131 is ensured when the registration pins are placed into the registration orifices.

Referring still to FIG. 2, registration pins 151, 161, and 171 are of a length (L) perpendicular to the plane of surfaces 111, 131, and 141 such that the pins extend from the bottom surface of base plate 110 to above surface 141. Registration pins 151, 161, and 171 are of a size and shape in the plane defined by surfaces 111, 131, and 141 in relation to registration orifices 150, 160 170, 152, 162, and 172 such that alignment between the components of the device within 200 microns, preferably within 100 microns, more preferably within 50 or fewer microns in all directions in the plane defined by surfaces 111, 141, and 131 is ensured when the registration pins are placed into the registration orifices.

As can be seen in FIG. 2, registration pins 151, 161, and 171 are preferably placed into orifices 150, 160, and 170 before removable member 140 is placed into contact with surface 131—in such a method of assembly, registration pins 151, 161, and 171 are placed into orifices 152, 162, and 172 as removable member 140 is placed into contact with surface 131. Alternatively, registration pins 151, 161, and 171 may be placed into orifices 152, 162, and 172 before removable member is placed into contact with surface 131—in such a method of assembly, registration pins 151, 161, and 171 are placed into orifices 150, 160, and 170 as removable member 140 is placed into contact with surface 131. The above methods of assembly are particularly desirable for uses of the device or steps of a method using the device in which it is desired to align removable member 140 with a pattern of material, such as biomolecules, already immobilized on surface 131. In other instances, such as uses of the device or steps of a method using the device in which no material has yet been immobilized on surface 131 or material has been immobilized in a uniform layer, it may be desirable to place removable member 140 into contact with surface 131 then place registration pins 151, 161, and 171 into orifices 150 and 152, 160 and 162, and 170 and 172.

As is taught herein, devices of the present invention preferably comprise registration means capable of ensuring alignment between the components of the device within 200 μm preferably within 100 μm, more preferably within 50 or fewer microns in all directions in the plane defined by surfaces 111, 141, and 131. As will be clear to the skilled user, the embodiment depicted in FIG. 2 is only one example of an arrangement of registration orifices and pins which are useful in devices according to the present invention.

As another example, registration orifices that are elongated on one axis in relation to registration pins may be located in a removable member and corresponding registration orifices that are not so elongated may be located in a base plate and any layers thereon.

Registration pins according to the present invention are preferably formed of a material and via a manufacturing method that provides sufficient rigidity to avoid bending of the pins as they are inserted into registration holes and to prevent shifting of the components of a device according to the present invention in the plane defined by the interface between a removable member and a base plate, or coatings or surfaces thereon, of the present invention. Registration pins may be made by any suitable technique, many of which are known in the art. Examples of suitable methods include those described herein for the fabrication of removable members according to the present invention. Registration pins of the present invention are preferably fabricated of a length in the plane perpendicular to the interface between a removable member and a base plate, or coatings or surfaces thereon, sufficient to permit ease of handling.

The sealable, removable, and resealable properties of removable members according to the present invention facilitate both the performance of assays and the reading, observation, and measurement of the results of assays performed using devices according to the present invention.

Materials of interest may be immobilized on surface 111 or 131. Materials of interest include biological materials such as biological molecules, organic molecules, and cells. More specific examples of biological materials which may be immobilized include proteins, nucleic acids, antibodies, biologically-active small molecules, enzymes, glycoproteins, peptides, proteoglycans, and other biological materials, as well as chemical or biochemical substances. Surface chemistries for the immobilization of various materials are also known in the art. One preferable example is immobilization via self-assembled monolayers (SAMs) comprising alkanethiols on gold.

As depicted in FIG. 1, the walls 144 of well orifices 143 may be substantially normal (i.e., from about 88° to about 92°) with respect to surfaces 141 and 142. Alternatively, walls 144 of well orifices 143 may form obtuse or acute angles with surfaces 141 and 142.

Figure 3:
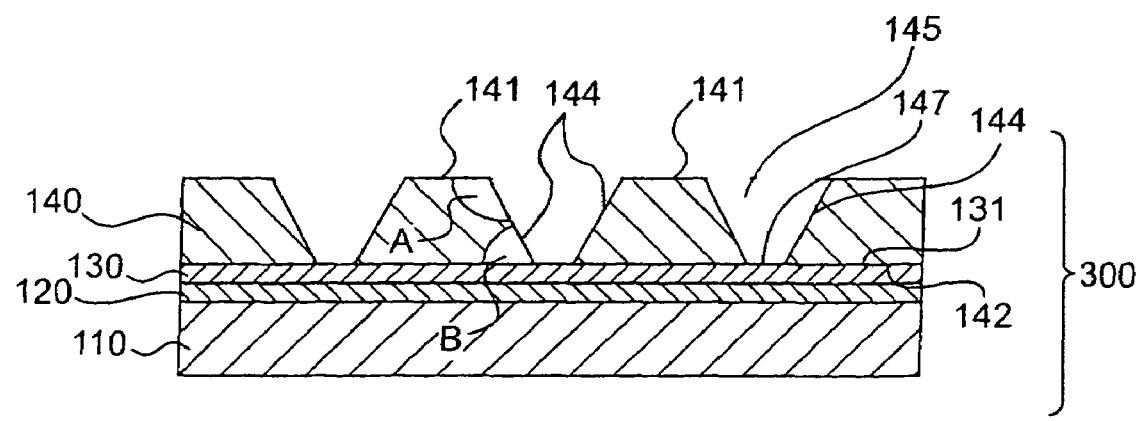
FIG. 3 shows a cross-sectional view of an assembled device according to another example embodiment of the present invention.

Device 300 of FIG. 3 is very similar to device 100 of FIG. 1 and comprises base plate 110, layer 120, layer 130, and removable member 140, which defines a plurality of well orifices 143. FIG. 3 depicts a cross sectional view of an embodiment in which walls 144 of well orifices 143 may form obtuse or acute angles with surfaces 141 and 142. As is depicted in FIG. 3, where walls 144 form angles with surfaces 141 and 142, walls 144 form obtuse angles (A) with surface 141 and acute angles (B) with surface 142, such that walls 144 taper downwardly inward with respect to well orifices 143 and wells 145 are in the shape of an inverted truncated pyramid. Preferably walls 144 taper inward with respect to well orifices 143. The degree of tapering can be adjusted as desired for particular applications. It will be appreciated that when walls 144 are tapered the size of well orifice 143 varies between the plane of surface 141, the plane of surface 142, and intermediate planes.

Methods of patterning biological materials are known in the art and are discussed further herein. For example, biomolecules can be patterned via micropipetting manually or using automated micropipetting machines, via soft lithography, by binding to selective SAMs which are patterned on a surface, and by other suitable art-known methods. It may often be preferable to combine two or more patterning methods to achieve the desired results. See Xia, Y. and Whitesides, G., *Angew. Chem. Int. ed.* 37: 550-575 (1998), which is herein incorporated by reference. See also, Albert Folch and Mehmet Toner; Annu. Rev. Biomed. Eng., vol. 2(2000), pp.227-56, "Microengineering of Cellular Interactions."

Devices and methods of the present invention facilitate the performance of assays requiring exposure of immobilized material to other material, particularly material in solution. Exposure of immobilized materials to biomolecules (such as enzymes of interest or antibodies), washes, reactions with chemicals, exposure to reagents, fixation of immobilized materials, the addition of signaling molecules (such as antibodies, fluorescent molecules, colored molecules, molecules that become colored when exposed to particular chemicals, molecules that become fluorescent when exposed to particular chemicals), and the exposure of signaling molecules to ("developing agents") agents which cause them to change, for example, from non-colored to colored or from non-fluorescent to fluorescent, and the like are collectively referred to as "process steps". Examples of fluorescent dyes include Cy 3, Cy 5 (Amersham U.K.), and DELFIA-based labels. Biomolecules, signaling molecules, and the like are preferably in solution.

When it is desirable simultaneously to perform process or detection steps on all materials immobilized on surface 111 or 131, removable surface 140 may be removed and the desired process or detection steps may be performed on the entirety of surface 111 or 131 at one time. Process steps performed on all materials immobilized on surface 111 or 131 are referred to as "bulk process steps."

Examples of other processing steps that may be performed as bulk processing steps include, but are not limited to immersion by bath techniques in washes, solutions of reagents, solutions of biomolecules; incubation of material with antibody solution; wash steps to remove unbound antibody or other materials; fixing steps to fix immobilized materials; developing steps, such as the addition of a signaling molecule, or the exposure of signaling molecules to agents (e.g., "developing agents") which cause them to change, for example, from non-colored to colored or from non-fluorescent to fluorescent; photo-assisted chemistry; and the like.

Such bulk processing steps may also be automated, thus increasing speed and efficiency even further. For example, baths may be automated and many devices may be processed in serial.

As non-limiting examples, test substances, such as biomolecules may be applied to the entirety of surface 111 or 131 at one time. Reagents, washes, and/or biomolecules may be applied to the material immobilized on each of well bottoms 147 simultaneously; thus all material immobilized on well bottoms 147 may be rinsed or exposed to reagents or biomolecules simultaneously, without the need for pipetting into each individual well 145. Such an application is particularly useful when it is desired to expose all immobilized materials to one or more solutions, reagents, or washes or the like.

The condition or state of the immobilized materials may be detected, observed, read, recorded, or the like at any time desired. For example, in an assay comprising steps of exposing immobilized materials to reagent(s) of interest, the results of the assay may be observed after the desired exposure. Such detection, observation, measurement, recordation, reading, and the like may collectively be referred to as "detection steps."

Devices of the present invention are particularly useful for observing results, conditions, or the like, when instruments which function only, or which function better, when the items to be measured are on a unencumbered flat surface (i.e., a substantially planar surface not comprising portions protruding perpendicularly from the flat surface and preferably substantially free from particles or residue from removable members of the invention). Examples of such instruments include, but are not limited to, microscopes (including, but not limited to, bright field, phase contrast, and epi-illuminated fluorescence microscopes), MALDI (Matrix Assisted LASER Desorbtion Ionization) mass spectrometers (which are available from commercial sources, such as Applied Biosystems), ELISA-coupled document scanners, surface plasmon resonance (SPR) sensors (which are available from commercial sources, such as Biacore, GWC, Texas Instruments, and Leica), flat-bed laser confocal scanners (which are available from commercial sources, such as Fuji, Biorad and Molecular Dynamics (examples of instruments available include the Typhoon)), flat bed scanners (including, but not limited to, confocal flat bed laser scanners), calorimetric scanners, fluorometric scanners, phosphorous scanners (which, among other uses, are effective for flat phosphorous-based imaging of radioisotopes, as commonly used to read DNA arrays, which are available from commercial sources, such as Affymetrix and Agilent), and scanning probe microscopies (such as scanning electron microscopes (SEM) and atomic force microscopes (AFM)). As yet another example, where radioactive signaling molecules are used, a phosphorescent substrate may be placed on the surface (such as surface 111 or 131 of FIG. 1) of a device according to the present invention and allowed to develop.

It will be recognized that process and/or detection steps may also be performed when removable member 140 is sealed to surface 111 or 131, using, for example, conventional microtiter plate readers.

After process and/or detection steps, removable member 140 may be resealed onto surface 111 or surface 131 to re-form wells 145. When wells 145 are re-formed, additional process steps may be performed individually on materials immobilized on well bottoms 147 (and, it will be appreciated, detection steps may be performed). The cycle of sealing removable member 140 to surface 111 or 131 and immobilizing materials and/or performing steps on materials immobilized on individual well bottom(s) 147; removing removable member 140 and performing process or detection steps on materials immobilized in individual well bottom(s) 147; and resealing removable member 140 to surface 111 or 131 and performing steps on materials immobilized in individual well bottom(s) 147 may be repeated as many times as is desired.

Figure 4A:
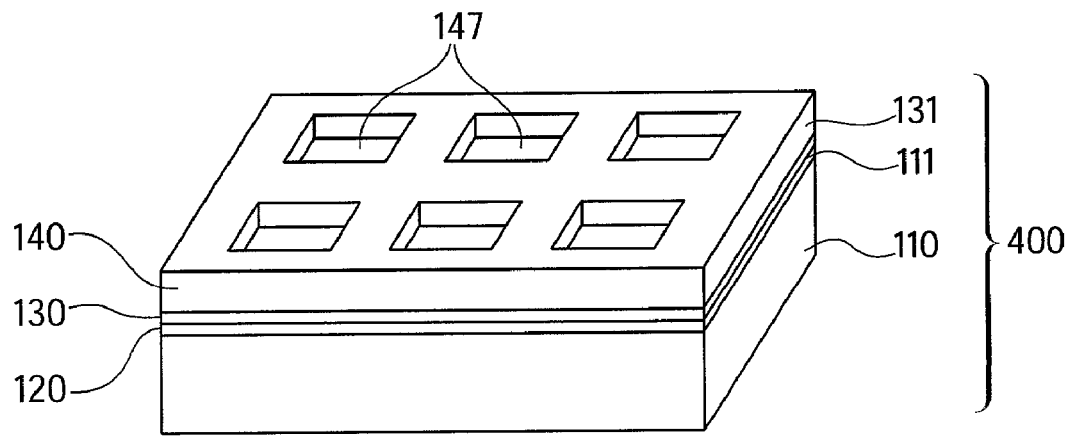
FIGS. 4A, 4B and 4C depicts a device according to the present invention.
Figure 4B:
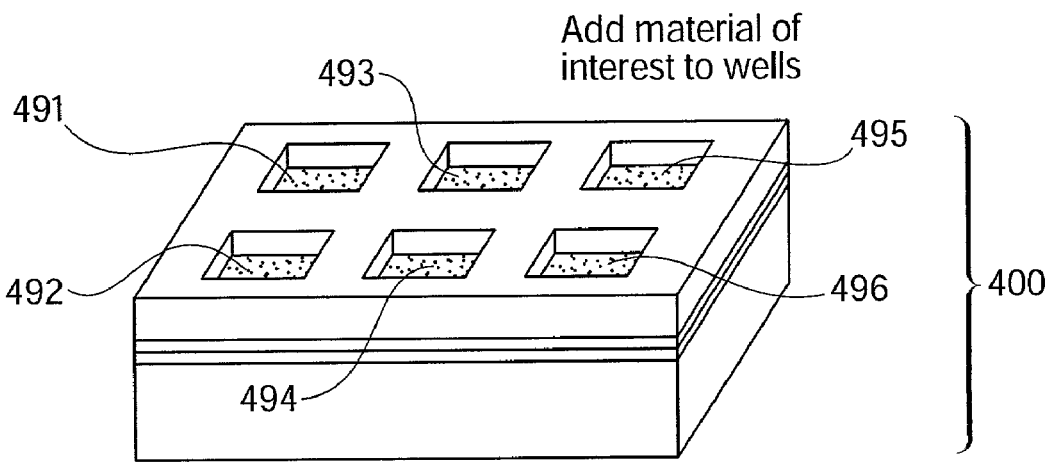
Figure 4C:
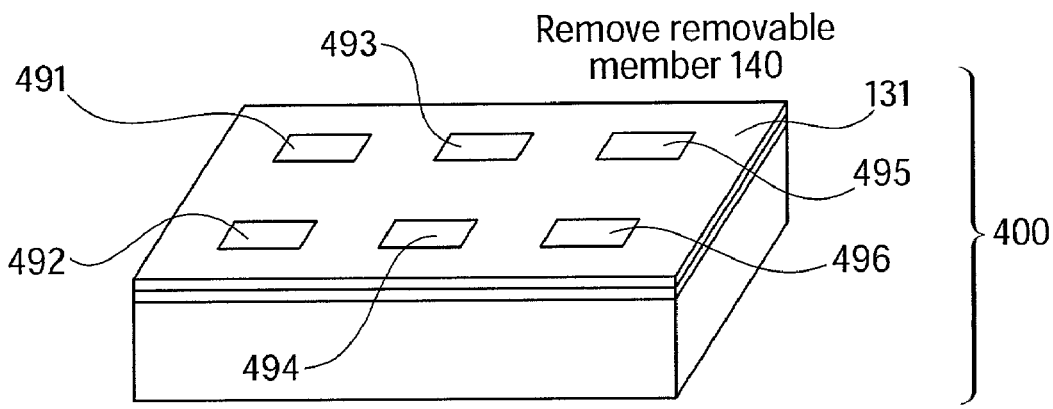

FIG. 4 depicts an embodiment according to the present invention. Device 400 of FIG. 4 is very similar to device 100 of FIG. 1 and comprises base plate 110, layer 120, layer 130, and removable member 140, which defines a plurality of well orifices 143. In FIG. 4, removable member 140 is sealed to surface 131 and materials of interest are immobilized on surface 131 in the spatial pattern defined by well orifices 143. Specifically, materials of interest 491-496 are immobilized on well bottoms 147 via the application of the materials of interest to well orifices 143. Device 400 with materials 491, 492, 493, 494, 495 and 496 immobilized on well bottoms 147 is depicted in FIG. 4(b), with removable member 140 sealed to surface 131, and in FIG. 4(c), with removable member 140 removed.

Methods for deposition of materials into orifices, or wells, are well-known in the art, and include both manual and automated techniques, such as pipetting, micropipetting, and the use of automated arrayers. Immobilized materials 491-496 may be the same or may differ from one another—thus, the material immobilized on each well bottom 147 may be the same or may vary between well bottoms 147. Although this is not illustrated in FIG. 4, more than one type of material of interest (such as a combination of two or more of materials 491-496) may be immobilized on a single well bottom 147. Device 400 may be used to perform assays and processes, such as those that are described in more detail herein.

Removable member 140 may be removed after immobilization of materials of interest (as is depicted in FIG. 4(c)), or may be left in place (as is depicted in FIG. 4(b)) for the performance of process and/or detection steps. In embodiments wherein removable member 140 is left in place, process and/or detection steps may be carried out within wells and may, therefore, vary between wells, allowing many different process and/or detection steps to be carried out on immobilized materials. Removable member 140 may be removed whenever it is desired simultaneously to perform a process step on all materials immobilized on surface 111 or 131. After being removed, removable member 140 may be resealed on surface 111 or 131 whenever it is desired separately to perform a process steps on materials immobilized in each of wells 145.

In other embodiments, materials of interest may be immobilized on surface 111 or surface 131 without removable member 140 being sealed to surface 111 or 131, and removable member 140 may then be sealed to surface 111 or surface 131 after the material is immobilized. Such a process and a device formed thereby are illustrated in FIG. 5. Device 500 of FIG. 5 is very similar to device 100 of FIG. 1 and comprises base plate 110, layer 120, layer 130, and removable member 140, which defines a plurality of well orifices 143.

Figure 5A:
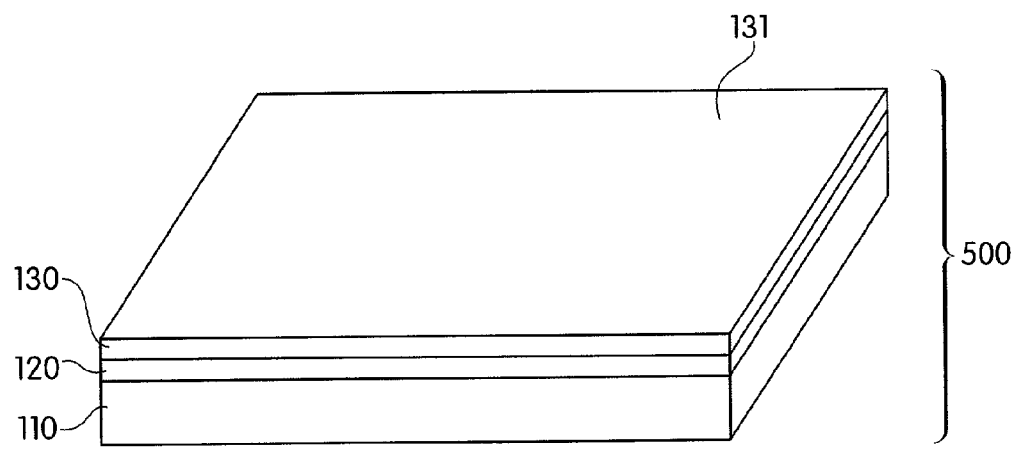
FIGS. 5A, 5B, and 5C depicts a device according to the present invention.
Figure 5B:
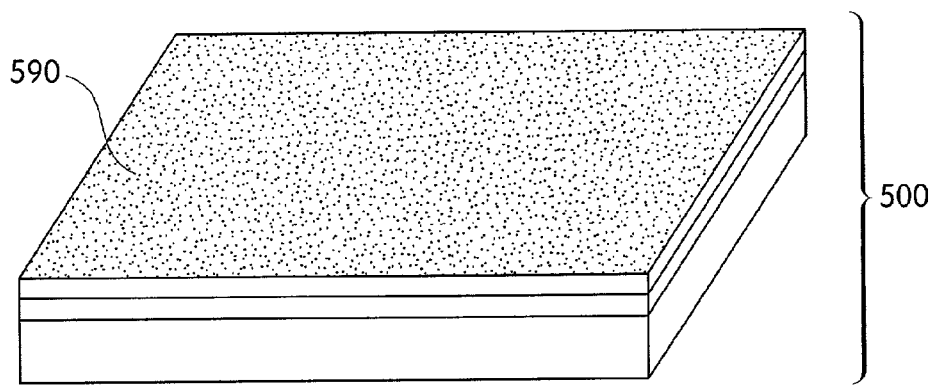
Figure 5C:
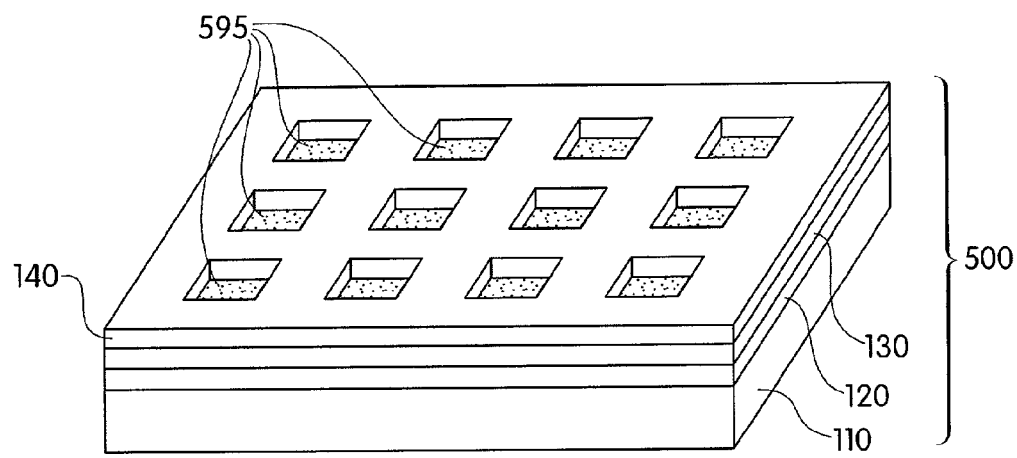

FIG. 5(a) depicts a device according to the present invention without removable member 140 sealed to surface 131. In the embodiment of FIG. 5(b), material of interest 590 is immobilized on surface 131 without the use of removable member 140. In the embodiment of the present invention illustrated in FIG. 5, removable member 140 having well orifices 143 is sealed to surface 131 on top of material of interest 590, as is depicted in FIG. 5(c). A plurality of discrete areas 595 of material of interest 590 are isolated by well orifices 143. Areas 595 are isolated from one another by the fluid-tight seal formed between removable member 140 and surface 131 and are accessible from above removable member upper surface 141 via well orifices 143.

The use of fluid-tight-seals allow the entire surface of the plate to be reproducibly modified into discrete areas 595, which could not be accomplished in a rigid plate without pipetting fluids into each well, thus potentially contaminating the wells.

Device 500 may be used to perform assays and processes, such as those that are described in more detail herein. Additional materials may be added to wells created by the well orifices 143 and surface 111 or 131 upon the sealing of removable member 140 to surface 111 or 131. Device 500 may be used to perform assays and processes, such as those that are described in more detail herein. Removable member may 140 may be removed from and resealed to surface 131 as desired.

Figure 6A:
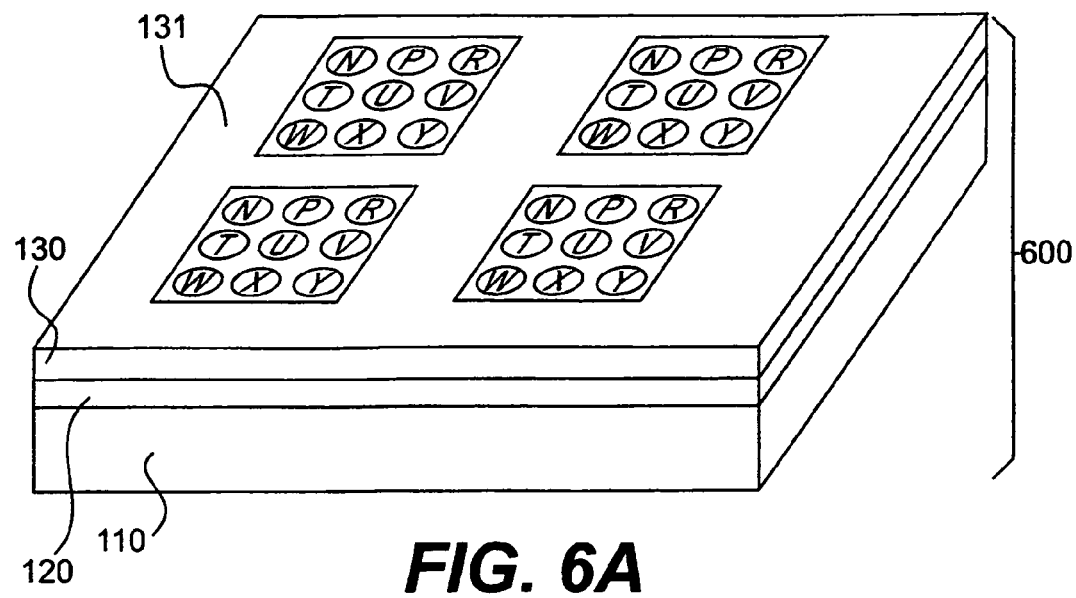
FIGS. 6A and 6B depicts an "array of arrays" according to the present invention
Figure 6B:
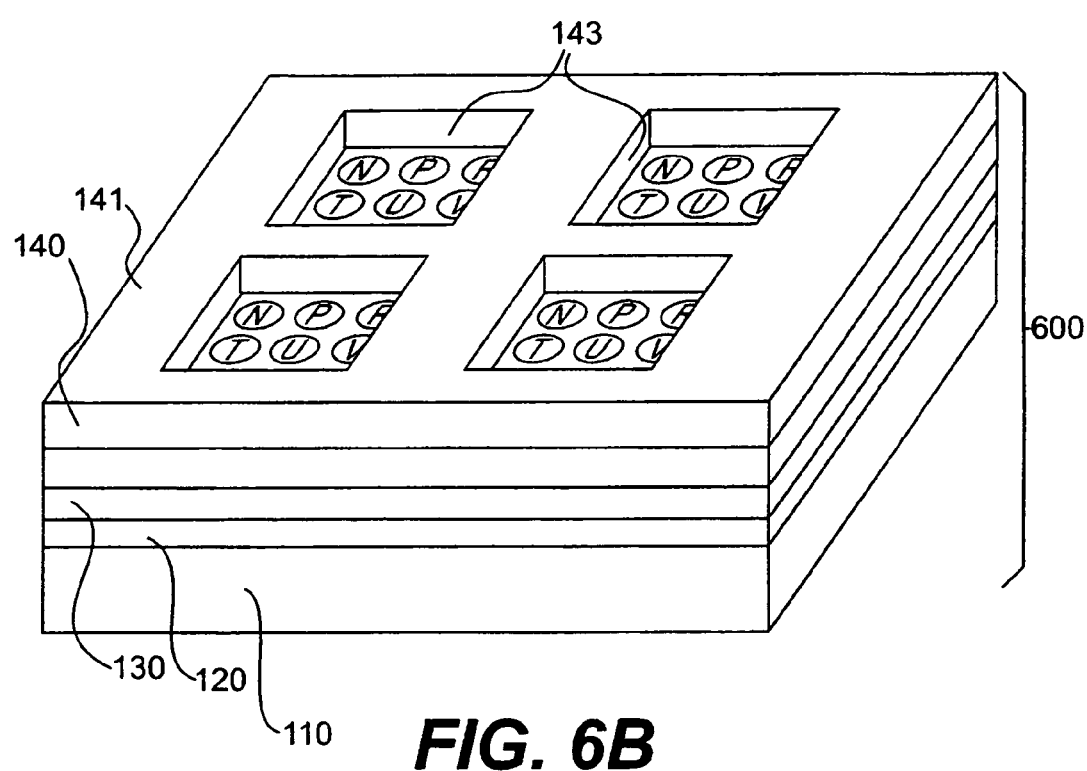

When materials of interest are immobilized to surface 111 or 131 without removable member sealed to surface 111 or 131, a single material may be immobilized on surface 111 or 131, as is illustrated in FIG. 5. Materials of interest may also be patterned on surface 111 or 131. For example, a self-assembled monolayer (SAM) that allows proteins or other biomolecules bind to specific areas, but not to others, may be patterned onto surface 111 or surface 131. Such monolayers can be patterned such that, for example, certain proteins may bind to one area, other proteins may bind to other areas, and other areas may remain free of bound proteins. FIG. 6 depicts such a process and device according to the present invention. Removable member 140 may be removed after immobilization of materials of interest, or may be left in place for the performance of process and/or detection steps. In embodiments wherein removable member 140 is left in place, process and/or detection steps may be carried out within wells and may, therefore, vary between wells, allowing many different process and/or detection steps to be carried out on immobilized materials. Removable member 140 may be removed whenever it is desired simultaneously to perform a process step on all materials immobilized on surface 111 or 131. After being removed, removable member 140 may be resealed on surface 111 or 131 whenever it is desired separately to perform a process steps on materials immobilized in each of wells 145.

In embodiments such as that depicted in FIG. 6, discrete islands of materials of interest, such as biomolecules, are immobilized in predetermined, spatially defined arrays. Each island is preferably surrounded by an area that is substantially free of biomolecules. It will generally be preferable to immobilize only one species of biomolecule in each island. It will also generally be preferable to immobilize different species of biomolecule in different islands, each surrounded by an area that is substantially free of biomolecules, such that an array of biomolecules islands is formed. This array pattern may repeated two or more times on surface 111 or 131, thus creating an "array of arrays," as can be seen in FIG. 6, FIG. 6 depicts an "array of arrays" according to the present invention and illustrates yet another device and process according to the present invention. Device 600 of FIG. 6 is very similar to device 100 of FIG. 1 and comprises base plate 110, layer 120, layer 130, and removable member 140, which defines a plurality of well orifices 143. In this embodiment, array(s) of discrete patterns of materials of interest are be immobilized on surface 131 without removable member 140 being sealed to surface 131, as is illustrated in FIG. 6(*a*), and removable member 140 having well orifices 143 is sealed to surface 131 after the material is immobilized, thereby forming wells 145 with surface 131, as is illustrated in FIG. 6(*b*). In the embodiment of the present invention depicted in FIG. 6, the letters N, P, R, T, U, V, W, X, and Z each represent an island of a particular species of biomolecule, with each of N, P, R, T, U, V W X, and Z representing a different species of biomolecule. Removable member 140 may be removed whenever it is desired simultaneously to perform a process step on all materials immobilized on surface 111 or 131. After being removed, removable member 140 may be resealed on surface 111 or 131 whenever it is desired separately to perform a process steps on materials immobilized in each of wells 145. Device 600 may be used to perform assays and processes, such as those that are described in more detail herein.

In such embodiments such as that depicted in FIG. 6, it is preferable that, when removable member 140 is sealed to surface 111 or 131, each of well orifices 143 encompasses at least one island of biomolecules surrounded by an area that is substantially free of biomolecules, as can be seen in FIG. 6(*b*). In more preferred embodiments, each of well orifices 143 encompasses more than one island of biomolecules, each surrounded by an area that is substantially free of biomolecules.

Figure 7A:
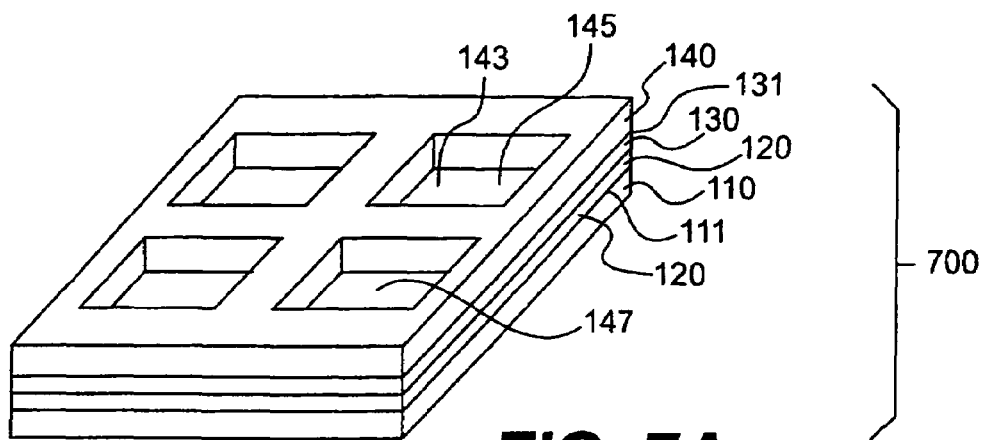
FIGS. 7(*a*)-(*c*) depict a process using two removable members, each having a plurality of well orifices, where the well orifices in one removable member are of a different size than the well orifices in the other removable member.
Figure 7B:
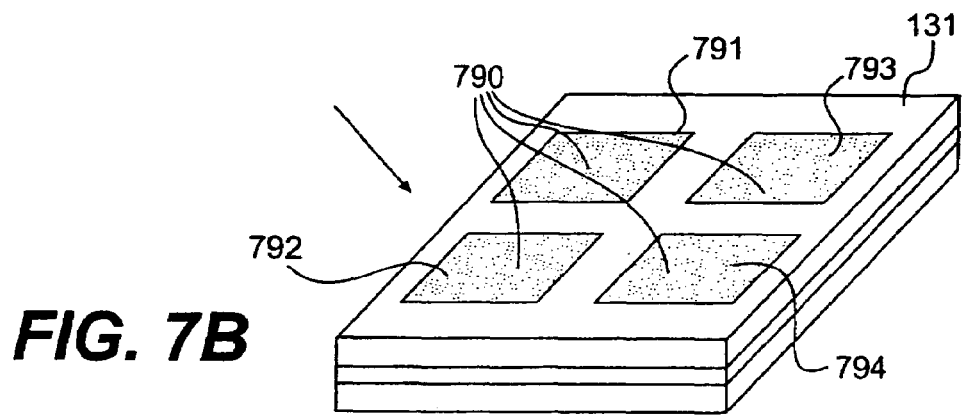
Figure 7C:
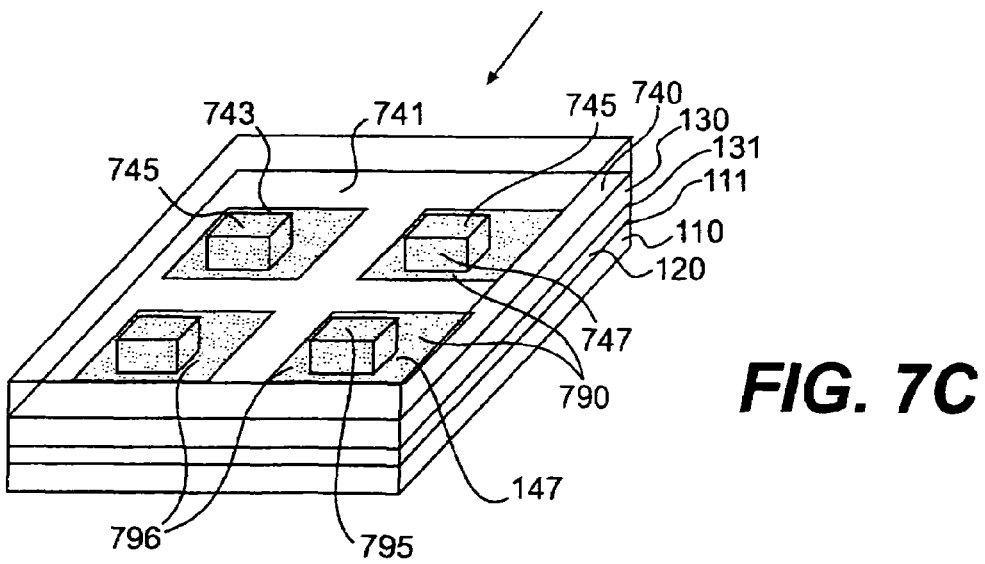

Devices according to the present invention may also be used to create and enable the use of local control regions for use in assays. FIG. 7 shows an exemplary device for creating and using such local control regions. Device 700 is very similar to device 100 of FIG. 1 and comprises base plate 110, layer 120, layer 130, and removable member 140, which defines a plurality of well orifices 143. Device 700 also comprises additional removable member 740, which may preferably be used sequentially with removable member 140.

As can be seen in FIG. 7(*a*), when removable member 140 is sealed to surface 131, a plurality of wells 145 having well bottoms 147 is formed. In the process illustrated in FIG. 7, islands 790 of materials of interest 791, 792, 793, and 794 are immobilized via wells 145 to form a pattern of material immobilized on well bottoms 147. Removable member 140 is then removed from surface 131, and a pattern of material corresponding to well bottom 147 remains immobilized on surface 131, as is depicted in FIG. 7(*b*). Materials of interest 791, 792, 793, and 794 may be the same material or may differ.

Removable member 740, depicted in FIG. 7(*c*), has structural, compositional, and sealing characteristics substantially the same as removable member 140 and may be manufactured using similar processes and materials.

Removable member 740 is formed of a material capable of forming a fluid-tight seal with surface 111, 131, or 141 when placed in contact with any of these surfaces. The fluid-tight seal is made without the use of adhesives, ultrasound, heat or other means of sealing external to removable members 740 or surfaces 111, 131, or 141. Therefore, removable member 740 is capable of being sealed to surface 111, 131, or 141, then removed therefrom without damaging or leaving residue on surface 111, 131, or 141. Surface 111, 131,or 141 is flat after removal of removable member 740. Likewise, removable member 740 is flat after being removed from surface 111, 131, or 141. Removable member 740 is also capable of being resealed to surface 111, 141 or 131, and a fluid-tight seal between removable member 740 and surface 111, 141 or 131 is made without the use of adhesives, ultrasound, heat or other means of sealing external to removable member 740 and surface 131, 141 or 111 when removable member 740 is placed into contact with surface 111, 131, or 141.

Removable member 740 has a top surface 741 and defines well orifices 743 which are smaller in the plane defined by surface 741, 131, and 111 than are well orifices 143. When removable member 740 is sealed to surface 131, as is illustrated in FIG. 7(*c*), wells 745 having wells bottoms 747 are formed. As can be seen in FIG. 7(*c*), well orifices 743 are preferably shaped, oriented, and sized in relation to well bottoms 147 such that well bottoms 747 encompass an exposed portion 795 of each of islands 790, and a protected border 796 of each of islands 790 surrounding well bottom 747 is covered by removable member 740.

When removable member 740 is sealed to surface 131, the seal is fluid-tight; thus, fluids can be added to wells 745, thereby exposing exposed portions 795 to the fluid, while protected borders 796 remains unexposed to the fluid. Process steps and/or detection steps may then be performed on exposed portions 795, while protected borders 796 are not exposed to the process or detection steps. In this way, a local control is formed for each well 745. Unlike assays in which a single unexposed well or well without protein must serve as a control for a whole plate of reactions, systems and devices of the present invention such as that shown in FIG. 7 allow the user to account for well-to-well variability.

Figure 8:
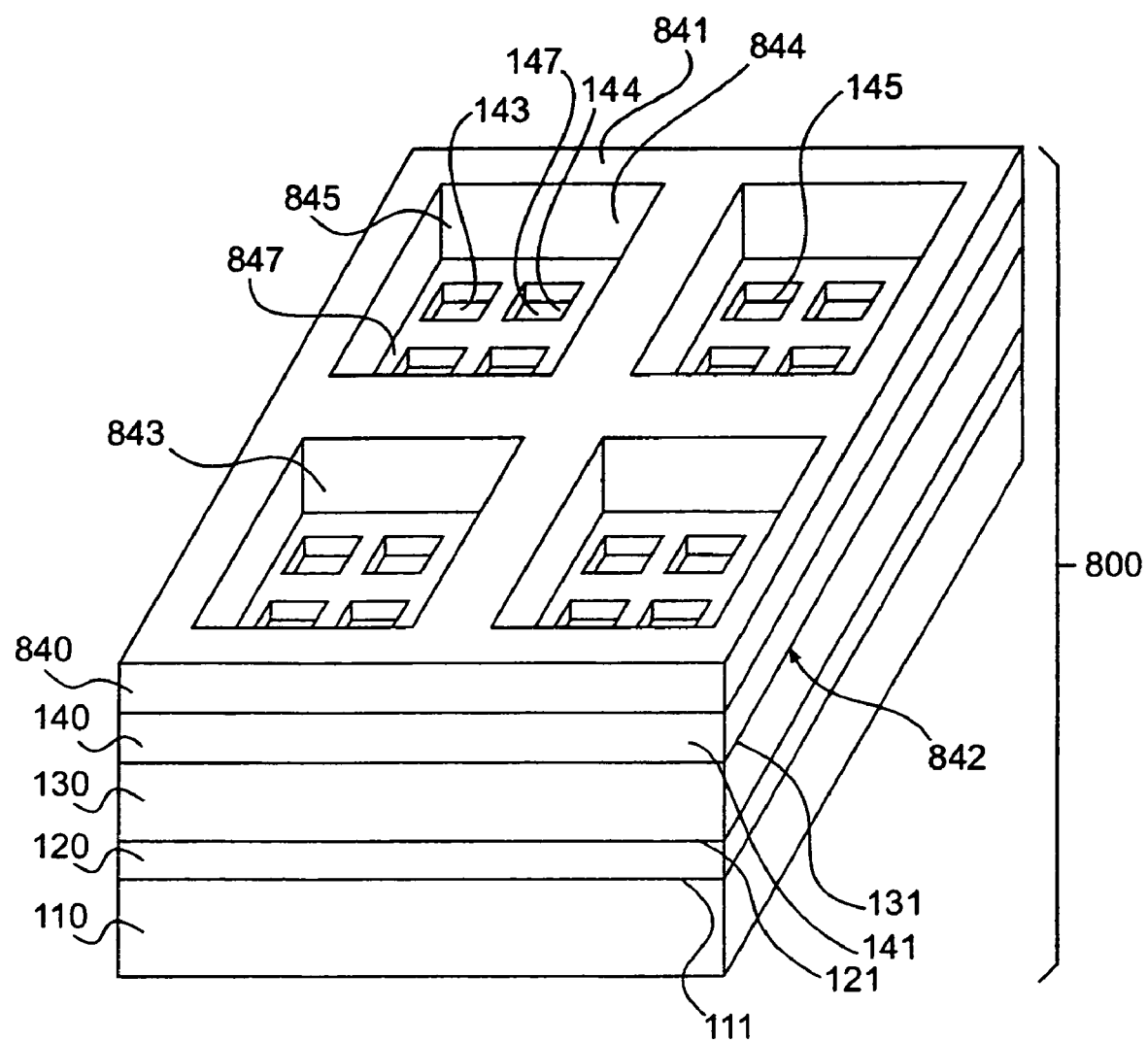
FIG. 8 shows an assembled view of a device according to an embodiment of the present invention comprising two removable members defining a plurality of well orifices.

FIG. 8 depicts a device that makes use of two removable members. Device 800 is very similar to device 100 of FIG. 1 and comprises base plate 110, layer 120, layer 130, and removable member 140, which defines a plurality of well orifices 143. Device 800 may be used, for example, to create wells within wells (for example, by using two membranes simultaneously). Device 800 also comprises removable member 840 comprising upper surface 841 and lower surface 842. Removable member 840 defines a plurality of well orifices 843. Removable member 840 has structural, compositional, and sealing characteristics substantially the same as removable member 140 and may be manufactured using similar processes and materials.

Removable member 840 is formed of a material capable of forming a fluid-tight seal with surface 111, 131, or 141 when placed in contact with any of these surfaces. The fluid-tight seal is made without the use of adhesives, ultrasound, heat or other means of sealing external to removable members 840 or surfaces 111, 131, or 141. Therefore, removable member 840 is capable of being sealed to surface 111, 131, or 141, then removed therefrom without damaging or leaving residue on surface 111, 131, or 141. Surface 111, 131, or 141 is flat after removal of removable member 840. Likewise, removable member 840 is flat after being removed from surface 111, 131, or 141. Removable member 840 is also capable of being resealed to surface 111, 131, or 141 and a fluid-tight seal between removable member 840 and surface 111, 131, or 141 is made without the use of adhesives, ultrasound, heat or other means of sealing external to removable member 840 and surface 111, 131, or 141 when removable member 840 is placed into contact with surface 111, 131, or 141.

As depicted in FIG. 8, a first well 145 is defined as a well bounded on sides thereof by walls 144 corresponding to one of the plurality of first well orifices 143 and a bottom 147 thereof by a corresponding first exposed region on the surface 11 or 131. A second well 845 is defined as a well bounded on sides thereof at least partially by walls 844 corresponding to one of the plurality of second orifices 843 and a respective bottom 847 thereof by a corresponding second exposed region on the first removable member 140 and/or the surface 111 or 131. An exposed region of an element is a region of the element exposed by an orifice of an orifice defining member by virtue of the orifice defining member having been disposed on the element.

As can be seen in FIG. 8, well orifices 843 are larger than well orifices 143 in the plane defined by surfaces 111, 131, 141, and 841, and well orifices 843 encompass more than one of well orifices 143 when resealable members 140 and 840 are placed in contact with one another.

Regardless of whether second removable member 840 is sealed to surface 111 or 131 (when removable member 140 is not sealed to surface 111 or 131) or second removable member 840 is sealed to surface 141, the spatial arrangement and shape of wells 845 correspond to the spatial arrangement and shape of orifices 843. The spatial arrangement and location of well bottoms 847 correspond to the spatial arrangement and dimensions of orifices 843 in the plane defined by surface 141, 131, 111, and 841. It will be appreciated that well bottoms 847 are constant in size, shape, and spatial arrangement, regardless of whether removable member 840 is sealed to surface 111 or 131 or is not so sealed and regardless of whether second removable member 840 is sealed to surface 141 or is not so sealed. Therefore, well bottoms 847 as used herein describe the portions of surface 111 or 131 corresponding in spatial arrangement and shape of orifices 843 in the plane defined by surface 841, 141, 131 or 111, regardless of whether removable member 140 is sealed to surface 111 or 131 or is not so sealed and regardless of whether second removable member 840 is sealed to surface 111, surface 131, or surface 141, or is not so sealed. It will also be recognized that in embodiments in which each orifice 843 encompasses a plurality of orifices 143, each well bottom 847 encompasses a plurality of well bottoms 147.

The sealable, removable, and resealable properties of removable members 140 and 840 facilitate both the performance of assays and the reading, observation, and measurement of the results of assays performed using device 800.

For example, as depicted in FIG. 8, removable member 140 is sealed to surface 131, and removable member 840 is sealed to surface 141. A plurality of wells 145, having well bottoms 147, are formed by well orifices 143 and surface 141. A plurality of wells 845 is also formed. The walls of wells 845 are formed by well orifices 843, and the bottom of wells 845 are formed by surface 141 or surface 131. Wells 845 encompass more than one well 145.

Device 800 is useful for performing assays, such as biological assays. As an example, when device 800 is configured as in FIG. 8, materials of interest may be immobilized on well bottoms 147 through wells 145, then multiple wells 145 may be simultaneously exposed to liquids via wells 845.

In many preferable embodiments, removable member 140 and removable member 840 will be interchangeably sealed, removed, and resealed to surface 131 one or more times during the course of an assay or procedure.

For example, removable member 140 may be sealed to surface 131 and biological molecules, organic molecules, cells or other materials of interest may immobilized on surface 131 in the defined spatial pattern defined by well orifices 143. Specifically, materials of interest are immobilized on well bottoms 147 via the application of the materials of interest to well orifices 143. Further examples of materials which may be immobilized include proteins, nucleic acids, antibodies, biologically-active small molecules, enzymes, glycoproteins, peptides, proteoglycans, and other biological materials, as well as chemical or biochemical substances. Methods for deposition of materials into orifices, or wells, are well-known in the art, and include both manual and automated techniques, such as pipetting, micropipetting, and the use of automated arrayers. Surface chemistries for the immobilization of various materials are also known in the art and discussed herein. Immobilized materials may be the same on each well bottom 147 or vary between well bottoms 147. Likewise, more than one material of interest may be immobilized on any single well bottom 147.

After immobilization of materials of interest, removable member 140 may be removed from surface 131 or may be left in place (as is depicted in FIG. 8), and second removable member 840 may be sealed to surface 131 or to surface 141. Process steps may then be performed in each of wells 845. In this way, different process steps may be carried out on each group of materials immobilized on each well bottom 847. It will be appreciated that the process steps performed on a given well bottom 847 are performed on each well bottom 147 encompassed by the given well 845. Thus, one process step(s) may simultaneously be performed on a group of materials immobilized on well bottoms 147 within a given well bottom 847; and a second process step(s) be performed on a second group of materials immobilized on well bottoms 147 within a second given well bottom 847.

When it is desirable to perform detection steps and/or the same process step(s) on material immobilized on each of all well bottoms 847, both removable member 140 and second removable member 840 may be removed.

Again, sealing, removing, and resealing removable member 140 and/or second removable member 840, immobilizing materials, and/or performing process and/or detection steps on materials immobilized on individual well bottom(s) 147 and/or 847 may be repeated as many times as is desired. It will be appreciated that additional removable members having different arrangements of orifices therethrough may be assembled and used according to the present invention.

Device 800 may be used, for example, to create wells within wells (for example, by simultaneously using two members) or to pattern spots, groups of which are then confined within wells within wells (for example, by patterning with one member, removing the first member, then placing another member to form wells).

When more than one removable member is used in a device according to the present invention, the walls of the well orifices defined by one or more removable member may be substantially normal (i.e., from about 88° to about 92°) with respect to the upper and lower surfaces of the removable members, as is depicted in FIG. 8.

Figure 9:
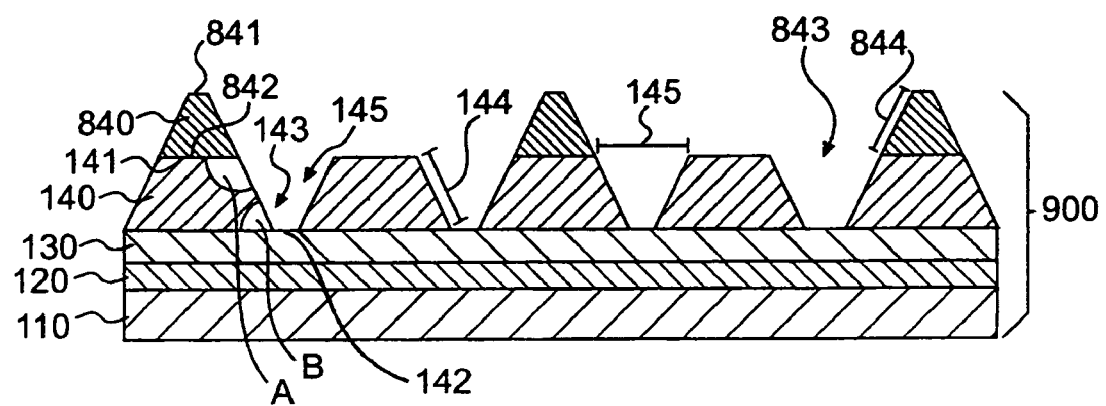
FIG. 9 shows a cross section of a device according to an embodiment of the present invention.

Alternatively, the walls of the well orifices defined by one or more removable member may define obtuse or acute angles with the upper and lower surfaces of the removable members. Such non-perpendicular well orifices may be used in any embodiment of the present invention where desired. FIG. 9 depicts a cross section of a device that makes use of two removable members that define well orifices having walls that define obtuse or acute angles with the upper and lower surfaces of the removable members. Device 900 is very similar to device 800 of FIG. 1 and comprises base plate 110, layer 120, layer 130, removable member 140, which defines a plurality of well orifices 143, removable layer 840, which comprises upper surface 841 and lower surface 842 and defines a plurality of well orifices 843. Device 900 may be used, for example, to create wells within wells (for example, by simultaneously using two members).

As is illustrated in FIG. 9, where walls 144 form angles with surfaces 142 and 141, preferably walls 144 form obtuse angles (A) with surface 142 and acute angles (B) with surface 141, such that walls 144 taper downwardly inward with respect to well orifices 143 and wells 145 are in the shape of an inverted truncated pyramid. The degree of the tapering can be adjusted as desired for particular applications.

Preferably, and as can be seen in FIG. 9, the dimensions and spatial arrangement of well orifices 843 are such that when second removable member 840 is sealed to surface 141, each well orifice 843 encompasses at least one well orifice, and preferably a plurality of well orifices 143.

A can be seen in FIG. 9, the dimensions and shape of well orifices 843 and well orifices 143 may be chosen so that, when second removable member 840 is sealed to surface 141, well walls 144 and well walls 844 form a substantially smooth and continuous surface, such that substantially no part of surface 141 is exposed.

Figure 10:
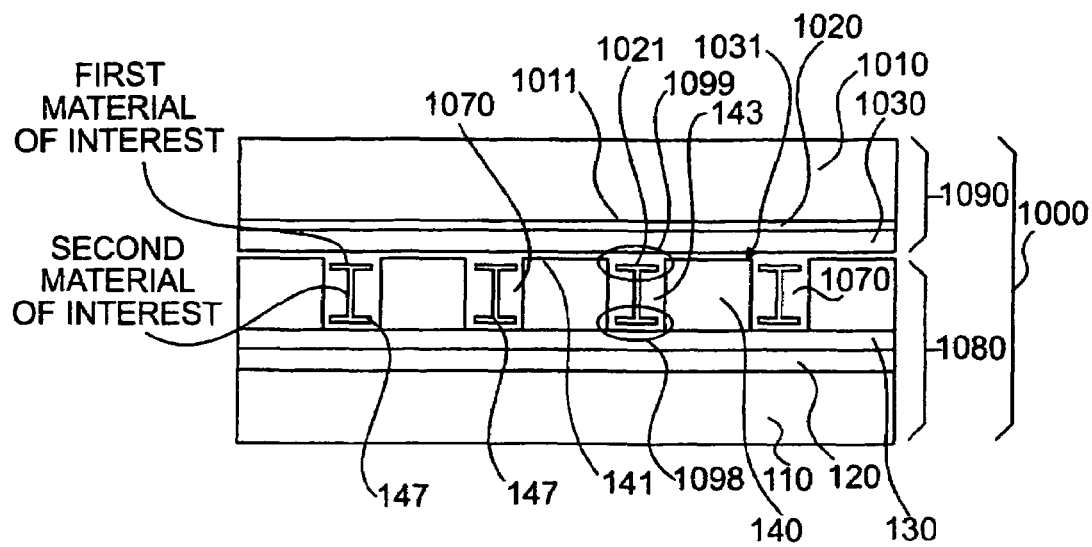
FIG. 10 depicts an embodiment of the present invention wherein a removable member forms a channel between two base plates. Different materials of interest may be immobilized on the surface of each base plate and allowed to interact through fluid or other materials in the channel.

Turning now to FIG. 10, device 1000 is another embodiment of the present invention. Device 1000 comprises lower assembly 1080 and upper assembly 1090. Lower assembly 1080 of device 1000 is very similar to device 100 of FIG. 1 and comprises base plate 110, layer 120, layer 130, and removable member 140, which defines a plurality of well orifices 143. Assembly 1080 may be similar to device 100, device 500, or to a device comprising or making use of more than two removable members defining well orifices. As can be seen from FIG. 10, removable member 140 defines well orifices 143.

Upper assembly 1090 of device 1000 comprises base plate 1010, which is similar in characteristics, materials, and manufacture as base plate 110, with surface 1011; layer 1020, which is similar in characteristics, materials, and manufacture as layer 120, with surface 1021; and layer 1030, which is similar in characteristics, materials, and manufacture as layer 130, with surface 1031. Removable member 140 is capable of self-sealing to surface 1031 in the same maimer as removable member 140 is capable of binding to surface 131.

As can be seen from FIG. 10, assemblies 1080 and 1090 preferably have the same footprint as one another. When surface 141 of removable member 140 is sealed to surface 1031, well orifices 143 of removable member 140, surface 141 of removable member 140, and surface_1031 form a plurality of fluid-tight passageways 1070. Fluid-tight passageways 1070 and are fluidly connected with each other and fluidly sealed from the outside surroundings.

A device such as 1000 may be used, for example, to culture populations of cells such that molecules released by cells 1098, or other materials, immobilized on one assembly can interact with cells, or other materials, 1099 immobilized on the other assembly, but the cells themselves cannot physically interact. As a plurality of fluid-tight passageways 1070 are formed, a plurality of cellular interactions can be studied simultaneously. Interactions between cells and immobilized materials of interest, as discussed herein, may similarly be studied. The sealable, removable, and removable properties of removable member 140 facilitate the collection, addition, and changing of media and the like. Additionally, materials immobilized on one assembly and exposed to materials immobilized on a second assembly can easily and simultaneously be removed from exposure to materials immobilized on the second assembly and exposed to materials immobilized on a third assembly, thus creating an interchangeable system.

Figure 11:
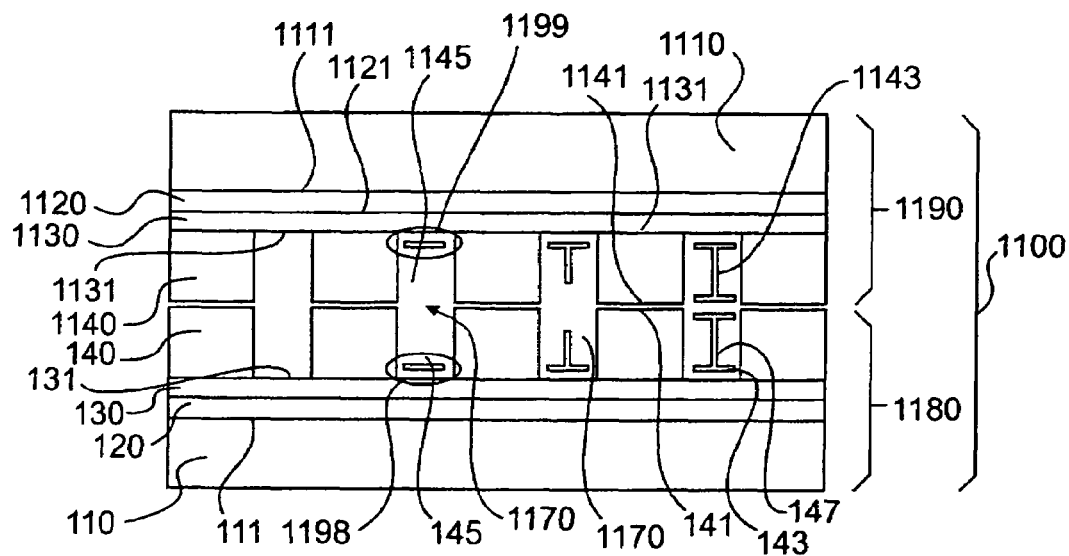
FIG. 11 depicts an embodiment of the present invention wherein two removable members are sealed together to form a channel.

Turning now to FIG. 11, device 1100 is another embodiment of the present invention. Device 1100 comprises lower assembly 1180 and upper assembly 1190. Lower assembly 1180 of device 1100 is very similar to device 100 of FIG. 1 and comprises base plate 110, layer 120, layer 130, and removable member 140, which defines a plurality of well orifices 143.

Upper assembly 1190 of device 1100 comprises base plate 1110, which is similar in characteristics, materials, and manufacture as base plate 110, with surface 1111; layer 1120, which is similar in characteristics, materials, and manufacture as layer 120, with surface 1121; layer 1130, which is similar in characteristics, materials, and manufacture as layer 130, with surface 1131; and removable member 1140, which is similar in characteristics, materials, and manufacture as removable member 140.

Removable member 1140 is formed of a material capable of forming a fluid-tight seal with surface 111, 131, 1111, 1131, or 141 when placed in contact with any f these surfaces. The fluid-tight seal is made without the use of adhesives, ultrasound, heat or other means of sealing external to removable members 1140 or surfaces 111, 131, 1111, 1131, or 141. Therefore, removable member 1140 is capable of being sealed to surface 111, 131, 1111, 1131, or 141, then removed therefrom without damaging or leaving residue on surface 111, 131, 1111, 1131, or 141. Surface 111, 131, 1111, 1131, or 141 is flat after removal of removable member 1140. Likewise, removable member 1140 is flat after being removed from surface 111, 131, 1111, 1131, or 141. Removable member 1140 is also capable of being resealed to surface 111, 131, 1111, 1131, or 141, and a fluid-tight seal between removable member 1140 and surface 111, 131, 1111, 1131, or 141 is made without the use of adhesives, ultrasound, heat or other means of sealing external to removable member 1140 and surface 111, 131, 1111, 1131, or 141 when removable member 1140 is placed into contact with surface 111, 131, 1111, 1131, or 141.

Each of assembly 1180 and assembly 1190 may be similar to device 100, device 500, or to a device comprising or making use of more than two removable members defining well orifices. As can be seen from FIG. 11, removable member 140 defines well orifices 143 with well bottoms 147, and removable member 1140 defines well orifices 1143.

As can be seen from FIG. 11, assemblies 1180 and 1190 preferably have the same footprint as one another. When surface 1141 of removable member 1140 is sealed to surface 141 of removable member 140, wells 145 (formed by removable member 140 and surface 131) and wells 1145 (formed by removable member 1140 and surface 1131) form a plurality of fluid-tight passageways 1170 and are fluidly connected with each other and fluidly sealed from the outside surroundings.

A device such as 1100 may be used, for example, to culture populations of cells such that molecules released by cells, or other materials, (1198) immobilized on one assembly can interact with cells, or other materials, (1199) immobilized on the other assembly, but the cells themselves cannot physically interact. As a plurality of fluid-tight passageways 1170 are formed, a plurality of cellular interactions can be studied simultaneously. Interactions between cells and immobilized materials of interest, as discussed herein, may similarly be studied. The sealable, removable, and removable properties of removable members 140 and 1140 facilitate the collection, addition, and changing of media and the like. Additionally, materials immobilized on one assembly and exposed to materials immobilized on a second assembly can easily and simultaneously be removed from exposure to materials immobilized on the second assembly and exposed to materials immobilized on a third assembly.

Devices of the present invention may be rotated by any suitable means, such as manually or by using a motor. Such rotation may be for any number of repetitions desired. For example, device 1100, as depicted in FIG. 11, may be continuously rotated so that liquid in well orifice 143 flows into well orifice 1143. Such rotation would be useful in operations such as culturing a first type of cells on well bottom 147 and a second type of cells on well bottom 1147 such that the first and second types of cells remain physically separated, but fluid in which they are grown is exposed to both types of cell.

Figure 12:
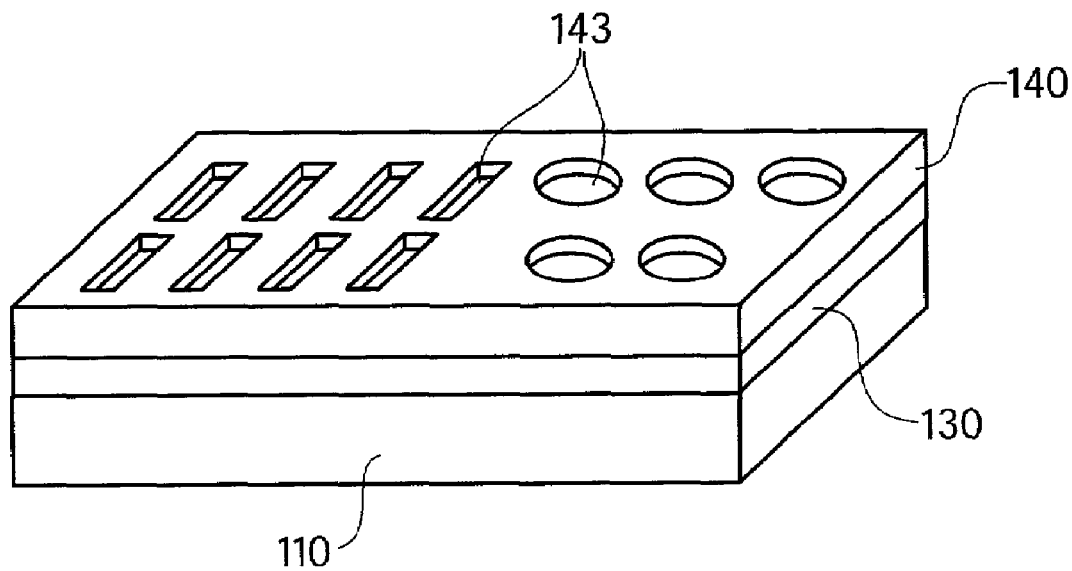
FIG. 12 depicts a removable member defining non-uniform well orifices, according to an embodiment of the invention.
Figure 13:
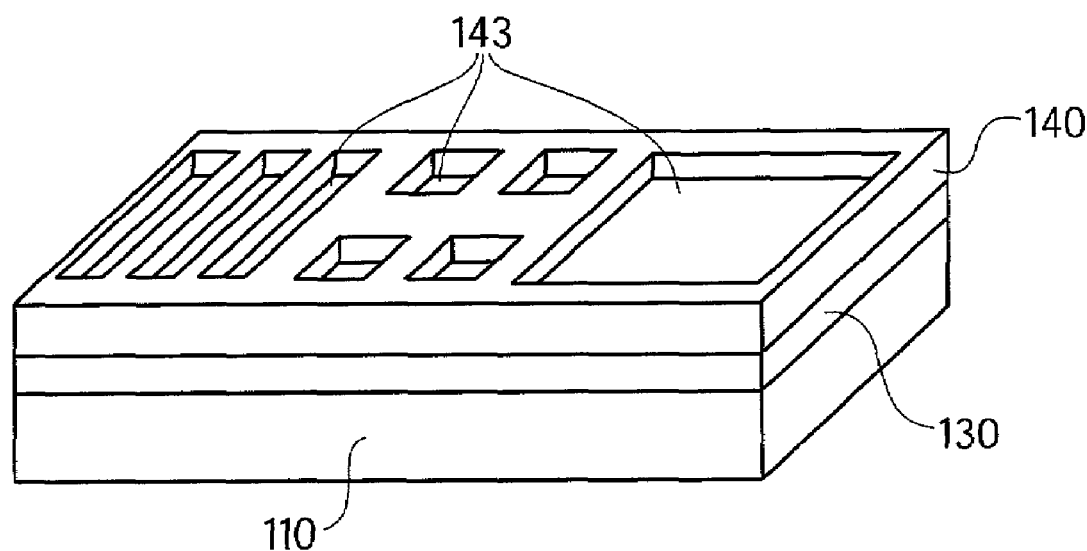
FIG. 13 depicts a removable member defining non-uniform well orifices, according to an embodiment of the invention.

It will be appreciated that any of the removable members described herein may define well orifices in non-uniform spatial arrangements. For example, a removable member may define well orifices corresponding in spatial arrangement and dimensions to the wells of a 96-well microtiter plate in one area, while defining well orifices corresponding in spatial arrangement and dimensions to the wells of a 384-well microtiter plate in another area. FIG. 12 and FIG. 13 depict exemplary removable members 140 defining well orifices in non-uniform spatial arrangements.

It will also be appreciated that well orifices 143, wells 145, and well bottoms 147 may be of any desired shape. The "shape" of well orifices 143, and of wells 145 and well bottoms 147, refers to the geometric shape of the well orifice in the plane defined by or parallel to surfaces 111, 131, 141 and/or 142. Preferred shapes include circles, squares, and rectangles. Embodiments of the invention having well orifices 143 in various shapes are depicted in FIG. 12 and FIG. 13.

Figure 14:
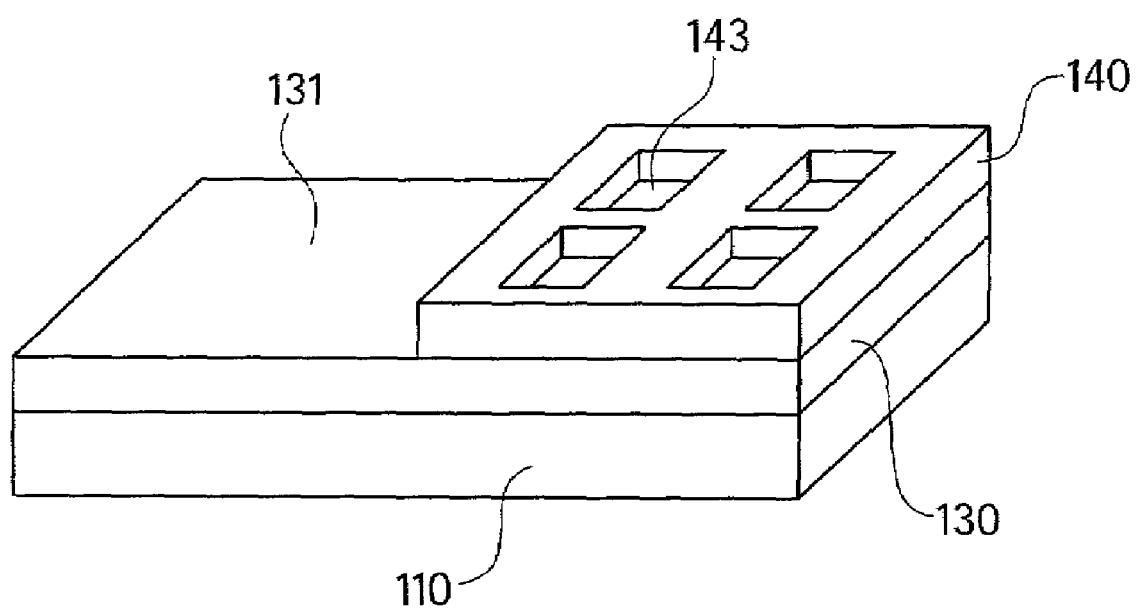
FIG. 14 depicts a device according to an embodiment of the present invention which comprises a removable member that does not have the same footprint as the base plate, but rather has a smaller footprint than the base plate.

Similarly, a device according to the present invention may comprise a removable member which does not have the same footprint as the base plate, but rather has a smaller footprint than the base plate. An example of such a device is depicted in FIG. 14.

FIG. 19 depicts a process according to the present invention in which removable member 140 is sealed to surface 131, biomolecules are pipetted into wells 145 (which are formed when removable member 140 is sealed to surface 131) using an automated or manual pipetting device and immobilized on surface 131, a biological assay is performed on the immobilized biological material, removable member 140 is removed from surface 131, an assay and the results are read using a flat-bed fluorescence scanner. FIG. 19(*a*) depicts an example of the use of a pipetting device to add material of interest to wells 145. The pipetting device may conveniently be a standard pipetting device used with microtiter plates, such as 384-well microtiter plates, being used to deliver fluids into wells defined by well orifices in a removable member and a base plate of a device according to the present invention. Process steps may be performed within individual wells while removable member 140 is sealed to surface 131, and/or may be performed in bulk while removable member 140 is not so sealed. FIG. 19(*b*) depicts the removal, or peeling, of the removable member from surface 131, thus providing a flat surface with material of interest 1990 immobilized thereon. FIG. 19(*c*) depicts the detection of changes in material of interest 1990 via scanning using a flat-bed scanner. The device is placed on the scanner with surface 131 contacting the scanner the lower surface 112 of base plate 110 facing upward.

As can be seen in FIG. 19, devices of the present invention enable the combination of the convenience of microwells for separation of materials during process step and detection using instruments that, like flat bed scanners, require or prefer a flat surface. Other examples of such instruments include surface plasmon resonance (SPR) instruments and mass spectrometers such as matrix assisted laser desorption ionization (MALDI) spectrometers.

Figure 24:
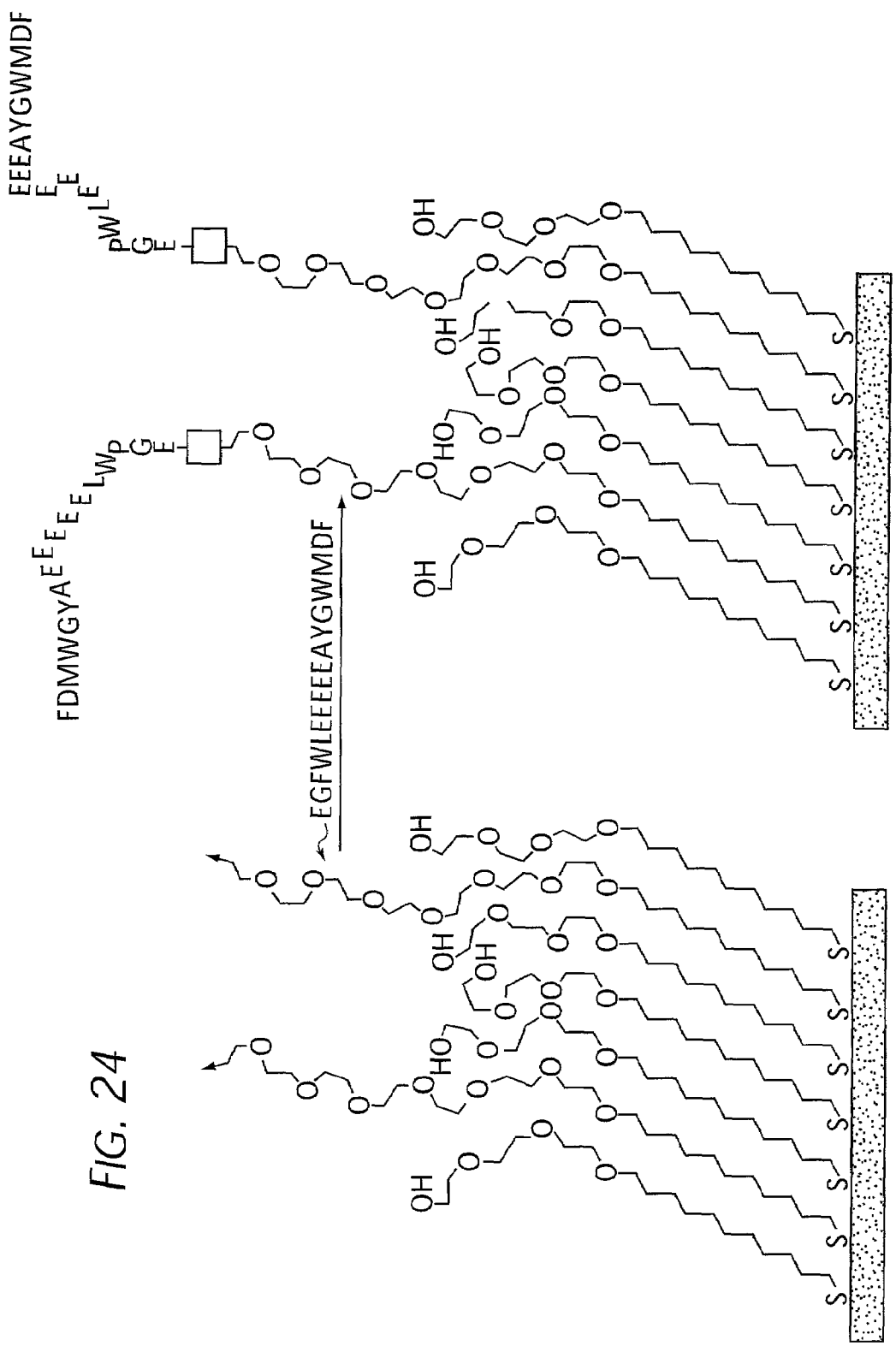
FIG. 24 is a representation of an exemplary technique, which may be used to immobilize biomolecules on surface 131.

FIG. 24 is a schematic representation of an example of surface chemistry which may be used to immobilize peptides, amino acids, and proteins on a base plate according to the present invention. The self-assembled monolayer (SAM) depicted comprises alkanethiols. Molecules ending in a hydroxy (—OH) group do not bind biomolecules. Molecules having chemoselective termini are dispersed among the inert molecules. In the monolayer depicted, the chemoselective molecules act as tethers to bind a peptide. The peptides to be bound are engineered so that they bind at a particular location. In FIG. 24, the peptide EGPWLEEEEEAYGW-MDF binds to the chemoselective SAMs at the terminal E. Since the chemoselective molecules are surrounded by inert molecules, peptides bound to the chemoselective molecules do not bind non-selectively to other molecules.

FIG. 25 depicts an embodiment according to the present invention. Device 2500 makes use of four removable members to pattern immobilized materials of interest to surface 131. Device 2500 of FIG. 25 is very similar to device 100 of FIG. 1 and comprises a base plate 110, layer 120, layer 130, and removable members 2540, 2550, 2560, and 2570, which defines a plurality of well orifices 2543, 2553, 2563, and 2573. In FIG. 25(a), removable member 2540 is sealed to surface 131, and material of interest is immobilized on surface 131 in the spatial pattern defined by well orifices 2543. Specifically, material of interest A is immobilized on well bottoms 2547 via the application of the material of interest to well orifices 2543. Device 2500 with material A immobilized on well bottoms 2547 is depicted in FIG. 25(b), with removable member 2540 sealed to surface 131, and in FIG. 25(c) with removable member 2540 removed.

As depicted in FIG. 25(d), after immobilization of material of interest A and removal of removable member 2540, a second removable member 2550 is sealed to surface 131 and material of interest B is immobilized on surface 131 in the spatial pattern defined by well orifices 2553. Specifically, material of interest B is immobilized on well bottoms 2557 via the application of the material of interest to well orifices 2553. Device 2500 with material of interest B immobilized on well bottoms 2557 is depicted in FIG. 25(d), with removable member 2550 sealed to surface 131, and in FIG. 25(e) with removable member 2550 removed.

Figure 25F:
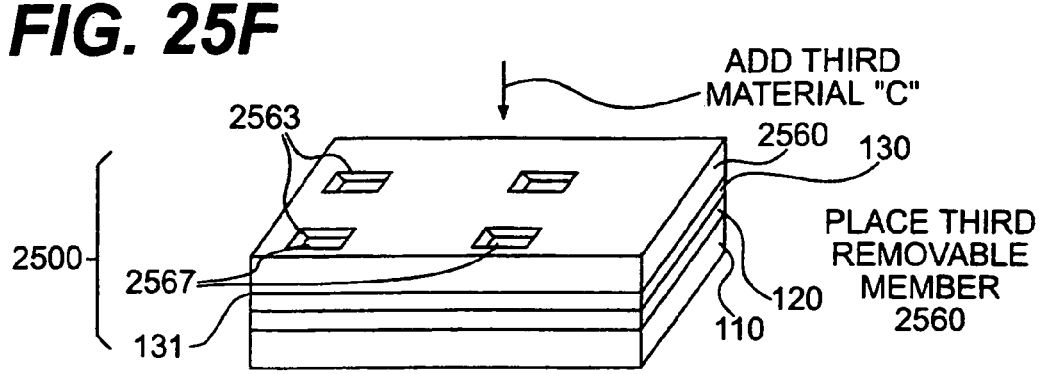
Figure 25G:
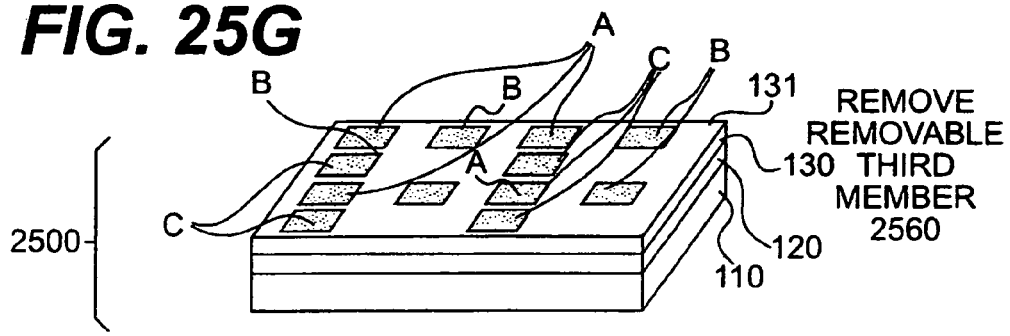

After removable member 2550 is removed after immobilization of material of interest B, as depicted in FIG. 25(f), a third removable member 2560 is sealed to surface 131 and material of interest C is immobilized on surface 131 in the spatial pattern defined by well orifices 2563. Specifically, material of interest C is immobilized on well bottoms 2567 via the application of the material of interest to well orifices 2563. Device 2500 with material of interest C immobilized on well bottoms 2567 is depicted in FIG. 25(f), with removable member 2560 sealed to surface 131, and in FIG. 25(g) with removable member 2560 removed.

Figure 25H:
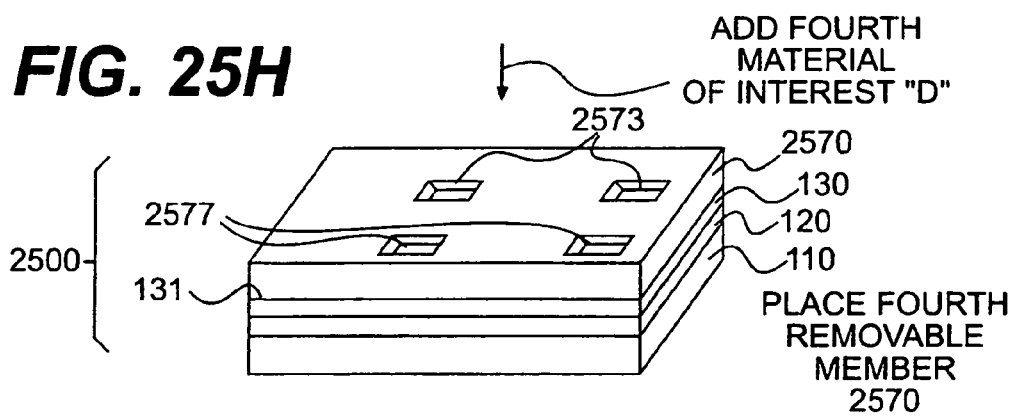
Figure 25I:
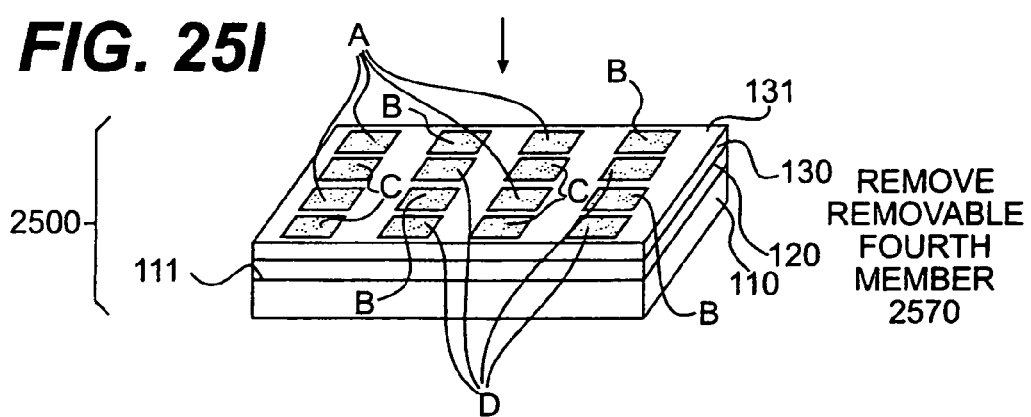

As depicted in FIG. 25(h), after immobilization of material of interest C and removal of removable member 2560, a fourth removable member 2570 is sealed to surface 131 and material of interest D is immobilized on surface 131 in the spatial pattern defined by well orifices 2573. Specifically, material of interest D is immobilized on well bottoms 2577 via the application of the material of interest to well orifices 2573. Device 2500 with material of interest D immobilized on well bottoms 2577 is depicted in FIG. 25(h), with removable member 2550 sealed to surface 131, and in FIG. 25(i) with removable member 2550 removed.

Device 2500 may be used to perform assays and processes, such as those that are described in more detail herein.

Figure 26:
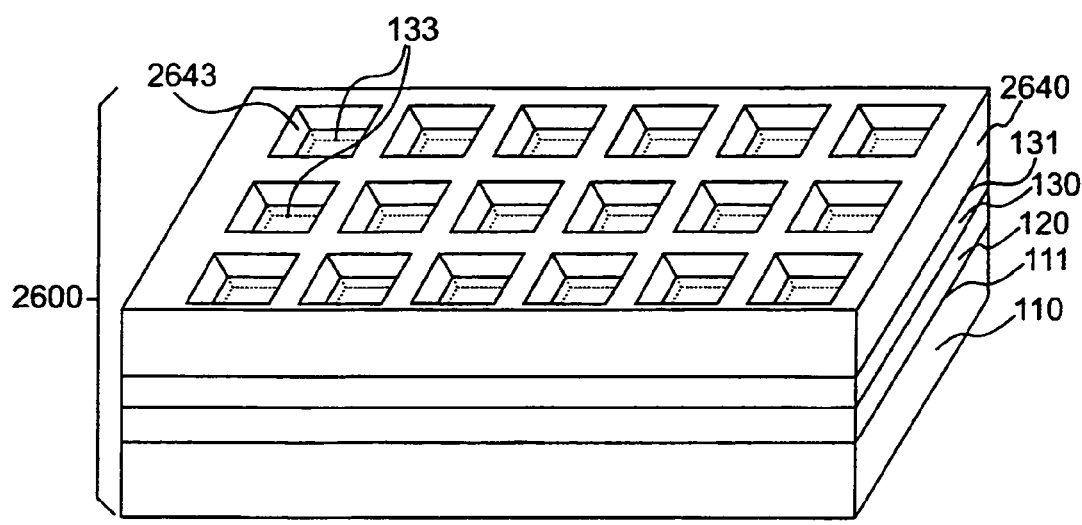
FIG. 26 depicts a device according to the present invention.

FIG. 26 depicts a device with a non-planar base plate according to the present invention. Device 2600 is very similar to device 100 of FIG. 1 and comprises base plate 110, layer 120, layer 130, and removable member 2640, which defines a plurality of well orifices 2643. Device 2600 may be used, for example, to pattern areas defined on non-planar base plates.

As can be seen in FIG. 26, the spatial arrangement and shape of orifices 2643 correspond to the arrangement and location of well bottoms 133 defined by surface 131 or surface 111 in the absence of layer 120 and layer 130. Dimensions and spatial arrangement of well bottoms 133, formed in the plane defined by surface 131 and 111, are such that the device of the present invention may be used for detection steps using instruments that include, but are not limited to, microscopes (including, but not limited to, bright field, phase contrast, and epi-illuminated fluorescence microscopes), MALDI (Matrix Assisted LASER Desorbtion Ionization) mass spectrometers (which are available from commercial sources, such as Applied Biosystems), ELISA-coupled document scanners, surface plasmon resonance (SPR) sensors (which are available from commercial sources, such as Biacore, GWC, Texas Instruments, and Leica), flat-bed laser confocal scanners (which are available from commercial sources, such as Fuji, Biorad and Molecular Dynamics (examples of instruments available include the Typhoon)), flat bed scanners (including, but not limited to, confocal flat bed laser scanners), colorimetric scanners, fluorometric scanners, phosphorous scanners (which, among other uses, are effective for flat phosphorous-based imaging of radioisotopes, as commonly used to read DNA arrays, which are available from commercial sources, such as Affymetrix and Agilent), and scanning probe microscopies (such as scanning electron microscopes (SEM) and atomic force microscopes (AFM)). As yet another example, where radioactive signaling molecules are used, a phosphorescent substrate may be placed on the surface (such as surface 111 or 131 of FIG. 26) of a device according to the present invention and allowed to develop.

Figure 27:
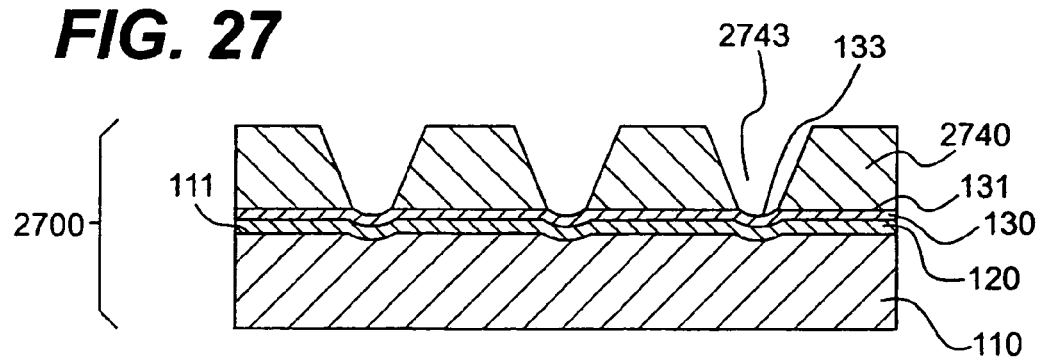
FIG. 27 shows a cross section of a device according to the present invention.

Devices according to the present invention may also be used to create patterned regions on planar and non-planar surfaces. FIG. 27 depicts a cross section of a device that has a non-planar surface 131 and surface 111. Device 2700 is very similar to device 100 of FIG. 1 and comprises base plate 110, layer 120, layer 130, and removable member 2740, which define a plurality of well orifices 2743. Device 2700 may be used, for example, to perform assays and processes, such as those that are described in more detail herein.

As can be seen in FIG. 27, the spatial arrangement and shape of orifices 2743 correspond to the arrangement and location of well bottoms 133 defined by surface 131 and 111, such that when member 2740 is sealed to surface 131, each well orifice 2743 encompasses one well bottom 133.

Figure 28A:
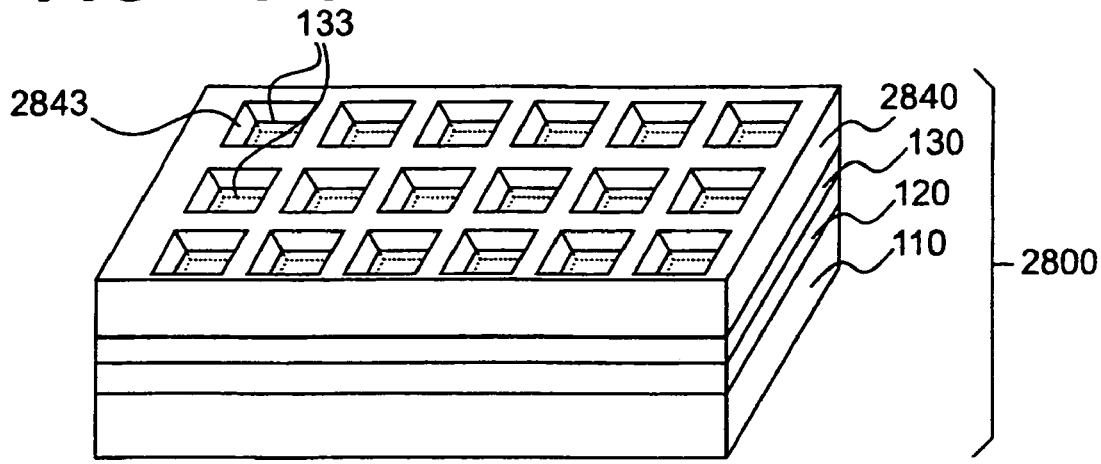
FIGS. 28A, 28B and 28C depicts a device according to the present invention.
Figure 28B:
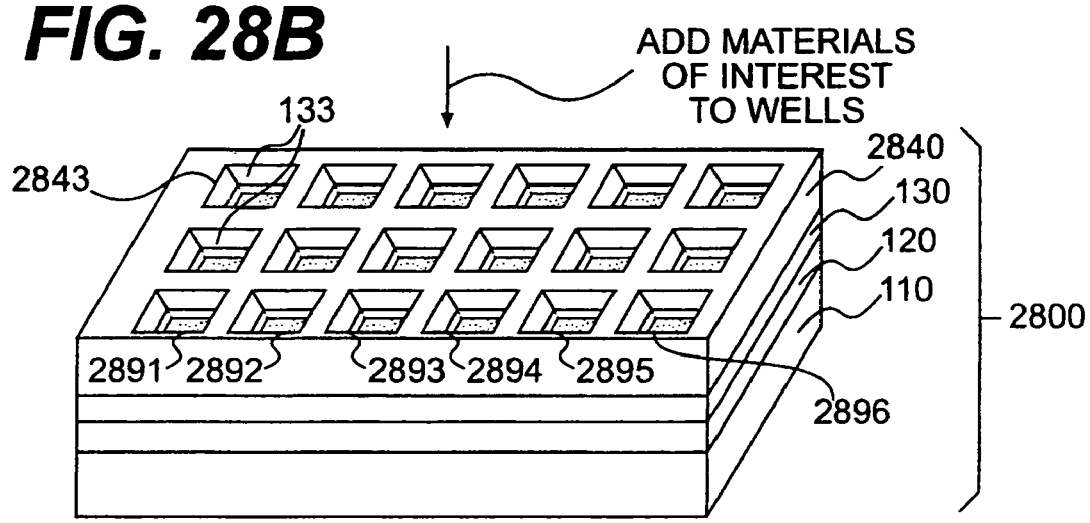
Figure 28C:
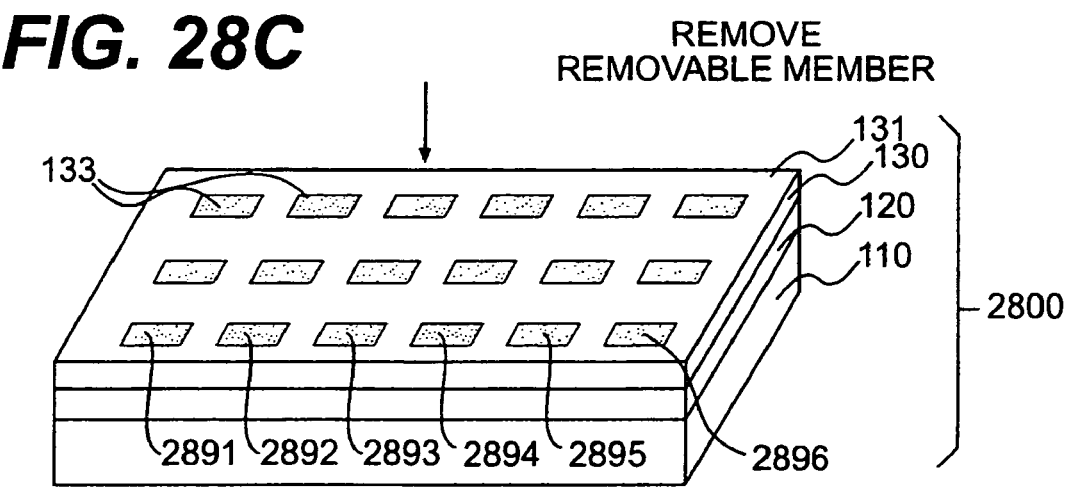

Turning now to FIG. 28, device 2800 is another embodiment of the present invention. Device 2800 is very similar to device 100 of FIG. 1 and comprises base plate 110, layer 120, layer 130, and removable member 2840, which defines a plurality of well orifices 2843. In FIG. 28, removable member 2840 is sealed to portions of surface 131 which are flat and materials of interest are immobilized on surface 131 which defines the spatial pattern of well bottoms 133 as well as the spatial patter of well orifices 2843. Specifically, materials of interest 2891, 2892, 2893, 2894, 2895 and 2896 are immobilized on well bottoms 133 via the application of the materials of interest to well orifices 2843. Device 2800 with materials 2891-2896 immobilized on well bottoms 133 is depicted in FIG. 28(b), with removable member 2840 sealed to surface 131, and in FIG. 28(c), with removable member 2840 removed.

Methods for deposition of materials into orifices, or wells, are well-known in the art, and include both manual and automated techniques, such as pipetting, micropipetting, and the use of automated arrayers. Immobilized materials 2891-2896 may be the same or may differ from one another—thus, the material immobilized on each well bottom 133 may be the same or may vary between well bottoms 133. Although this is not illustrated in FIG. 28, more than one type of material of interest (such as a combination of two or more of materials 2891-2896) may be immobilized on a single well bottom 133. Device 2800 may be used to perform assays and processes, such as those that are described in more detail herein.

As with the device shown in FIG. 4, removable member 2840 may be removed after immobilization of materials of interest (as is depicted in FIG. 28(c)), or may be left in place (as is depicted in FIG. 28(b)) for the performance of process and/or detection steps. In embodiments wherein removable member 2840 is left in place, process and/or detection steps may be carried out within wells and may, therefore, vary between wells, allowing many different process and/or detection steps to be carried out on immobilized materials. Removable member 2840 may be removed whenever it is desired simultaneously to perform a process step on all materials immobilized on surface 111 or 131. After being removed, removable member 2840 may be resealed on surface 111 or 131 whenever it is desired separately to perform a process steps on materials immobilized in each of wells 133.

Devices according to the present invention may also have non-planar base plates. FIG. 29 depicts a cross section of a device that has a non-planar base plate 110 and surface 111. Device 2900 is very similar to device 100 of FIG. 1 and comprises base plate 110, layer 120, layer 130, and removable layer 2940 with well orifices 2943. Device 2900 may be used, for example, to perform processes and immobilize various biomolecules, such as those that are described in more detail herein.

Figure 29A:
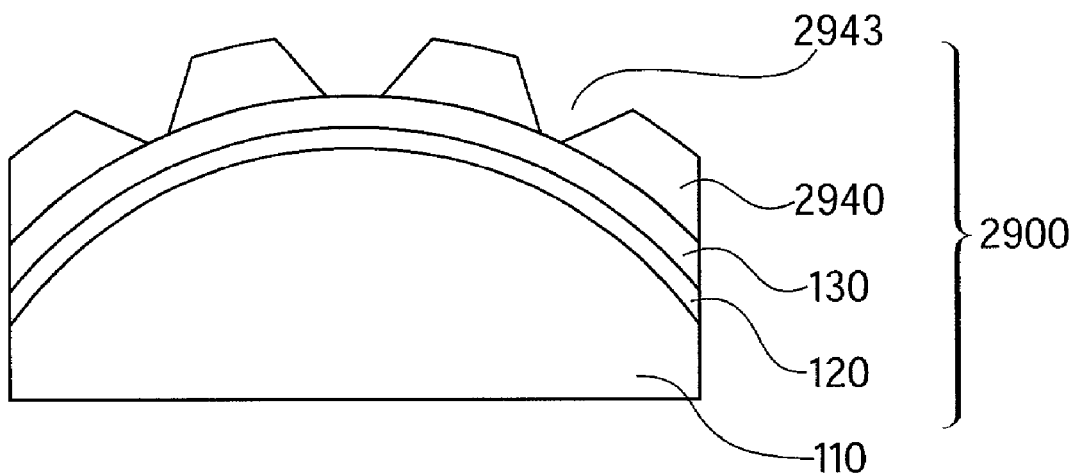
FIG. 29A, 29B 29C, 29D, 29E shows cross sections of devices according to the present invention.
Figure 29B:
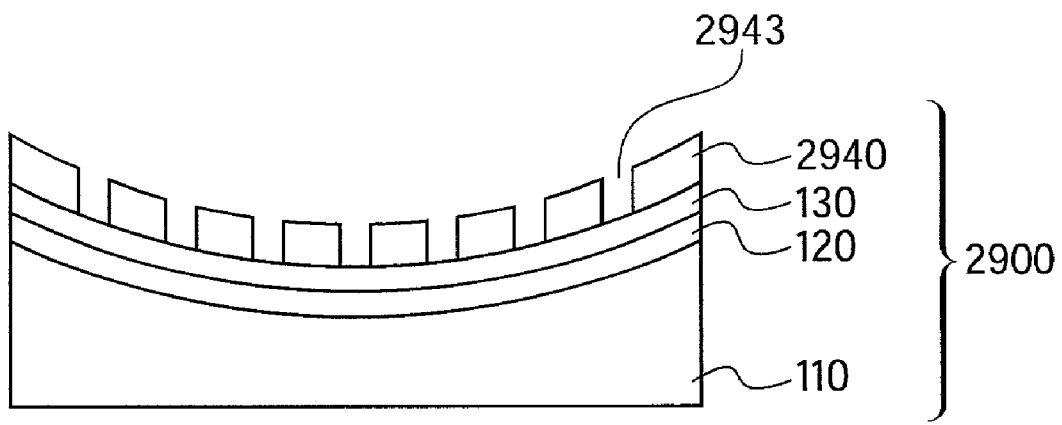
Figure 29C:
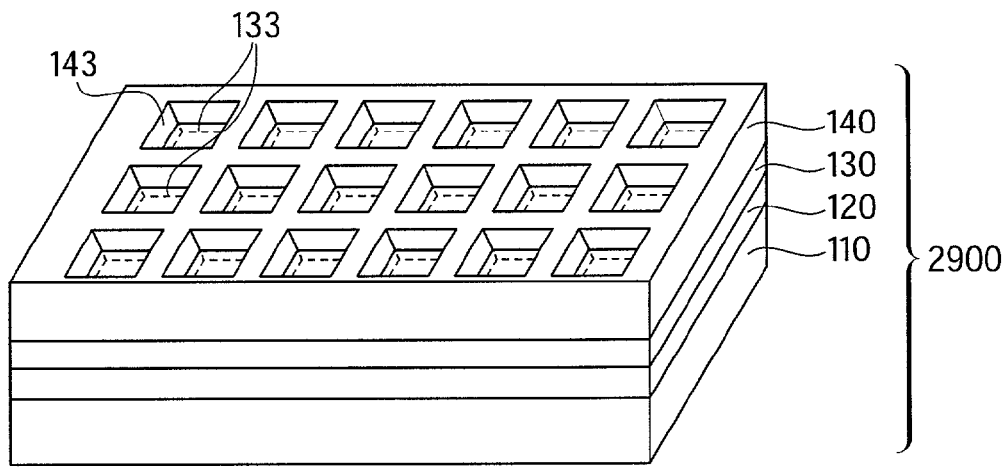
Figure 29D:
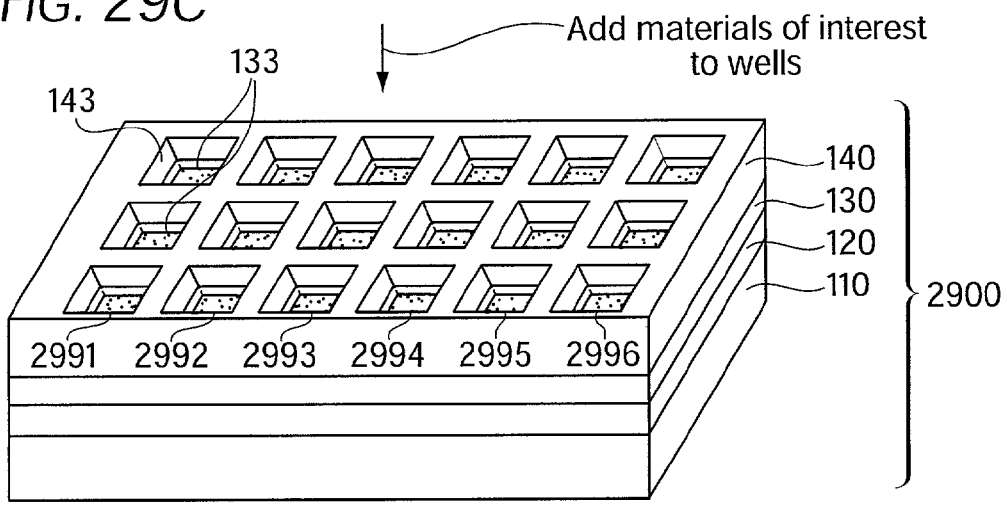
Figure 29E:
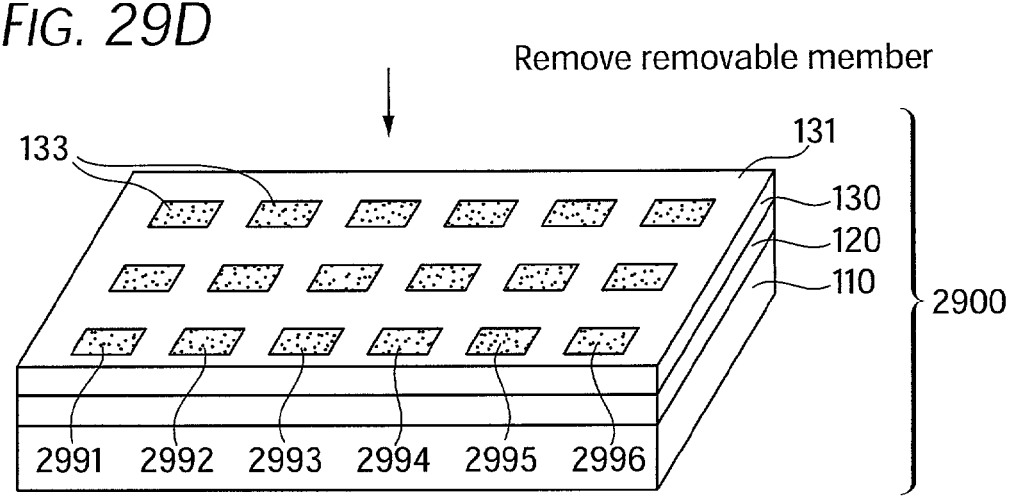

Non-planar base plate may have any desired geometry. For example, as depicted in FIG. 29(a), non-planar base plate 110 may be concave, or as depicted in FIG. 29(b), non-planar base plate 110 may be convex.

As is described and depicted herein, immobilization and/or patterning of materials of interest, particularly biomolecules, on surfaces is particularly important in devices and methods according to the present invention.

The use of self-assembled monolayers (SAMs) provides a preferred method for immobilization and/or patterning of material, particularly biomolecules. SAMs are the most widely studied and best developed examples of nonbiological, self-assembling systems. They form spontaneously by chemisorption and self-organization of functionalized, long-chain organic molecules onto the surfaces of appropriate substrates. SAMS are usually prepared by immersing a substrate in the solution containing a ligand that is reactive toward the surface, or by exposing the substrate to the vapor of the reactive species. There are many systems known in the art to produce SAMs.

The best characterized systems of SAMs are alkanethiolates $CH_3(CH_2)_nS-$ on gold. Alkanethiols chemisorb spontaneously on a gold surface from solution and form adsorbed alkanethiolates. Sulfur atoms bonded to the gold surface bring the alkyl chains in close contact—these contacts freeze out configurational entropy and lead to an ordered structure. For carbon chains of up to approximately 20 atoms, the degree of interaction in a SAM increases with the density of molecules on the surface and the length of the alkyl backbones. Only alkanethiolates with n>11 form the closely packed and essentially two-dimensional organic quasi-crystals supported on gold that characterize the SAMs most useful in soft lithography. The formation of ordered SAMs on gold from alkanethiols is a relatively fast process. Highly ordered SAMs of hexanedecanethiolate on gold can be prepared by immersing a gold substrate in a solution of hexadecanethiold in ethanol (ca. 2 mM) for several minutes, and formation of SAMs during microcontact printing may occur in seconds.

In certain embodiments, it may be desirable to pattern the SAM to have an arrayed surface. Patterning SAMs in the plane defined by a surface has been achieved by a wide variety of techniques, including micro-contact printing, photo-oxidation, photo-cross-linking, photo-activation, photolithography/plating, electron beam writing, focused ion beam writing, neutral metastable atom writing, SPM lithography, micro-machining, micro-pen writing. A preferred method is micro-contract printing. Micro-contact printing is described in U.S. Pat. No. 5,776,748 and is herein incorporated in its entirety.

In another embodiment, a coating comprising SAMs is "patterned" by micro-contract printing. The SAM patterns are applied to the support using a stamp in a "printing" process in which the "ink" consists of a solution including a compound capable of chemisorbing to form a SAM. The ink is applied to the surface of a plate using the stamp and deposits a SAM on the support in a pattern determined by the pattern on the stamp. The support may be stamped repeatedly with the same or different stamps in various orientations and with the same or different SAM-forming solutions. In addition, after stamping, the portions of the support which remain bare or uncovered by a SAM may be derivatized. Such derivatization may conveniently include exposure to another solution including a SAM-forming compound. The SAM-forming or derivatizing solutions are chosen such that the regions of the finished support defined by the patterns differ from each other in their ability to bind biological materials. Thus, for example, a grid pattern may be created in which the square regions of the grid bind to specific biomolecules, or biomolecules generally, but the linear regions of the grid substantially bioinert, and few or no biomolecules bind in those areas.

A simple description of the general process of microcontact printing is as follows. A polymeric material is cast onto a mold with raised features defining a pattern to form a stamp. The stamp with the stamping surface after curing is separated from the mold. The stamp is inked with a desired "ink," which includes a SAM-forming compound. The "inked" stamp is brought into contact with a plate comprising a substrate and optionally, coated with a thin coating of surface material. The SAM forming compound of the ink chemisorbs to the material surface to form a SAM with surface regions in a pattern corresponding to the stamping surface of the stamp. The plate can then be exposed to a second or filling solution including a SAM-forming compound. The second solution has filled the bare regions of the surface material with a second or filling SAM. The plate having the patterned SAM can then have a material selectively bound to the surface regions of the first SAM but not bound the surface regions of the second SAM and vice-versa.

The stamp is inked with a solution capable of forming a SAM by chemisorption to a surface. The inking may, for example, be accomplished by (1) contacting the stamp with a piece of lint-free paper moistened with the ink, (2) pouring the ink directly onto the stamp or (3) applying the ink to the stamp with a cotton swab. The ink is then allowed to dry on the stamp or is blown dry so that no ink in liquid form, which may cause blurring, remains on the stamp. The SAM-forming compound may be very rapidly transferred to the stamping surface. For example, contacting the stamping surface with the compound for a period of time of approximately 2 seconds is generally adequate to effect sufficient transfer, or contact may be maintained for substantially longer periods of time. The SAM-forming compound may be dissolved in a solvent for such transfer, and this is often advantageous in the present invention. Any organic solvent within which the compound dissolves may be employed but, preferably, one is chosen which aids in the absorption of the SAM-forming compound by the stamping surface. Thus, for example, ethanol, THF, acetone, diethyl ether, toluene, isooctane and the like may be employed. For use with a PDMS stamp, ethanol is particularly preferred, and toluene and isooctane are not preferred as they are not well absorbed. The concentration of the SAM-forming compound in the ink solution may be as low as 1 µM. A concentration of 1-10 mM is preferred and concentrations above 100 mM are not recommended.

The support is then contacted with the stamp such that the inked stamping surface bearing the pattern contacts the surface material of the plate. This may be accomplished by hand with the application of slight finger pressure or by a mechanical device. The stamp and plate need not be held in contact for an extended period; contact times between 1 second and 1 hour result in apparently identical patterns for hexadecanethiol (1-10 mM in ethanol) ink applied to a plate with a gold surface. During contact, the SAM-forming compound of the ink reacts with the surface of the plate such that, when the stamp is gently removed, a SAM is chemisorbed to the plate in a pattern corresponding to the stamp.

A variety of compounds may be used in solution as the ink and a variety of materials may provide the surface material onto which the ink is stamped and the SAM is formed. In general, the choice of ink will depend on the surface material to be stamped. In general, the surface material and SAM-forming compound are selected such that the SAM-forming compound terminates at a first end in a functional group that binds or chemisorbs to the surface of the surface material. As used herein, the terminology "end" of a compound is meant to include both the physical terminus of a molecule as well as any portion of a molecule available for forming a bond with the surface in a way that the compound can form a SAM. The compound may comprise a molecule having first and second terminal ends, separated by a spacer portion, the first terminal end comprising a first functional group selected to bond to the surface material of the plate, and the second terminal end optionally including a second functional group selected to provide a SAM on the material surface having a desirable exposed functionality. The spacer portion of the molecule may be selected to provide a particular thickness of the resultant SAM, as well as to facilitate SAM formation. Although SAMs of the present invention may vary in thickness, as described below, SAMs having a thickness of less than about 50 Angstroms are generally preferred, more preferably those having a thickness of less than about 30 Angstroms and more preferably those having a thickness of less than about 15 Angstroms. These dimensions are generally dictated by the selection of the compound and in particular the spacer portion thereof.

A wide variety of surface materials and SAM-forming compounds are suitable for use in the present invention. A non-limiting exemplary list of combinations of surface materials and functional groups which will bind to those surface materials follows. Although the following list categorizes certain preferred materials with certain preferred functional groups which firmly bind thereto, many of the following functional groups would be suitable for use with exemplary materials with which they are not categorized, and any and all such combinations are within the scope of the present invention. Preferred materials for use as the surface material include metals such as gold, silver, copper, cadmium, zinc, palladium, platinum, mercury, lead, iron, chromium, manganese, tungsten, and any alloys of the above when employed with sulfur-containing functional groups such as thiols, sulfides, disulfides, and the like; doped or undoped silicon employed with silanes and chlorosilanes; metal oxides such as silica, alumina, quartz, glass, and the like employed with carboxylic acids; platinum and palladium employed with nitrites and isonitriles; and copper employed with hydroxamic acids. Additional suitable functional groups include acid chlorides, anhydrides, sulfonyl groups, phosphoryl groups, hydroxyl groups and amino acid groups. Additional surface materials include germanium, gallium, arsenic, and gallium arsenide. Additionally, epoxy compounds, polysulfone compounds, plastics and other polymers may find use as the surface material in the present invention. Polymers used to form bioerodable articles, including but not limited to polyanhydrides, and polylactic and polyglycolic acids, are also suitable. Additional materials and functional groups suitable for use in the present invention can be found in U.S. Pat. No. 5,079,600, issued 7 Jan. 1992, and incorporated herein by reference.

According to a particularly preferred embodiment, a combination of gold as the surface material and a SAM-forming compound having at least one sulfur-containing functional group such as a thiol, sulfide, or disulfide is selected.

The SAM-forming compound may terminate in a second end or "head group," opposite to the end bearing the functional group selected to bind to the surface material, with any of a variety of functionalities. That is, the compound may include a functionality that, when the compound forms a SAM on the surface material, is exposed. Such a functionality may be selected to create a SAM that is hydrophobic, hydrophilic, that selectively binds various biological or other chemical species, or the like. For example, ionic, nonionic, polar, nonpolar, halogenated, alkyl, aryl or other functionalities may exist at the exposed portion of the compound. A non-limiting, exemplary list of such functional groups includes those described above with respect to the functional group for attachment to the surface material in addition to: —OH, —CONH—, —CONHCO—, —NH$_2$, —NH—, —COOH, —COOR, —CSNH—, —NO$_2^-$, —SO$_2^-$, —RCOR—, —RCSR—, —RSR, —ROR—, —PO$_4^{-3}$, —OSO$_3^{-2}$, —SO3—, —NH$_x$R$_4$ _x$^+$, —COO$^-$, —SOO$^-$, —RSOR—, —CONR$_2$, —O(CH$_2$CH$_2$)OR—, —(OCH$_2$CH$_2$)$_n$ OH (where n=1–20, preferably 1–8), —CH$_3$, —PO$_3$ H$^-$, —2-imidazole, —N(CH$_3$)$_2$, —NR$_2$, —PO$_3$H$_2$, —CN, —(CF$_2$)$_n$CF$_3$(where n=1–20, preferably 1–8), olefins, and the like. In the above list, R is hydrogen or an organic group such as a hydrocarbon or fluorinated hydrocarbon.

As additional examples, SAMS to which biomolecules are to be attached may terminate in moieties such as biotin, avidin, glutathione, and nitriloacetic acid. Biomolecules ending in moieties such as avidin, biotin, His-tag, glutathione-S-transferase (GST) tag, glutathione, and nitriloacetic acid, may then be bound specifically to their respective binding partner (e.g., biotin-avidin, glutathione-glutathione-S-transferase-tag, nitriloacetic acid-His-tag).

As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups.

In addition, the functional group may be chosen from a wide variety of compounds or fragments thereof which will render the SAM generally or specifically "biophilic" as those terms are defined below. Generally biophilic functional groups are those that would generally promote the binding, adherence, or adsorption of biological materials such as, for example, intact cells, fractionated cells, cellular organelles, proteins, polypeptides, small molecules, lipids, polysaccharides, simple carbohydrates, complex carbohydrates, and/or nucleic acids. Generally biophilic functional groups include hydrophobic groups or alkyl groups with charged moieties such as —COO$^-$, —PO$^3$H$^-$ or 2-imidazolo groups, and compounds or fragments of compounds such as extracellular matrix proteins, fibronectin, collagen, laminin, serum albumin, polygalactose, sialic acid, and various lectin binding sugars. Specifically biophilic functional groups are those that selectively or preferentially bind, adhere or adsorb a specific type or types of biological material so as, for example, to identify or isolate the specific material from a mixture of materials. Specific biophilic materials include antibodies or fragments of antibodies and their antigens, cell surface receptors and their ligands, nucleic acid sequences and many others that are known to those of ordinary skill in the art. The choice of an appropriate biophilic functional group depends on considerations of the biological material sought to be bound, the affinity of the binding required, availability, facility of ease, effect on the ability of the SAM-forming compound to effectively form a SAM, and cost. Such a choice is within the knowledge, ability and discretion of one of ordinary skill in the art.

Alternatively, the functional group may be chosen from a wide variety of compounds or fragments thereof which will render the SAM "biophobic" as that term is defined below. Biophobic SAMs are those with a generally low affinity for binding, adhering, or adsorbing biological materials such as, for example, intact cells, fractionated cells, cellular organelles, proteins, lipids, polysaccharides, simple carbohydrates, complex carbohydrates, and/or nucleic acids. Biophobic functional groups include polar but uncharged groups including unsaturated hydrocarbons. A particularly preferred biophobic functional group is polyethylene glycol (PEG).

The central portion of the molecules comprising the SAM-forming compound generally includes a spacer functionality connecting the functional group selected to bind the to surface material and the exposed functionality. Alternately, the spacer may essentially comprise the exposed functionality, if no particular functional group is selected other than the spacer. Any spacer that does not disrupt SAM packing and that allows the SAM layer to be somewhat impermeable to various reagents such as etching reagents, as described below, in addition to organic or aqueous environments, is suitable. The spacer may be polar; non-polar; halogenated or, in particular, fluorinated; positively charged; negatively charged; or uncharged. For example, a saturated or unsaturated, linear or branched alkyl, aryl, or other hydrocarbon spacer may be used.

A variety of lengths of the SAM-forming compound may be employed in the present invention. For example, if mixed SAM of two or more compounds are used in the ink, it is often advantageous that the active molecule be longer than the inert molecule (non-binding), which enables the former compound that has the conformational order to interact with biological molecules, to "stick out" into the solution.

As another example, when a two or more step process is used in which a first SAM is provided on a surface and at least a second SAM is provided on the surface, the various SAMs being continuous or noncontinuous, it may be advantageous in some circumstances to select molecular species for formation of the various SAMs that have different lengths. For example, if the SAM formed by stamping has a first molecular length and the SAM subsequently derivatized to the surface has a second molecular length greater than that of the stamped SAM, a continuous SAM having a plurality of "wells" results. These wells are the result of the stamped SAM being surrounded by the second SAM having a longer chain length. Such wells may be advantageously fabricated according to certain embodiments, for example, when it is desirable to add greater lateral stability to particular biological materials, such as cells, which have been captured in the wells. Such wells may also form the basis for reaction vessels.

Additionally, SAMs formed on the surface material may be modified after such formation for a variety of purposes. For example, a SAM-forming compound may be deposited on the surface material in a SAM, the compound having an exposed functionality including a protecting group which may be removed to effect further modification of the SAM. For example, a photoremovable protecting group may be used, the group being advantageously selected such that it may be removed without disturbance of the SAM of which it is a part. For example, a protective group may be selected from a wide variety of positive light-reactive groups preferably including nitroaromatic compounds such as o-nitrobenzyl derivatives or benzylsulfonyl. Photo-removable protective groups are described in, for example, U.S. Pat. No. 5,143,854, and incorporated herein by reference, as well as an article by Patchornik, JACS, 92, 6333 (1970) and Amit et al., JOC, 39, 192, (1974), both of which are incorporated herein by reference. Alternately, a reactive group may be provided on an exposed portion of a SAM that may be activated or deactivated by electron beam lithography, x-ray lithography, or any other radiation. Such protections and deprotections may aid in chemical or physical modification of an existing surface-bound SAM, for example in lengthening existing molecular species forming the SAM. Such modification is described in U.S. Pat. No. 5,143,857, referenced above.

Another preferred method of patterning the SAM to have an array matching the cell patterning layer, for example, is through soft lithography methods known in the art. Soft lithography has been exploited by George M. Whitesides and is described in U.S. Pat. No. 5,976,826 and PCT WO 01/70389, herein incorporated by reference in their entirety. For example, the cell patterning layer having micro-orifices is placed over the SAM. The cell patterning membrane forms a conformal seal on the SAM. A modifying solution is then placed on the cell patterning membrane and allowed to contact the SAM surface exposed by the micro orifices. A "modifying" solution is one that modifies the head group of the SAM to achieve a desired characteristic or that adds or removes a desired biomolecule to the head group. For example, a tether may be added to the exposed SAMs head groups, which in turn captures a protein, which in turns provides an affinity for the cell to be patterned subsequently through a well-defining layer.

Preferred surface portions of the patterned SAM are cytophilic, that is, adapted to promote cell attachment. Molecular entities creating cytophilic surfaces are well known to these of ordinary skill in the art and include antigens, antibodies, cell adhesion molecules, extracellular matrix molecules such as laminin, fibronectin, synthetic peptides, carbohydrates and the like.

In methods and devices according to the present invention, a flat surface (such as surface 131, referring to FIG. 10 as an example, and/or surface 1031, referring to FIG. 1 as an example) is preferably coated with a SAM, and materials of interest, such as biomolecules, are immobilized on the SAM. It will generally be preferable to apply a mixed SAM comprising from about 0.1% to about 10%, more preferably from about 0.5% to about 5%, most preferably from about 1% to about 2% SAM-forming molecules that terminate in chemical groups that are capable of binding to a specific chemical group. The remainder of the mixed SAM will preferably be a SAM-forming molecule that is terminated in a chemical group that is substantially inert towards biological molecules. An example of such a mixture is a mixed SAM containing 2% maleimide-terminal groups, which couple specifically to thiol groups, in a background of tri(ethylene glycol) terminal groups, which are substantially inert. In this way, molecules containing thiol can be immobilized on the SAM-coated surface at via a specific site on the molecule itself and at a known density (corresponding to the density of maleimide-terminated SAM-forming molecules). The inert background reduces or eliminates non-specific binding.

A preferred method of immobilizing biolomolecules involves the formation of SAMs of thiolate functionalized with Michael Acceptors. A more detailed description of such embodiment is included below following the description of the peelable and releasable devices.

Devices and methods according to the present invention find particular application in the biological and pharmaceutical sciences, such as in the fields of biochemistry, molecular biology, cell biology, clinical diagnostics, environmental screening, immunology, genomics, microscopy, and proteomics. These devices and methods are particularly useful in the area of drug discovery, finding application in, for example, identification and validation of target compounds, toxicity screening, and the like.

Devices and methods of the present invention are suitable for high throughput assays, and also allow assays to be performed using new and improved techniques. Significantly, devices and methods according to the present invention combine the advantages of a flat surface with the advantages of a well structure. Using the devices and methods of the present invention, the user can pattern materials of interest in a predetermined, spatially defined manner, utilize a well structure in which to perform assays, and successfully and accurately read, detect, or monitor the results of the assays using devices and techniques that require the surfaces to be read be flat, or that function optimally when the surfaces to be read are flat. As an alternative to patterning materials of interest on a surface, the user can immobilize materials of interest over an entire surface, then use devices and methods according to the present invention to isolate certain areas from others.

As another example, using a device such as that illustrated in FIG. 8, a user can perform an assay with a local control for each test well. Unlike assays in which a single unexposed well or well without protein must serve as a control for a whole plate of reactions, the methods and devices of the present invention allow the user to account for well-to-well variability.

In a preferred embodiment of the present invention, the self-assembled monolayers are modified to have "switchable surfaces." For example, self-assembled monolayers can be designed with a "head group" that will capture a desired molecule. The head group is then subsequently modified at a desired point in time to release the captured molecule. In a preferred embodiment of the present invention, the head group is modified such that after release of the captured cell, the head group no longer will attract and attach subsequent cells. This release is important to allow the patterned cells to migrate. If a self-assembled monolayer did not have a "switchable" head group, the migration of the cell may be hindered. An example of a "switchable" control is depicted in FIG. 14. This figure depicts a particular peptide-presenting compound that allows cells to attach to itself. Upon application of an electrical potential, the peptide presenting compound is cleaved causing the release of cells from the support. Importantly, the portion of the peptide presenting compound that remains after application of the electrical potential is unable to bind cells, and thus eliminates the potential for non-specific cell binding.

It is also often desirable to utilize a bioinert support material to resist non-specific adsorption of cells, proteins, or any other biological material. The most successful method to confer this resistance to the adsorption of protein has been to coat the surface with poly(ethylene glycol) PEG. A variety of methods, including adsorption, covalent immobilization, and radiation cross-linking, have been used to modify surfaces with PEG. Polymers that comprise carbohydrate units also passivate surfaces, but these material are less stable and less effective than PEG. A widely used strategy is to pre-adsorb a protein—usually bovine serum albumin—that resists adsorption of other proteins. In addition, self-assembled monolayers that are prepared from alkanethiols terminated in short oligomers of the ethylene glycol group $[HS(CH_2)_{11}(OCH_2CH_2)_n, OH:n=2-7]$ resist the adsorption of several model proteins. Even self-assembled monolayers that contain as much as 50% methyl-terminated alkanethiolates, if mixed with oligo(ethylene glycol)-terminated alkanethiolates, resist the adsorption of protein. Further, self-assembled monolayers that are terminated in oligo(ethylene glycol) groups may have broad usefulness as inert supports, because a variety of reactive groups can be incorporated in self-assembled monolayers in controlled environments.

In contrast to using a bioinert treatment or support material, by choosing an appropriate support or treatment, the surface can be modified to have any desired functionality. For example, the support can be treated to have immobilized biomolecules such as other cells, DNA/RNA, chemicals, or other biological or chemical entity.

A preferred embodiment uses the self assembled monolayer technology of thiol molecules bonded to coinage metal surfaces to immobilize proteins and carbohydrates in spatially defined and predetermined areas on surfaces. Provisional application, 60/356,765 and 60/357,136 (filed on February 15) entitled "Formation of self assembled monolayers of thiolate functionalized with Michael acceptors and immobilization of biological molecules onto surfaces coated with monolayers," which are herein incorporated by reference in their entirety, provide for the immobilization of proteins and carbohydrates onto SAMS, and further provide for the controlled immobilization of such biomolecules.

Gold/thiolate monolayers are described in Whitesides, G. M.; Gorman, C. G. *Handbook of Surface Imaging and Visualization* 713-733 (CRC Press: Boca Raton, FL 1995); Ulman, *A Chem. Rev.* 1996, 96, 1533-54; DuBois, L. H. et al. *Annu. Rev. Phys. Chem.* 1992, 43, 437-463; Mrksich, M.; Whitesides, G. M. *Trends Biotechnol.* 1995, 13, 228-235; Y. Xia, G. M. Whitesides *Angew. Chem. Int. Ed.*, 1998, 37, 550-575; C. D. Bain, G. M. Whitesides, *Agnew, Chem. Int. Ed*, Engl. 1989, 28, 506-512; G. M. Whitesides, P. E., Laibinis, *Langmuir* 1990, 6, 87-96; A. Ulman, *Introduction to Thin Organic Films: From Langmuir-Blodgett to Self-Assembly* (Academic Press: Boston, 1991); J. D. Swalen, *Annu, Rev. Phys. Chem.* 1992, 43, 437-463; J. Xu, H.-L. Li, *J. Coll. Interf. Sci.* 1995,176, 138-149; A. Ulmam, *MRS Bull.* i, 30(6), 46-51; A. R. Bishop, R. G. Nuzzo, *Curr. Opin. Coll. Interf. Sci.* 1996, 1, 127-136; E. Delamarche, B. Michel, H. A. Biebuyck, C. Gerber, *Adv. Mater.* 1996, 8, 719-729; U.S. Pat. Nos. 5,512,131; 5,776,748 and 5,900,160. Surfaces of self assembled thiolate monolayers adsorbed onto coinage metals offer several advantages over other platforms for immobilizing molecules like proteins. One significant advantage that they have over polymer supports like that of the '697 patent is that the surface itself is a complete barrier to penetration by molecules regardless of size. A linker molecule like the perfluoroazide of Example 9 of the '697 patent may penetrate into the matrix of the polymer support before binding to the polymer. Linker molecules that bind within the polymer matrix would be unavailable for covalent bonding with a large molecule that is unable to penetrate the polymer matrix.

His-tagged proteins have been immobilized on a flat gold surface by forming Nickel metal chelate complexes via the imidazole rings of histidine and the carboxyl groups of a thiol bound to the surface through sulfur. Sigal G. B.; Bamdad, C.; Barberis, A.; Strominger, J.; Whitesides, G. M. *Anal. Chem* 1996, 68, 490-97. The thiol of formula:

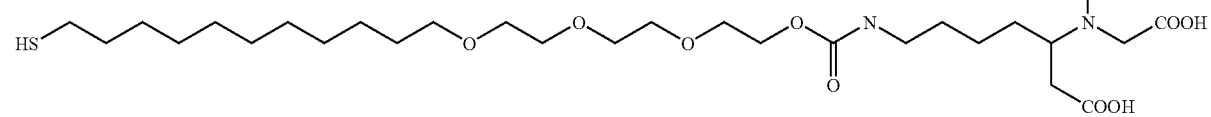

was immobilized on gold coated glass slides by immersing the glass slide in a solution containing the linker molecule in ethanol. The density of the linker molecules on the surface was adjusted by providing another, triethylene glycol terminated, thiol (HS—(CH$_2$)$_{11}$—(OCH$_2$CH$_2$)$_3$—OH) in the solution, hereafter referred to as a "diluent thiol."

Wilner et al. discloses separating thiol and maleimide groups on separate molecules that were attached to the surface in serial fashion. Willner, I; Heleg-Shabtai, V.; Katz, E.; Rau, H. K.; Haehnel, W. *J. Am. Chem. Soc.* 1999, 121, 6455-6468. Wilner et al. were investigating the electrochemical behavior of a gold electrode that had been coated with an electrically active protein. The protein was bound to the gold electrode by first immersing the electrode in a solution of cystamine to coat the electrode with cysteamine (—SCH$_2$—CH$_2$NH$_2$). The cysteamines were then reacted with the heterobifunctional linker N-succinimidyl-3-maleimidopropionate to produce a maleimide-modified surface. The two step sequence is depicted below.

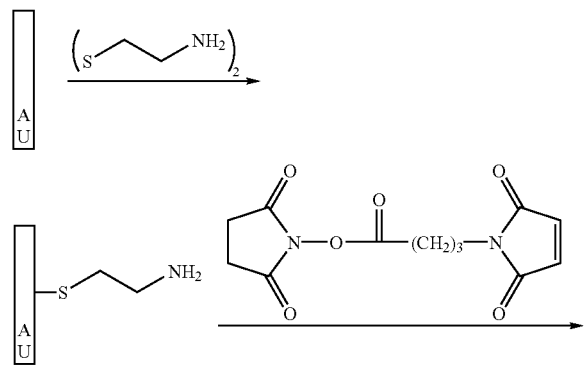

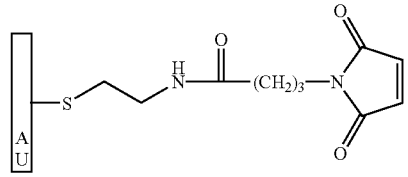

The amount of protein bound to the maleimide surface was characterized by coulometric assay that gave an estimated surface coverage of $4.8 \times 10^{-11}$ mol cm$^{-2}$. The formation of a tightly packed monolayer of thiolates generally requires more extensive Van der Waals contact between adjacent molecules than is provided by the ethyl group of cysteamine.

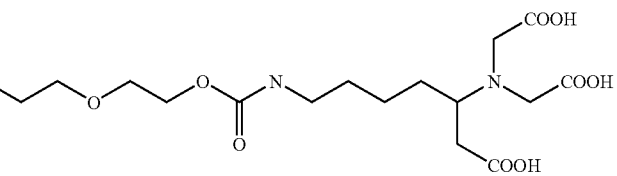

Studies on the adsorption of linear alkanethiolates onto gold surfaces have demonstrated that self-assembled monolayers tend to develop from nuclei of adsorbed thiolate molecules. Van der Waals interactions between the alkyl chains stabilize the monolayer and promote tight packing. Ulman, A., *Introduction to Thin Organic Films: From Langmuir-Blodgett to Self-Assembly* (Academic Press: Boston, 1991). For these reasons, reducing the thiol concentration of a solution used to coat the surface would be ineffective for producing a surface uniformly coated with a monolayer of thiolate at a correspondingly lower density.

Though non-specific adsorption has been used to immobilize proteins purposefully in some research studies, Blawas A. S. et al. *Langmuir* 1998, 14, 4243-4250, when a covalent immobilization technique is used to immobilize proteins in a pattern on a surface, non-specific protein adsorption may be problematic. It can reduce the sensitivity of an assay. Further, when surface-bound protein is used to attach cells to a surface, non-specific protein binding may cause cells to adhere randomly to the surface. Blawas, A. S.; Reichert "Protein Patterning" *Biomaterials,* 1998, 19, 595-609.

Another method for resisting non-specific adsorption of peptides, polypeptides, proteins, nucleotides, cells and the like involves the use of thiols having a proximal linear alkyl segment for promoting self assembly and a distal polyethylene glycol (polyethoxy) segment to resist non-specific adsorption of biological materials. Singhvi R. et al. "Engineering Cell Shape and Function" *Science,* 1994, 264, 696-698.

U.S. Pat. No. 5,843,650 describes a method of amplifying target nucleic acids in a test sample. In the method, a pair of oligonucleotide probes are used. When the probe pairs are hybridized to a target polynucleotide, chemical functional groups on the probes reacted to bind the probes together. This patent discloses that functional groups that can be used to bind the probes together while hybridized to the target include nucleophilic/electrophilic pairs, like thiol and maleimide, and Diels Alder reacting pairs.

International Publication No. WO 98/30575 describes the Diels Alder reaction as a way to conjugate macromolecules with other molecular entities.

Some of the terms used in this disclosure have the following ascribed meanings.

An "aglycone" is the component of a glycoside, which is not a sugar.

An "asymmetric" disulfide is a disulfide that may be viewed as formed by covalent bonding of the sulfur atoms of two different thiyl radicals.

A "carbohydrate" is a polyhydroxy aldehyde or ketone, or a substance that yields such compounds upon hydrolysis. Non-limiting examples of carbohydrates are monosaccharides, disaccharides, oligosaccharides, glycopeptides, glycoproteins, glycolipids and their derivatives. As used in this disclosure carbohydrates include polyhydroxy aldehydes and ketones whose aldehyde or ketone functionality is reduced, such as alditols, cyclitols and their derivatives, and oxidized forms such as aldonic acids, uronic acids, aldaric acids, keto acids and their derivatives. M. Sznaidman, *Introduction to Carbohydrates in Bioorganic Chemistry: Carbohydrates*, p. 1-55 (S. M. Hecht, Ed, Oxford Press, 1999).

A "carboxylic acid derivative" is a carboxylic acid and "derivatives" thereof. Carboxylic acid derivatives include esters, amides, carbamates, nitrites, acyl halides and imidazolides.

A "coinage metal" is gold, silver, platinum and copper.

A "derivative" is a compound that can be obtained from another compound by a simple chemical process. *Grant & Hackh's Chemical Dictionary* 5th ed. (1987).

A "monolayer forming moiety" is a moiety that is a precursor molecule to a "monolayer moiety." For example, a "monolayer forming disulfide moiety" is a precursor molecule that when brought into contact with a coinage metal surface, forms a bond with the coinage metal to form a thiolate monolayer, herein referred to as a "monolayer thiolate moiety."

A "monolayer forming moiety bearing an inert group" is a precursor molecule to a "monolayer moiety bearing an inert group." For example, if the monolayer forming moiety bearing an inert group is a disulfide compound bearing an inert group, upon contact with a coinage metal surface, the disulfide compound bearing an inert group becomes a thiolate bearing an inert group or, as referred to herein as a "monolayer thiolate moiety bearing an inert group." Exemplary "monolayer forming disulfide moieties bearing an inert group" are disulfides of the formula $R-(O-(CH_2)_y)_z-(CH_2)_x-S-S-(CH_2)_x-((CH_2)_y-O)_z-H$, wherein x is a number from 10 to 24, y is preferably 2, z is a number from 1 to 10, and R is H or CH3 or any inert group that resists non-specific adsorption of a biomolecule. A "monolayer forming disulfide moiety bearing an inert group" will also be referred to interchangeably throughout the specification as a "diluent disulfide." Similarly, a "monolayer thiolate moiety bearing an inert group" will also be referred to interchangeably throughout the specification as a "diluent thiolate."

A "monolayer forming moiety bearing a covalent bond forming reactive group" is a precursor molecule to a "monolayer moiety bearing a covalent bond forming reactive group." For example, if the monolayer forming moiety bearing a covalent bond forming reactive group is a disulfide compound bearing a covalent bond forming reactive group, upon contact with a coinage metal surface, the disulfide compound becomes a thiolate bearing a covalent bond forming reactive group or, as referred to herein as a "monolayer thiolate moiety bearing a covalent bond forming reactive group."

A "covalent bond forming reactive group" is any group that will react with a reaction partner to form a covalent bond. The covalent bond forming reactive group on a monolayer moiety will react with a reaction partner on a functional organic molecule to form a covalent bond and immobilize a functional organic molecule on the monolayer. Exemplary reactions include, but are not limited to Michael additions or Diels Alder reactions. In the case of a Michael addition, an exemplary covalent bond forming reactive group may be a maleimide, which will react with a thiol on a functional organic molecule. The functional organic molecule may have to be derivatized to contain a thiol group. Other exemplary covalent bond forming reactive groups include, but are not limited to: carboxylic acids and amines; phosphonyl groups and esters; thiols and carboxylic acids; free amino groups and carboxylic acids; free amino groups and dicarboxylic acids; and sulfonyl groups and esters. For simplification and for purposes of illustration only, the figures depict the covalent bond forming reactive group as a maleimide that reacts in a Michael addition with a thiol group on a functional organic molecule. One skilled in the art will appreciate that any number of suitable chemistries may be employed to form a covalent bond. Some non-limiting examples are included above. Preferred chemistries include those where the reaction has well behaved, and well understood reaction kinetics. Preferably the reaction goes to completion.

"Electron withdrawing groups" (alternatively "EWG") are well understood by those in the art to be collections of atoms (functional groups) that tend to withdraw electron density from atoms to which they are bonded. Non-limiting examples of EWGs include carboxylic acid derivatives, keto groups, nitro groups, such as but not limited to esters, amides, carbamates, nitrites, acyl halides, and imidazoles.

A "functional organic molecule" means an organic molecule that has a role in the functioning of a biological organism and molecules that selectively bond to such organic molecules. Functional organic molecules include oligopeptides, peptides, polypeptides, proteins (large polypeptides with tertiary structure), nucleotides, nucleosides, carbohydrates, lipids enzymes, enzyme substrates, ligands, receptors, antibodies, antigens, small molecules, and nucleic acids. These broad classifications of polymers and oligomers assume functional forms in organisms. Some proteins are enzymes, receptors or antibodies. Some carbohydrates are involved in cell surface recognition and therefore function as ligands to which receptor proteins bind. Functional organic molecules further include ligands and receptors, antibodies and antigens, enzymes and the like.

A "hydrocarbyl" means a fragment of a molecule that contains carbon and hydrogen. The term is intended to have a broad meaning that includes fragments comprising the elements carbon and hydrogen. Hydrocarbyl groups may have any number of heteroatoms in addition to carbon and hydrogen. Heteroatoms may be pendant, such as a carbonyl oxygen or the fluorine atoms of difluoromethylene. Heteroatoms also may be incorporated into a hydrocarbyl fragment, such as the nitrogen of triethylamine or the oxygen atom of diethyl ether or a polylalkoxy fragment.

A "ligand" is a molecule that binds specifically to another molecule.

A "Michael addition" is a conjugate addition reaction of a nucleophile to a carbon-carbon double bond conjugated to an electron withdrawing group. The nucleophilic addition is often followed by proton abstraction or trapping of an electrophile by the carbon atom across the double bond from the carbon atom undergoing the addition. See generally, Mundy, B. P.; Ellerd, M. G. *Name Reactions and Reagents in Organic Synthesis* (John Wiley & Sons: New York 1988) and March, *J. Advanced Organic Chemistry: Reactions Mechanisms and Structure* (John Wiley & Sons: New York, 4th ed. 1992).

A "Michael acceptor" is an electrophilic compound having a carbon-carbon double bond conjugated to an electron withdrawing group that can participate in a Michael addition. Michael acceptors include, but are not limited to quinones, maleimides, α-β unsaturated ketones, α-β unsaturated amides, and α-β unsaturated esters.

A "polypeptide" is an oligomer or polymer of amino acids bound by peptide bonds formed by the condensation of the amino group of one amino acid with the carboxyl group of another. The term "peptide" is also used in this disclosure to refer to amino acid oligomers and short chained polymers of less than about 50 amino acids. These terms have well understood meaning to those skilled in the art. When peptides containing ten amino acids or less are intended, the term "oligopeptide" shall be used. Hawley, G. G. *The Condensed Chemical Dictionary* 759 (Van Nostrand Reinhold Co.: New York 1981).

A "small molecule" as used herein means small organic or non-organic structures having molecular weights of 1,000 daltons or less.

A "switchable covalent bond forming group" as used herein means a group that, upon the introduction of a certain stimulus, is activated to bond to a functional organic molecule through various chemical reactions to achieve a covalent bond. For example, the stimulus may be an electrical impulse, a change in temperature, pH or the like. A "reversible switching group," is one that can be switched on to an active state from an unreactive state, and that can be switched off from an active state to an unreactive state. A signal that turns the active state on is referred to herein as an "activating signal." A signal that turns the active state off is referred to herein as a "quieting signal." An exemplary reversible switchable group is a quinone. Quinones can be modulated electrochemically—they can be turned on or off by either adding or removing electrons. When a quinone is in its oxidized state (electrons are removed), it is in its active state. When the quinone is reduced (electrons are added), it is in its unreactive state. An "irreversible switching group" is one that is initially unreactive, but upon exposure to a signal, it changes to its active state. Often the signal works to break a bond and release a group that rendered the compound unreactive. For example, nitroveratryloxycarbonyl ("NVOC") is a photolabile group that is removable by light. NVOC groups are commonly used in photochemistry to protect amines, carboxylic acids or hydroxyl groups. A compound is prepared to have a covalent attachment of a NVOC group at these sites. The NVOC group renders the compound unreactive at these sites. When it is desired to activate the compound, light is used to cleave off the NVOC groups and render the compounds active. When a light is shined on these compounds, the NVOC group is released to expose the amines, carboxylic acids or hydroxyl groups thus allowing them to participate in a subsequent reaction.

A "thiol" is an organic compound that contains a —SH functional group, also known as a mercaptan. In this disclosure, thiol is also used to refer to the —SH functional group as is conventional in the art. The thiol functional group is also known as sulfhydryl and mercapto. Whether the term thiol refers to a compound or a functional group will be clear from the context.

"Thiolate" refers to a sulfur anion singly bonded to a carbon atom and to compounds containing a sulfur anion singly bonded to a carbon atom. The term thiolate is also used to refer to the organic constituent of a self assembled monolayer formed by contacting a thiol or disulfide with a coinage metal, without inferring anything about the distribution of electrons in the Au—S bond.

The term "thiyl fragment" is used to refer to a fragment (syn. moiety, radical) of a disulfide that includes one of the sulfur atoms of the disulfide group and the substituent bonded to that sulfur atom.

Those skilled in the art of surface chemistry will appreciate that the products of reactions performed on surfaces can be difficult to characterize. Routine solution phase characterization techniques like $^1$H NMR are not available for characterization of surface bound reaction products. An improvement that reduces the number of chemical reactions that are performed on surfaces to prepare them for a particular application should provide surfaces with more well-defined characteristics and more reproducible characteristics between surfaces prepared in the same manner. The present invention fulfills this need.

The present invention provides a process for making an article useful for the immobilization of biomolecules. This process uses a technique of forming a self assembled monolayer of thiolates on a coinage metal surface. The inventive method enables the immobilization of covalent bond forming reactive groups, such as Michael acceptors and others, with fewer manipulative steps on the surface than are required by methods known in the art. The need to derivatize a preformed SAM with a covalent bond forming reactive group is avoided. Avoiding the derivatization step obviates concern about the completeness of the derivatization and the composition of the surface after the derivatization.

Accordingly, in a first aspect, the present invention provides a process for immobilizing a functional organic molecule on a coinage metal surface by forming a monolayer of thiolates on the surface wherein at least a portion of the thiolates are functionalized with a covalent bond forming reactive group. A significant feature of the invention is that the monolayer is formed in one step by reacting the surface with a disulfide compound bearing a covalent bond forming reactive group. The covalent bond forming reactive group reacts with a functional organic molecule to covalently bond it to the thiolate (FIG. 30), resulting in immobilization of the functional organic molecule on the surface.

The invention will be further illustrated with gold surfaces since gold/thiolate monolayers are the most thoroughly studied self assembled monolayers with which the present invention is most immediately concerned. While a gold surface may be the surface of a solid gold article, gold surfaces produced by surface engineering are conventionally gold coatings over substrates like glass. Glass articles, like microscope slides and coverslips, can be coated with a layer of gold by vapor deposition of an adhesive layer of titanium onto a clean glass surface of the article followed by vapor deposition of gold onto the adhesive layer. Instrumentation for applying a gold coating to a glass substrate is commercially available from Pharmacia Biosensors.

Underneath the gold surface, the article may comprise any material whatsoever so long as the gold surface is not so poorly adherent to the article that it makes the article unsuitable as a support for immobilizing functional organic molecules and then using the article as a research or diagnostic tool, or other appropriate application that may be found for the article. For instance, polycarbonate and polyurethane, in addition to glass, are suitable substrates that can be coated with gold according to methods well known in the art.

According to the process, the gold surface is contacted, e.g. by immersion, with a solution of the disulfide. Conventionally, disulfide and thiol solutions that are used to prepare self assembled monolayers are dilute, on the order of $10^{-3}$ M. Thus, the solution concentration is preferably about $9 \times 10^{-3}$ M in total disulfide concentration or less, more preferably about $1 \times 10^{-3}$ M or less. An advantage of using disulfides as the monolayer forming moiety rather than thiols is that when using a thiol, a self-reaction may occur to produce an ill-defined monolayer having a dimer and oligomer molecules incorporated therein. By using a disulfide rather than a thiol as the molecule precursor for forming the monolayer, the invention prevents self-reaction of the precursor. Further, providing a disulfide functionalized with a covalent bond forming reactive group as the precursor, a thiolate monolayer will be formed having the covalent bond forming reactive group present at the surface.

Accordingly, one embodiment of the preset invention provides a process for making an article having a coinage metal surface region and a mixed self-assembled monolayer of thiolate on the surface region. The process involves contacting the coinage metal surface with a solution containing a mixture of two monolayer forming disulfide moieties in an inert solvent.

The solvent is one that allows the disulfides to form a monolayer when they contact the coinage metal surface. Ethanol and methanol are two such solvents. One skilled in the art will appreciate and understand other solvents that may work. For instance, a solvent such as DMSO is not suitable as it will not allow a monolayer to form.

The first monolayer forming disulfide moiety bears a covalent bond forming reactive group. The second monolayer forming disulfide moiety in the solution mixture bears an inert group. For simplification and ease of understanding, the monolayer forming disulfide moiety bearing an inert group may be referred to herein as a diluent disulfide, since it will not be able to react with a functional organic molecule to form a covalent bond to immobilize the functional organic biomolecule. When the monolayer forming disulfide moieties contact the surface region, a mixed self-assembled monolayer of thiolates is formed on the surface region. The first monolayer forming disulfide moiety bearing a covalent bond forming reactive group reacts with a coinage metal surface region to form a first monolayer thiolate moiety bearing a covalent bond forming reactive group. The second monolayer forming disulfide moiety reacts with the coinage metal surface region to form a second monolayer thiolate moiety bearing an inert group (also referred to as a diluent thiolate).

Any disulfides can be used in the present invention. Non-limiting examples include symmetric and asymmetric disulfides. Preferably, the disulfide used as the monolayer forming moiety bearing the covalent bond reacting group will be an asymmetric disulfide. This asymmetric disulfide preferably has at one end a covalent bond forming reactive group and at the other end an inert group.

Figure 31:
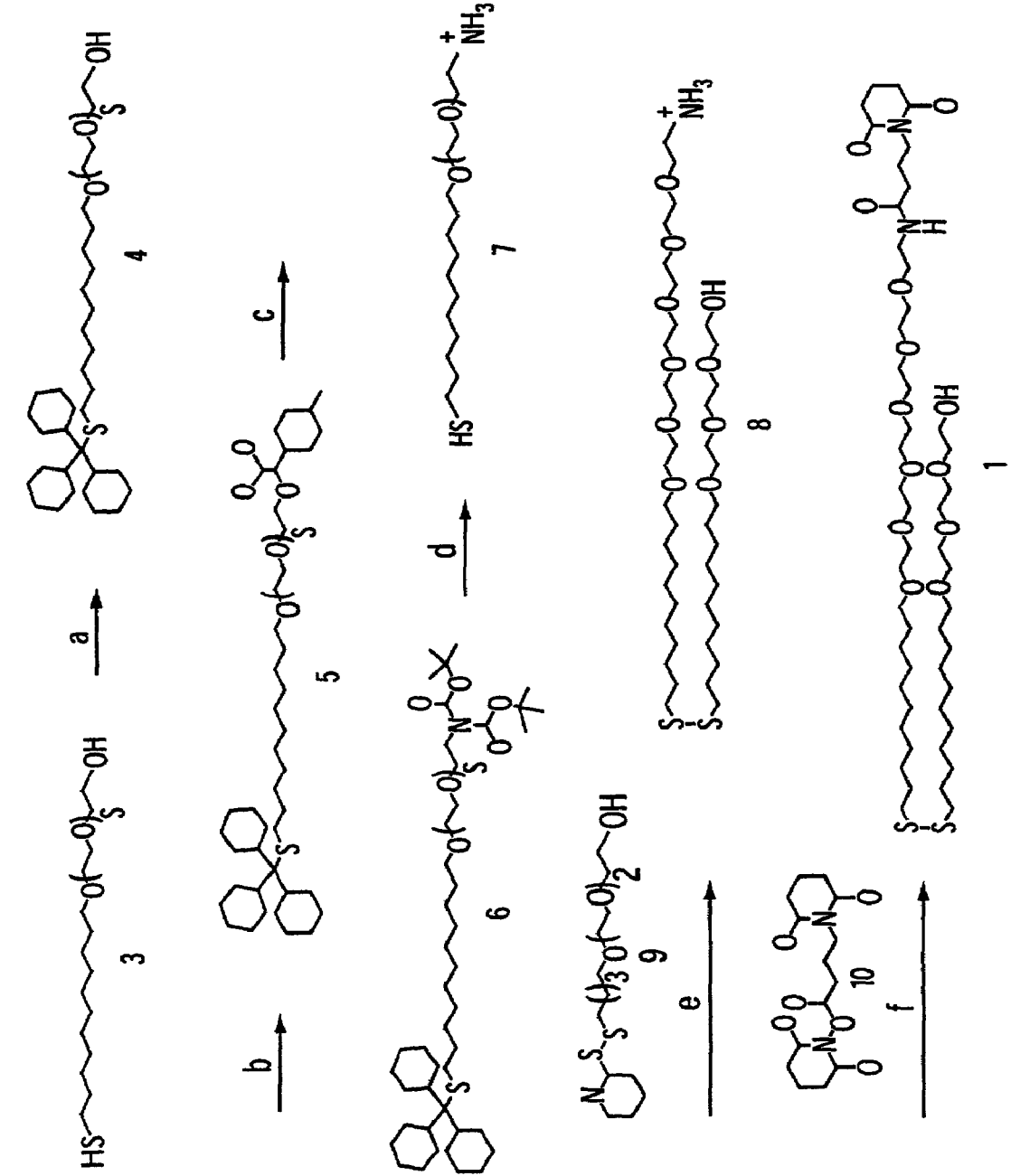
FIG. 31 schematically depicts the synthetic route used to prepare asymmetric disulfide 1 used for forming surfaces presenting maleimide groups. (a) trityl chloride, THF, 49%; (b) TsCl, pyr., $CH_2Cl_2$, 91%; (c) $HN(CO_2tBu)_2$, NaH, DMF, 72%; (d) TFA, EDT, PhOH, PhSMe, $H_2O$; (e) 9, $Et_3N$, MeOH; (f) 10, $Et_3N$, DMF.

Symmetric disulfides may be prepared conventionally by oxidizing an -amino-functionalized thiol like $HS-(CH_2)_a-(OCH_2CH_2)_b-NH_2$, wherein a and b each independently may vary widely, e.g. from 0 to 24 (but a orb can not both be 0) or higher homologs thereof (but wherein a is preferable 6-24 and b is preferably 1-10) to form a disulfide and then reacting the amine group with a compound having a covalent bond forming reactive group, such as a Michael acceptor, and an activated carboxyl group such as compound 10 in FIG. 31. By using a symmetric disulfide, the gold surface can be coated exclusively with thiolates that present the covalent bond forming reactive groups, or in this case the Michael acceptor, at the surface. For some applications, such high density may be desirable, but for providing a surface to covalently immobilize proteins, carbohydrates and other biological material a much lower density is preferred. Thus, asymmetric disulfides are preferred in these cases.

The disulfide compounds may also be asymmetric, preferably having one covalent bond forming reactive group such as a Michael acceptor on one end and an inert group on the other. Preferred asymmetric disulfides are maleimide substituted disulfides of formula:

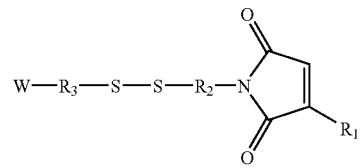

wherein $R_2$ and $R_3$ are saturated or unsaturated, substituted or unsubstituted hydrocarbyl and $R_1$ is a hydrogen or an electron withdrawing group and W is a hydrophilic or hydrophobic substituent. W may also be selected from the group consisting of hydroxyl, sulfonate, hydroxy substituted $C_1$-$C_4$ alkyl and methyl. $R_2$ may be a chain of the formula $-(CH_2)_m-(O(CH_2)_n)_o-NHC(O)-(CH_2)_p-$ wherein m is a number from 10 to 24, n is preferably 2, o is a number from 1 to 10 and p is a number from 1 to 16. Preferably, $R_3$ is of the formula $-(O-(CH_2)_j)_k-(CH_2)_i-$, wherein i is a number from 10 to 24, j is preferably 2, and k is a number from 1 to 10. W is preferably hydroxyl, sulfonate or methyl, more preferably hydroxyl. In one embodiment, $R_2$ and $R_3$ each are linear and formed of an alkyl segment bonded to a sulfur atom and a second segment selected from the group consisting of polyalkoxy, polyperfluoroalkyl, poly(vinyl alcohol) and polypropylene sulfoxide bonded to the alkyl segment.

Asymmetric disulfides may be formed conventionally by exposing a mixture of two thiols to oxidative conditions and recovering the mixed disulfide. However, if the covalent bond forming reactive group is a Michael acceptor, since Michael addition between the thiol and Michael acceptor can occur at this stage, and since the statistical yield of mixed oxidative coupling is inherently low, it is preferred to use a protection strategy such as the strategy depicted in FIG. 31. That figure shows schematically a preparation of an asymmetric disulfide bearing a terminal maleimide Michael acceptor functional group on one thiolate moiety and a hydroxy terminated polyethoxy-alkyl segment on the other.

Referring to FIG. 31, an co-hydroxy polyalkoxy-alkyl thiol 3 is protected as its trityl thioether. The hydroxy group of thioether 4 is converted into its sulfonate 5. The sulfonate is displaced with di-tert-butyl iminodicarboxylate to give protected amine thiol 6. The trityl and Boc groups are cleaved to give ω-ammonium thiol 7. The resulting ω-ammonium thiol is then reacted with (polyalkoxy-alkyl)-(2-pyridyl) disulfide 9 to form asymmetric disulfide 8 having an ammonium group on one terminus and a hydroxy group on the other. Treatment of 8 with γ-maleimidobutyric acid N-hydroxysuccinimide ester 10 in the presence of a non-nucleophilic base yields asymmetric disulfide precursor compound 1. Those skilled in the art will appreciate that this preparation is highly versatile. ω-Hydroxy polyalkoxy-alkyl thiol 3 may be substituted by another co-hydroxy thiol of a different desired overall chain length and/or having alkyl or polyalkoxy chain segments of different chain length. A compound having another Michael acceptor, chain length or amine-reactive functionality may be substituted for compound 10 to prepare a variety of precursor compounds presenting a variety of Michael acceptors in a variety of ways on the surface.

Further, a disulfide having a different thiyl fragment in place of the polyalkoxy-alkyl thiyl fragment of compound 9 may be substituted for compound 9 in step (e). For instance, a pyridinium disulfide having a linear alkyl thiyl fragment may be substituted. For another instance, the thiyl fragment could be a polyalkoxy-alkyl chain with any of a wide variety of terminal groups.

Using asymmetric disulfides described above, another aspect of the invention provides a uniformly mixed monolayer of a thiolates bearing a covalent bond forming reactive group dispersed in a thiolate bearing an inert group (or more than one diluent thiolate), wherein the thiolates are all derived from disulfide precursors. According to this aspect of the invention, an asymmetric disulfide precursor bearing one covalent bond forming reactive group is contacted with the surface to synchronously and proximally adsorb thiolate bearing a covalent bond forming reactive group and one thiolate bearing an inert group onto the surface. This process provides more uniform initial dispersion of the thiolate bearing a covalent bond forming reactive group in thiolates bearing an inert group on the surface, which is expected to lead to a more uniform monolayer and more reproducible characteristics between monolayers prepared by the inventive process.

In gold/thiolate monolayers, individual thiolates are hindered from migration across the surface by neighboring molecules. According to studies of alkanethiolate monolayers on gold, monolayer formation occurs in two kinetically distinct stages. Initial adsorption from a millimolar solution of thiol occurs within minutes. After the initial adsorption, the thiolates reorient to maximize Van der Waals interactions and other stabilizing interactions, which is thought to occur over several hours. The reorientation phenomenon has been detected as a slow increase in thickness of the monolayer. During both these kinetic phases, the thiolates are less constrained by neighboring molecules from migration across the surface than they are after reorientation. Mixed monolayers tend to form microdomains enriched in one type of thiolate. Stranick, S. J.; Parikh, A. N.; Tao, Y. T.; Allara, D. L.; Weiss, P. S. *J. Phys. Chem.* 1994, 98, 7636. Microdomains reduce the uniformity of the surface. They also introduce an uncontrolled element that can effect the reproducibility of the surface characteristics obtained in repetitions of the same procedure. Surface migration of thiolates appears to be an important factor that allows microdomains to form. By more uniformly distributing thiolates bearing a covalent bond forming reactive groups and thiolates bearing an inert group in the monolayer using an asymmetric disulfide precursor, microdomain formation should be suppressed resulting in more uniform and reproducible surface characteristics.

As discussed above, covalent bond forming reactive groups can be any group that will react with a reaction partner to form a covalent bond. A non-limiting example of a covalent bond forming reactive groups is a Michael acceptor. Michael acceptors will participate in a Michael addition (a conjugate addition reaction of a nucleophile to a carbon-carbon double bond conjugated to an electron withdrawing group). Michael acceptors include quinones, maleimides and others. A preferred Michael addition involves a maleimide and a thiol. Non-limiting example of Michael acceptor functional groups are maleimide groups of the formula:

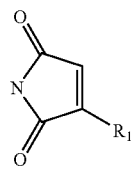

wherein the maleimide group is bonded to the residuum of the disulfide through nitrogen, and substituent $R_1$ is either hydrogen or an electron withdrawing group. It may be desirable to modify the reactivity of maleimide so as to accelerate a subsequent immobilization reaction. Thus, suitable maleimide groups include, in addition to maleimide itself, derivatives of maleimide having an electron withdrawing group on no more than one of the vinylic carbons. Preferred electron withdrawing groups are carboxylic acid derivatives, keto groups, nitro groups, esters, amides, carbamates, nitriles, acyl halides and imidazolides. Since Michael acceptors, like maleimide, behave as dienophiles, the MAB thiolates can be used to covalently immobilize functional organic molecules that have conjugated carbon-carbon double bonds by Diels Alder or other cycloaddition reaction.

Since the rate of addition of the reaction partner (thiols) to maleimide (R1=H) is quite rapid, and for reasons of commercial availability and cost of the starting materials, a most preferred maleimide derivative is maleimide itself when the functional organic molecule is to be immobilized by Michael addition of a thiol group to the maleimide group. Alternative Michael acceptor functional groups include ortho- and para-quinones and quinone derivatives, acrylic acids and their derivatives, vinyl sulfones, enamines and enamides.

In contrast to the covalent bond forming reactive group on one monolayer forming moiety, the other monolayer forming moiety will have an inert group. The inert group is a group that resists non-specific adsorption ("NSA") or non-specific binding ("NSB") of a biomolecule. In particular, when the article or methods of the present invention are to be used to immobilize proteins, it is preferred that the inert group resists non-specific adsorption of proteins. Often hydrophilic group resists such NSA. One preferred inert group is a polyethylene glycol, such as triethylene glycol ("EG3").

According to the present invention, the monolayer thiolate moiety bearing an inert group may be derived from a monolayer forming disulfide moiety bearing an inert group. The disulfide bearing an inert group may be any disulfide capable of forming a SAM on the gold surface. Further it may be any disulfide discussed above. Symmetric linear alkane disulfides are one example. Preferred disulfides bearing an inert group impart resistance against non-specific biomolecule adsorption to the surface. More particularly preferred disulfides bearing an inert group are of the formula W—$R_4$—S—S—$R_4$—W wherein $R_4$ is a hydrocarbyl having an alkyl segment bonded to sulfur and a linear polyalkoxy segment bonded to the alkyl segment and to W. Substituent W may be either a hydrophilic or hydrophobic group, and preferably is a functional group that resists adsorption of proteins. More preferably, W is hydrophilic group such as hydroxyl or sulfonate, most preferably hydroxyl. The polyalkoxy segment resists protein adhesion. A preferred polyalkoxy is polyethoxy. Especially preferred diluent disulfides are of the formula H—(O—(CH$_2$)$_y$)$_z$—(CH$_2$)$_x$—S—S—(CH$_2$)$_x$—((CH$_2$)$_y$—O)$_z$—H, wherein x is a number from 10 to 24, y is preferably 2, and z is a number from 1 to 10. Other suitable disulfides bearing an inert group have in place of the polyalkoxy segment and W, a polyperfluoroalkyl, poly(vinyl alcohol) or polypropylene sulfoxide segment, each of which has been shown to resist protein adhesion. Folch, A.; Toner, M. *Annu. Rev. Biomed. Eng.* 2000, 2, 227-56.

The present invention also provides an article useful for immobilizing functional organic biomolecules. The article is comprised of a coinage metal surface and a mixed self-assembled monolayer surface covering at least a portion of the coinage metal surface. The mixed self-assembled monolayer surface comprises a first monolayer moiety and a second monolayer moiety. The first monolayer moiety comprises a thiolate bearing a covalent bond forming reactive group, and the second monolayer moiety comprises a thiolate bearing an inert group. As discussed above, the covalent bond forming reactive group may be any group that can participate in a reaction with its reaction partner to form a covalent bond. The covalent bond forming reactive groups and the inert groups are as discussed above.

Critical to the ability to faithfully reproduce a range of different ligand densities on surfaces is the ability to measure the absolute density of immobilized functional organic molecules. The present invention further provides a convenient method for electrochemically assaying and quantifying the density of covalent bond forming reactive groups, specifically Michael acceptors, in a mixed self-assembled thiolate monolayer on a coinage metal surface. In this embodiment of the present invention, an electrically active compound is reacted with the covalent bond forming reactive group to form a surface having an electrochemical activity. See FIG. 61. The electrochemical activity of the surface is measured, and the density of the covalent bond forming reactive group on the surface is determined from the measurement. Once the density of the covalent bond forming reactive group on the surface is known, this density can be correlated to the density of immobilized functional organic molecules, assuming that the covalent bond forming reaction has gone to completion and all of the covalent bond forming reactive groups have an immobilized functional organic molecule.

Figure 35:
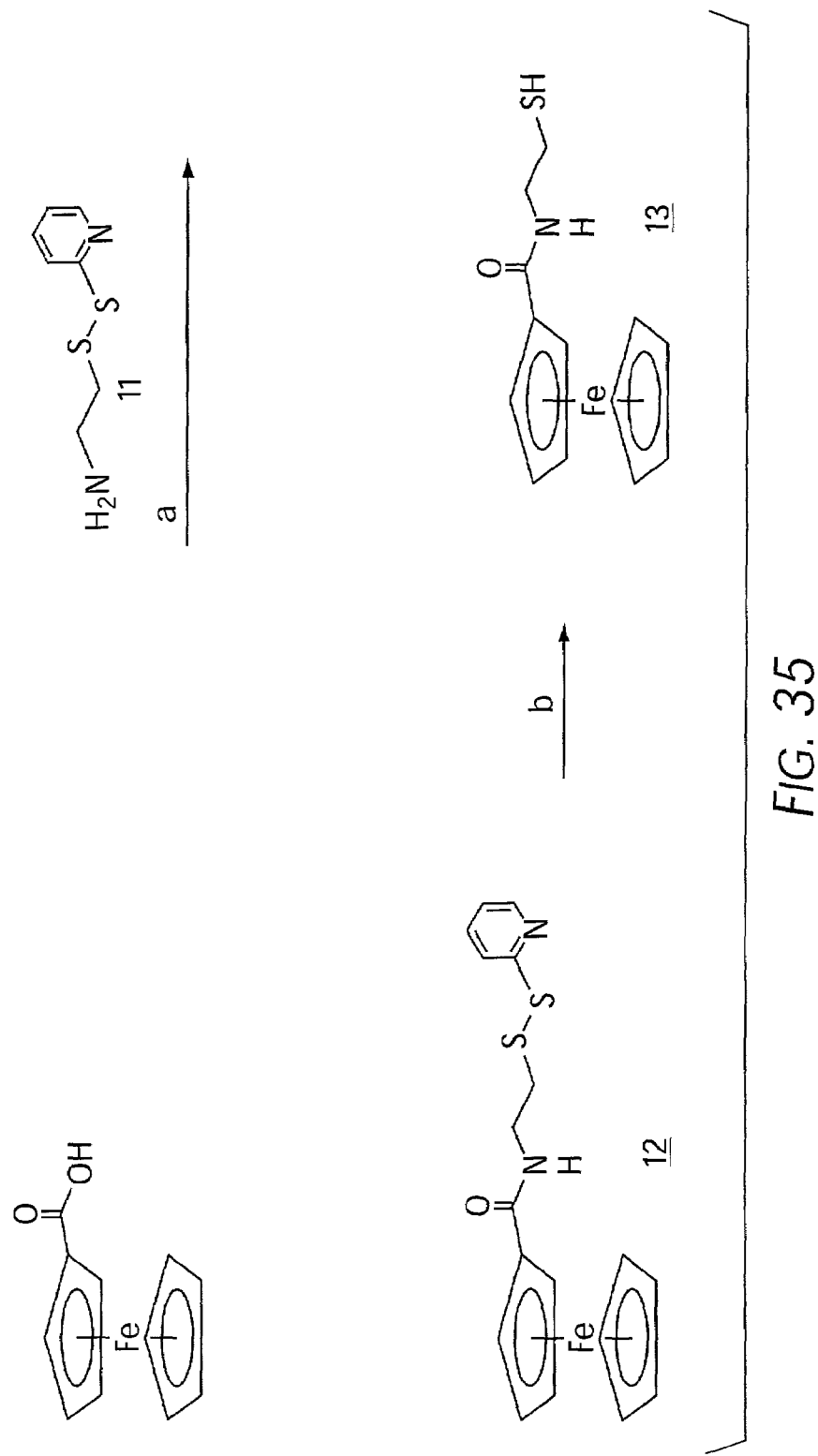
FIG. 35 schematically depicts the synthetic route used to prepare ferrocene-thiol 13, which was used as an electrochemical tag to determine the density of maleimide groups within monolayers. (a) (i) EDC, NHS, $CH_2Cl_2$; (ii) 11, $Et_3N$, DMF; (b) dithiothreitol ("DTT"), $Et_3N$, MeOH.

Non-limiting examples of electrically active compounds include any Ru2+ compounds and hydroquinones. A particularly useful electrically active compound is a bis-cyclopentadienyl metallocene having a cyclopentadienyl ring with a substituent that contains a thiol group. A preferred electrically active compound is ferrocene-thiol 13 (FIG. 35)(ferrocene-2-carboxylic acid (2-mercapto-ethyl)-amide). Ferrocene-thiol 13 is accessible in two steps from commercially available ferrocene carboxylic acid. Referring to the schematic depiction of the preparation of ferrocene 13 in FIG. 35, the carboxylic acid of ferrocene carboxylic acid is transformed to its NHS ester, which is then reacted with the free amine of (2-aminoetyl) -(2-pyridyl) disulfide 11. The disulfide bond of direct product 12 was then reduced with dithiothreitol.

Ferrocene-thiol 13 may be used to test the density of thiolates bearing a maleimide group in a mixed self-assembled monolayer containing a diluent thiolate by taking advantage of its electrical activity. Cyclic voltammetry of mixed thiolate monolayers functionalized with Ferrocene-thiol 13 yields voltammagrams wherein the area under the redox waves is proportional to the density of ferrocene on the surface. It has been found that this technique provides accurate and reliable quantitation of the density of maleimide groups on the surface. Reaction of an excess of ferrocene-thiol 13 with a SAM presenting maleimide is rapid and complete and therefore provides a 1:1 correspondence between the ferrocene density detected by cyclic voltammetry and the density of maleimide functional groups available for reaction with ferrocene-thiol 13. This method of measuring the density of maleimides on the surface is convenient because it requires only one chemical reaction to derivatize the maleimide bearing surface to one that is electrochemically active.

Figure 36A:
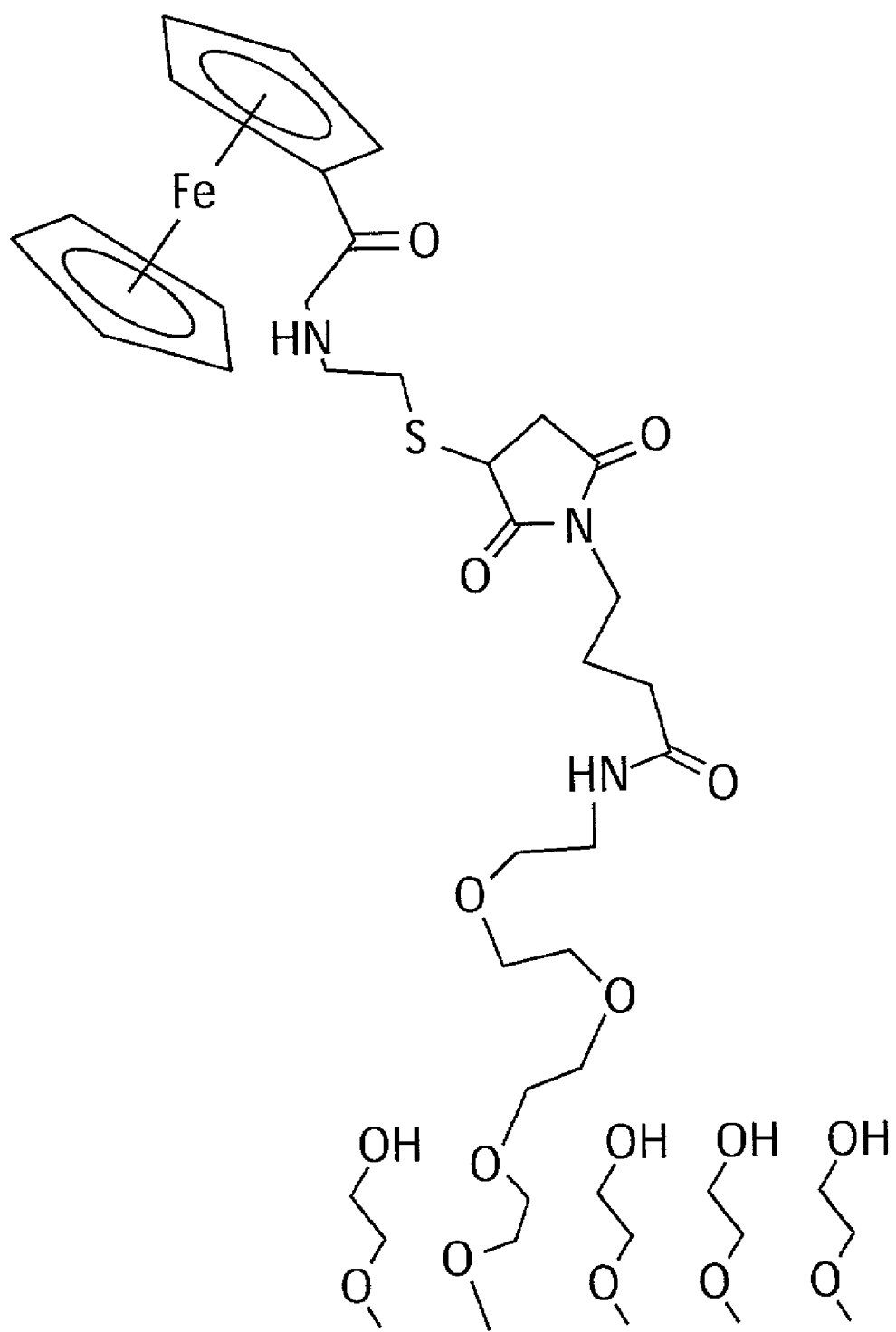
FIGS. 36A, 36B and 36C relates to the determination of the density of maleimide groups within monolayers. SAMs formed from different ratios of disulfides 1 and 2 were treated with a solution of ferrocene-2-carboxylic acid (2-mercapto-ethyl) amide (hereinafter "ferrocene 13"), and then analyzed using cyclic voltammetry in 0.5 M KNO3 at a scan rate of 200 mV/s.
Figure 36B:
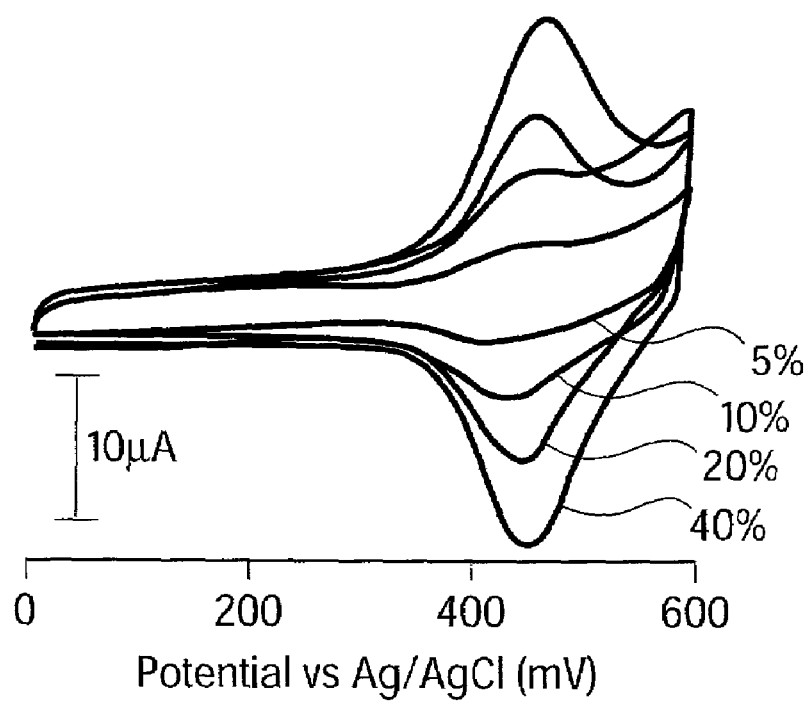
Figure 36C:
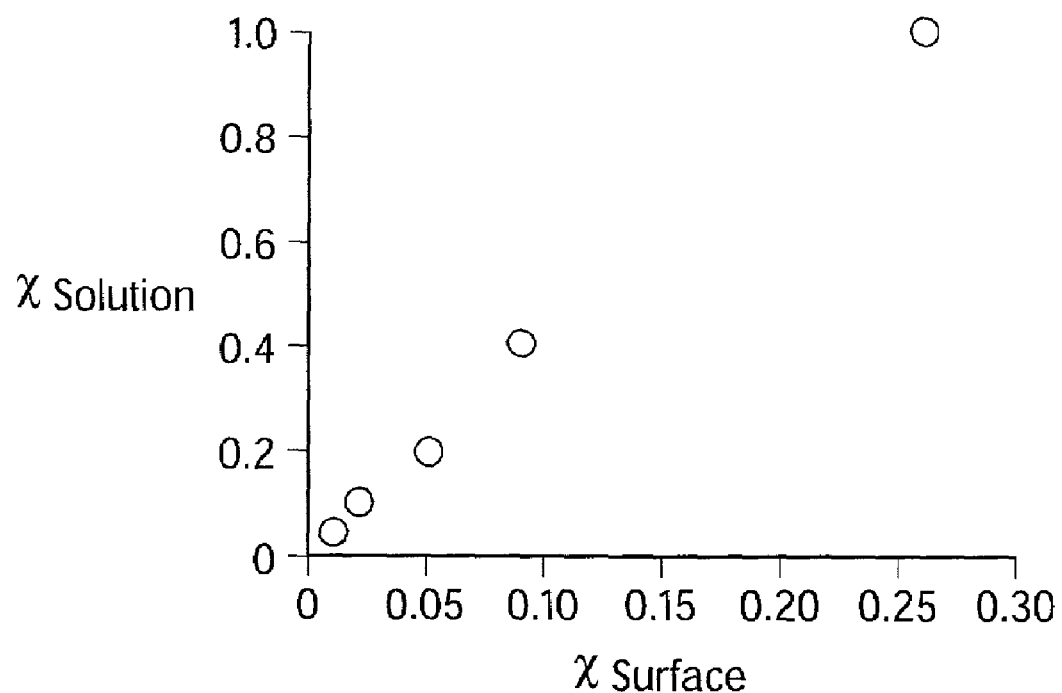

The overlay of cyclic voltammagrams in FIG. 36(A), was obtained from a surface that had been treated with solutions of a disulfides bearing a maleimide and a diluent disulfide in different ratios (indicated on the figure as percent disulfide 1 in disulfide 2 (v/v)). The resulting SAMs were treated with a solution of ferrocene-thiol 13, and then analyzed using cyclic voltammetry in 0.5 M KNO$_3$ at a scan rate of 200 mV/s. The two waves centered at 480 mV correspond to the oxidation and reduction of the immobilized ferrocene molecules. The density of immobilized ferrocene group, and therefore maleimide, can be determined from the normalized areas under the redox waves. The plot of FIG. 36(B) was produced in this manner. FIG. 36(C) is a plot of $X_{solution}$, the mole fraction of disulfide 1 relative to disulfide 2 in the solution from which the monolayers were formed, versus $X_{surface}$, the mole fraction of maleimide incorporated into the surface. As can be seen, the mole fraction of thiolate bearing the maleimide on the surface varies linearly with the mole fraction of disulfide bearing the maleimide in the treatment solution. Therefore, by using the invention's maleimide quantitation technique employing a ferrocene-thiol such as compound 13 and cyclic voltammetry, those skilled in the art may quantitate the maleimide density of a mixed SAM under any desired conditions. This technique provides for a quality control protocol for the production of surfaces presenting Michael acceptors in a manufacturing setting. Further, this aspect of the invention provides a technique for normalizing results of research experiments performed on surfaces prepared according to the invention or other surfaces presenting Michael acceptors.

The present invention also provides measuring the relative density of immobilized ligand by other means known in the art, such as, but not limited to, matrix assisted laser desorption ionization (MALDI), mass spectrometry (MS), and surface plasmon resonance.

Figure 30:
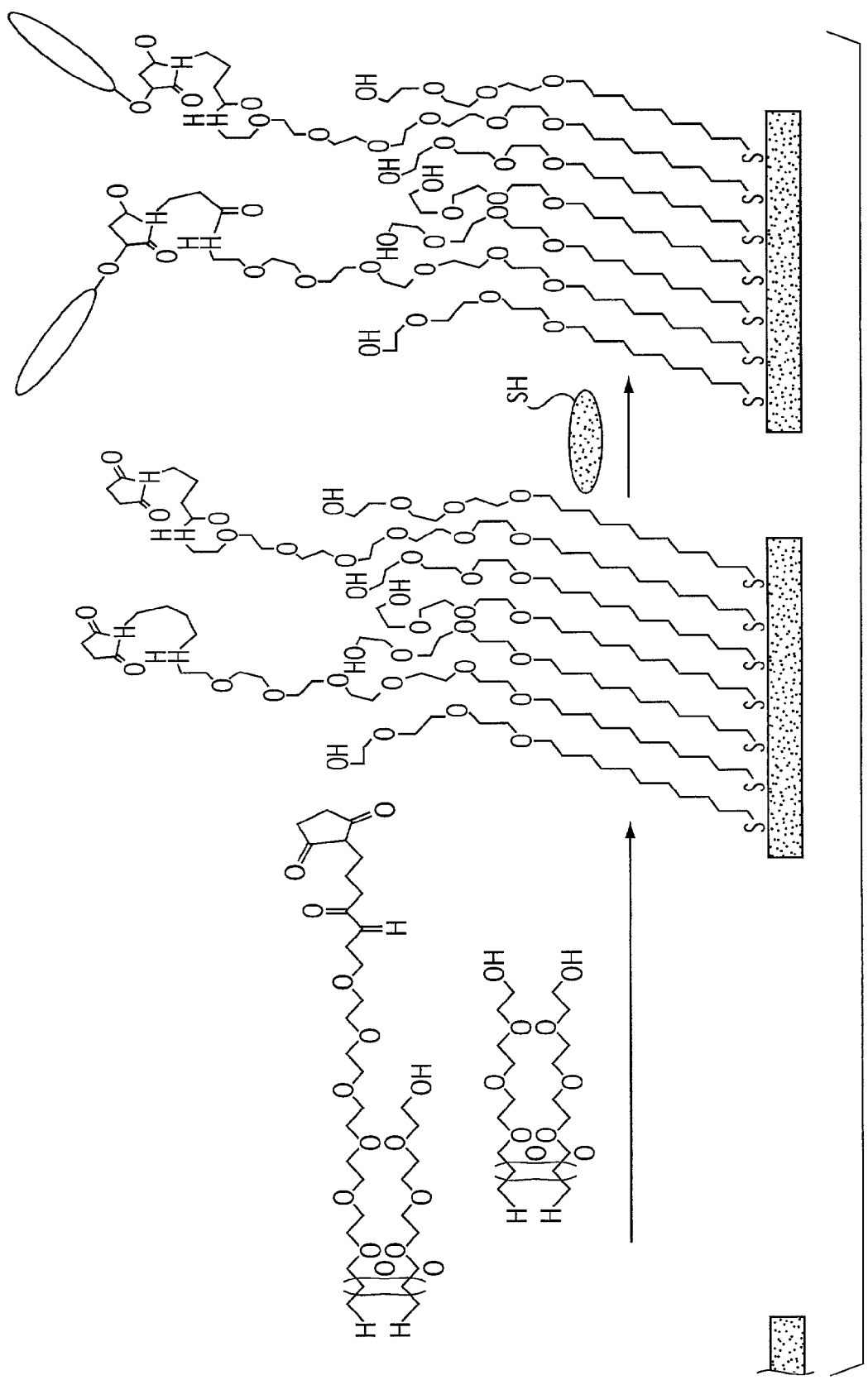
FIG. 30 is a molecular scale representation of the structure of a self assembled monolayer prepared according to the invention.
Figure 32:
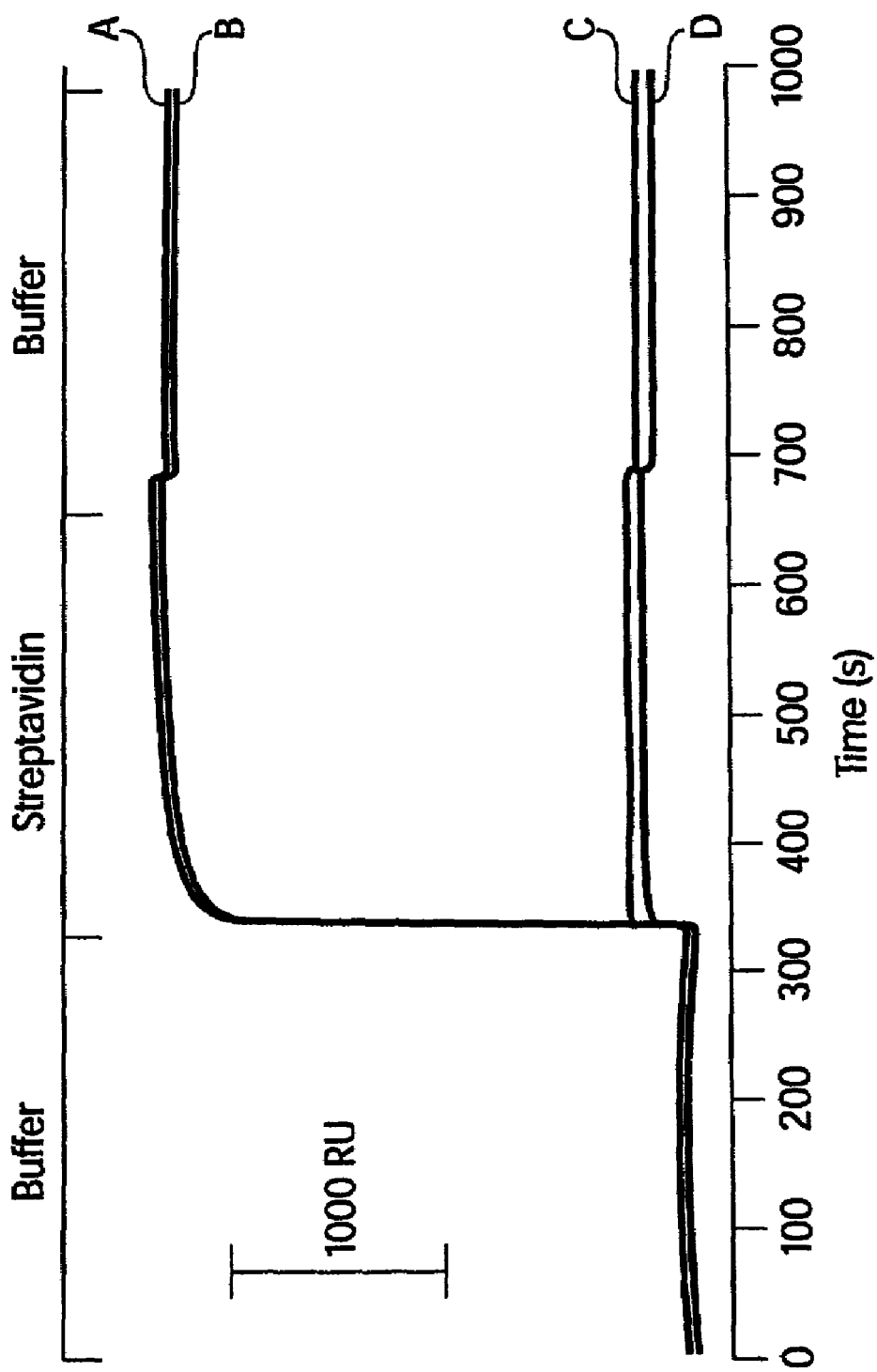
FIG. 32 is an overlay of surface plasmon resonance sensorgrams showing the selectivity of binding to a maleimide-derivatized surface prepared according to the invention after treatment with: (A) a biotinylated, thiol-containing peptide and then streptavidin, (B) a mixture of lysine and biotinylated, thiol-containing peptide, and then streptavidin, (C) mercaptoethanol, then the biotinylated, cysteine-containing peptide and then streptavidin and (D) a biotinylated peptide having no free thiol functionality and then streptavidin.
Figure 33:
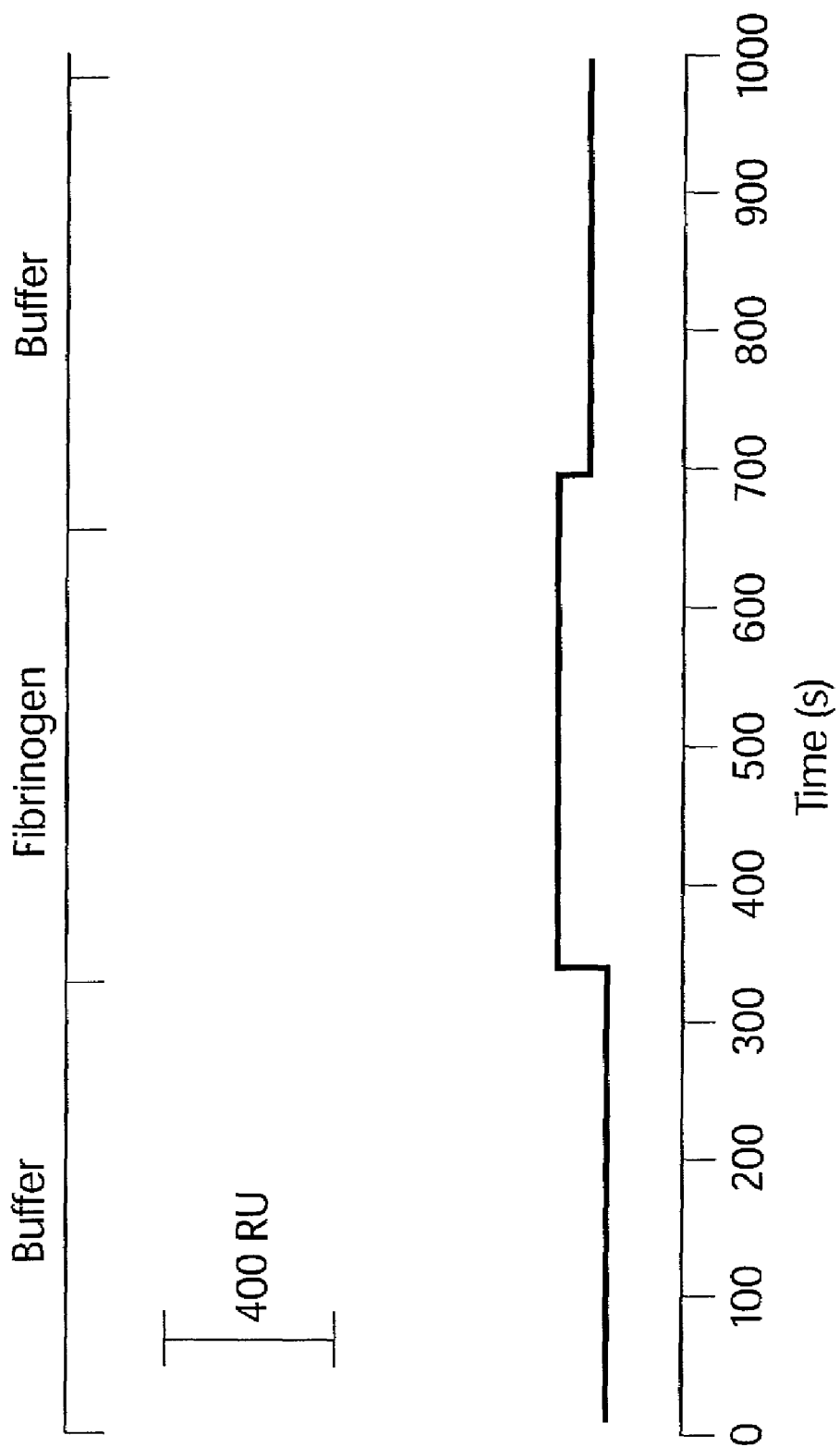
FIG. 33 is a surface plasmon resonance sensorgram showing the lack of non-specific protein binding of a maleimide-derivatized surface prepared according to the invention. The SPR sensorgram was taken after the surface was treated with a biotinylated, thiol-containing peptide and a solution of the sticky protein fibrinogen.
Figure 34:
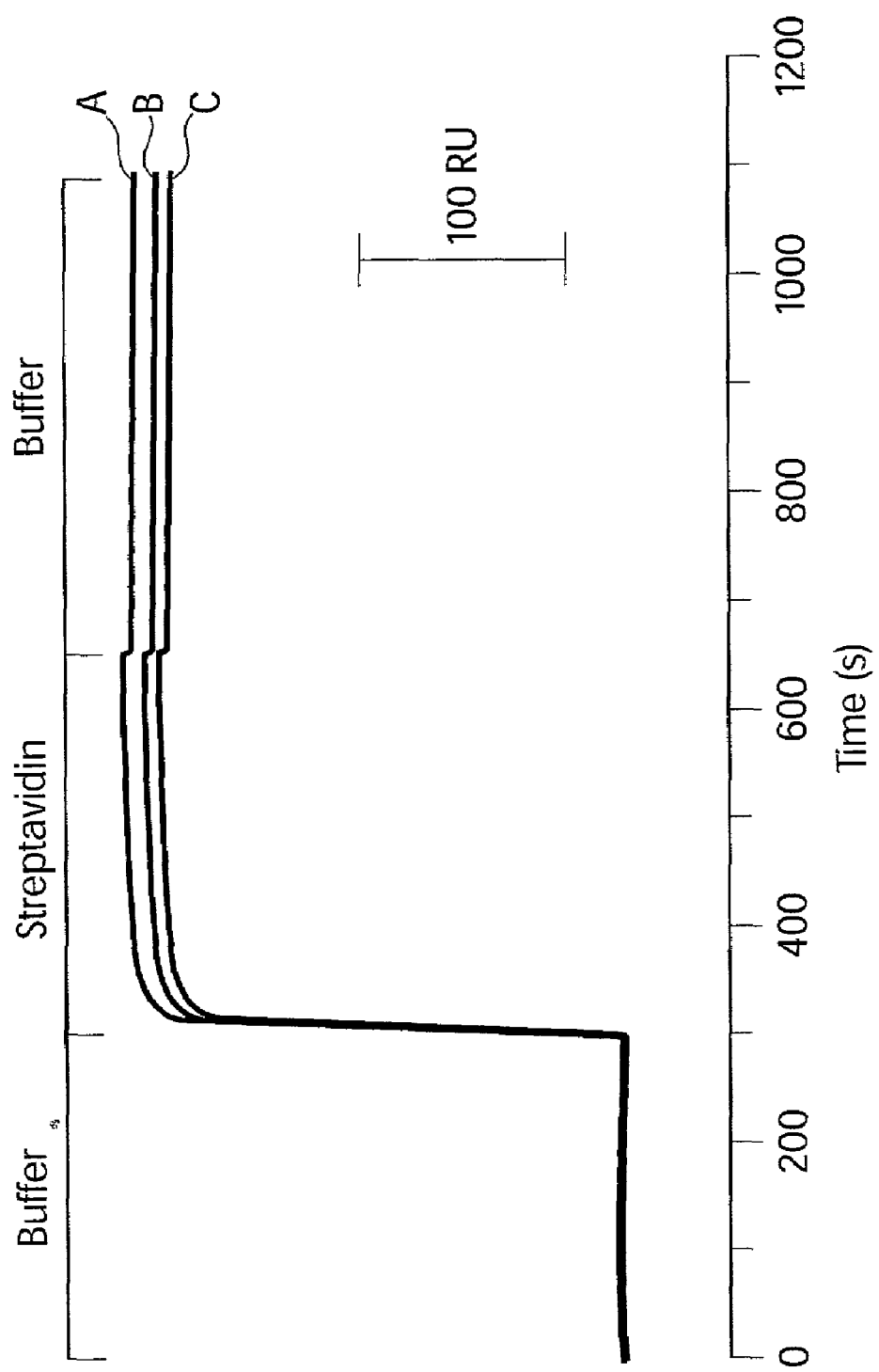
FIG. 34 is an overlay of surface plasmon resonance sensorgrams showing the robustness of surfaces prepared according to the invention under typical assay conditions. Three maleimide-functionalized surfaces were treated with biotinylated, thiol-containing peptide and then exposed to the following conditions: (A) After treatment in PBS buffer for 4 h, (B) control, no exposure, (C) After treatment with a solution of dithreitol and lysine in PBS buffer for 2 h. Each surface was then treated with streptavidin and analyzed by SPR to assay for the proportion of biotinylated peptide remaining on the surface after exposure.

Michael acceptor-derivatized surfaces like that depicted in FIG. 30 are well adapted for selectively immobilizing and orienting functional organic molecules for such uses as biosensors, high throughput assays, binding assays, enzymatic assays and cell cultures. FIGS. 32-34 depict surface plasmon resonance ("SPR") sensorgrams that demonstrate the selectivity of covalent immobilization by the present invention and the robustness of the surface. Surface binding was detected using biotinylated, cysteine-containing peptides and streptavidin. SAMs presenting the maleimide group at a density of 2% were applied to gold-coated coverslips according to the Examples. The SAM coated coverslips were each treated with solutions containing various reactive molecules dissolved in phosphate buffer (pH 6), and the reactivity of the surface was characterized by flowing the protein streptavidin, which selectively binds biotin, over the SAM. Streptavidin binding was quantitated by surface plasmon resonance.

Referring to FIG. 32 sensorgram (A), the SAM-coated coverslip was treated with a solution of the model biotinylated peptide biotin-NH-Arg-Asp-Cys-CONH2 (1.2 mM) for 12 minutes. 2280 RU of streptavidin binding was observed. Sensorgram (B) was obtained using a solution containing a mixture of the model peptide (0.6 mM) and lysine (16 mM). The SAM-coated coverslip was immersed in the solution for 12 minutes and then treated with streptavidin. Sensorgram (B) shows the same amount of streptavidin binding and therefore the same amount of bound model peptide as in (A) when a pure solution of the model peptide was used. These results indicate that an amine group, like the amine group of the lysine side chain, is essentially non-competitive with thiol as a Michael donor. Sensorgram (C) was obtained from a SAM-coated coverslip that was treated first with a solution of mercaptoethanol (1 mM) for 12 minutes and then with the solution of model peptide for 12 minutes as in (A). As can be seen, the pretreatment blocked streptavidin binding by inactivating the Michael acceptors with the hydrophilic Michael donor mercaptoethanol, thus preventing the immobilization of the biotinylated model peptide. Sensorgram (D) was obtained from a SAM-coated coverslip that was treated with a solution of a different model biotinylated peptide (biotin-NH-Arg-Asp-Lys-CONH 2) that lacks a thiol group. Treatment of the SAM-coated coverslip with a solution containing the model peptide biotin-NH-Arg-Asp-Lys-CONH2 (4 mM) for 12 minutes resulted in no streptavidin binding, showing that the surface is not reactive toward amines.

FIG. 33 shows that surfaces prepared according to the invention are inert to non-specific protein adsorption. FIG. 33 is a surface plasmon resonance sensorgram of a SAM presenting maleimide at a density of 2%. The SAM-coated coverslip was treated with the biotinylated, thiol-containing, model peptide biotin-NH-Arg-Asp-Cys-CONH$_2$ (1.2 mM) for 12 minutes. Afterwards, a solution of the "sticky" protein fibrinogen (0.5 mg/mL) was flowed over the surface. Only 60 RU of adsorption was observed. Another coverslip was treated with the model peptide solution and then treated with streptavidin that had been pre-incubated with biotin. Surface plasmon resonance of that coverslip showed that the streptavidin also did not attach to the surface.

FIG. 34 demonstrates the stability of surfaces prepared according to the invention under normal assay conditions. Each of three coverslips presenting maleimide at 2% density was treated with a solution of the peptide biotin-NH-Arg-Asp-Cys-CONH 2 (1.2 mM) for 12 minutes to afford a surface presenting biotin and the peptide. One of the coverslips was set aside as a control and the other two were immersed in solutions selected to mimic conditions to which surfaces for immobilized proteins would be exposed during use. One of the test coverslips was immersed in PBS buffer (pH 7.4) for 4 hours. The other test coverslip was immersed in a solution of DTT (5 mM) and lysine (5 mM) in PBS buffer (pH 7.4) for 2 hours. Afterwards, the test surfaces and control surfaces were rinsed and then treated with streptavidin and then analyzed by SPR. Since the SPR response is proportional to the amount of streptavidin bound to the surface, the response reflects the proportion of biotinylated peptide remaining on the surface after exposure. Sensorgram (B) was taken of the control. Sensorgram (A) was taken of the coverslip that was exposed to PBS buffer. Sensorgram (C) was taken of the coverslip that had been exposed to DTT and lysine in PBS buffer. These sensorgrams show nearly equal SPR response between the exposed surfaces and the control surface, thus demonstrating that the monolayers were stable under these conditions.

Accordingly one embodiment of the present invention provides a process for measuring density of covalent bond forming reaction groups on a mixed monolayer surface. The mixed monolayer surface comprises a first monolayer moiety and a second monolayer moiety. The first monolayer moiety has an electrically active compound to provide a detectable signal as well as a covalent bond forming reactive group. The second monolayer moiety has an inert group. The process comprises measuring the detectable signal, and correlating the measurement of the signal to the density of the first monolayer moiety. Then the density of the first monolayer moiety may be correlated to the density of the covalent bond forming reaction groups.

The electrically active compound is preferable a bis-cyclopentadienyl metallocene having a cyclopentadienyl ring with a substituent that contains a thiol group such as ferrocene-2-carboxylic acid (2-mercapto-ethyl)-amide. Preferably the detectable signal is measured by cyclic voltammetry.

In another embodiment, there is provided process for measuring density of immobilized functional organic molecules on a mixed monolayer surface. The mixed monolayer surface is as described above. The process comprises measuring the detectable signal, and correlating the measurement of the detectable signal to the density of the first monolayer moiety, and correlating the density of the first monolayer moiety to the density of the immobilized functional organic molecules. Preferably the detectable signal is measured by cyclic voltammetry. The preferred electrochemical groups are described above.

Using the above embodiments relating to characterizing the density of covalent bond forming reactive groups on the thiolate monolayer surface, it was discovered that the ratio of the monolayer forming disulfide moieties in solution does not produce a monolayer thiolate surface having the exact same ratio. For example, if the ratio of the first monolayer forming disulfide moiety bearing a covalent bond forming reactive group to the second monolayer forming disulfide moiety bearing an inert group is 2:98 in solution, the surface formed after contacting the monolayer forming disulfides with the coinage metal surface will not be exactly at the same 2:98 ratio. In other words, just because the solution contained 2% monolayer forming disulfide moieties bearing a covalent reactive group, the monolayer thiolate surface will not have exactly 2% thiolates bearing a covalent bond forming reactive group. Thus, the inventors have discovered that there is a solution to surface variability. This appears to be due to the fact that impurities in the solution may alter the ratio of thiolates formed. In addition, since the two monolayer forming disulfide moieties have different structures, they will have slightly different reactivities with the surface. For example, one group might be more or less soluble in the solvent system and therefore may have a higher or lower kinetic constant relative to the other disulfide. Typically, if it the disulfide is less soluble, it tends to be more reactive with the coinage metal surface.

Nevertheless, the inventors have discovered that once the solution is used to form the thiolate monolayer, and the monolayer is characterized, preferably using the methods described above, there is virtually no surface to surface variability. Thus, for example, if a solution of first and second monolayer forming disulfide moieties were present at a 2:98 ratio in solution, and that solution was contacted with a coinage metal surface to produce a mixed self-assembled thiolate monolayer having a density ratio of 2.5:97:5, the next time that same solution was used to prepare another thiolate monolayer, the surface would again have the 2:5:97.5 ratio of the two thiolates.

Thus, to achieve the desired surface density, the ratio in solution can be tweaked and altered until it produces the desired ratio on the surface. Once that desired density is achieved on the surface, that same solution may be used over and over to produce a surface with a known density.

It is important to note that due to impurities, different batches of solutions having a certain ratio will not always produce the same density on the surface. Thus, the methods of the present invention relating to characterizing the surface should be used to characterize the density of the surface every time a new batch of solution is made.

Accordingly, one embodiment of the present invention provides a process for making an article having a coinage metal surface region and a mixed self-assembled monolayer of thiolate, wherein the surface will have a predetermined density of covalent bond forming reactive groups, and thus have a predetermined density of groups available for binding/immobilizing functional organic molecules. This process comprises contacting the coinage metal surface with a solution of a mixture of a first monolayer forming disulfide moiety bearing a covalent bond forming reactive group, and a second monolayer forming disulfide moiety bearing an inert group. The mixture of monolayer forming disulfide moieties is in a solution of an inert solvent as described above. The solution comprises the first and second monolayer forming disulfide moieties in a predetermined ratio of the first monolayer forming disulfide moiety to the second monolayer forming disulfide moiety. When the solution of the monolayer forming disulfide moieties contact the coinage metal surface region, a mixed self-assembled monolayer of thiolates is formed on the surface region to form a self-assembled thiolate monolayer. The predetermined ratio of the first and second monolayer forming disulfide moieties in the solution determines the ratio of the first and second monolayer thiolate moieties on the coinage metal surface region.

The present invention further provides an article having a coinage metal surface and a mixed self-assembled monolayer surface. The mixed self-assembled monolayer surface comprises a first and second monolayer moiety. The first monolayer moiety comprises a thiolate bearing a covalent bond forming reactive group. The second monolayer moiety comprises a thiolate bearing an inert group. The first and second monolayer moieties are present in a predetermined ratio of the first monolayer moiety to the second monolayer moiety. In preferred embodiments, the first monolayer moiety is 20 mole percent of less of the total of the first and second monolayer moieties on the surface. In a more preferred embodiment, the first monolayer moiety is 5 mole percent of less of the total of the first and second monolayer moieties on the surface. In a most preferred embodiment, the first monolayer moiety is 0.01_mole percent to about 2 mole percent of the total of the first and second monolayer moieties on the surface.

The present invention also provides a process for immobilizing a functional organic molecule in a predetermined density on a mixed monolayer surface. The mixed monolayer surface comprising a first monolayer moiety having a covalent bond forming reactive group and a second monolayer moiety having an inert group. The first monolayer moiety is present in a predetermined density in the mixed monolayer surface. This process comprises the step of contacting the mixed monolayer surface with the functional organic molecule, wherein the contacting step forms a covalent bond between the functional organic molecule and the covalent bond forming reactive group of the first monolayer moiety to immobilize the functional organic molecule. The density of the immobilized functional organic molecule is determined by the density of the first monolayer moiety in the mixed monolayer surface. In a preferred embodiment the covalent bond formation does not require an enzymatic reaction.

The present invention provides yet another method of controlling the density of immobilized functional organic molecules on a coinage metal surface. In this embodiment, the density of immobilized functional organic molecules is determined by adjusting the ratios of three different monolayer forming moieties (two monolayer forming disulfides moities, each bearing a different covalent bond forming reactive group, and one monolayer forming disulfide moiety bearing an inert group) in solution and thus, on the surface. Preferably, each of the different covalent bond forming reactive groups bind to a functional organic molecule using a different chemistry. Non-limiting chemistries include immobilization of a nucleophile through a Michael addition reaction and immobilization of an alkene functioning as a dienophile in a Diels Alder reaction. Those skilled in the art would appreciate the use of other chemistries achieving covalent bond formation.

Another non-limiting example of two different covalent bond forming reaction chemistries is where one covalent bond forming group is a maleimide; the other covalent bond forming group is an acetophenone; and the inert group is as a tri(ethylene glycol). The acetophenone selectively reacts with a hydrazide tagged molecule in a nucleophilic addition, and the maleimide selectively reacts with a thiol in a Michael addition. The density of the maleimide and the acetophenone is determined by the ratio of the monolayer forming disulfide moieties bearing these groups in solution. Further, the density of various immobilized functional molecules also depends on selectively reacting the maleimide and/or the acetophenone with immobilized groups carrying thiol and/or hydrazide respectively.

The present invention provides yet another method of controlling the density of immobilized functional organic molecules on a coinage metal surface. In this embodiment, the density of immobilized functional organic molecules is determined by switching on or off an electrochemically switchable group after a desired amount of a functionalized organic molecule has been immobilized. See, Yousaf & Mrksich, *J. Am. Chem. Soc.* (1999) Vol. 121, 14286-14287, hereby incorporated by reference.

This process involves the use of a switchable covalent bond forming reactive group and a second monolayer moiety having an inert group in the mixed monolayer surface. The switchable covalent bond forming reactive group has a reactive state and an unreactive state. An activating signal turns the unreactive state to the active state to turn on the switchable covalent bond forming reactive group. A quieting signal turns the reactive state to the unreactive state to turn off the switchable covalent bond forming reactive group. In this process an activating signal is used to turn on the switchable covalent bond forming reactive group to allow a covalent bond to form between the covalent bond forming reactive group of the first monolayer moiety and the functional organic molecule to immobilize the functional organic molecule. The covalent bond formation to is allowed to take place for a length of time. After the length of time, a quieting signal is provided to turn off the switchable covalent bond forming reactive group. The length of time the that the switchable covalent bond forming reactive group remains on determines the density of the immobilized functional organic molecule on the mixed monolayer surface. As discussed above, preferably the covalent bond formation does not require an enzymatic reaction. The covalent bond forming reactive groups, the inert groups and the functional organic molecule are as discussed above.

In yet another embodiment involving a switchable covalent bond forming reactive group, a mixture of a first disulfide compound bearing a switchable group having a covalent bond forming reactive group and a disulfide compound bearing an inert group are contacted with a coinage metal surface to form a mixed monolayer of thiolates on the surface. The proportion of thiolates bearing the switchable group on the surface is determined by the predetermined ratio of the first disulfide compound and the second disulfide compound in the mixture. A first reaction is then performed for a predetermined length of time to allow a first functional organic molecule to bond with the switchable group. Then the chemical reactivity of the switchable group is temporarily turned off to inhibit further reaction of a first functional organic molecule with the switchable group. Any unbound first functional organic molecules may be washed away. The chemical reactivity of the switchable group is then turned back on, a second functional organic molecule is allowed to bond with the switchable group. The ratio of the first and the second functional organic molecules on the surface is determined by the length of time of the first reaction is allowed to proceed resulting in a surface presenting two different ligand types, each at a controlled density.

For immobilizing functional organic molecules such as peptides, oligopeptides, polypeptides, proteins, carbohydrates, cells and the like, it is preferred to use a mixed monolayer composed of a thiolate bearing an inert group and less than about 20 mole percent, more preferably less than about 5 mole percent and, most preferably from about 0.01 to about 2 mole percent of the thiolate bearing a covalent bond forming reactive group. At higher densities of the covalent bond forming reactive group, such as a maleimide, some non-specific protein adsorption can occur. A surface presenting thiolate bearing a maleimide at about 2% density in a self assembled monolayer derived from disulfides bearing an inert group of the formula: H—(O—(CH$_2$)$_y$)$_z$—(CH$_2$)$_x$—S—S—(CH$_2$)$_x$—((CH$_2$)$_y$—O)$_z$—H, wherein x, y and z are as previously defined, allows for selective covalent immobilization with very low non-specific binding.

It will be appreciated by one skilled in the art that in order to correlate the density of the covalent bond forming reactive groups on the surface to the amount of immobilized functional organic molecule, the reaction between the covalent bond forming reactive group and the functional organic molecule must be well behaved and go to completion. Hence, a reaction such as Michael addition between a maleimide group on the monolayer thiolate, with a thiol group on a functional organic molecule is especially preferred as this reaction is well characterized, well behaved and goes to completion. Further, the relative rarity of thiol groups on exposed surfaces of proteins and other complex biological materials like oligonucleotides, carbohydrates, co-factors and small molecule drugs favors selectively in immobilizing such materials on a surface by direct Michael addition to the surface bound Michael acceptor.

Accordingly, to immobilize functional organic molecules according to an embodiment of the invention wherein the covalent bond forming reactive group is a Michael acceptor, the functional organic molecule may be functionalized with a thiol group. The functional organic molecule may be functionalized with conjugated carbon-carbon double bonds. In this embodiment, the reacting step involves a cycloaddition reaction between the Michael acceptor and the conjugated carbon-carbon double bonds.

Since Michael acceptors like maleimide behave as dienophiles, the monolayer thiolate moieties can be used to covalently immobilize functional organic molecules that have conjugated carbon-carbon double bonds by Diels Alder or other cycloaddition reaction. Immobilization by cycloaddition is a highly chemoselective method of immobilizing peptides, polypeptides, carbohydrates, oligonucleotides and oligonucleosides since dienyl is not a naturally occurring functionality of these biomolecules. Consequently, such naturally occurring biomolecules must be derivatized with a diene. Peptides and polypeptides can be derivatized with a dienyl group by chain extension with an amino acid-bearing dienyl group on its side chain. There is a rich literature on derivatizing functional organic molecules so as to contain conjugated carbon-carbon double bonds. A couple of patents/publications with teachings on the subject of derivatizing oligonucleotides and polypeptides with dienes are U.S. Pat. No. 5,843,650 and International Publication No. WO 98/30575, which are incorporated by reference herein. See also, Bergstrom et al *J. Am. Chem. Soc.* 1977, 100, 8206.

Many techniques are known in the art for thiolating compounds. See generally, Hermanson, G. T. *Bioconjugate Techniques* (Academic Press: New York 1996). For instance, free amine groups can be substituted with thiol-bearing substituents using Traut's reagent, N-succinamidyl-S-acetylthioacetate (SADA), N-succinimidyl 3-(2-pyridyldithio)propionate (SPDP)/DTT, CMPT, N-acetylhomosysteinthiolacetone, and S-acetylmercaptosuccinic anhydride to name but a few. In some cases the direct product is a thioacetate that must be hydrolyzed to reveal the free thiol. Aldehydes and ketones may be thiolated with 2-acetamido-4-mercaptobutyric acid anhydride ("AMBH"). Carboxylic acids may be derivatized to an N-(2-thioethyl) amide by diimide (e.g. EDC) coupling with cystamine and then reducing the disulfide bond. Common mild S—S bond reductants for use in biological system are mercaptoethanol, 2-mercaptoethylamine ("2-MEA"), DTT, dithiocrythritol ("DTE") and NaBH$_4$. Diimide catalyzed coupling of cystamine also can be used to attach thiol groups to the phosphate groups of an oligonucleotide. Cystamine bonds directly to phosphorous displacing oxygen. The cystamine is then reductively cleaved to reveal the thiol. These and other procedures for thiolating compounds are well known and accessible in reference works known to those in the art, such as *Bioconjugate Techniques* and others.

In another embodiment, an oligopeptide, peptide or polypeptide may be conveniently derivatized by coupling to a cysteine. Indirect immobilization of a protein via a ligand allows the thiolation reaction, if necessary, to be performed on a small molecule that is likely to have less interfering functionality than, for example, a large protein or oligonucleotide. Thus, such a ligand may be derivatized with thiol according to, for example, the methods previously described. A technique for thiolation that is also well adapted for thiolation of small molecules involves first derivatization of the molecule with a vinyl substituent. For instance, if the ligand is provided with a moderately nucleophilic substituent such as amine or hydroxyl, a vinyl group may be conventionally installed by reaction with an allyl halide or sulfonate. The vinyl group is then reacted with thioacetic acid under free radical conditions to add thioacetate to the vinyl group. Removal of the acetate group by hydrolysis leaves either a 3-thiopropyl substituent or a 2-thioethyl substituent on the ligand, depending on where the R group is on the vinyl group.

Carbohydrates can also be designed with a thiol-containing aglycone. Appropriate carbohydrate derivatives suitable for immobilization have been described or can be prepared easily by one skilled in the art. See, e.g. Liang et al. *PNAS* 2000, 97, 13092-96, Horan et al. *PNAS* 1999, 96, 11782-86.

In a preferred method, carbohydrates are derivatized to have a thiol chemical tag that will react with a covalent bond forming reactive group (such as a maleimide) on the monolayer surface. In this method, the ligation chemistry is selective, and thus helps to ensure that non-specific chemical reactions with functional groups on or within the carbohydrate do not occur. Such selective ligation chemistry results in oriented immobilization of carbohydrates. This is advantageous, for example, when examining specific protein binding to an immobilized carbohydrate because all binding interactions with the carbohydrate are the result of specific protein binding to the carbohydrates and not due to nonspecific binding.

In a preferred embodiment of the present invention, the thiol chemical tag is produced in the following manner. The carbohydrates to be immobilized are derivatized by converting a peracetylated sugar, having an n-pentenyl group on the reducing end, to a thiolacetate derivative. See FIG. 39. The thioacetate sugars are preferably saponified under oxygen-free conditions to yield, after neutralization, the fully deprotected carbohydrate containing a thiol group at the reducing end. (Hereinafter, referred to as thiol-carbohydrate.)

Figure 40:
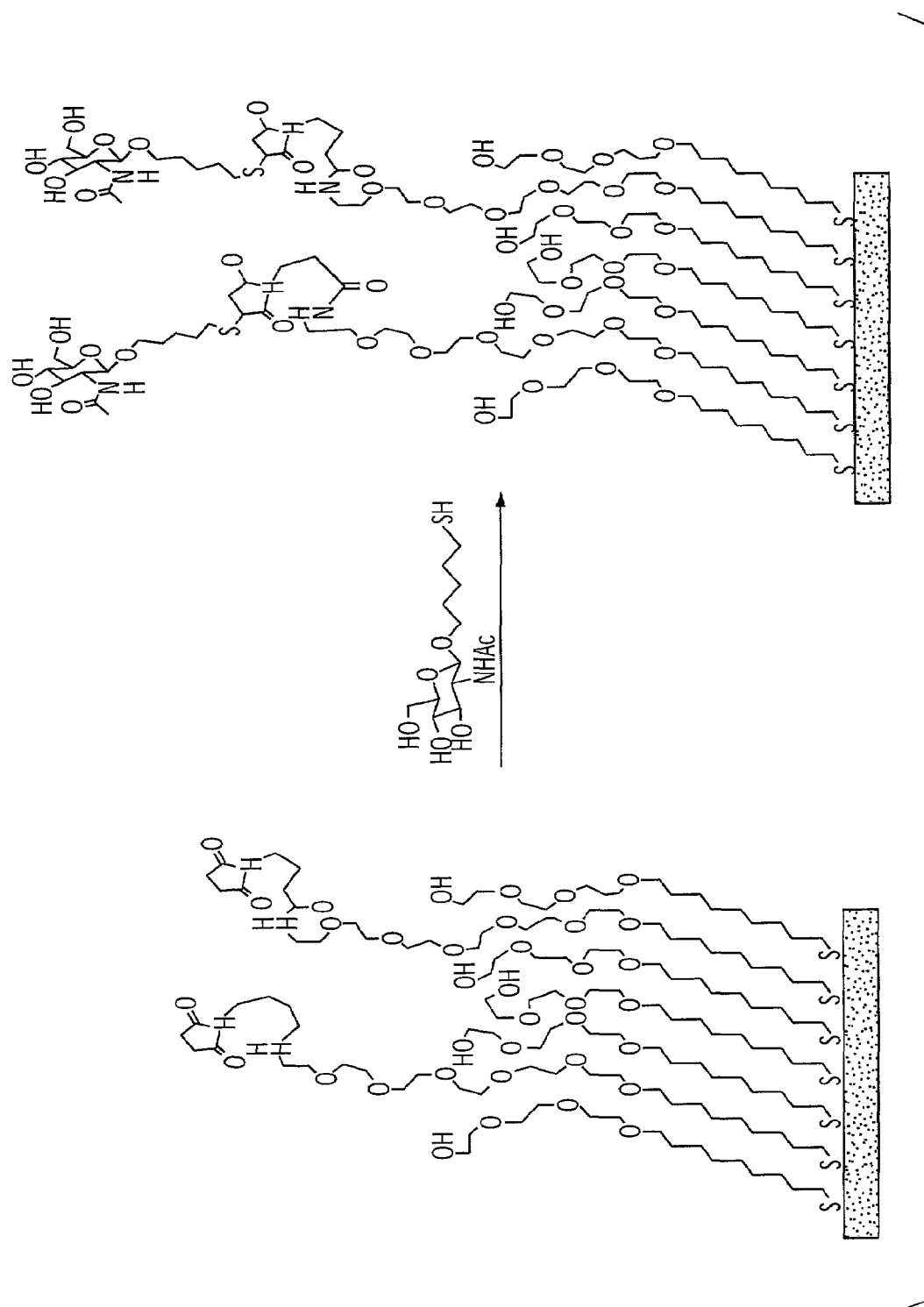
FIG. 40 illustrates the formation of surface presenting immobilized carbohydrates. SAMs presenting maleimide at 1-2% density are contacted with solutions (pH 6) containing thiol-tagged carbohydrates for 30 min. The resulting surface presents the carbohydrates in a well-defined orientation at controlled densities.

This thiol-carbohydrate may covalently attach to monolayers of a SAM presenting a maleimide. See FIG. 40. Preferably, the SAM presenting maleimide contains maleimide at a density of from about 0.1 to about 50% in a inert tri(ethylene glycol) matrix. More preferably, the maleimide density is from about 1% to about 10%.

To ensure a complete immobilization reaction, a solution containing the dissolved thiol-carbohydrate and SAM are incubated for about 1 hour. Preferably the thiol-carbohydrate in the solution is at a concentration of from about 0.01 mM to about 100 mM. More preferably, the concentration of thiol-carbonate is from about 0.1 mM to about 5 mM. Most preferably the thiol-carbohydrate is at a concentration of about 1 mM.

The derivatization reaction is performed in a solvent such as methanol or water and is preferably performed at a pH range from about pH 4 to about pH 10. The solvents used are preferably methanol or water. More preferably the pH is from about 5 to about 8. Most preferably the pH is about 6.0. The optimal temperature range is from about 0 C. to about 60 C. More preferably, the optimal temperature range is from about 10 C. to about 40 C. Following the derivatization reaction, the surface is preferably rinsed with water and ethanol and dried under a stream of nitrogen.

By providing for the immobilization of carbohydrates, the present invention provides carbohydrate-based assay surfaces. For example, an immobilized thiol-carbohydrate can be used in various enzymatic assays such as a glycosyltransferase assay. See FIG. 41 and Example 13.

Figure 41:
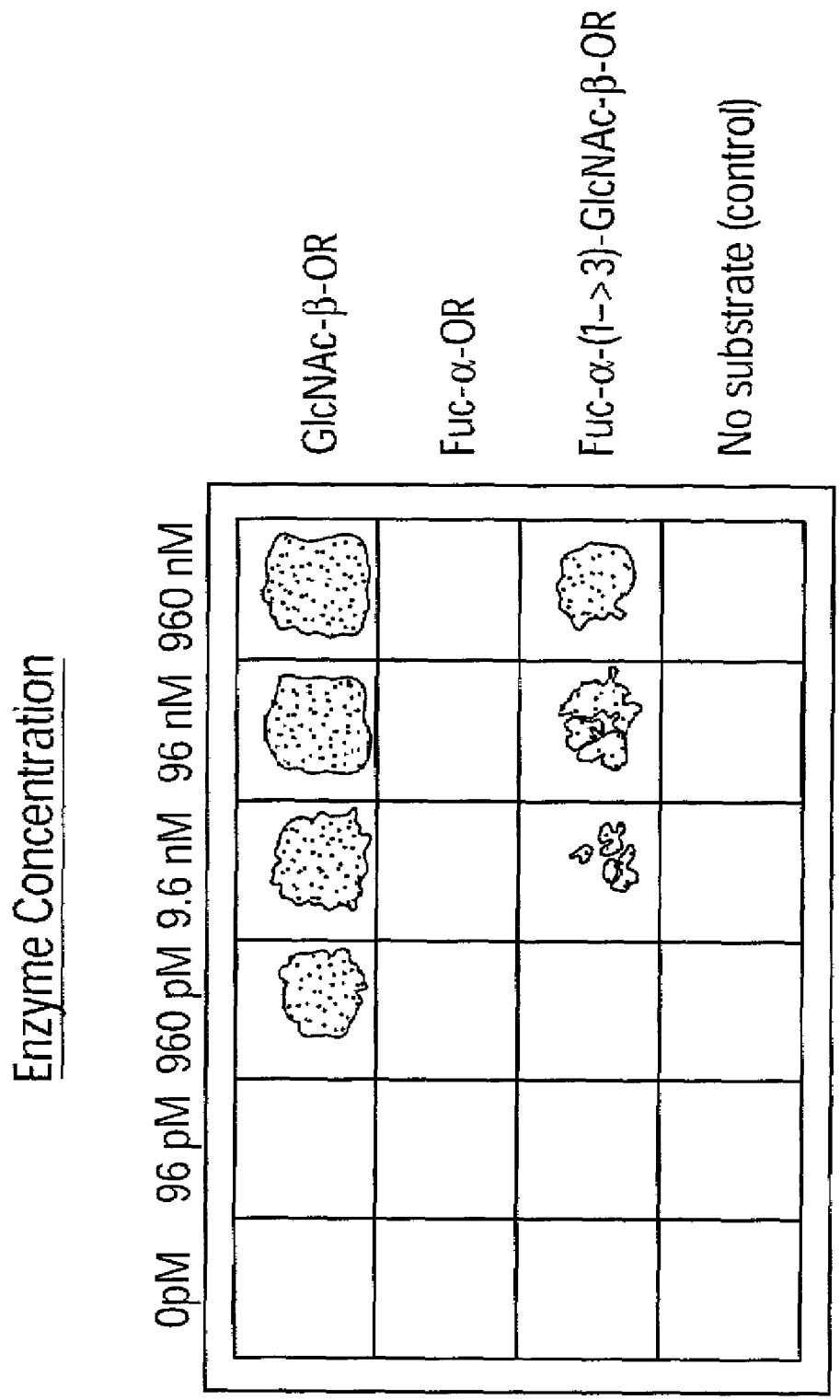
FIG. 41 represents the results of a glycosyltransferase assay. The surface comprises 3 different carbohydrate substrates defined by columns and a control column (no substrate). Each row was reacted with a different concentration of β1,4-galactosyltransferase and a constant concentration of sugar donor (UDP [$^{14}$C] galactose, 3.5 µM). The reaction was detected by phosphorimaging. It is clear that only the immobilized GlcNAc was a substrate for this particular enzyme.
Figure 42:
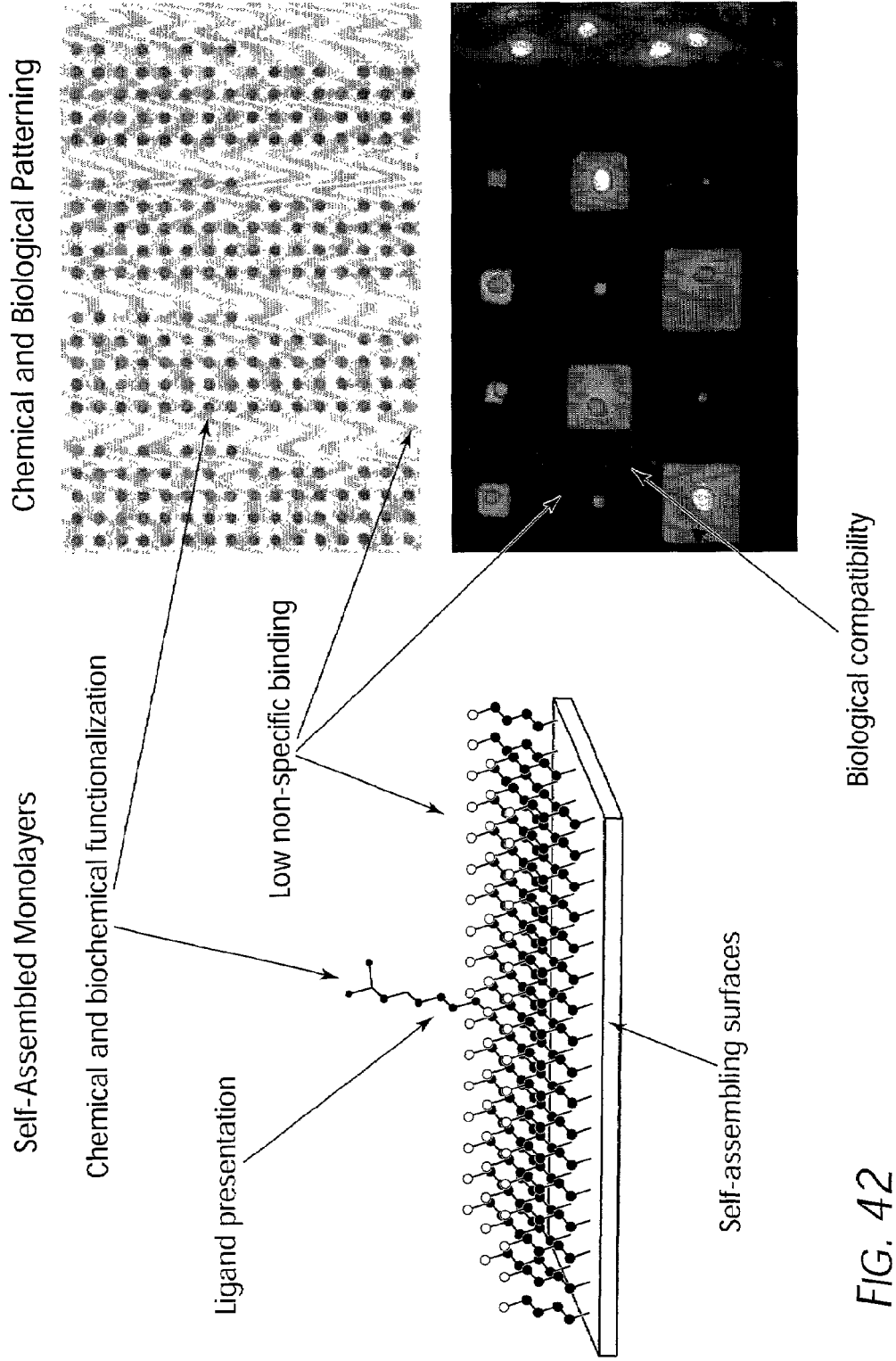
FIG. 42 depicts the use of soft lithography to create self-assembled monolayers and chemical and biological patterning of device surfaces. The combination of chemical and biochemical functionalization, ligand presentation, low non-specific binding, self-assembling surfaces and biological compatibility provides a highly reproducible, highly sensitive platform for performing quantitative assays.
Figure 43:
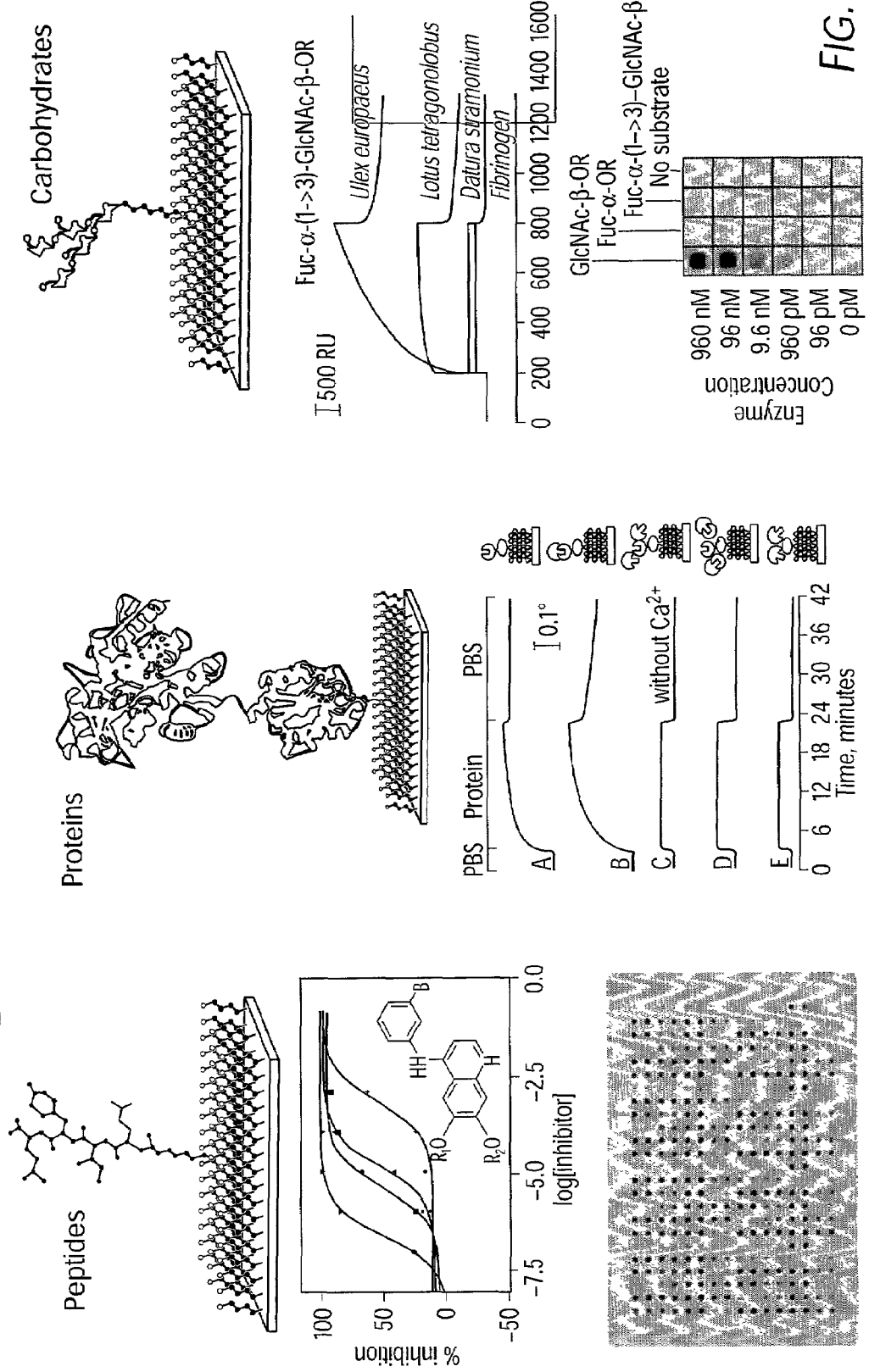
FIG. 43 depicts various surface chemistries for use in quantitative biochemical assays. The immobilization methods and devices can be used for a number of different applications. For example, these methods and devices are useful for immobilization peptides for binding assays, immobilization of proteins for protein-protein interaction assays, or immobilized carbohydrates for protein-carbohydrate interaction assays.
Figure 44:
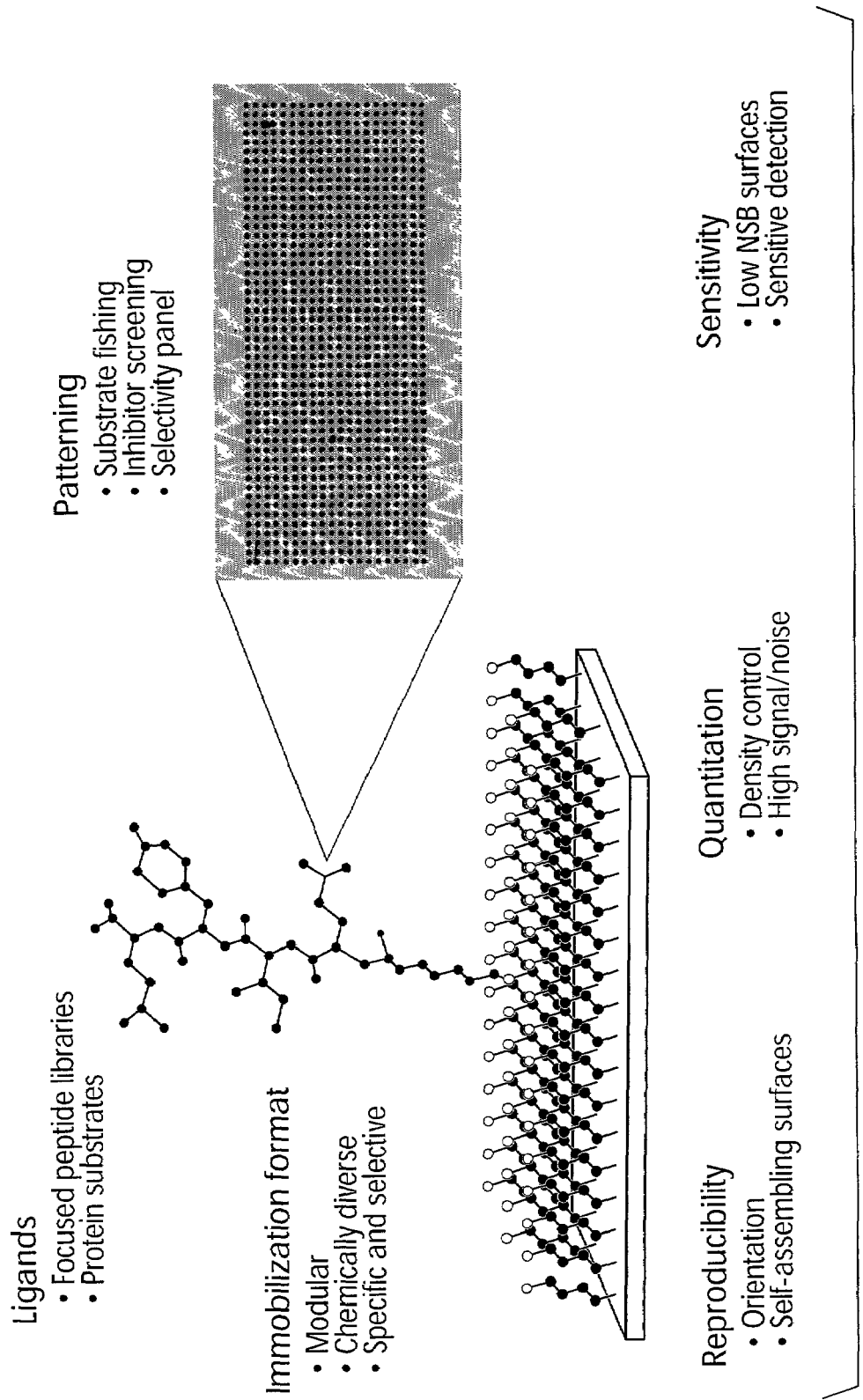
FIG. 44 depicts features and applications of kinase assays. The present invention provides for kinase assays useful for improving the reproducibility of test results and detection sensitivity. Unlike standard methods used in industry for screening inhibitors against a kinase, the present invention allows for simultaneous screening of different kinases and conditions on a single plate, for example, muliplex kinases and conditions for a single kinase inhibitor on a single plate.

Referring to FIG. 41, in the glycosyltransferase assay, various carbohydrates were immobilized using a thiol chemical tag to bond to a monolayer thiolate bearing a maleimide group. A glycosyltransferase enzyme was added to the immobilized carbohydrates. The ability of the enzyme to add radioactively labeled sugars to the immobilized carbohydrates was measured. In the glycosyltransferase assay the enzyme that was employed is bovine recombinant β1,4-galactosyltransferase. Preferably, the enzyme is at a concentration of about 10 pM to about 100 uM. More preferably, the enzyme is at a concentration of about 100 pM to about 1 uM.

The concentration of radioactively labeled donor sugar is preferably from about 0.1 uM to about 1000 uM. Preferably, the concentration is from about 1 uM to about 10 uM. A preferred temperature for the glycosyltransferase assay is from about 0 C. to about 60 C. More preferably the temperature range is from about 20 C. to about 40 C.

The density of the monolayer thiolate groups bearing a maleimide on the substrates in a glycosyltransferase assay is limited by steric factors with regard to the accessibility of substrate to enzyme. Therefore, it is preferable that the immobilized monolayer thiolate groups bearing a maleimide are from about 0.1% to about 50%. More preferably, the immobilized substrate is from about 1% to about 10%.

Detection of glycosylation of the immobilized carbohydrate substrates on the base plate was performed radiometrically. The incorporation of $^{14}C$ was quantified by exposing a storage phosphor screen to the plate and then imaging it on a Variable Mode Imager (Typhoon 8600; Molecular Dynamics, Sunnyvale, Calif.).

In yet another embodiment, the present invention provides for immobilizing a fusion protein on a mixed monolayer surface. The fusion protein comprises a reactive group and a display protein or peptide. The process comprises the step of contacting the mixed monolayer surface with a bifunctional affinity tag and the fusion protein. The mixed monolayer surface has a first monolayer moiety having a covalent bond forming reactive group, and a second monolayer moiety bearing an inert group. The covalent bond forming reactive groups, the inert groups and the monolayer moieties are as described above. The density may also be controlled and determined as described above.

The bifunctional affinity tag comprises a first reactive group and a second reactive group, the first reactive group has a covalent bond forming reaction partner to react with the covalent bond forming reactive group of the first monolayer moiety. The second reactive group has a reaction partner to react with the reactive group of the fusion protein. The contacting step forms a covalent bond between the first reactive group of the bifunctional affinity tag and the covalent bond forming reactive group of the first monolayer moiety to immobilize the bifunctional affinity tag. Also, the contacting step forms an association between the second reactive group of the bifunctional affinity tag and the reactive group of the fusion protein to immobilize the fusion protein.

In one embodiment the reactive group of the fusion protein comprises a histidine, and the second reactive group of the bifunctional affinity tag is a metal ion, thus allowing an ionic association between the fusion protein and the affinity tag to provide the immobilization chemistry and thus immobilize the fusion protein.

Further, the reactive group of the fusion protein may be an antibody. In this embodiment, the second reactive group of the bifunctional affinity tag is an antigen target of the antibody. The antibody and target antigen will associate in an antibody-antigen association to immobilize the fusion protein. Alternatively, the reactive group of the fusion protein may be a target antigen and the second reactive group of the bifunctional affinity tag may be an antibody that will recognize the target antigen. An antibody as used herein does not necessarily have to be the whole antibody. It may also be an antibody fragment such as a Fab, $Fab_2$, or a ScFv and the like.

In another embodiment the reactive group of the fusion protein is a biotin molecule, and the second reactive group of the bifunctional affinity tag is an avidin or streptavidin. Alternatively, the reactive group of the fusion protein may be an avidin or streptavidin, and the second reactive group of the bifunctional affinity tag may be a biotin. Other known binding target/ligand associations may be used to allow the second reactive group of the bifunctional affinity tag to bind to the reactive group of the fusion protein.

The present invention provides yet another process for immobilizing a fusion protein in a predetermined density on a mixed monolayer surface. The fusion protein is as described above except that the reactive group of the fusion protein is a covalent bond forming reactive group (as described earlier). The process is similar as the process described above, but the second reactive groups of the bifunctional affinity tag has a covalent bond forming reaction partner to react with a covalent bond forming group of the fusion protein.

In the process described above, in a preferred embodiment, the covalent bond forming group of the fusion protein is cutinase, and the first reactive group of the bifunctional affinity tag is a thiol. The second reactive group of the bifunctional affinity tag is paranitrophenolphosphate ("PNPP"). In this embodiment, the PNPP will bind covalently to the cutinase to immobilize the fusion protein.

As discussed above, the fusion protein comprises a covalent bond forming group and a display protein/peptide (hereinafter "display polypeptide"). The covalent bond forming reactive group is as described above. The display polypeptide is a peptide, polypeptide, or protein of interest to be immobilized. The two components of the fusion protein may be linked to each other in a variety of ways, such as by recombinant techniques and by native chemical ligation (Kent et al., U.S. Pat. No. 6,184,344B1) or any other methods known in the art. Preferably, both the display polypeptide and the covalent bond forming reactive group retain their respective biochemical properties in the fusion polypeptide.

These and other uses for the devices and methods of the present invention will be apparent from the examples that follow. Further, additional uses for and embodiments of the present invention will be readily apparent to those of skill in the art.

Any combination of the components described above may be provided in a kit format, as readily recognizable by one skilled in the art.

The chemistries and devices described herein are useful to perform many of the steps involved in drug discovery. For example, the peelable and resealable devices and methods of use are used to perform protein profiling which aids in choosing a target. The chemotactic invasion assay device and methods described or known in the arts are used in drug discovery systems and improve such systems as well as are useful for performing cellular validation. The peelable and resealable devices and methods of use are useful to perform primary biochemical assays and secondary cellular assays. Cell motility assay device and methods described or known in the arts are used for performing a variety of cellular studies.

All citations throughout the specification and the references cited therein are hereby expressly incorporated by reference.

The examples that follow are set forth to aid in understanding the invention but are not intended to, and should not be construed to limit its scope in any way. The Examples do not include detailed descriptions of conventional methods. Such methods are well known to those of ordinary skill in the art and are described in numerous publications

EXAMPLES

Example 1

A base plate according to the present invention, comprising a glass slide coated with a thin (45 nm) layer of gold, was coated with a mixed self-assembled monolayer (SAM) containing 2% maleimide-terminal groups in a background of tri(ethylene glycol) terminal groups. This entire surface was then exposed to a 500-µM solution of a peptide (Ip-YGEFKKKC) that was phosphorylated on its tyrosine residue. This peptide reacted with the maleimide groups on the surface via its terminal cysteine group to yield a surface composed of 2% of a monolayer of phospho-peptide. A PDMS removable member comprising 10 well orifices was removably sealed to the base plate, and the phospho-peptide exposed by the well orifices was exposed to different concentrations of protein tyrosine phosphatase (PTP-1B) via the well orifices. The plate was then incubated at 37° C. for 30 minutes to allow the enzymatic cleavage of the phosphoryl group from the immobilized peptide by PTP-1B.

The PDMS removable member was removed, the plate was washed in sodium dodecyl sulfate (SDS) and tris-buffered saline (TBS) solution, and the decrease in phosphotyrosine in the well-bottom areas was quantified by developing the plate using a primary anti-phosphotyrosine antibody (rabbit host) and a secondary Cy-3-labeled anti-rabbit antibody. The amount of fluorescence from the Cy-3-labeled antibody—which is proportional to the number of phosphotyrosine groups at the surface—was measured using a Molecular Dynamics Typhoon™ fluorescence confocal flat-bed scanner ($\lambda_{ex}$=532 nm; $\lambda_{em}$=555±20 nm; PMT voltage=650 V; scan resolution=50 µm).

Figure 16B:
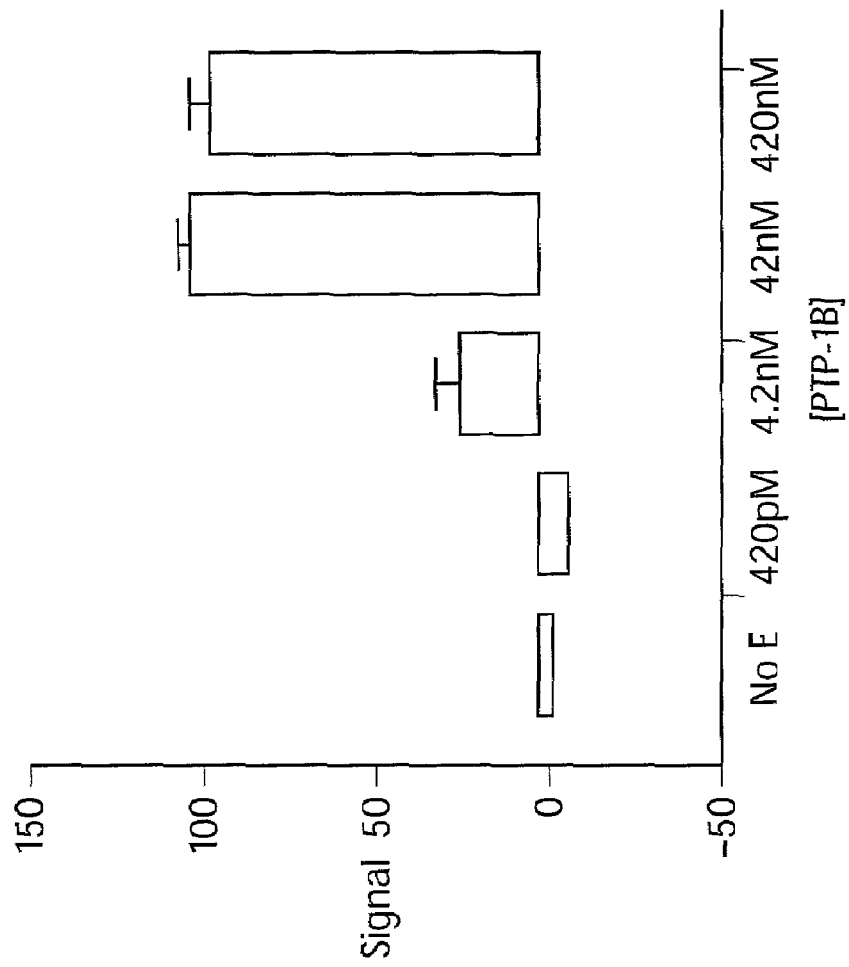
FIGS. 16A and 16B depicts results of an assay performed using a device according to the present invention.
Figure 16A:
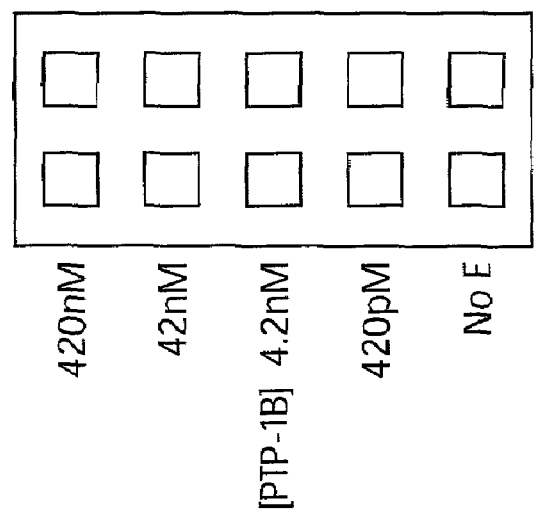

FIG. 16(a) depicts the fluorescence image of the developed base plate produced by the confocal scanner. FIG. 16(b) depicts a graph of the signal intensity produced by analyzing the image in FIG. 16(a). The greater the intensity of the signal, the greater the concentration of phosphotyrosine remaining. As would be expected from a phosphatase enzyme, it can be seen that the concentration of PTP-1B to which the phosphopeptides in each well were exposed is inversely correlated with the concentration of phospho-tyrosine remaining in the protein in each well.

Example 2

A base plate according to the present invention, comprising a glass slide coated with a thin (45 nm) layer of gold, was coated with a mixed self-assembled monolayer (SAM) containing 2% maleimide-terminal groups in a background of tri(ethylene glycol) terminal groups. Solutions of seven tyrosine-containing peptides in a buffer solution were then arrayed onto the base plate using a robotic split-pin arrayer (PixSys 5500, Cartesian Technologies). The robot was programmed to create a rectangular 5×12 set of microarrays spaced by 4.5 mm, each microarray being composed of 4×4 100 µm spots (2 spots of each peptide and 2 of buffer) spaced by 300 µm. The peptides were then allowed to attach via their terminal-cysteine residues and the plate was washed in SDS and water.

A PDMS removable member according to the present invention that contained a set of 5×12 well orifices spaced by 4.5 mm was then aligned and sealed to the base plate so that each microarray had a liquid-tight well defined around it.

The plate was aligned by placing a print-out of the pattern arrayed by the robot below the base plate and aligning the PDMS membrane to this pattern. Solutions comprising 12 different kinases (Abl, Fyn, Lck, Lyn, Src, ZAP-70, EGFR, FGFR, Met, PDGFR, Tek, VEGFR) at 5 different concentrations, ATP, and other co-factors were applied to the 5×12 well orifices in the removable member, the Walls of which, with the base plate, defined wells around each microarray of the 7 peptides.

Figure 17B:
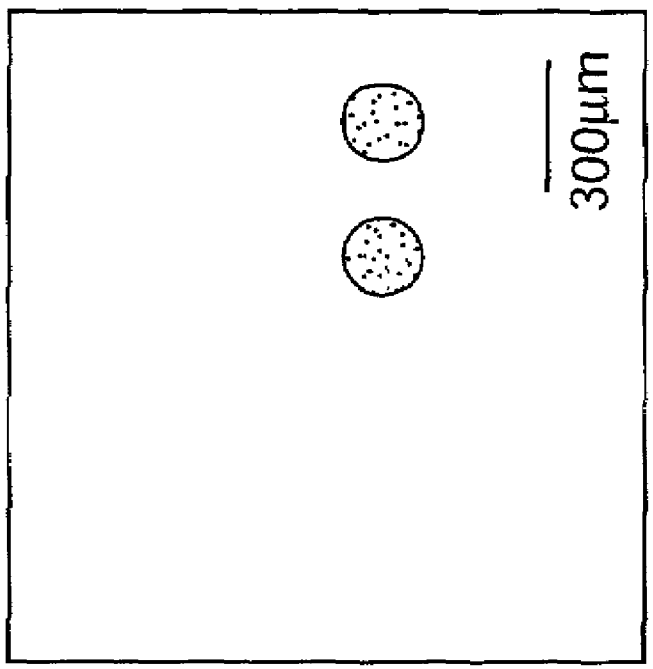
FIG. 17(*a*) depicts an array according to the present invention.
Figure 17A:
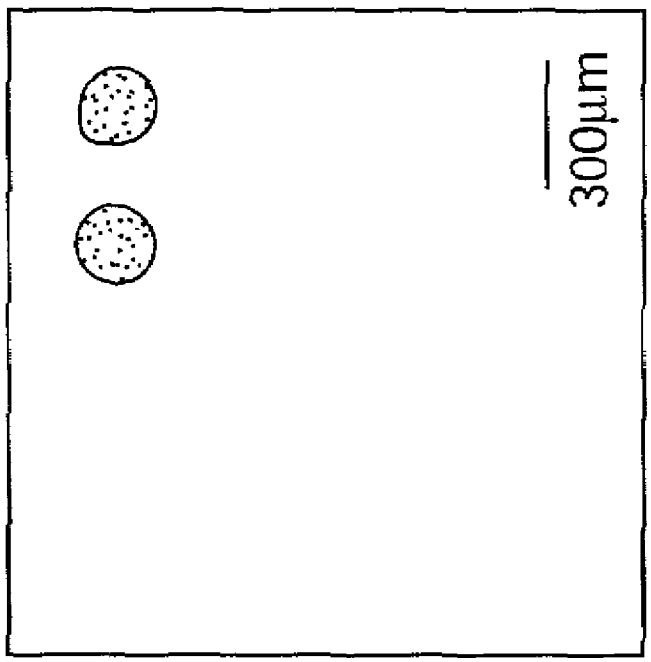

After incubation of the plate at 37° C. for 30 min, the removable member was removed, the plate was washed in SDS and TBS, and the plate was incubated first with a primary anti-phosphotyrosine antibody (rabbit host) and then a secondary anti-rabbit antibody that was conjugated to alkaline phosphatase (AP). The amount of secondary antibody and, hence, the number of phosphotyrosine groups in each element of each array, was quantified using a substrate to AP that generated a colored (blue) precipitate and imaging the microarrays on an optical microscope. FIG. 17 depicts a image of two sets of these arrays that were exposed to 13 pM Src kinase and 2 nm Abl kinase. The two dark spots in each of the 4×4 arrays correspond to the two different peptides that were phosphorylated sufficiently to be detected.

Example 3

Base plates according to the present invention, comprising glass slides coated with a thin (45 nm) layer of gold, were coated with a mixed self-assembled monolayer (SAM) containing 2% maleimide-terminal groups in a background of tri(ethylene glycol) terminal groups. These surfaces were then exposed to a 500-μM solution of a peptide (CEQEDEPEGIYGVLF) that is a good substrate for Lck kinase. The peptide reacted with the maleimide groups on the surface via its terminal cysteine group to yield a surface composed of 2% of a monolayer of peptide.

PDMS removable members comprising well orifices were removably sealed to the base plates, and the peptide exposed by the well orifices was exposed to different lysates of cell lines that over-express a kinase, ATP, and other co-factors. The plate was then incubated at 37° C. for 30 min to allow the enzymatic transfer of a phosphate group from ATP to the immobilized peptide by the kinase. The increase in phosphotyrosine in the well-bottom areas was quantified by developing the plate using a primary anti-phosphotyrosine antibody (rabbit host) and a secondary Cy-3-labeled anti-rabbit antibody, and detection of fluorescence on a confocal scanner as described in Example 1.

FIG. 18(a) shows the fluorescence image of a plate treated with a lysate of cells over-expressing $p56^{Lck}$ (upper spot, labeled "+lysate") and a control lysate of cells that do not over-express this kinase (lower spot, labeled "−lysate"). FIG. 18(b) shows the fluorescence image of a plate treated with various concentrations of a lysate of an epidermal carcinoma cell line (A431) that is known to over-express EGFR kinase and a control, wild-type cell line (WS1) that does not over-express this kinase. As can be seen in both examples, devices and methods of the present invention can be used to measure kinase activity from a cell lysate.

Example 4

A base plate according to the present invention, comprising a glass slide coated with a thin (45 nm) layer of gold, was coated with a mixed self-assembled monolayer (SAM) containing 2% maleimide-terminal groups in a background of tri(ethylene glycol) terminal groups. This surface was then exposed to a 500-μM solution of a peptide substrate for kinases (CEQEDEPEGIYGVLF). The peptide reacted with the maleimide groups on the surface via its terminal cysteine group to yield a surface composed of 2% of a monolayer of the peptide.

A PDMS removable member comprising 20 well orifices was removably sealed to the base plate, and the peptide exposed by the well orifices was exposed to different concentrations of Src kinase, ATP, and other co-factors. The plate was then incubated at 37° C. for 30 minutes to allow the enzymatic transfer of a phosphate group from ATP to the immobilized peptide by the kinase. The increase in phosphotyrosine in the well-bottom areas was quantified by developing the plate using a primary anti-phosphotyrosine antibody (rabbit host) and a secondary Cy-3-labeled anti-rabbit antibody, and detection of fluorescence on a confocal scanner as described in Example 1.

Figure 20B:
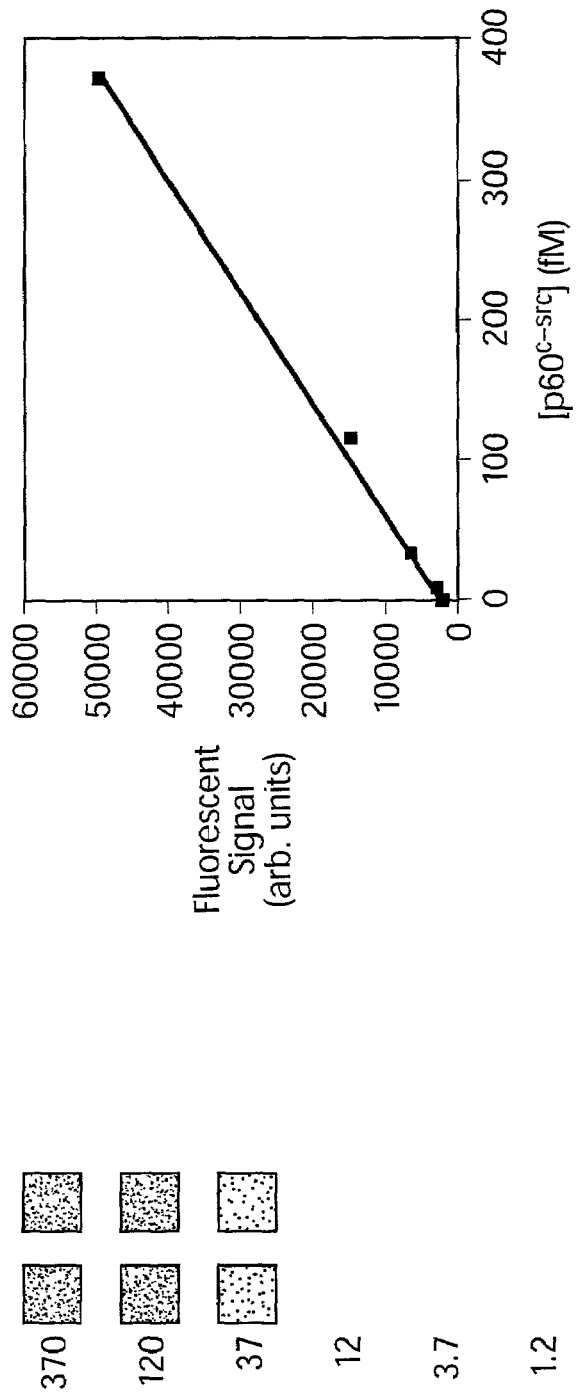
FIGS. 20A and 20B depicts results of an assay demonstrating the sensitivity of assays performed using devices according to the present invention.
Figure 20A:
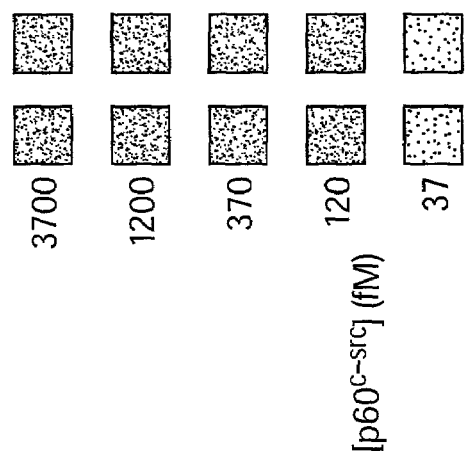

FIG. 20(a) shows a fluorescence image from this developed plate. The results demonstrate that, using assays according to the present invention, Src activity can be detected at concentrations as low as 4 femtomolar. These results demonstrate the extremely high level of sensitivity achievable using assays according to the present invention. Furthermore, a high level of anti-phosphotyrosine antibody bound in the area corresponding to the well having immobilized peptide and exposed to 0.37 to 3.7 pM Src kinase. In contrast, anti-phosphotyrosine antibody did not bind in the areas corresponding to the control wells. These results demonstrate the extremely low level of non-specific binding and high level of sensitivity achievable using assays according to the present invention. Such low levels of non-specific binding allow for and facilitate a high level of sensitivity, which is achievable using assays according to the present invention. FIG. 20(b) shows an analysis of the image in FIG. 20(a) and demonstrates that these assays produce a signal that is linear with the concentration of enzyme.

Example 5

A base plate according to the present invention, comprising a glass slide coated with a thin (45 nm) layer of gold, was coated with a mixed self-assembled monolayer (SAM) containing 2% maleimide-terminal groups in a background of tri(ethylene glycol) terminal groups. This surface were then exposed to a 500-μM solution of a peptide substrate for Src kinase (IYGEFKKKC). The peptide reacted with the maleimide groups on the surface via its terminal cysteine group to yield a surface composed of 2% of a monolayer of the peptide.

A PDMS removable member comprising 3×8 well orifices was removably sealed to the base plate, and the peptide exposed by the well orifices was exposed to solutions containing 3.7 pM Src kinase, ATP, other co-factors, and different concentrations of an inhibitor of Src, namely, staurosporine. Wells receiving Src but receiving no inhibitor, and wells receiving inhibitor but no Src were used as controls. The plate was then incubated at 37° C. for 30 min to allow the enzymatic transfer of a phosphate group from ATP to the immobilized peptide by the kinase. The increase in phospho-tyrosine in the well-bottom areas was quantified by developing the plate using a primary anti-phosphotyrosine antibody (rabbit host) and a secondary AP-conjugated anti-rabbit antibody, and a substrate to AP that generated a colored (blue) precipitate. The amount of blue precipitate and, hence, the number of phosphor-tyrosine groups was quantified using a conventional PC flat-bed scanner.

The level of Src inhibition by staurosporine correlates directly with the concentration of inhibitor added. FIG. 21(c) shows an image of the developed base plate scanned on a flat bed scanner. FIG. 21(a) shows a detail of this plate. FIG. 21(b) is a graph of the results of the assay. Assays such as this can be used to assess inhibition by potential inhibitors of kinases or other enzymes.

The effect of a potential inhibitor may be simultaneously tested on a large number of kinases or other enzymes. Likewise, the effect of a large number of potential inhibitors on a single kinase or other enzyme may simultaneously be tested. In an even more complex assay, the effects of a large number of inhibitors on a large number of kinases or other enzymes could be evaluated. Such assays are particularly useful in the field of drug screening, where, for example, the specific enzymatic reaction at which an inhibitor blocks a pathway often determines the side effects of the inhibitor.

Example 6

The effects of 12 different kinases (6 receptor tyrosine kinases and 6 kinases of the src family) on 7 peptide substrates were simultaneously measured. A 12×5 array of each peptide was patterned onto a base plate according to the present invention, to form an array of 12×35 spots of peptide.

A removable member comprising 420 well orifices, according to the present invention, was used to pattern the peptides. A base plate according to the present invention, comprising a glass slide coated with a thin (45 nm) layer of gold, was coated with a mixed self-assembled monolayer (SAM) containing 2% maleimide-terminal groups in a background of tri(ethylene glycol) terminal groups. The SAM-covered surface of the base plate was then exposed to 500 μM solutions of seven different peptide substrate for kinases (the same seven as used in Example 2) to create a 12×5 pattern of spots of each substrate in an overall array of 12×35 spots of kinase substrate. The peptides reacted with the maleimide groups on the surface via its terminal cysteine group to yield surfaces composed of 2% of a monolayer of the various peptide substrates.

A PDMS removable member comprising 5×12 well orifices were removably sealed to the base plate, and the peptide substrates exposed by the well orifices were exposed to different concentrations of the 12 kinases, and other co-factors. The plate was then incubated at 37° C. for 30 min to allow the enzymatic transfer of a phosphate group from ATP to the immobilized peptides by the kinases. The increase in phospho-tyrosine in the well-bottom areas was quantified by developing the plate using a primary anti-phosphotyrosine antibody (rabbit host) and a secondary Cy-3-labeled anti-rabbit antibody, and detection of fluorescence on a confocal scanner as described in Example 1.

Figure 22A:
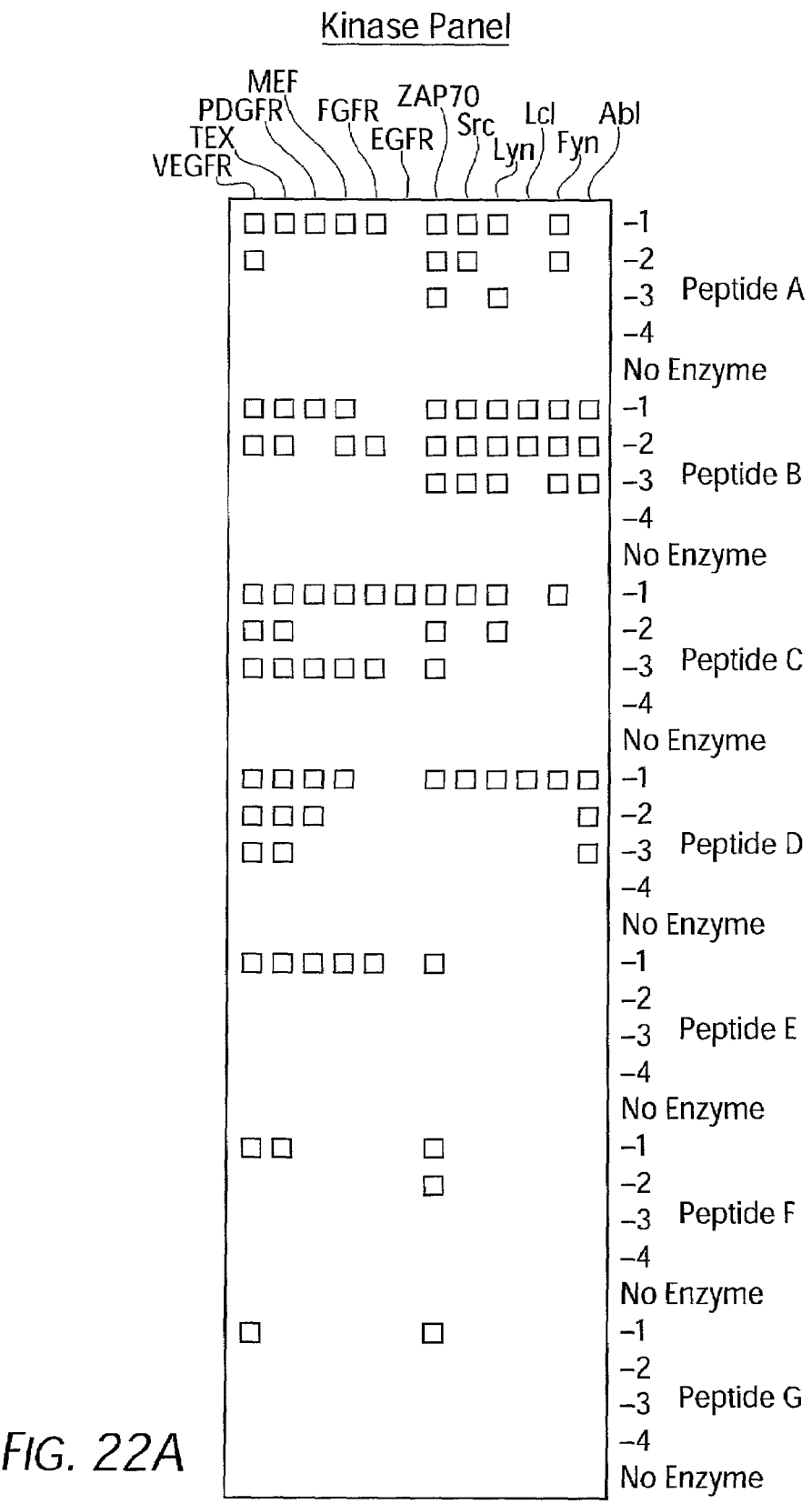
FIGS. 22A and 22B depicts results of assays demonstrating the use of a device according to the present invention to perform many assays simultaneously.
Figure 22B:
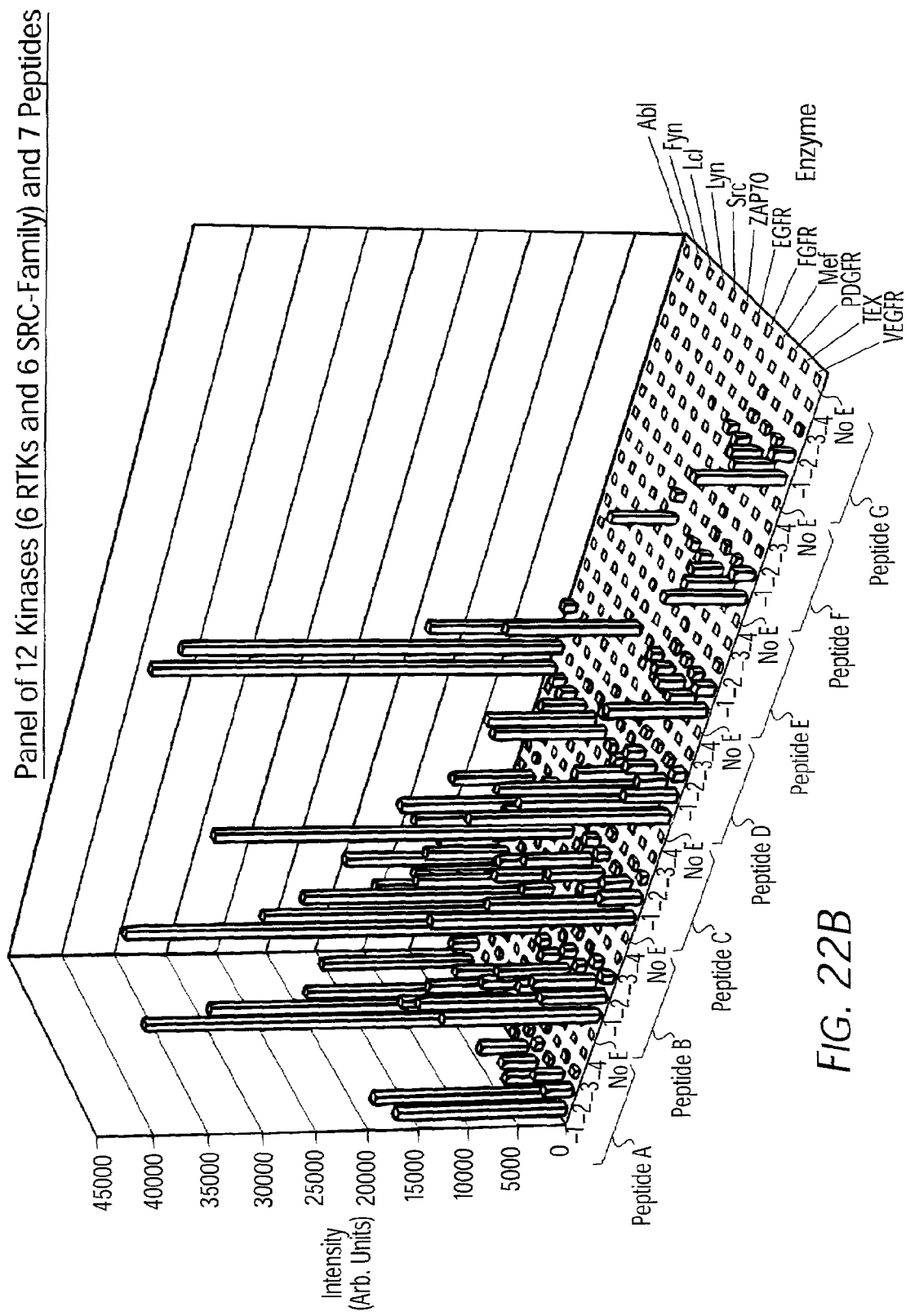

FIG. 22(a) depicts a fluorescence image of the developed base plate. FIG. 22(b) is a graphical representation of the signal intensity. In this way, 420 different assays were simultaneously performed—the effect of each of the 12 kinases in each of 5 different concentrations (including no kinase) was simultaneously tested on each of 7 peptides.

This experiment demonstrated the use a device according to the present invention to perform many assays simultaneously. Such performance of multiple assays simultaneously may be referred to as "multiplexing."

Example 7

Removable and resealable PDMS members of the present invention can be used to pattern different peptides in spatially defined and predetermined areas on surfaces, thus enabling the performance of assays on multiple peptides. A base plate according to the present invention, comprising a glass slide coated with a thin (45 nm) layer of gold, was coated with a mixed self-assembled monolayer (SAM) containing 2% maleimide-terminal groups in a background of tri(ethylene glycol) terminal groups.

Figure 23:
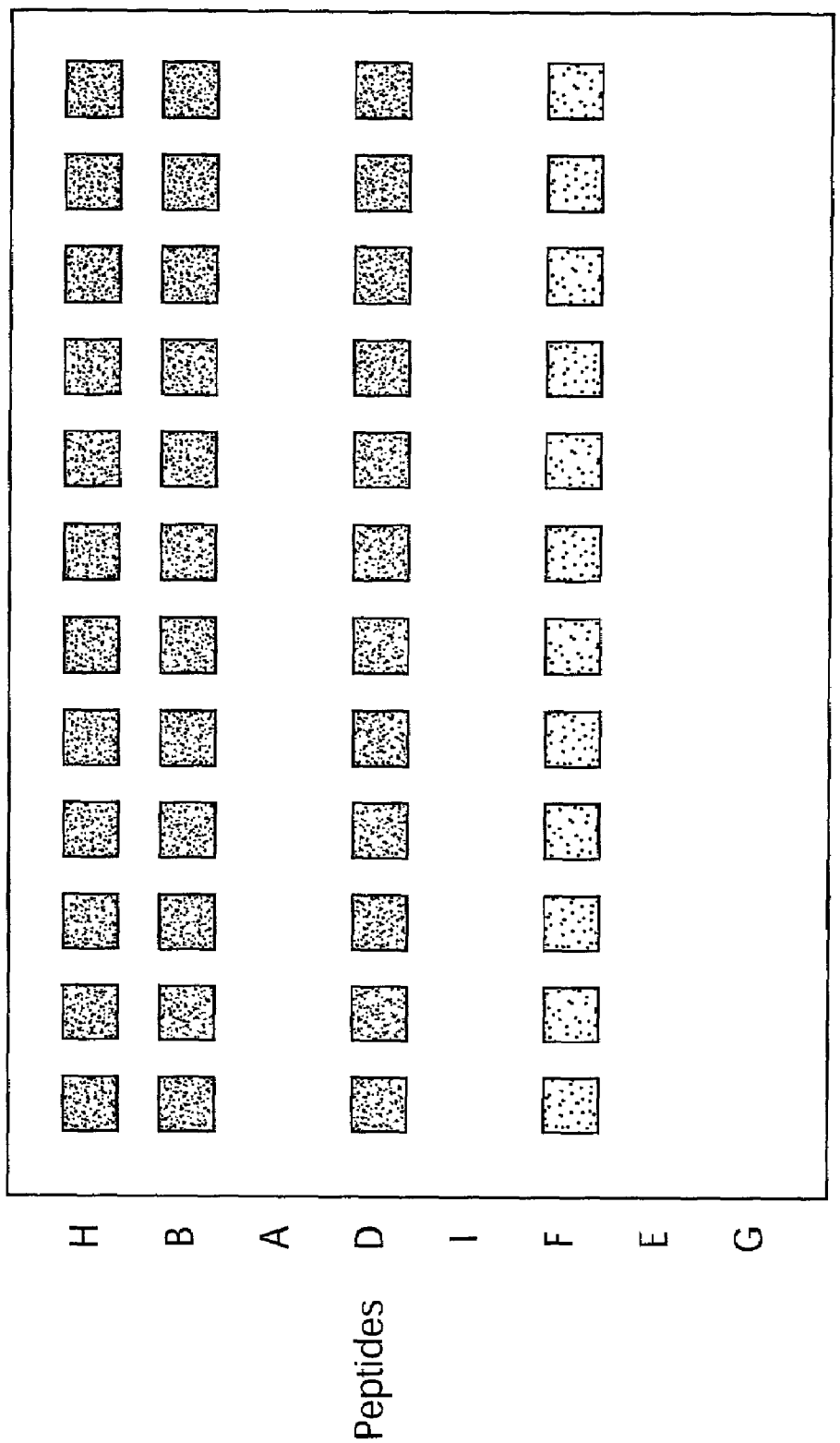
FIG. 23 depicts the results of an assay performed according to the present invention.

A PDMS removable member comprising 8×12 well orifices was removably sealed to the base plate, and 8 columns (of 12 wells each) of different solutions of peptides were then delivered to each of the wells defined by the PDMS member. The 8 peptides reacted with the maleimide groups on the surface via its terminal cysteine group for 30 min to yield a surface composed of 2% of a monolayer of the different peptides. The PDMS member was then removed and washed to define 96 separate islands of peptide on the base plate. The plate was then incubated at 37° C. for 30 min with 21 nM Abl kinase, ATP, and cofactors to allow the enzymatic transfer of a phosphate group from ATP to the immobilized peptides by the kinase. The increase in phospho-tyrosine in the well-bottom areas was quantified by developing the plate using a primary anti-phosphotyrosine antibody (rabbit host) and a secondary Cy-3-labeled anti-rabbit antibody, and detection of fluorescence on a confocal scanner as described in Example 1. FIG. 23 shows the fluorescence image of the plate after development and shows that removable and resealable members according to the present invention can be used to define separate islands of peptides for kinase assays. These assays are multiplexed in terms of being useful to assay many peptides.

Example 8

A base plate according to the present invention, comprising a polycarbonate plate coated with a thin (45 nm) layer of gold, is coated with a mixed self-assembled monolayer (SAM) containing 2% maleimide-terminal groups in a background of tri(ethylene glycol) terminal groups. A PDMS removable member having an array of well orifices corresponding to a 384-well microtiter plate is sealed to the base plate coated with gold. 384 different potential peptide targets are immobilized, one type of protein in each of 384 wells. The peptides are immobilized via reaction between the maleimide groups on the base plate and a terminal cysteine group of each peptide.

After the immobilization, the removable member is removed from the gold surface and the a candidate drug is applied to the entirety of the gold surface, thus the candidate drug is applied to each of the 384 types of proteins simultaneously, without the need for micropipetting. The gold surface is washed, again without the need for micropipetting. A detecting agent, such as an antibody or fluorescent dye, that can detect which proteins the candidate drug has affected, is applied to each of the 384 types of proteins simultaneously, yet again without the need for micropipetting. The binding of the detecting agent is measured using a flat bed scanner. Because the removable member is removed, the gold surface is flat and the use of the scanner is not hindered by structures protruding perpendicularly from the surface to which the material to be observed is attached.

Example 9

A base plate according to the present invention, comprising a glass slide coated with a thin (45 nm) layer of gold, is coated with a mixed self-assembled monolayer (SAM) containing 2% maleimide-terminal groups in a background of tri(ethylene glycol) terminal groups.

A first PDMS removable member having an array of well orifices corresponding to a 1536-well microtiter plate is sealed the base plate, forming a flat gold surface. Four different potential peptide targets are immobilized in groups of four, such that 384 groups of four are formed. The peptides are immobilized via reaction between the maleimide groups on the base plate and a terminal cysteine group of each peptide.

The first removable member is removed and a second PDMS removable member having an array of 384 well orifices, aligned such that each of the 384 well orifices encompasses a group of four well orifices of the first removable member and therefore, a group of four different potential target proteins, is sealed on gold surface.

candidate drugs are then applied to the device, with one candidate drug being added to each of the 384 wells formed by the second removable member. After the candidate drugs and potential protein targets have been exposed to each, the 384-well orifice removable member is removed from the gold surface the gold surface is washed, without the need for micropipetting.

A detecting agent, such as an antibody or fluorescent dye, that can detect which proteins the candidate drug has affected, is applied to the entirety of the gold surface, thus being applied to each of the 1536 spots of proteins simultaneously, again without the need for micropipetting. The binding of the detecting agent is measured using a flat bed scanner. Because both removable members are removed, the gold surface is flat and the use of the scanner is not hindered by structures protruding perpendicularly from the surface to which the material to be observed is attached.

Example 10

A base plate according to the present invention, comprising a glass slide coated with a thin (45 nm) layer of gold, is coated with a mixed self-assembled monolayer (SAM) containing 2% maleimide-terminal groups in a background of tri(ethylene glycol) terminal groups. A first PDMS removable member having an array of well orifices corresponding to a 96-well microtiter plate is sealed to a base plate coated with gold, forming a flat gold surface. Peptides of interest, that are potential targets for an enzyme of interest, are immobilized on the gold surface, with one protein being immobilized per microwell. The peptides are immobilized via reaction between the maleimide groups on the base plate and a terminal cysteine group of each peptide.

The first removable member is removed, and a second PDMS removable member having an array of well orifices corresponding in orientation to a 96-well microtiter plate, but having well orifices smaller in the plane defined by the gold surface than the first removable member, is sealed to the gold surface. A solution containing the enzyme of interest is pipetted into each of the wells. After an appropriate incubation time, the solution containing the enzyme is rinsed away and enzymatic reactions are detected, using appropriate detection methods. Preferably, the second membrane is removed before the washing and detection are performed. The area of unexposed peptide surrounding each area of exposed peptide will have been subjected to all processing and detection steps, with the exception that it will not have been exposed to the enzyme of interest. Thus, each unexposed area will act as an accurate control for each exposed area.

Example 11

NMR $^1$H NMR spectra were recorded on a Varian 400 MHz spectrometer in $CDCl_3$, $CD_3OD$ or $D_2O$, with chemical shifts reported relative to the residual peak of the respective solvent. Reactions were performed under an argon atmosphere. Reagents were used as received unless otherwise stated.

Chromatography

Flash chromatography was carried out using Merck Silica gel 60 (230-400) mesh. Thin-layer chromatography (TLC) was performed on EM Science silica gel 60 plates (0.25 mm thickness). All compounds were visualized with either shortwave ultraviolet light, ninhydrin staining solution, or a cerium sulfate/ammonium heptamolybdate tetrahydrate staining solution. All reagents were purchased from Aldrich or VWR.

Substrate Preparation

Gold substrates were prepared by evaporation of an adhesive layer of titanium (1.5 nm) followed by a layer of gold (45 nm) onto microscope cover glass (VWR 24×50 mm #2) or coverslips (VWR 25×75 mm). Prior to evaporation, the substrates were cleaned by sonication in hexanes (20 min) and 95% EtOH (20 min), followed by drying in a stream of nitrogen. Evaporations were performed using a thermal evaporator (Edwards Auto 306) at a pressure of $6 \times 10^{-6}$ Torr and at a rate of 0.3 nm/s. The gold-coated substrates were cut into ca. 1×1 cm pieces, washed with absolute ethanol and dried under a stream of nitrogen. The monolayers were formed by immersion of the clean gold substrates in ethanolic solutions of mixtures of disulfides 1 and 2 in various ratios (0.2 mM total disulfide concentration). After 16 hours, the monolayers were rinsed with absolute ethanol and dried under a stream of nitrogen gas.

Quality Control of Maleimide/EG3 Mixed SAM Surface

A gold chip that presents 1.5% maleimide groups in a background of EG3 was loaded into an SPR machine (Biacore 3000). Two flow channels over this chip were simultaneously exposed to cysteine-biotin that reacts with the maleimide in order to present 1.5% biotin at the surface. Subsequently, one channel was exposed to 70 μg/mL of streptavidin and then one channel was exposed to 500 μg/mL of fibrinogen. The large signal change caused by the adsorption of streptavidin (2100 RU) indicated a large specific binding capacity of biotin; the small signal change caused by the adsorption of fibrinogen (90RU) indicated that the surface had retained a low non-specific binding (NSB). This experiment indicated that this batch of maleimide/EG3 surfaces were suitable for protein immobilization (see below).

Surface Plasmon Resonance Spectroscopy

SPR was performed with a Biacore 3000 instrument. Gold-coated glass microscope cover glass presenting SAMs to be analyzed were mounted in SPR cartridges as previously described. All experiments used a flow rate of 10 mL/min.

Electrochemistry

Electrochemical studies were performed using a BAS Epsilon potentiostat. Electrochemistry on SAMs was performed in water containing 0.5 M KNO3 as the electrolyte using the gold substrate as the working electrode, a platinum wire as the counter electrode, and a Ag/AgCl/KCl reference electrode. All experiments were performed in the cyclic voltammetry mode, at a scan rate of 200 mV/s.

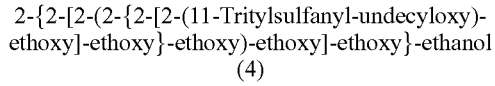

$$Q = nF; F = 96{,}500 \text{ C/mol} \quad (1)$$
$$\text{Density} = n/\text{cm}^2 \quad (2)$$
$$0.78 \text{ nmol/cm}^2$$

The determination of the density of the maleimide group incorporated into the SAM was determined electrochemically. SAMs of variable densities of maleimide were immersed in a solution of electroactive ferrocene 13 (1 mM in absolute EtOH) for 2 h, followed by extensive rinsing with EtOH. After drying the SAMs under nitrogen, cyclic voltammetry was performed.

From the area under the redox waves, total charge (Q) can be determined (Equation 1), which is proportional to the number of moles (n) of redox-active molecule on the surface. The density is determined by dividing the moles of redox active molecule by the total moles of molecule on the surface (after the two numbers are normalized to SAM surface area) (Equation 2). We assume that all of the maleimide groups on the surface react with the ferrocene-thiol molecule, so from the density of ferrocene on the surface, we infer that the density of maleimide is the same.

Kinase Assay. Peptide Immobilization. An src peptide substrate with a C-terminal cysteine (IYGEFKKKC) was covalently immobilized to monolayers presenting maleimide at a density of 2% by incubation with a 1 mM peptide solution (pH 6) for 1 hour, followed by rinsing with water and drying with a stream of nitrogen.

Kinase Inhibitor Assays. Staurosporine (Calbiochem) was prepared at various concentrations in DMSO. Active $p60^{c\text{-}src}$ was purchased from Upstate Biotechnology, and diluted with equal parts kinase assay buffer (KAB) (50 mM HEPES pH 7.4, 0.1 mM EDTA, 0.015% Brij 35) and kinase dilution buffer (KDB) (KAB with 0.1 mg/ml BSA and 0.2% b-mercaptoethanol) for a final assay concentration of 20 pM.

Kinase reactions were set up by premixing 0.6ml of a staurosporine dilution with 4 ml of $p60^{c\text{-}src}$ dilution, and started by adding ATP/$Mg^{2+}$cocktail (made in KAB) to final concentrations of 50 mM ATP and 10 mM $Mg^{2+}$. 6 ml of reaction mixture were immediately delivered to each well, and the sample was incubated for 30 min at 37° C. After incubation, the sample was washed for 1 min in 8 mM SDS, 3×3 min in TBST (TBS (10 mM Tris pH 7.4, 150 mM NaCl) with 0.05% Tween-20), and 2×3 min in TBS. Phosphorylation of the substrate peptide was detected by incubation for 1 hour with polyclonal anti-phosphotyrosine (Calbiochem) diluted to 1 mg/ml in TBS with 3% (w/v) BSA. After washing again for 2×3 min in TBST and 2×3 min in TBS, the sample was incubated for 1 hour with alkaline phosphatase conjuagated anti-rabbit (Rockland Immunochemicals) diluted to 2 mg/ml in TBST with 1% (w/v) BSA, and developed with the BCIP/NBT alkaline phosphatase substrate (reference). The resulting sample was scanned in 16-bit greyscale using a conventional flatbed document scanner, and the average greyscale pixel value in each spot was obtained using standard image analysis software.

Figure 37B:
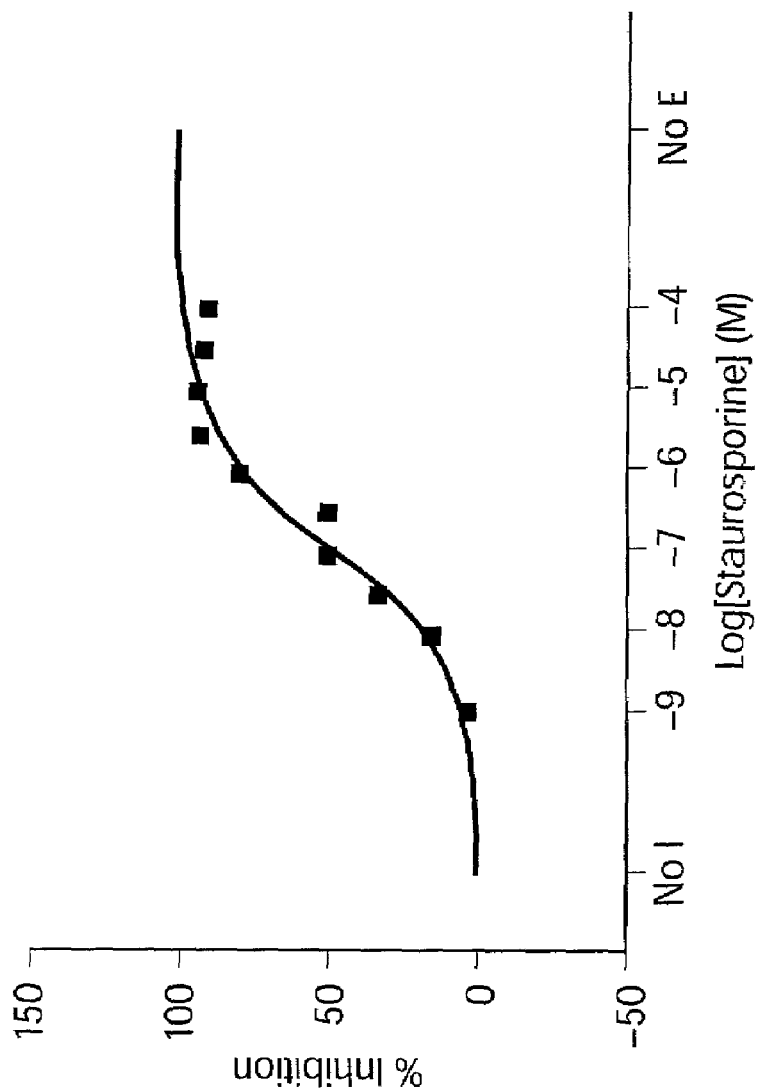
FIG. 37 illustrates the use of the maleimide SAM in a kinase assay. A peptide substrate (IYGEFKKKC) of an src kinase was immobilized to the maleimide surface through the C-terminal cysteine residue, and the inhibition of the kinase by the drug staurosporine was monitored.
FIG. 37(A) scan of $p60^{c-src}$ staurosporine $IC_{50}$ results, FIG. 37(B) plot of spot intensity, converted to % inhibition.
Figure 37A:
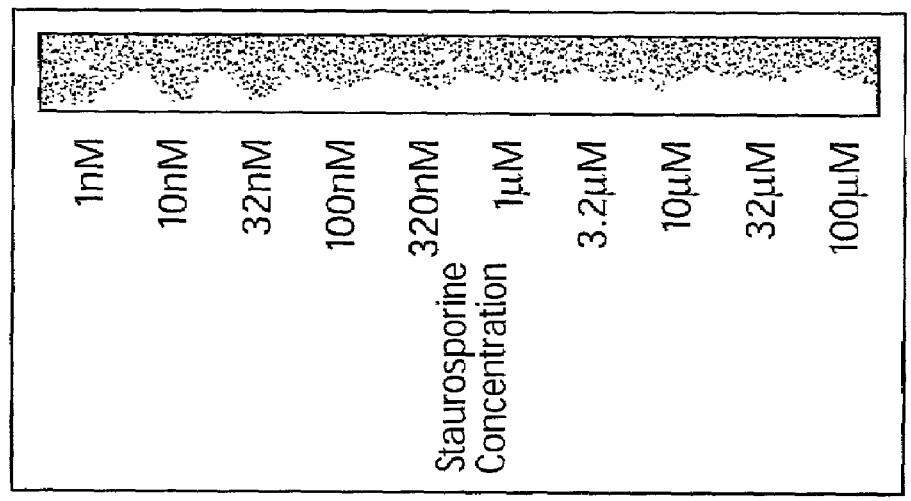
Figure 38:
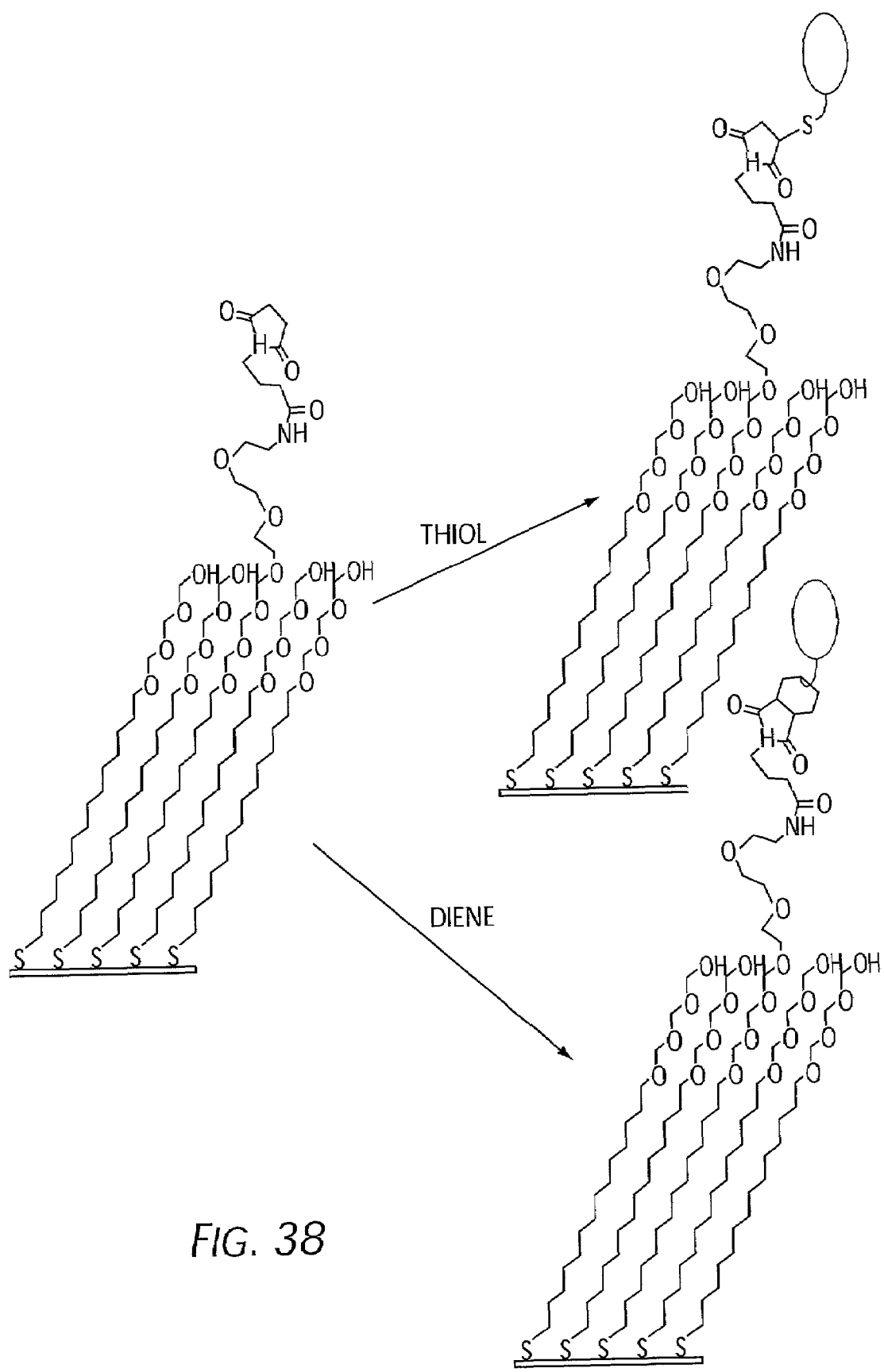
FIG. 38 illustrates that a tethered maleimide can react with a thiol to form a stable alkyl-thiol bond or with a diene to form new stable carbon-carbon bonds via a Diels-Alder reaction.

The intensity of color (blue) is proportional to the kinase activity. FIG. 37(A) is gray scale image of the substrates after development. FIG. 37(B) is a plot of spot intensity converted to percent inhibition. By fitting a sigmoidal dose-response curve to the plot, the log $IC_{50}$ (M) of staurosporine for $p60^{c\text{-}src}$ was determined to be −6.9|0.09.

Example 12

Preparation of Compounds

Synthesis of Disulfides for Preparation of SAMS

2-{2-[2-(2-{2-[2-(11-Tritylsulfanyl-undecyloxy)-ethoxy]-ethoxy}-ethoxy)-ethoxy]-ethoxy}-ethanol (4)

To a solution of 2-{2-[2-(2-{2-[2-(11-mercapto-undecyloxy)-ethoxy]-ethoxyl}-ethoxy)-ethoxy]-ethoxy}-ethanol (3) (1.22 g, 2.6 mmol) prepared according to the method of Pale-Grosdemange et al.†, dissolved in 10 mL of THF was added triphenylmethyl chloride (1.46 g, 5.2 mmol). After stirring at room temperature for 48 hours, the reaction mixture was concentrated. The crude residue was purified by flash chromatography (gradient elution, EtOAc to 20:1 EtOAc/MeOH) to afford 910 mg (49%) of 4. $^1$H NMR (CDCl$_3$, 400 MHz) d 7.36 (d, J=X Hz, 6H), 7.22 (t, J=X Hz, 6H), 7.15 (t, J=X Hz, 3H), 3.72-3.48 (br m, 24H), 3.40 (t, J=X Hz, 2H), 2.08 (t, J=X Hz, 2H), 1.52 (m, 2H), 1.4-0.9 (br, 16H). ES-MS: m/z 733.4 (M+Na$^+$). †Pale-Grosdemange, C.; Simon, E. S.; Prime, K. L.; Whitesides, G. M. *J. Am. Chem. Soc,* 1991, 113,12-20.

Toluene-4-sulfonic acid 2-{2-[2-(2-{2-[2-(11-tritylsulfanyl-undecyloxy)-ethoxyl ethoxy]-ethoxy}-ethoxy)-ethoxy]-ethoxy}-ethyl ester (5)

p-Toluenesulfonyl chloride (900 mg, 4.7 mmol) was added to a solution of alcohol 4 (910 mg, 1.28 mmol) dissolved in 12 mL of CH$_2$Cl$_2$ and 2 mL of pyridine at 0° C. The solution was warmed to room temperature and stirred for 16 hours. The reaction mixture was rinsed with brine (2×30 mL) and H20 (2×30 mL), and then the organics were dried over MgSO$_4$. After the solvent was evaporated, the crude residue was purified by flash chromatography (gradient, 1:1 hexanes/EtOAc to EtOAc) to afford 1.01 g (91%) of pure 5. $^1$H NMR (CDCl$_3$, 400 MHz) d 7.79 (d, J =8.0 Hz, 2H), 7.40 (d, J=7.8 Hz, 6H), 7.33 (d, J=8.0 Hz, 2H), 7.26 (t, J=7.8 Hz, 6H), 7.19 (t, J=7.8 Hz, 3H), 4.15 (t, J=4.8 Hz, 2H), 3.67 (t, J=5.2 Hz, 2H), 3.64-3.54 (br m, 20H), 3.43 (t, J=6.8 Hz, 2H), 2.45 (s, 3H), 2.12 (t, J=7.2 Hz, 2H), 1.56 (m, 2H), 1.42-0.90 (br, 16H).

DiBOC Protected Amine (6)

To a solution of Di-tert-butyl iminodicarboxylate (136 mg, 0.63 mmol) in 10 mL of DMF at 0° C. was added sodium hydride (60%, 25 mg, 0.63 mmol). After stirring at room temperature for 40 min, a solution of 5 (452 mg, 0.52 mmol) in 3 mL of DMF was added dropwise. The solution was stirred for 45 h, and then the solvent was evaporated in vacuo. The crude residue was dissolved in 30 mL of CH$_2$Cl$_2$ and rinsed with H$_2$O (2×10 mL). After drying the organic layer over MgSO$_4$ and evaporating the solvent, the residue was purified by column chromatography (hexanes/EtOAc, 1:1, v/v) to give 343 mg (72%) of pure 6. $^1$H NMR (CDCl$_3$, 400 MHz) δ 7.39 (d, J=7.6 Hz, 6H), 7.26 (t, J=7.6 Hz, 6H), 7.18 (t, J=7.6 Hz, 3H), 3.77 (t, J=6.4 Hz, 2H), 3.65-3.54 (br m, 22H), 3.43 (t, J=6.4 Hz, 2H), 2.11 (t, J =7.6 Hz, 2H), 1.54 (m, 2H), 1.49 (s, 18H), 1.4-1.0 (br, 16H).

2-{2-[2-(2-{2-[2-(11-Mercapto-undecyloxy)-ethoxy]-ethoxy}-ethoxy)-ethoxy]-ethoxy}-ethyl-ammonium trifluoro-acetate (7)

A solution of ethanedithiol (0.5 mL), H$_2$O (0.5 mL), phenol (1 g), and thioanisole (0.5 mL) dissolved in 10 mL of trifluoroacetic acid was added to 6 (247 mg, 0.27 mmol). After stirring for 6 h at room temperature, the reaction mixture was concentrated and purified by column chromatography (gradient elution, $CH_2Cl_2$/MeOH 20:1, v/v to 10:1 to 5:1) to give 147 mg of a mixture of 7 (ca. 75%) and trityl protected thiol (ca. 25%). Continued to the next step without further purification. $^1$H NMR (CDCl$_3$, 400 MHz) δ 3.87 (t, J=4.8 Hz, 2H), 3.74 (t, J=4.2 Hz, 2H), 3.71-3.62 (m, 16H), 3.57 (t, J=4.0 Hz, 2H), 3.42 (t, J=7.0 Hz, 2H), 3.14 (br, 2H), 2.50 (q, J=7.2 Hz, 2H), 1.62-1.47 (br m, 4H), 1.40-1.18 (m, 14H).

2-(2-{2-[11-(Pyridin-2-yldisulfanyl)-undecyloxy]-ethoxy}-ethoxy)-ethanol (9)

Aldrithiol-2 (145 mg, 0.66 mmol) was added to a solution of 2-{2-[2-(11-mercapto-undecyloxy) -ethoxy]-ethoxy}-ethanol (201 mg, 0.66 mmol) in 5 mL of MeOH. After stirring the solution for 18 h at room temperature, the solvent was evaporated, and the residue was purified by flash chromatography (gradient elution, hexanes/EtOAc 1:1, v/v to EtOAc) to afford 9 148 mg (56%). $^1$H NMR 400 MHz (CDCl$_3$) d 8.44 (s, 1H), 7.74 (br s, 1H), 7.60 (br s, 1H), 7.07 (br s, 1H), 3.75-355 (br, 12H), 3.43 (t, J=7 Hz, 2H), 2.77 (t, J=7.0 Hz, 2H), 1.65 (m, 2H), 1.55 m, 2H), 1.41-1.17 (br, 14H).

2-(2-{2-[2-(2-{2-[11-(11-{2-[2-(2-Hydroxy-ethoxy)-ethoxy]-ethoxy}-undecyldisulfanyl)-undecyloxy]-ethoxy}-ethoxy)-ethoxy]-ethoxy}-ethoxy-ethyl-ammonium trifluoro-acetate (8)

To a solution of 7 (120 mg, 0.2 mmol) in 5 mL of MeOH was added 9 (101 mg, 0.22 mmol). The solution was stirred at room temperature for 33 hours. After concentration, the reaction mixture was purified by flash chromatography (gradient: $CH_2Cl_2$/MeOH, 20:1 to 10:1 to 5:1, v/v) to afford 137 mg of impure 8. $^1$H NMR 400 MHz (CD$_3$OD) d 3.85 (t, J=4.8 Hz, 2H), 3.76-3.52 (m, 32H), 3.42 (m, 4H), 3.14 (t, J=4.8 Hz, 2H), 2.65 (t, J=7.4 Hz, 4H), 1.67 (m, 2H), 1.55 (m, 2H), 1.40-1.18 (br m, 32H).

4-(2,5-Dioxo-2,5-dihydro-pyrrol-1-yl)-N-[2-(2-{2-[2-(2-{2-[11-(11{2-[2-(2-hydroxy-ethoxy) -ethoxy]-ethoxy}-undecyldisulfanyl)-undecyloxy]-ethoxy}-ethoxy) -ethoxy]-ethoxy}-ethoxy)-ethyl]-butyramide (1)

To a solution of crude 8 (137 mg, 0.2 mmol) in 4 mL of anhydrous DMF was added g-malcimidebutyric acid N-hydroxysuccinimide ester (10) (58 mg, 0.21 mmol) and Et$_3$N (48 mL, 0.34 mmol). The solution was stirred at room temperature for 24 hours. After concentration, the reaction mixture was purified by flash chromatography (EtOAc/MeOH, 10:1, v/v) to afford 22 mg of 1. $^1$H NMR 400 MHz (CDCl$_3$) d 6.69 (s, 2H), 6.48 (br, 1H), 3.72 (t, J=X Hz, 2H), 3.68-3.52 (br m, 32H), 3.42 (m, 4H), 2.65 (t, J=X Hz, 4H), 2.15 (t, J=X Hz, 2H), 1.91 (m, 2H), 1.7-1.5 (m, 8H), 1.4-1.2 (br, 28H). ES-MS: m/z 967.8 (MH$^+$).

2-(2-{2-[11-(11-{2-[2-(2-Hydroxy-ethoxy)-ethoxyl-ethoxy}-undecyl disulfanyl)-undecyloxy]-ethoxy}-ethoxy)-ethanol (2)

To a solution of 2-{2-[2-]11-mercapto-undecyloxy)-ethoxy]-ethoxy}-ethanol (145 mg, 0.43 mmol) dissolved in 5 mL of THF was added 1 mL of a NaOH solution (0.1 M), followed by iodine (5 crystals). The solution was stirred at room temperature for 24 h and added to 20 mL of $CH_2Cl_2$. After the solution was rinsed with $H_2O$ (2×5 mL), the organics were dried over MgSO$_4$ and concentrated. The crude residue was purified by flash chromatography ($CH_2Cl_2$/MeOH, 20:1, v/v) to afford 78 mg (54%) of 2. $^1$H NMR 400 MHz (CDCl$_3$) d 3.72-3.52 (br, 24H), 3.44 (t, J=7.2 Hz, 4H), 2.66 (t, J=7.0 Hz, 2H), 2.41 (br s, 2H), 1.65 (m, 4H), 1.57 (m, 4H), 1.41-1.20 (br, 28H).

Ferrocene-2-carboxylic acid [2-(pyridin-2-yldisulfanyl)-ethyl]-amide (12)

EDC (213 mg, 1.1 mmol) was added to a solution of ferrocenecarboxylic acid (232 mg, 1.0 mmol) and N-hydroxysuccinimide (128 mg, 1.1 mmol) dissolved in 20 mL of $CH_2Cl_2$. The solution was stirred at room temperature for 5 h and concentrated. The crude residue was dissolved in 8 mL of DMF and 2-(pyridin-2-yldisulfanyl) -ethyl-ammonium chloride (222 mg, 1.0 mmol) was added followed by Et$_3$N (0.14 mL, 1.0 mmol). After stirring for 48 h, the solvent was evaporated in vacuo. The crude residue was purified by flash chromatography (gradient: hexanes/EtOAc, 1:1, v/v to EtOAc) to afford 113 mg (28% over 2 steps) of 12. $^1$H NMR 400 MHz (CDCl$_3$) d 8.56 (m, 1H), 7.61 (m, 1H), 7.52 (m, 1H), 7.43 (t, J=6.8 Hz, 1H), 7.15 (m, 1H), 4.75 (m, 2H), 4.34 (m, 2H), 4.20 (s, 5H), 3.63 (q, J=6.0 Hz, 2H), 2.98 (t, J=6.0 Hz, 2H).

Ferrocene-2-carboxylic acid (2-mercapto-ethyl)-amide (13)

To a solution of 12 (113 mg, 0.28 mmol) dissolved in 6 mL of MeOH was added DTT (438 mg, 2.8 mmol) and Et$_3$N (79 mL, 0.57 mmol). The solution was stirred at room temperature for 18 h, followed by evaporation of the solvent. The residue was dissolved in 15 mL of EtOAc and rinsed with $H_{20}$ (8×15 mL) to remove excess DTT. After drying over MgSO$_4$ and concentrating, the residue was purified by flash chromatography (hexanes/EtOAc, 1:1, v/v) to afford 46 mg (57%) of 13. $^1$H NMR 400 MHz (CDCl$_3$) d 6.16 (br s, 1H), 4.66 (t, J=1.8 Hz, 2H), 4.33 (t, J=1.8 Hz, 2H), 4.19 (s, 5H), 3.53 (q, J=6.4 Hz, 2H), 2.75 (m, 2H).

Synthesis of Ethyl-4-nitrophenyl(8-mercapto-octyl) phosphonate Diethyl(7-octene)phosphonate (15)

A mixture of 8-bromo-1-octene (14) (5 g, 26.16 mmol) and triethyl phosphite (8.69 g, 52.32 mmol) was slowly heated to 156° C. The reaction mixture was stirred overnight at this temperature under Argon. The ethyl bromide that evolved was trapped with a condenser and a receiving flask in an ice bath. Excess triethyl phosphite was removed in vacuo and the residual oil was distilled under high vacuum (~160° C.) to give (15) as a colorless oil (6.22 g, 96%). 1H NMR (400 MHz, CDCl$_3$) 1.2-1.4 (m, 12H), 1.5 (m, 2H), 2.0 (δ, 2H), 4.1 (m, 4H), 4.9 (q, 2H), 5.8 (m, 1H). $^{31}$P(400 MHz, CDCl$_3$) δ 33.3.

Ethyl-4-nitrophenyl(7-octene)phosphonate (16)

Compound (15) (1.00 g, 4.03 mmol) was dissolved in dry $CH_2Cl_2$ (30 mL). After the mixture was cooled to 0° C. under Argon, oxalyl chloride (1.28 g, 10.07 mmol) was added drop wise. The mixture was slowly allowed to reach room temperature and stirred for 16 hours. Excess oxalyl chloride and the solvent were removed in vacuo. The intermediate mono-chlorophosphate and 4-nitrophenol (561 mg, 4.03 mmol) were dissolved in dry $CH_2Cl_2$ (30 mL). Triethylamine (816 mg, 8.06 mmol) was added drop wise and the mixture was stirred at room temperature for 5 hours. This was concentrated in vacuo to obtain a yellow oil, which was purified by flash chromatography (silica gel, Hex: EtOAc (1:1)) to give pure (3) as an oil (1.06 g, 77%). $^1$H NMR (400 MHz, $CDCl_3$) δ 1.2-1.5 (m, 9H), 1.7 (m, 2H), 2.0 (m, 2H), 4.2 (m, 2H), 5.0 (m, 2H), 5.8 (m, 1H), 7.4 (6, 2H), 8.2 (δ, 2H).

Ethyl-4-nitrophenyl(8-thioacetate-octyl)phosphonate (17)

A solution of (16) (161 mg, 0.47 mmol) in dry 1,4-dioxane (5 mL) containing thioacetic acid (359 mg, 4,72 mmol) and AIBN (15.4 mg, 0.094 mmol) was stirred at reflux under Argon for 2.5 hours. The mixture was concentrated, and was purified by flash chromatography (silica gel, CH2Cl2:EtOAc (4:1)) to give compound (4) as a yellow oil (149 mg, 76%). $^1$H NMR (400 MHz, CDCl3) δ 6 1.2-1.5 (m, 9H), 1.5-1.6 (m, 2H), 1.9-2.0 (m, 2H), 2.35 (s, 3H), 2.85 (t, 2H), 4.1-4.3 (m, 2H), 7.4 (δ, 2H), 8.25 (δ, 2H).

Ethyl-4-nitrophenyl(8-mercapto-octyl)phosphonate (18)

A solution of compound (17) (1.14 g, 2.72 mmol) in MeOH (30 mL) containing concentrated HCl (545 mL, 13.6 mmol) was stirred at 40° C. for 16 hours. The mixture was concentrated in vacuo, re-dissolved in CH2Cl2 and washed with saturated sodium bicarbonate (2×20 mL) and brine (1×20 mL). The organic layer was dried over $Na_2SO_4$ and concentrated to give a pure (18) as a yellow oil. $^1$H NMR (400MHz, $CDCl_3$) 8 1.2-1.5 (m, 11H), 1.7 (m, 2H), 1.9 (m, 2H), 2.5 (q, 2H), 4.1-4.3 (m, 2H), 5.0 (m, 2H), 5.8 (m, 1H), 7.4 (δ, 2H), 8.25 (δ, 2H).

Example 13

Immobilization of Carbohydrates

Carbohydrate Tagging

All carbohydrates were derivatized by converting the peracetylated sugar, having an n-pentenyl group on the reducing end, to a thiolacetate derivative. The sugars were then saponified under oxygen-free conditions to afford, after neutralization, the fully deprotected carbohydrate containing a thiol group at the reducing end. See FIG. 39.

Carbohydrate Immobilization

Carbohydrates were covalently immobilized to a monolayers (on a microscope slide) presenting maleimide at a density of 2% by incubation with a solution of fully deprotected carbohydrate comprising a reducing end pentane thiol group (1 mM carbohydrate in pH 6 phosphate buffer) for 1 hour. After rinsing with water and ethanol, the monolayers were dried under a stream of nitrogen. See FIG. 40.

Example 14

Gycosyltransferase Assay

A surface presenting 3 different substrates for a glycosyltransferase assay was formed by contacting a maleimide surface with 3 different carbohydrate-thiol solution. The carbohydrates were immobilized in discrete locations on the slide by confining the solutions using a peelable and resealable device. See FIG. 41.

The invention claimed is:

1. A method for performing at least one bulk process step on a biological material comprising:
   a) chemically treating a base plate to enhance immobilization of kinase substrates thereon with a solution of mixed self-assembled monolayer (SAM) comprising about 0.1 to 20% maleimide-terminal groups in a background of tri(ethylene glycol) terminal groups;
   b) placing a first removable member on the base plate for establishing self-sealing contact of the first removable member on the base plate,
      the first removable member being adapted to repeatedly self-seal on the base plate,
      the first removable member further defining a plurality of first orifices therein, each having a plurality of first walls bounding respective ones of the plurality of first orifices,
      the first removable member further being configured such that, when placed in self-sealing contact with the base plate, the first removable member defines a plurality of first wells therewith corresponding to respective ones of the plurality of first orifices;
   c) immobilizing a biological material on a plurality of first regions of the base plate exposed by the plurality of first orifices;
   d) removing the first removable member from the base plate such that the biological material is arrayed on the base plate in an array that corresponds to the plurality of first orifices; and
   e) performing at least one bulk process step on the entire array of biological material on the base plate simultaneously.

2. The method of claim 1, wherein step e) comprises washing the array of biological material on the base plate.

3. The method of claim 1, wherein step e) comprises incubating the array of biological material on the base plate with a reagent.

4. The method of claim 1, wherein step e) comprises fixing the array of biological material on the base plate.

5. The method of claim 1, wherein step e) comprises developing the array of biological material.

6. The method of claim 1, further comprising before step e): modifying the biological material.

7. The method of claim 1, further comprising:
   f) placing a second removable member on the base plate for establishing self-sealing contact of the second removable member on the base plate,
      the second removable member being adapted to repeatedly self-seal on the base plate,
      the second removable member further defining a plurality of second orifices therein, each having a plurality of second walls bounding respective ones of the plurality of second orifices,
      the second removable member further being configured such that, when placed in self-sealing contact with the base plate, the second removable member defines a plurality of second wells therewith,
      the second wells being arrayed such that at least a portion of the first regions of biological material on the base plate are within respective ones of the plurality of second wells.

8. The method of claim 7, further comprising:
g) performing at least one bulk process step on the regions of biological material revealed by the second wells.

9. The method of claim 7, further comprising:
performing step e) before step d).

10. The method of claim 1, wherein step e) comprises exposing the array of biological material to at least one of a biomolecule or a reagent.

11. The method of claim 1, wherein step e) includes at least one of washing the array of biological material, fixing the array of biological material and developing the array of biological material.

12. The method of claim 8, further comprising:
performing step e) before step d).

13. The method of claim 12, wherein step g) comprises exposing the array of biological material to at least one of a biomolecule, a reagent, an enzyme or an antibody.

14. The method of claim 12, wherein step g) includes at least one of washing the array of biological material, fixing the array of biological material and developing the array of biological material.

15. The method of claim 1, further comprising:
performing step f) before step e); and
performing step e) before step d).

16. The method of claim 1, further comprising:
performing step e) before step b).

17. The method of claim 1, further comprising:
performing step e) before step d); and
h) measuring a change in the immobilized biological material resulting from step e).

18. The method of claim 8, further comprising:
performing step e) before step d); and
h) measuring a change in the immobilized biological material resulting from step e) and step g).

19. The method of claim 1, wherein step a) comprises a solution of mixed self-assembled monolayer (SAM), such that binding of kinase substrates is enhanced in discrete areas and reduced or eliminated in others.

20. The method of claim 19, wherein specific binding of kinase substrates in desired orientations is enhanced and non-specific binding of kinase substrates is reduced or eliminated.

21. The method of claim 8, further comprising:
i) removing the second removable member.

22. The method of claim 7, wherein the plurality of second orifices are configured such that each second region on the base plate exposed by a respective one of the second plurality of orifices is smaller than each first region on the base plate exposed by a respective one of the first plurality of orifices.

23. The method of claim 7, wherein the plurality of second orifices are configured such that each second region on the base plate exposed by a respective one of the second plurality of orifices is larger than each first region on the base plate exposed by a respective one of the first plurality of orifices.

24. The method of claim 10, wherein the biomolecule comprises an enzyme or an antibody.

* * * * *